US011717452B2

(12) United States Patent
Monson et al.

(10) Patent No.: US 11,717,452 B2
(45) Date of Patent: *Aug. 8, 2023

(54) INCONTINENCE DETECTION SYSTEMS FOR HOSPITAL BEDS

(71) Applicant: Hill-Rom Services, Inc., Batesville, IN (US)

(72) Inventors: Gavin M. Monson, Oxford, OH (US); Todd P. O'Neal, Fairfield, OH (US); David Lance Ribble, Indianapolis, IN (US); Dan R. Tallent, Hope, IN (US); John D. Christie, Batesville, IN (US); Kirsten M. Emmons, Batesville, IN (US); Yongji Fu, Harrison, OH (US); Michael Scott Hood, Batesville, IN (US); Douglas A. Seim, Okeana, OH (US); Ryan S. Severns, Grand Rapids, MI (US); James D. Voll, Columbus, IN (US); Gregory Wiley, Indianapolis, IN (US); Steven Alan Dixon, Riverview, FL (US); Bryan Weidman, Columbus, IN (US); Eric David Benz, Sunman, IN (US); Brett Knittle, Oldenburg, IN (US); Marwan Nusair, Cincinnati, OH (US); Neal Wiggermann, Batesville, IN (US); John V. Harmeyer, Cleves, OH (US); Joshua A. Williams, Harrison, OH (US)

(73) Assignee: Hill-Rom Services, Inc., Batesville, IN (US)

( * ) Notice: Subject to any disclaimer, the term of this patent is extended or adjusted under 35 U.S.C. 154(b) by 113 days.

This patent is subject to a terminal disclaimer.

(21) Appl. No.: 17/478,114

(22) Filed: Sep. 17, 2021

(65) Prior Publication Data

US 2022/0000678 A1  Jan. 6, 2022

Related U.S. Application Data

(63) Continuation of application No. 15/775,882, filed as application No. PCT/US2016/062167 on Nov. 16, 2016, now Pat. No. 11,147,719.

(Continued)

(51) Int. Cl.
*A61F 13/42* (2006.01)
*A61B 5/00* (2006.01)
(Continued)

(52) U.S. Cl.
CPC .............. *A61F 13/42* (2013.01); *A61B 5/207* (2013.01); *A61B 5/6802* (2013.01);
(Continued)

(58) Field of Classification Search
CPC .... A61F 13/42; A61F 2013/424; A61B 5/207; A61B 5/6802; A61B 5/6804;
(Continued)

(56) References Cited

U.S. PATENT DOCUMENTS

| | | |
|---|---|---|
| 1,772,232 A | 8/1930 | Guilder |
| 2,127,538 A | 8/1938 | Seiger |

(Continued)

FOREIGN PATENT DOCUMENTS

| | | |
|---|---|---|
| CA | 2361145 | 12/1999 |
| CA | 2494896 | 12/1999 |

(Continued)

OTHER PUBLICATIONS

Extended EP Search Report for European Patent Application No. 16866993.5 dated Jul. 16, 2018; 8 pages.

(Continued)

*Primary Examiner* — Nabil H Syed
*Assistant Examiner* — Cal J Eustaquio
(74) *Attorney, Agent, or Firm* — Barnes & Thornburg LLP

(57) ABSTRACT

An incontinence detection system monitors an area for moisture events and wirelessly transmits moisture-related information to one or more notification devices. The system has a pad that includes a substrate and one or more sensors supported by the substrate. The sensor(s) emit wireless signals indicative of the moisture-related information. A sensor event communication system forwards the sensor signals to another device, such as a notification device. Portions of the system are included in a patient support apparatus, such as a bed.

20 Claims, 90 Drawing Sheets

Related U.S. Application Data

(60) Provisional application No. 62/255,592, filed on Nov. 16, 2015.

(51) Int. Cl.

| | |
|---|---|
| G16H 40/20 | (2018.01) |
| A61G 7/015 | (2006.01) |
| A61G 7/05 | (2006.01) |
| G06K 7/10 | (2006.01) |
| H01Q 1/22 | (2006.01) |
| H01Q 9/04 | (2006.01) |
| A61B 5/20 | (2006.01) |
| G06K 19/077 | (2006.01) |
| G08B 21/20 | (2006.01) |
| G06K 7/00 | (2006.01) |
| G01M 3/04 | (2006.01) |
| A61B 5/05 | (2021.01) |

(52) U.S. Cl.
CPC .......... *A61B 5/6804* (2013.01); *A61B 5/6808* (2013.01); *A61B 5/6892* (2013.01); *A61B 5/7465* (2013.01); *A61G 7/015* (2013.01); *A61G 7/05* (2013.01); *G06K 7/10069* (2013.01); *G06K 7/10168* (2013.01); *G06K 7/10356* (2013.01); *G06K 7/10366* (2013.01); *G16H 40/20* (2018.01); *H01Q 1/2216* (2013.01); *H01Q 9/0407* (2013.01); *H01Q 9/0457* (2013.01); *A61B 5/0022* (2013.01); *A61B 5/05* (2013.01); *A61B 5/202* (2013.01); *A61B 2503/08* (2013.01); *A61B 2560/0468* (2013.01); *A61B 2562/164* (2013.01); *A61F 2013/424* (2013.01); *A61G 2203/30* (2013.01); *A61G 2203/70* (2013.01); *A61G 2205/60* (2013.01); *G01M 3/045* (2013.01); *G06K 7/0095* (2013.01); *G06K 19/07718* (2013.01); *G08B 21/20* (2013.01); *Y10T 156/1052* (2015.01); *Y10T 156/1056* (2015.01)

(58) Field of Classification Search
CPC ... A61B 5/6808; A61B 5/6892; A61B 5/7465; A61B 5/0022; A61B 5/05; A61B 5/202; A61B 2503/08; A61B 2560/0468; A61B 2562/164; A61G 7/015; A61G 7/05; A61G 2203/30; A61G 2203/70; A61G 2205/60; G06K 7/10069; G06K 7/10168; G06K 7/10356; G06K 7/10366; G06K 7/0095; G06K 19/07718; G16H 40/20; H01Q 1/2216; H01Q 9/0407; H01Q 9/0457; G01M 3/045; G08B 21/20; Y10T 156/1052; Y10T 156/1056

See application file for complete search history.

(56) References Cited

U.S. PATENT DOCUMENTS

| | | |
|---|---|---|
| 2,644,050 A | 6/1953 | Seiger |
| 2,668,202 A | 2/1954 | Kaplan |
| 2,726,294 A | 12/1955 | Kroening et al. |
| 2,766,463 A | 10/1956 | Bendersky |
| 2,907,841 A | 10/1959 | Campbell |
| 3,199,095 A | 8/1965 | Ashida |
| 3,971,371 A | 7/1976 | Bloom |
| 4,069,817 A | 1/1978 | Fenote et al. |
| 4,106,001 A | 8/1978 | Mahoney |
| 4,163,449 A | 8/1979 | Regal |
| 4,191,950 A | 3/1980 | Levin et al. |
| 4,212,295 A | 7/1980 | Snyder |
| 4,228,426 A | 10/1980 | Roberts |
| 4,347,503 A | 8/1982 | Uyehara |
| 4,529,087 A | 7/1985 | Neal |
| 4,539,559 A | 9/1985 | Kelley et al. |
| 4,610,685 A | 9/1986 | Raley |
| 4,747,166 A | 5/1988 | Kuntz |
| 4,965,554 A | 10/1990 | Darling |
| 5,081,422 A | 1/1992 | Shih |
| 5,086,294 A | 2/1992 | Schwab, Jr. |
| 5,137,033 A | 8/1992 | Norton |
| 5,144,284 A | 9/1992 | Hammett |
| 5,291,181 A | 3/1994 | De Ponte |
| 5,438,721 A | 8/1995 | Pahno et al. |
| 5,459,452 A | 10/1995 | DePonte |
| 5,491,609 A | 2/1996 | Dankman et al. |
| 5,537,095 A | 7/1996 | Dick et al. |
| 5,570,082 A | 10/1996 | Mahgerefteh et al. |
| 5,675,854 A | 10/1997 | Zibelin |
| 5,760,694 A | 6/1998 | Nissim |
| 5,790,035 A | 8/1998 | Ho |
| 5,824,883 A | 10/1998 | Park et al. |
| 5,827,254 A | 10/1998 | Trombetta et al. |
| 5,910,080 A | 6/1999 | Selton |
| 5,947,943 A | 9/1999 | Lee |
| 6,028,241 A | 2/2000 | Armstead |
| 6,047,419 A | 4/2000 | Fergusaon |
| 6,104,311 A | 8/2000 | Lastinger |
| 6,200,250 B1 | 3/2001 | Janszen |
| 6,235,011 B1 | 5/2001 | O'Connell |
| 6,292,102 B1 | 9/2001 | Smith |
| 6,340,932 B1 | 1/2002 | Rodgers et al. |
| 6,341,393 B1 | 1/2002 | Votel |
| 6,351,215 B2 | 2/2002 | Rodgers et al. |
| 6,362,737 B1 | 3/2002 | Rodgers et al. |
| 6,384,728 B1 | 5/2002 | Kanor et al. |
| 6,544,200 B1 | 4/2003 | Smith et al. |
| 6,552,661 B1 | 4/2003 | Lastinger et al. |
| 6,559,772 B2 | 5/2003 | Zand et al. |
| 6,583,722 B2 | 6/2003 | Jeutter et al. |
| 6,603,403 B2 | 8/2003 | Jeutter et al. |
| 6,621,410 B1 | 9/2003 | Lastinger et al. |
| 6,639,517 B1 | 10/2003 | Chapman et al. |
| 6,774,800 B2 | 8/2004 | Friedman et al. |
| 6,831,562 B2 | 12/2004 | Rodgers et al. |
| 6,832,507 B1 | 12/2004 | van de Berg et al. |
| 6,933,849 B2 | 8/2005 | Sawyer |
| 6,948,205 B2 | 9/2005 | Van Der Wurf et al. |
| 6,982,646 B2 | 1/2006 | Rodgers et al. |
| 7,017,213 B2 | 3/2006 | Chisari |
| 7,030,731 B2 | 4/2006 | Lastinger et al. |
| 7,071,830 B2 | 7/2006 | Sahiberg et al. |
| 7,120,952 B1 | 10/2006 | Bass et al. |
| 7,141,715 B2 | 11/2006 | Shapira |
| 7,181,206 B2 | 2/2007 | Pedersen |
| 7,250,547 B1 | 7/2007 | Hofmeister et al. |
| 7,253,729 B2 | 8/2007 | Lastinger et al. |
| 7,274,944 B2 | 9/2007 | Lastinger et al. |
| 7,302,278 B2 | 11/2007 | Lastinger et al. |
| 7,305,246 B2 | 12/2007 | Lastinger et al. |
| 7,308,270 B2 | 12/2007 | Lastinger et al. |
| 7,348,930 B2 | 3/2008 | Lastinger et al. |
| 7,349,701 B2 | 3/2008 | Lastinger et al. |
| 7,355,090 B2 | 4/2008 | Ales, III et al. |

(56) References Cited

U.S. PATENT DOCUMENTS

| | | |
|---|---|---|
| 7,359,675 B2 | 4/2008 | Lastinger et al. |
| 7,400,860 B2 | 7/2008 | Lastinger et al. |
| 7,424,298 B2 | 9/2008 | Lastinger et al. |
| 7,489,252 B2 | 2/2009 | Long et al. |
| 7,489,282 B2 | 2/2009 | Lastinger et al. |
| 7,498,478 B2 | 3/2009 | Long et al. |
| 7,551,089 B2 | 6/2009 | Sawyer |
| 7,586,385 B2 | 9/2009 | Rokhsaz |
| 7,595,734 B2 | 9/2009 | Long et al. |
| 7,595,756 B2 | 9/2009 | Lastinger et al. |
| 7,598,853 B2 | 10/2009 | Becker et al. |
| 7,598,862 B2 | 10/2009 | Lastinger et al. |
| 7,599,699 B2 | 10/2009 | Lastinger et al. |
| 7,616,959 B2 | 11/2009 | Spenik et al. |
| 7,633,378 B2 | 12/2009 | Rodgers et al. |
| 7,649,125 B2 | 1/2010 | Ales, III et al. |
| 7,663,483 B2 | 2/2010 | Spenik et al. |
| 7,667,600 B2 | 2/2010 | Woodbury et al. |
| 7,812,731 B2 | 10/2010 | Bunza et al. |
| 7,822,386 B2 | 10/2010 | Lastinger et al. |
| 7,834,234 B2 | 11/2010 | Roe et al. |
| 7,834,235 B2 | 11/2010 | Long et al. |
| 7,834,765 B2 | 11/2010 | Sawyer |
| 7,834,766 B2 | 11/2010 | Sawyer |
| 7,838,720 B2 | 11/2010 | Roe et al. |
| 7,849,544 B2 | 12/2010 | Flocard et al. |
| 7,873,319 B2 | 1/2011 | Lastinger et al. |
| 7,977,529 B2 | 7/2011 | Bergman et al. |
| 8,009,646 B2 | 8/2011 | Lastinger et al. |
| 8,073,386 B2 | 12/2011 | Pedersen |
| 8,081,043 B2 | 12/2011 | Rokhsaz |
| 8,102,254 B2 | 1/2012 | Becker et al. |
| 8,104,126 B2 | 1/2012 | Caminade et al. |
| 8,106,782 B2 | 1/2012 | Fredriksson et al. |
| 8,111,165 B2 | 2/2012 | Ortega et al. |
| 8,111,678 B2 | 2/2012 | Lastinger et al. |
| 8,121,856 B2 | 2/2012 | Huster et al. |
| 8,181,290 B2 | 5/2012 | Brykalski et al. |
| 8,191,187 B2 | 6/2012 | Brykalski et al. |
| 8,196,809 B2 | 6/2012 | Thorstensson |
| 8,237,572 B2 | 8/2012 | Clement et al. |
| 8,248,249 B2 | 8/2012 | Clement et al. |
| 8,270,383 B2 | 8/2012 | Lastinger et al. |
| 8,279,069 B2 | 10/2012 | Sawyer |
| 8,319,633 B2 | 11/2012 | Becker et al. |
| 8,325,695 B2 | 12/2012 | Lastinger et al. |
| 8,332,975 B2 | 12/2012 | Brykalski et al. |
| 8,345,651 B2 | 1/2013 | Lastinger et al. |
| 8,395,014 B2 | 3/2013 | Helmer et al. |
| 8,428,039 B2 | 4/2013 | Lastinger et al. |
| 8,428,605 B2 | 4/2013 | Pedersen et al. |
| 8,461,982 B2 | 6/2013 | Becker et al. |
| 8,471,715 B2 | 6/2013 | Solazzo et al. |
| 8,482,305 B2 | 7/2013 | Johnson |
| 8,487,774 B2 | 7/2013 | Reeder et al. |
| 8,502,684 B2 | 8/2013 | Bunza et al. |
| 8,628,506 B2 | 1/2014 | Ales, III et al. |
| 8,674,826 B2 | 3/2014 | Becker et al. |
| 8,742,929 B2 | 6/2014 | Sawyer |
| 8,749,319 B2 | 6/2014 | Rokhsaz et al. |
| 8,766,804 B2 | 7/2014 | Reeder et al. |
| 8,842,013 B2 | 9/2014 | Sawyer |
| 8,855,089 B2 | 10/2014 | Lastinger et al. |
| 8,866,615 B2 | 10/2014 | Sawyer |
| 8,878,557 B2 | 11/2014 | Kristiansen et al. |
| 8,878,676 B2 | 11/2014 | Koblasz |
| 8,896,449 B2 | 11/2014 | Sawyer |
| 8,914,923 B2 | 12/2014 | Smith |
| 8,933,292 B2 | 1/2015 | Abraham et al. |
| 8,962,909 B2 | 2/2015 | Groosman et al. |
| 9,048,819 B2 | 6/2015 | Rokhsaz et al. |
| 9,107,776 B2 | 8/2015 | Bergman et al. |
| 9,366,644 B1 | 6/2016 | Lastinger et al. |
| 9,506,886 B1 | 11/2016 | Woodbury et al. |
| 9,649,230 B1 | 5/2017 | Li |
| 9,681,996 B2 | 6/2017 | Prioleau et al. |
| 10,022,277 B2 | 7/2018 | Heil et al. |
| 11,147,719 B2 | 10/2021 | Monson et al. |
| 2002/0011932 A1 | 1/2002 | Rodgers et al. |
| 2002/0033757 A1 | 3/2002 | Rodgers et al. |
| 2002/0145526 A1 | 10/2002 | Friedman et al. |
| 2003/0030568 A1 | 2/2003 | Lastinger et al. |
| 2005/0003763 A1 | 1/2005 | Lastinger et al. |
| 2005/0003865 A1 | 1/2005 | Lastinger et al. |
| 2005/0052282 A1 | 3/2005 | Rodgers et al. |
| 2005/0060246 A1 | 3/2005 | Lastinger et al. |
| 2005/0174246 A1 | 8/2005 | Picco et al. |
| 2005/0242946 A1 | 11/2005 | Hubbard, Jr. et al. |
| 2005/0250453 A1 | 11/2005 | Lastinger et al. |
| 2005/0277441 A1 | 12/2005 | Lastinger et al. |
| 2005/0282545 A1 | 12/2005 | Lastinger et al. |
| 2005/0282553 A1 | 12/2005 | Lastinger et al. |
| 2006/0164320 A1 | 7/2006 | Lastinger et al. |
| 2006/0270351 A1 | 11/2006 | Lastinger et al. |
| 2007/0159332 A1 | 7/2007 | Koblasz |
| 2007/0202809 A1 | 8/2007 | Lastinger et al. |
| 2007/0270774 A1 | 11/2007 | Bergman et al. |
| 2008/0116990 A1 | 5/2008 | Rokhsaz |
| 2008/0204245 A1 | 8/2008 | Blair et al. |
| 2008/0262376 A1 | 10/2008 | Price |
| 2008/0263776 A1 | 10/2008 | O'Reagan et al. |
| 2008/0300559 A1 | 12/2008 | Gustafson et al. |
| 2009/0160648 A1 | 6/2009 | Rokhsaz |
| 2009/0221980 A1 | 9/2009 | Mosbacher et al. |
| 2009/0289743 A1 | 11/2009 | Rokhsaz |
| 2009/0292265 A1 | 11/2009 | Helmer et al. |
| 2009/0315728 A1 | 12/2009 | Ales, III et al. |
| 2009/0326417 A1 | 12/2009 | Ales, III et al. |
| 2010/0043143 A1 | 2/2010 | O'Reagan et al. |
| 2010/0069862 A1 | 3/2010 | Wada et al. |
| 2010/0125937 A1 | 5/2010 | Chen et al. |
| 2011/0025458 A1 | 2/2011 | Rokhsaz et al. |
| 2011/0025473 A1 | 2/2011 | Rokhsaz et al. |
| 2011/0092890 A1 | 4/2011 | Stryker et al. |
| 2011/0095884 A1 | 4/2011 | Xu et al. |
| 2011/0115635 A1 | 5/2011 | Petrovski et al. |
| 2011/0130732 A1 | 6/2011 | Jackels et al. |
| 2011/0174317 A1 | 7/2011 | Martin |
| 2011/0263952 A1 | 10/2011 | Bergman et al. |
| 2011/0283459 A1 | 11/2011 | Essers |
| 2011/0291810 A1 | 12/2011 | Rokhsaz et al. |
| 2011/0295619 A1 | 12/2011 | Tough |
| 2011/0300808 A1 | 12/2011 | Rokhsaz et al. |
| 2011/0302720 A1 | 12/2011 | Yakam et al. |
| 2012/0092027 A1 | 4/2012 | Forster |
| 2012/0105233 A1 | 5/2012 | Bobey et al. |
| 2012/0119912 A1 | 5/2012 | Ortega et al. |
| 2012/0130330 A1 | 5/2012 | Wilson et al. |
| 2012/0157947 A1 | 6/2012 | Nhan et al. |
| 2012/0165772 A1 | 6/2012 | Groosman et al. |
| 2012/0173249 A1 | 7/2012 | Popp et al. |
| 2012/0216607 A1 | 8/2012 | Sjoholm et al. |
| 2012/0217311 A1 | 8/2012 | Rokhsaz et al. |
| 2012/0268278 A1 | 10/2012 | Lewis et al. |
| 2012/0316048 A1 | 12/2012 | Oba |
| 2013/0019405 A1 | 1/2013 | Flanagan et al. |
| 2013/0079590 A1 | 3/2013 | Bengtson |
| 2013/0109929 A1 | 5/2013 | Menzel |
| 2013/0123726 A1 | 5/2013 | Yu et al. |
| 2013/0178811 A1 | 7/2013 | Kikuchi et al. |
| 2013/0254141 A1 | 9/2013 | Barda et al. |
| 2014/0120836 A1 | 5/2014 | Rokhsaz et al. |
| 2014/0148772 A1 | 5/2014 | Hu et al. |
| 2014/0152442 A1 | 6/2014 | Li |
| 2014/0200538 A1 | 7/2014 | Euliano et al. |
| 2014/0236629 A1 | 8/2014 | Kim et al. |
| 2014/0244644 A1 | 8/2014 | Mashinchi et al. |
| 2014/0247125 A1 | 9/2014 | Barsky |
| 2014/0266735 A1 | 9/2014 | Riggio et al. |
| 2014/0276504 A1 | 9/2014 | Heil et al. |
| 2014/0296808 A1 | 10/2014 | Curran et al. |
| 2014/0358099 A1 | 12/2014 | Durgin et al. |
| 2015/0080819 A1 | 3/2015 | Charna et al. |
| 2015/0080834 A1 | 3/2015 | Mills |

(56) References Cited

U.S. PATENT DOCUMENTS

| | | |
|---|---|---|
| 2015/0087935 A1 | 3/2015 | Davis et al. |
| 2016/0000291 A1 | 7/2016 | Calderas et al. |
| 2017/0065464 A1 | 3/2017 | Heil et al. |
| 2020/0060599 A1 | 2/2020 | Monson et al. |

FOREIGN PATENT DOCUMENTS

| | | |
|---|---|---|
| CN | 101304715 | 11/2008 |
| CN | 102568259 | 7/2012 |
| CN | 202711437 | 1/2013 |
| CN | 102985853 | 3/2013 |
| DE | 4137631 | 5/1992 |
| DE | 69906388 | 2/2004 |
| DE | 69915370 | 3/2005 |
| DE | 69917491 | 5/2005 |
| DE | 60016946 | 6/2006 |
| DE | 102007050074 | 4/2009 |
| EP | 0335279 | 10/1989 |
| EP | 1286179 | 12/1999 |
| EP | 1147603 | 10/2001 |
| EP | 1149305 | 10/2001 |
| EP | 1153317 | 11/2001 |
| EP | 1218771 | 7/2002 |
| EP | 1153317 | 3/2003 |
| EP | 1147603 | 3/2004 |
| EP | 1410353 | 4/2004 |
| EP | 1149305 | 5/2004 |
| EP | 1218771 | 12/2004 |
| EP | 1684615 | 8/2006 |
| EP | 2014267 | 6/2007 |
| EP | 1868553 | 12/2007 |
| EP | 1897278 | 3/2008 |
| EP | 1959900 | 8/2008 |
| EP | 1994650 | 11/2008 |
| EP | 2019659 | 2/2009 |
| EP | 1410353 | 12/2009 |
| EP | 1897278 | 1/2010 |
| EP | 1684615 | 2/2010 |
| EP | 2156222 | 2/2010 |
| EP | 2313044 | 4/2011 |
| EP | 2579069 | 6/2011 |
| EP | 2444039 | 8/2011 |
| EP | 1959900 | 2/2012 |
| EP | 2738748 | 4/2012 |
| EP | 2452183 | 5/2012 |
| EP | 2739254 | 7/2012 |
| EP | 2496197 | 9/2012 |
| EP | 1994650 | 12/2012 |
| EP | 2542200 | 1/2013 |
| EP | 2548473 | 1/2013 |
| EP | 2582341 | 4/2013 |
| EP | 2729107 | 5/2014 |
| EP | 2739254 | 6/2014 |
| EP | 2156222 | 8/2015 |
| EP | 2496197 | 8/2015 |
| EP | 2019659 | 4/2016 |
| EP | 2582341 | 4/2016 |
| GB | 145859 | 3/1919 |
| GB | 2145859 | 4/1985 |
| GB | 2408204 | 11/2003 |
| WO | 89/10110 | 4/1989 |
| WO | 94/20002 | 3/1994 |
| WO | 00/44091 | 7/2000 |
| WO | 01/25817 | 4/2001 |
| WO | 02/103645 | 12/2002 |
| WO | 2006/108540 | 10/2006 |
| WO | 2007/069968 | 6/2007 |
| WO | 2008/130298 | 10/2008 |
| WO | 2010/001271 | 1/2010 |
| WO | 2010/043368 | 4/2010 |
| WO | 2011/043724 | 4/2011 |
| WO | 2011/107580 | 9/2011 |
| WO | 2012/136157 | 10/2012 |
| WO | 2014/165041 | 10/2014 |
| WO | 2015/137999 | 9/2015 |

OTHER PUBLICATIONS

Non-Final Office Action for U.S. Appl. No. 15/708,589 dated May 23, 2018; 10 pages.
Amendment for U.S. Appl. No. 15/708,589 dated Aug. 8, 2018; 9 pages.
Notice of Allowance for U.S. Appl. No. 15/708,589 dated Sep. 6, 2018; 10 pages.
PCT Search Report and Written Opinion for PCT/US2016/062167, completed Feb. 20, 2017.

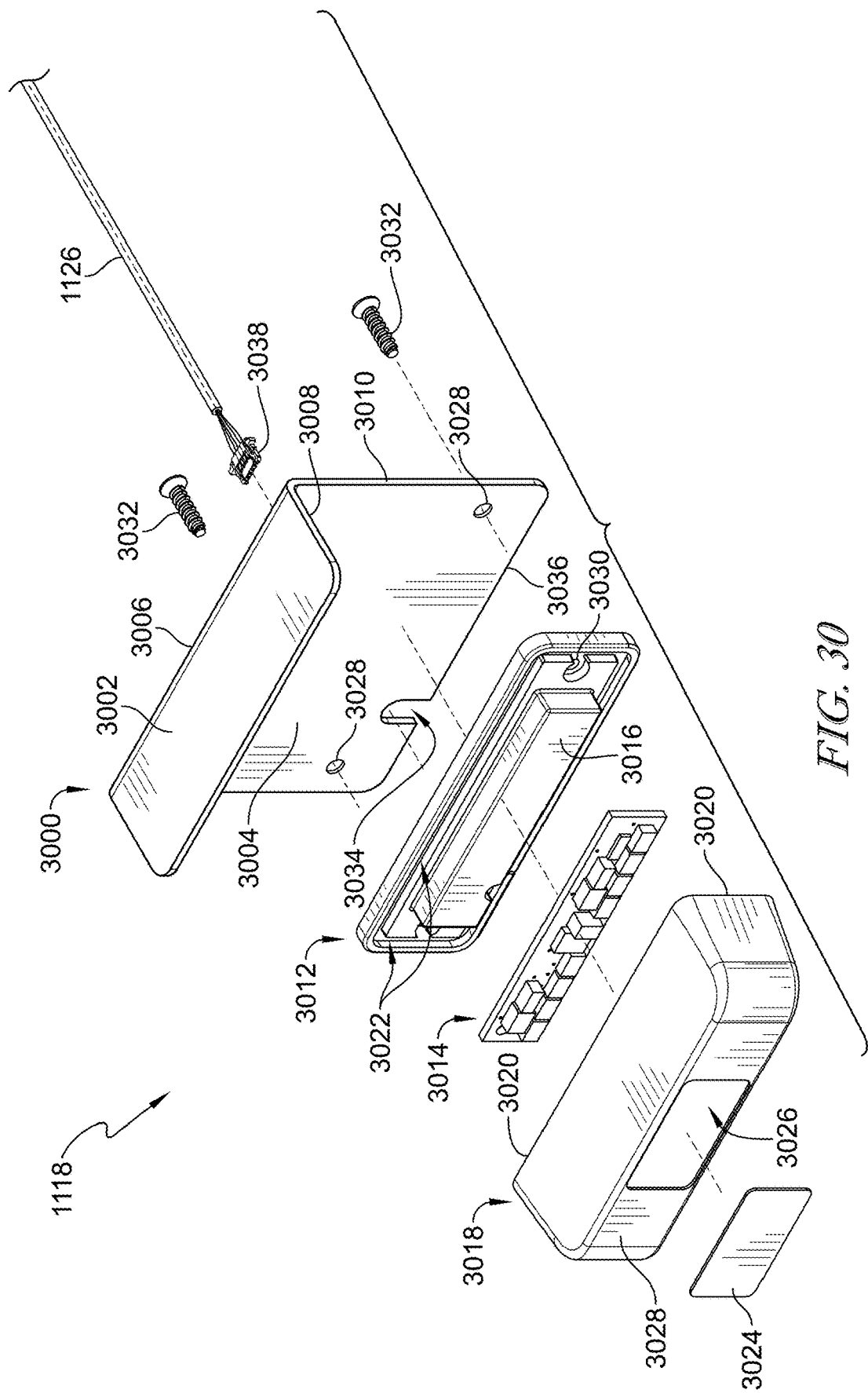

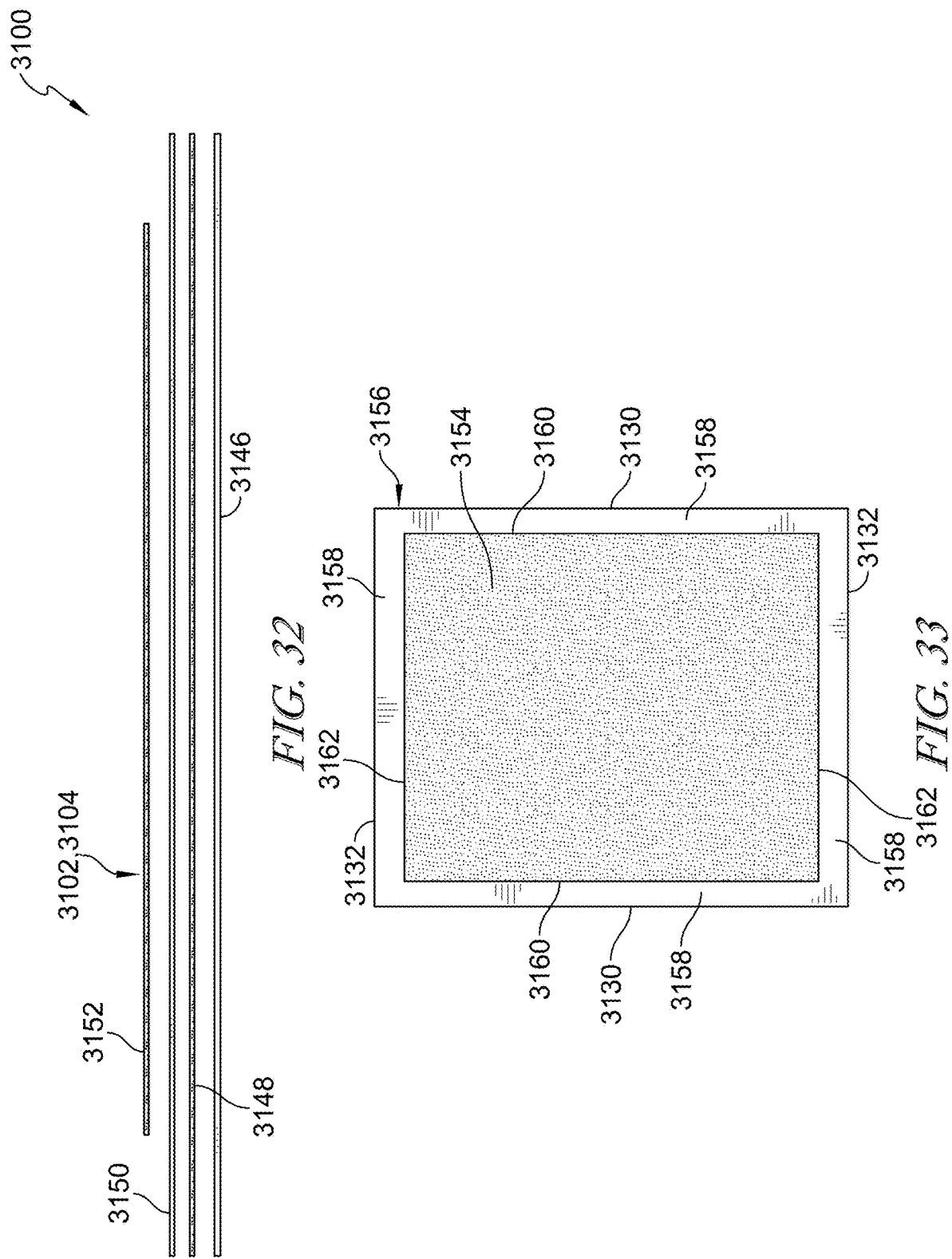

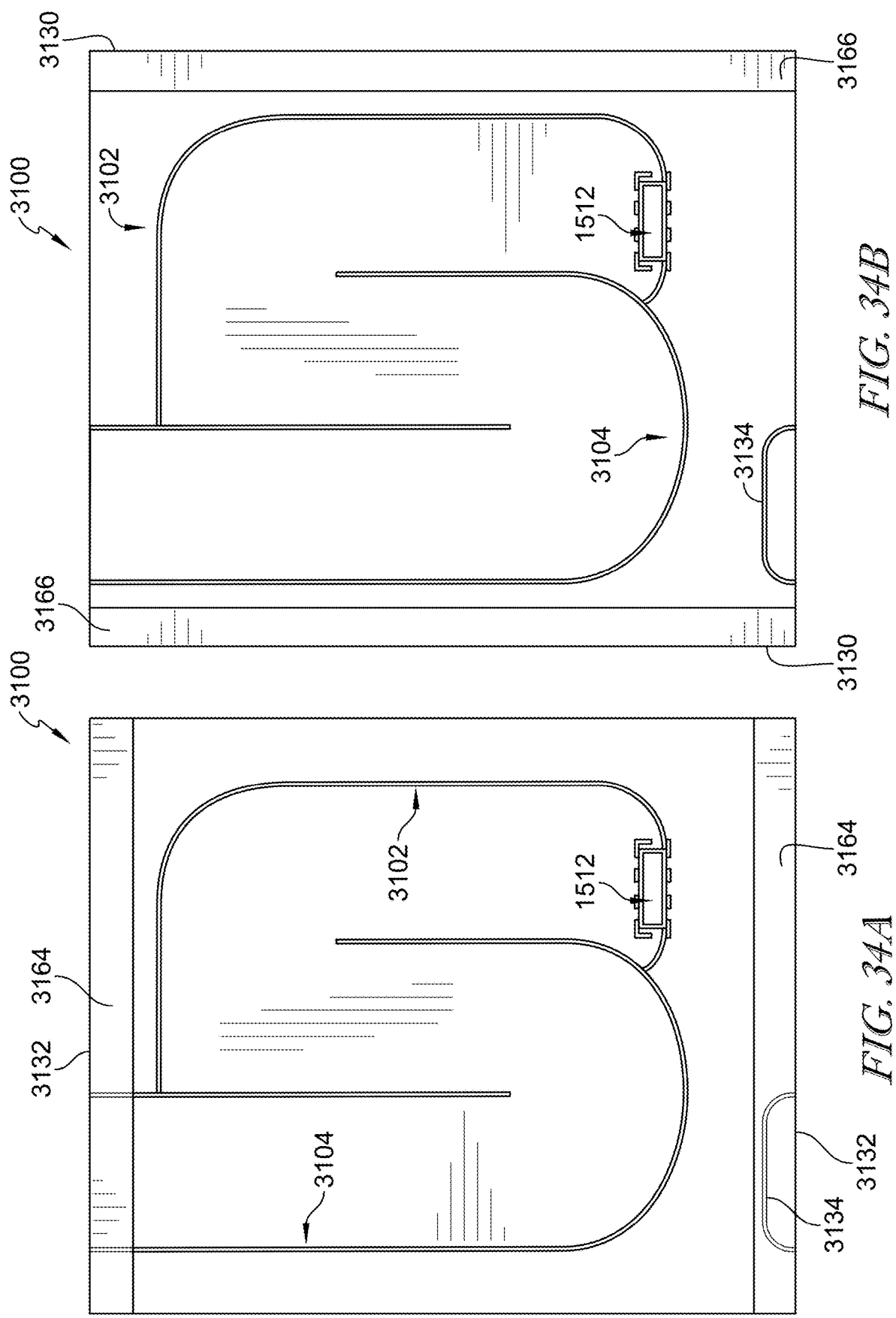

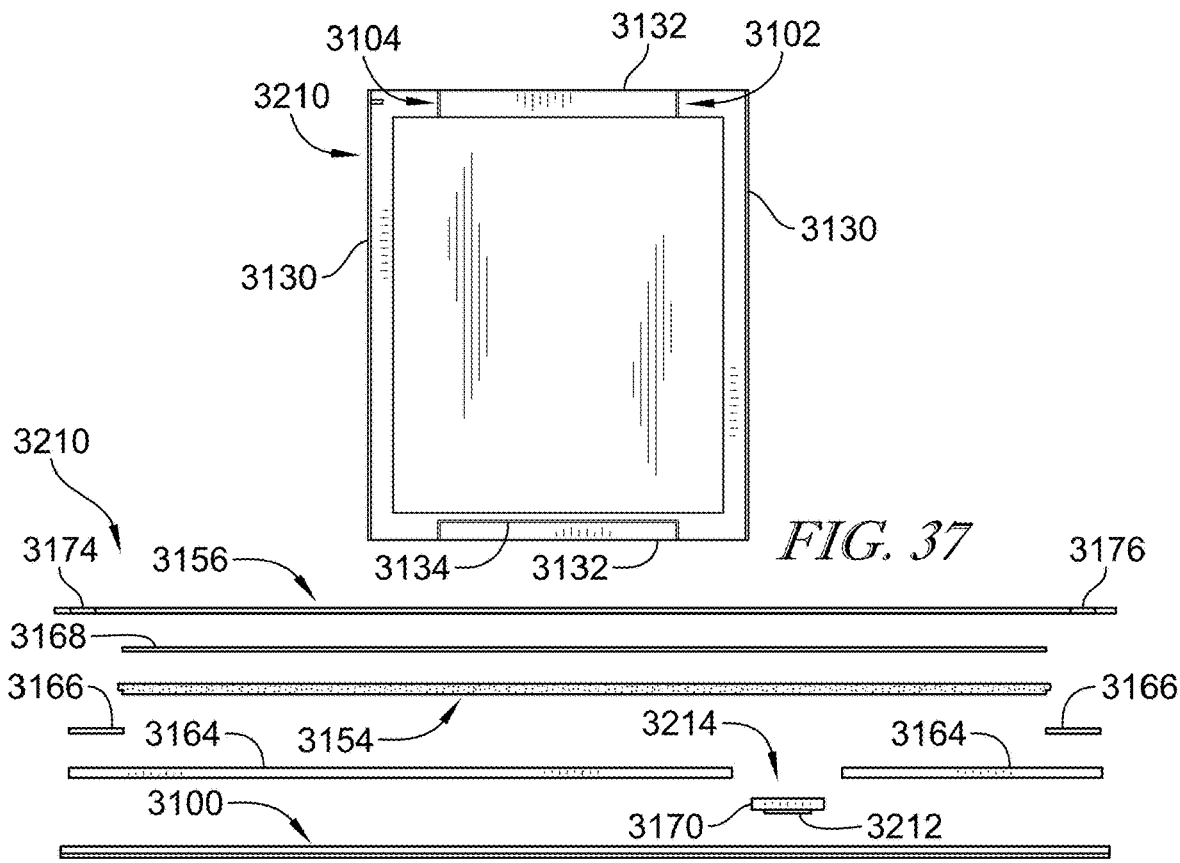
FIG. 37
FIG. 38
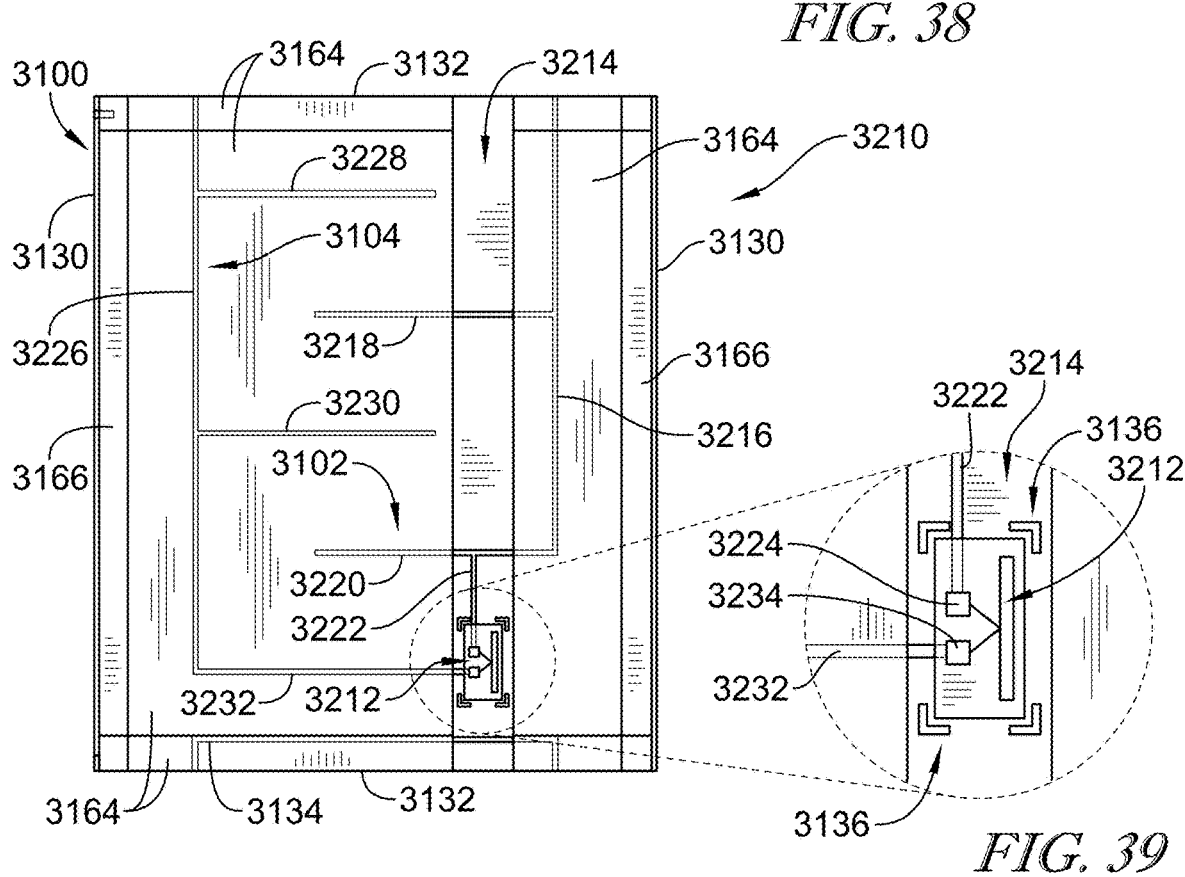
FIG. 39

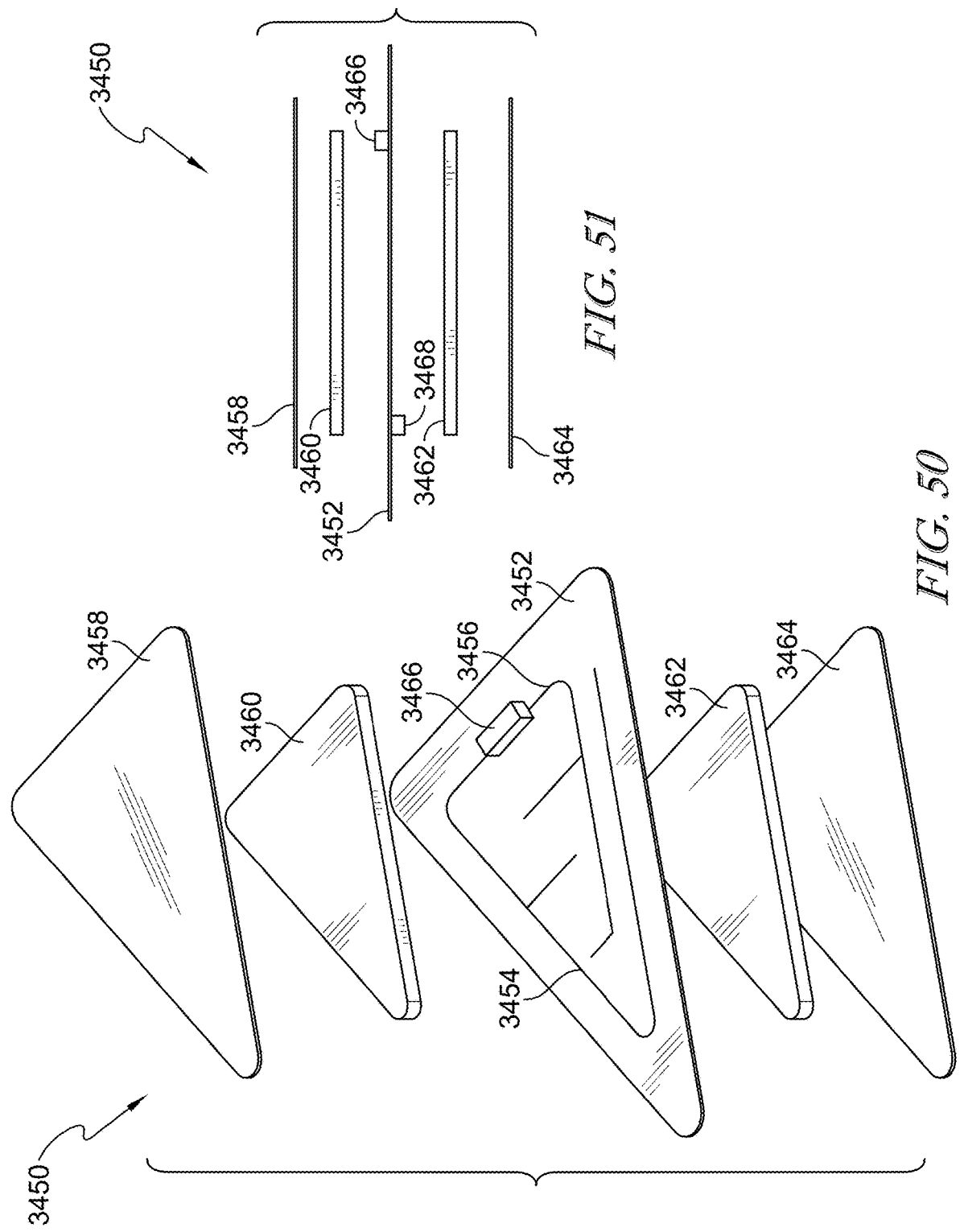

INCONTINENCE DETECTION SYSTEMS FOR HOSPITAL BEDS

This application is a continuation of U.S. application Ser. No. 15/775,882, filed May 14, 2018, now U.S. Pat. No. 11,147,719, which is a U.S. national phase of PCT/US2016/062167, filed Nov. 16, 2016, which claims the benefit, under 35 U.S.C. § 119(e), of U.S. Provisional Application No. 62/255,592, filed Nov. 16, 2015, and each of which is hereby incorporated by reference herein in its entirety.

BACKGROUND

The present disclosure relates to incontinence detection systems and particularly, to incontinence detection systems that use a pad beneath a person lying in a hospital bed. More particularly, the present disclosure relates to incontinence detection systems that are able to communicate wirelessly.

Good medical practice dictates that patients who are incontinent should be removed from the wet environment as soon as possible to avoid skin breakdown which can potentially lead to pressure ulcers. Prior art incontinent detection systems that generate an alarm when wetness is detected are known. False alarms are sometimes generated in such systems due to perspiration rather than biofluids from incontinent events. Thus, incontinence detection systems that reduce the number of false alarms would be appreciated caregivers. Also, caregivers will appreciate incontinence detection systems that communicate with other healthcare information systems due to the enhanced alerting and data collection that such systems will permit.

SUMMARY

The present application discloses one or more of the features recited in the appended claims and/or the following features which, alone or in any combination, may comprise patentable subject matter:

According to the present disclosure, an incontinence detection system for monitoring an area for the occurrence of incontinent events in the area may be provided. The incontinence detection system may include a substrate having a length and width defining a monitoring area. A sensor may be coupled to the monitoring area and may have a transmitter configured to transmit a wireless signal. The sensor may include a plurality of electrically conductive traces that may be coupled to inputs of the transmitter. Each trace of the plurality of electrically conductive traces may be arranged at measureable distances from each of the other traces of the plurality of traces on the substrate. A controller may be configured to determine a fluid volume in the substrate based on the wireless signal transmitted by the transmitter and the distances between the electrically conductive traces.

In some embodiments, the distances between each trace of the plurality of electrically conductive traces may correlate to predetermined volumes of moisture. Alternatively or additionally, the distances between each trace of the plurality of electrically conductive traces may be predetermined based on the area of the substrate and the absorption properties of the substrate. The plurality of electrically conductive traces includes may include at least three electrically conductive traces, for example. In some embodiments, the at least three electrically conductive traces may be positioned in predetermined parallel distances from each other in order to detect 50 mL and 100 mL moisture volumes. The transmitter may include a passive radio frequency identification (RFID) circuit.

In some embodiments, a fluid volume threshold may be variable among a plurality of fluid volume thresholds so that the controller may generate an alarm if the fluid volume exceeds a selected fluid volume threshold and so that the controller may not generate the alarm if the fluid volume is below the selected fluid volume threshold. The plurality of electrically conductive traces may be laid out in a grid pattern to define a plurality of sensing blocks and wherein the fluid volume may be estimated by the controller based on how many sensing blocks of the plurality of sensing blocks have been exposed to fluid. The selected fluid volume threshold may be selected automatically by the controller based on information received from a remote computer relating to a condition of a patient. For example, the selected fluid volume threshold may be smaller if the condition of the patient indicates that the patient may be at risk of developing pressure ulcers than if the condition of the patient indicates that the patient may not be at risk of developing pressure ulcers.

In some embodiments, first and second fluid volume thresholds may be selectable from among more than two fluid volume thresholds. The controller may generate a first alarm if the first fluid volume threshold is sensed and the controller may generate a second alarm if the second fluid volume threshold is sensed. The first alarm may be different than the second alarm. For example, the first alarm may include a visual alarm and the second alarm may include an audible alarm. Alternatively or additionally, the first alarm may include an audible alarm at a first volume of loudness and the second alarm may include an audible alarm at a second volume of loudness. The first volume of loudness may be different than the second volume of loudness.

In some embodiments, at least one of the first alarm and the second alarm may include a transmission to a nurse call system. Alternatively or additionally, the first alarm may include a first textual message presented on a display and the second alarm may include a second textual message presented on the display. Thus, the first alarm may include a first visual alarm and the second alarm may include a second visual alarm.

Further according to the present disclosure, a controller for an incontinence detection system may be provided and may include a processor and a memory that may have stored therein a plurality of instructions that when executed by the processor may cause the controller to: receive sensed data from a sensor that may include a plurality of electrically conductive traces; determine if incontinence is detected based on the received sensed data; determine a number of the electrically conductive traces that may have been exposed to a fluid based on the received sensed data; determine a volume of fluid based on the determined number of electrically conductive traces exposed to fluid; select an appropriate alert from a plurality of alerts based on the computed fluid volume; and transmit the appropriate alert.

In some embodiments, the appropriate alert may be a patient-specific alarm dependent on a patient condition. Alternatively or additionally, the appropriate alert may be a patient-specific alarm dependent upon a pre-defined moisture volume. The plurality of alerts may include a plurality of visual alerts indicative of no moisture, moisture volume up to a predefined threshold, and a moisture volume above the predefined threshold. Thus, the plurality of visual alerts may include a plurality of pre-assigned colors.

Also according to the present disclosure, an incontinence event communication system may include an antenna that may be configured to wirelessly receive a sensor signal that may be emitted by a sensor. The sensor signal may be indicative of a moisture event. A scanner may be configured to detect the physical presence of a caregiver in proximity to a patient. A controller may be configured to power the antenna to receive the sensor signal in response to detection of the caregiver in proximity to the patient by the scanner to cause the antenna to receive signals from the sensor.

In some embodiments, the scanner and controller may be integrated into a mobile device. The scanner may be further configured to scan a barcode. The barcode may be associated with one of the sensor, the patient, a location of the patient, and equipment holding the patient. The scanner may be configured to actively or passively detect the proximity of the caregiver to the patient. For example, the scanner may detect the caregiver by sensing the proximity of a caregiver access card or identification card. Upon detection of the caregiver in proximity to the patient by the scanner, the controller may provide power to the antenna and may report an incontinence status to the caregiver.

Further according to the present disclosure, an incontinence detection system for monitoring an area for the occurrence of moisture events in the area may be provided and may include a substrate having a length and width defining a monitoring area and a passive sensor that may include a first connection trace, a second connection trace, and a plurality of electrically conductive sensing traces that may be spaced apart from each other by measureable distances. Some of the sensing traces of the plurality of sensing traces may be coupled to the first connection trace and others of the sensing traces of the plurality of sensing traces may be coupled to the second connection trace. A shield may cover the first and second connection traces to prevent exposure of the first and second connection traces to moisture. The plurality of electrically conductive sensing traces may be arranged at measureable distances from one another on the substrate. A controller may be configured to detect moisture in the substrate based on a signal received from the wireless sensor in response to fluid bridging a space between at least one of the sensing traces coupled to the first connection trace and one of the sensing traces coupled to the second connection trace.

In some embodiments, the substrate is wearable. Each of the plurality of electrically conductive sensing traces may extend in substantially perpendicular relation from its respective first and second connection trace. The measurable distance between adjacent sensing traces may be such that the minimum volume of moisture detected is 150 mL.

According to another aspect of the present disclosure, an incontinence detection system may include a pad having a plurality of layers including a top non-woven layer configured to be contacted by a user of the pad and a sensor grid that may be printed onto one of the plurality layers of the pad and that may be configured to detect moisture in the pad. The sensor grid may be printed onto one of a barrier layer, a non-woven substrate layer, and a film substrate layer.

In some embodiments, the sensor grid may be printed on a layer positioned beneath an absorbent layer having a super absorbent polymer. The sensing grid may be printed on a surface of the non-woven substrate that contacts the absorbent layer. The sensing grid may be printed on a surface of the non-woven substrate that contacts the barrier layer. The sensor grid may be printed on the barrier layer. For example, the sensing grid layer may be printed on the film substrate layer of the barrier layer.

According to a further aspect of the present disclosure, an incontinence detection system may include at least one RFID sensor that may have a trace fluid detection grid that may be configured to detect a moisture event. A reader may be configured to poll the at least one sensor for detection of the moisture event. A controller may communicate the moisture event with one or more remote alert systems in response to a signal from the reader that a moisture event took place.

In some embodiments, the at least one RFID sensor may include two RFID sensors. Each sensor may include a fluid detection grid, a tuning circuit and a communications circuit, that may be mounted to a substrate for positioning beneath a user. The controller may communicate the moisture event to at least one of a nurse call system, an electronic medical record (EMR) system, an alert light, or a caregiver's mobile device.

In some embodiments, the incontinence detection system may include an analog-to-digital converter (ADC) that may be coupled to the sensor. The ADC may have an output that may provide an indication if the trace fluid detection grid is broken. The ADC may be included as part of an application specific integrated circuit (ASIC), for example. The incontinence detection system may also have an RF suppressor that may be coupled to the trace fluid detection grid and that may be coupled to the ADC. The trace fluid detection grid may form a loop. A resistance of the loop may change depending upon an amount and location of moisture on the loop. The ADC may have an output that correlates to the resistance of the loop.

According to an aspect of the present disclosure, a patient support apparatus may include a frame that may include a patient support deck that may have a plurality of deck sections. A first deck section of the plurality of deck sections may be movable relative to at least a second deck section. A mattress may be supported by the patient support deck. The mattress may have a portion that moves with the first deck section. The patient support apparatus may further include an incontinence detection pad for placement on an upper surface of the mattress. The incontinence detection pad may have a passive radio frequency identification (RFID) tag. A reader may be coupled to the frame and may be operable to read data from the RFID tag. A first antenna may coupled to an upper surface of the first deck section to move therewith. A second antenna may be coupled to an upper surface of the second deck section. The RFID tag may be excited by energy emitted from at least one of the first and second antennae through the mattress and data from the RFID tag of the incontinence pad may be reflected back to at least one of the first and second antennae through the mattress.

In some embodiments, the patient support deck may have a first side that may extend in a longitudinal dimension of the patient support apparatus and a second side that may extend in the longitudinal dimension of the patient support apparatus. The incontinence detection pad may be configured so that, when the incontinence detection pad is properly oriented on the mattress, the RFID tag may be closer to the first side of the patient support deck than the second side. The first and second antennae may be each positioned closer to the first side of the patient support deck than the second side.

It is contemplated that the frame may have a head end and a foot end. The incontinence detection pad may be generally quadrilateral in shape. In some embodiments, the incontinence detection pad may have first indicia indicating that a first edge of the quadrilateral should be oriented toward the head end of the frame. Alternatively or additionally, the incontinence detection pad may have second indicia indicating that a second edge of the quadrilateral, opposite the first edge, should be oriented toward the foot end of the frame. Stated another way, the incontinence detection pad may be generally quadrilateral in shape and may have first indicia indicating that a first edge of the quadrilateral should be oriented toward the foot end of the frame.

In some embodiments, the first and second deck sections each may have a hole therethrough. A first cable may couple the first antenna to the reader and a second cable may couple the second antenna to the reader. The first cable may be routed through the hole of the first deck section and/or the second cable may be routed through the hole of the second deck section.

In some embodiments, the second deck section may be movable relative to a third deck section. The third deck section may be situated between the first and second deck sections. For example, the first deck section may support a torso of a patient located on the mattress, the second deck section may support thighs of the patient located on the mattress, and the third deck section may support a buttocks of the patient located on the mattress. It is contemplated that a first gap may be defined between the first deck section and the third deck section and a second gap may be defined between the second deck section and the third deck section. A first cable may couple the first antenna to the reader and a second cable may couple the second antenna to the reader. The first cable may be routed through the first gap and the second cable being may be routed through the second gap.

In some embodiments, the frame may have a head end and a foot end and the patient support apparatus may further include an indicator unit that may be attached to the frame adjacent the foot end. The indicator unit may be signaled by the reader to provide a visual indication that the incontinence detection pad has detected incontinence. The indicator unit may have a light that is illuminated a first color in response to the incontinence detection pad detecting wetness, for example. The light may be illuminated a second color when the incontinence detection pad is in communication with the reader and the incontinence detection pad has not detected wetness. In some embodiments, the light may flash in response to the incontinence detection pad detecting wetness. The first color may comprise amber or yellow and the light may be illuminated green when the incontinence detection pad is in communication with the reader and the incontinence detection pad has not detected wetness. The light may be illuminated a third color when the reader is not in communication with the incontinence detection pad. For example, the first color may be amber or yellow, the second color may be green, and the third color may be white.

In some embodiments of the patient support apparatus, the first deck section may include a stationary portion and a translating portion that translates relative to the stationary portion as the first deck section is raised and lowered relative to at least one other portion of the frame. The first antenna may be coupled to the translating portion of the first deck section. The patient support deck may have a first side extending in a longitudinal dimension of the patient support apparatus. The first antenna may be located a first distance from the first side and the second antenna may be located a second distance from the first side. For example, the second distance may be larger than the first distance or vice versa.

The first deck section may support a torso of a patient located on the mattress. The second deck section may be a movable section that supports thighs of the patient located on the mattress. In some embodiments, the patient support deck may include stationary portions situated along opposite sides of the second section such that the second section may nest between the stationary portions when the second section is in a lowered position. The stationary portions of the patient support deck may be included as part of a seat section of the patient support deck, for example. The seat section may have a connecting portion that interconnects the stationary portions. Thus, the connecting portion may be located between the first and section sections of the patient support deck.

The patient support apparatus may further include an output port that is wired to the reader. The frame may have a head end and a foot end and the output port may be located adjacent the head end of the frame. In some embodiments, the frame may include a base frame and an upper frame that may support the patient support deck for upward and downward movement relative to the base frame. The reader may be coupled to the upper frame and the output port may be coupled to the base frame. The upper frame may include a longitudinally extending frame member and the reader may be coupled to the longitudinally extending frame member about midway between the head end and foot end of the frame, for example. In some embodiments, the output port comprises a female receptacle for a ¼ inch jack.

The patient support apparatus may further include bed circuitry that may be coupled to the frame and operable to control bed functions. The bed circuitry may have an output port through which bed data is transmitted. The reader may be coupled to the bed circuitry. Thus, in some embodiments, the reader may send to the bed circuitry detection information that may indicate whether the incontinence detection pad has detected wetness or has not detected wetness. The bed circuitry may transmit the detection information through the output port of the bed circuitry. For example, the detection information may be transmitted in one or more data packets that also include the bed data. Alternatively or additionally, the detection information may be transmitted in one or more data packets that do not include the bed data. In some embodiments, the reader may be configured to communicate wirelessly with a receiver of a network of a healthcare facility. Such wireless communication capability of the reader may be in lieu of, or in addition to, wired communication capability.

Accordance to a further aspect of the present disclosure, an incontinence detection system may be provided for use with a patient support apparatus that may have a head end and a foot end. Thus, the incontinence detection system may retrofit onto existing beds. The incontinence detection system may include an incontinence detection pad that may have a passive radio frequency identification (RFID) tag. The incontinence detection may also have a reader that may be attachable to the patient support apparatus and that may bed operable to read data from the passive RFID tag. A first antenna may be attachable to the patient support apparatus. A second antenna may be housed separately from the first antenna and may be attachable to the patient support apparatus at a location spaced from the first antenna.

The first and second antenna may be electrically coupled to the reader. The passive RFID tag may be excited by energy emitted from at least one of the first and second antennae and the data from the RFID tag of the incontinence pad may be reflected back to at least one of the first and second antennae. The incontinence detection system may further include a visual indicator that may be electrically coupled to the reader by a first cable that may have sufficient length to permit the visual indicator to be mounted adjacent the foot end of the patient support apparatus. The incontinence detection system may also have an output port that may be electrically coupled to the reader by a second cable that may have sufficient length to permit the output port to be mounted adjacent the head end of the patient support apparatus. In some embodiments, one or more of the visual indicator, the first cable, the visual indicator, and the second cable may be omitted from the incontinence detection system.

In some embodiments, the reader may be operable to write data to the passive RFID tag via the first and second antenna. A first bit of the data stored in the passive RFID tag may be set in response to the incontinence detection pad detecting wetness, for example. The first bit may not be set if the incontinence detection pad does not detect wetness. The first bit may change from being set to not being set in response to the incontinence detection pad becoming sufficiently dry after the incontinence detection pad has detected wetness. In some embodiments, a second bit of data stored in the passive RFID tag may be set in response to the incontinence detection pad detecting wetness and the second bit of data may remain set even after the incontinence detection pad becomes sufficiently dry after the incontinence detection pad has detected wetness to cause the first bit to change states back to not being set. Under such circumstances, the second bit may serve as a kill bit that indicates to the reader that the incontinence detection pad cannot be used again once it becomes dry after having been wet.

In some embodiments, at least a portion of the data transferred between the passive RFID tag and the reader may be encrypted. The incontinence detection pad may include a top sheet, a backsheet having a pair of electrodes that are printed on the backsheet and that are electrically coupled to the passive RFID tag, and an absorbent core sandwiched between the top sheet and the backsheet.

According to yet another aspect of the present disclosure, an antenna for use in an incontinence detection system may be provided. The antenna may include a housing and a ground plate that may be coupled to the housing and that may have a perimetral edge that has generally the same shape as is defined by a perimeteral side wall of the housing such that the ground plate may nest within the housing with minimal clearance between the perimetral edge and the perimetral side wall. For example, about one millimeter (mm) or less is within the scope of the term "minimal clearance" according to this disclosure.

The antenna may include a nonconductive substrate that may carry an antenna plate thereon. A set of spacers may support the nonconductive substrate in substantially parallel spaced relation with the ground plate to form a gap therebetween. A cable may extend through the perimetral side wall of the housing and into the gap in substantially parallel relation with the ground plate and the nonconductive substrate. The cable may have at its terminal end at least one first conductor that may be routed so as to be coupled to the antenna plate carried by the nonconductive substrate and at least one second conductor that may be routed so as to be coupled to the ground plate.

In some embodiments, the antenna plate carried by the nonconductive substrate may be substantially the same shape as the nonconductive substrate and may be located in the central region of the nonconductive substrate such that perimetral portions of the nonconductive substrate may extend beyond a perimeter of the antenna plate. The set of spacers may be attached to the perimetral portions of the nonconductive substrate and may be oriented in perpendicular relation therewith. Each spacer of the set of spacers may comprise a tubular member. A set of bolts may extend through respective apertures formed in the ground plate, through respective bores of the tubular members, through respective holes formed in the nonconductive substrate, and into threaded holes formed in the housing. The antenna may have a ground spacer that may extend between central regions of the nonconductive substrate and the ground plate in substantially perpendicular relation therewith. The ground spacer may be cylindrical and may be smaller in diameter than each spacer of the set of spacers.

In some embodiments, the shape defined by the perimetral side wall of the housing may be generally square. Alternatively or additionally, the shape of the ground plate may be generally square. Thus, the shape of the nonconductive substrate may be generally square and the shape of the antenna plate carried by the nonconductive substrate may be generally square. In some embodiments, a first length and a first width of the ground plate may be larger than a second length and a second width, respectively, of the nonconductive substrate. Optionally, the second length and the second width of the nonconductive substrate may be larger than a third length and a third width, respectively, of the antenna plate carried by the nonconductive substrate. If desired, the nonconductive substrate may be centered with respect to the ground plate. Alternatively or additionally, the antenna plate may be centered with respect to the nonconductive substrate.

In some embodiments, the antenna plate may be shaped as an elongated hexagon that may have first and second spaced apart side edges that are substantially parallel and that may be longer than four end edges of the elongated hexagon. Opposite pairs of the end edges may define opposite ends of the elongated hexagon. Such an antenna plate may have first and second elongated notches that may extend from the end edges of the elongated hexagon toward a central region of the antenna plate. For example, the first and second elongated notches may be substantially parallel with the first and second spaced apart side edges of the elongated hexagon. The notches may be open at the end edges of the elongated hexagon about midway between the first and second spaced apart side edges of the elongated hexagon. It is contemplated by this disclosure that the first and second notches may act as an electronic band gap.

According to still another aspect of the present disclosure, an incontinence detection pad may include a top sheet that may be made of a fluid permeable material and a backsheet that may have a first layer of fluid impermeable material. A conductive ink pattern may be provided on the first layer and may be configured to form a first electrode trace and a second electrode trace. A passive radio frequency identification (RFID) tag may be attached to the first layer and may have electrical contacts that couple to respective ends of the first and second electrode traces. An absorbent core may be situated between the top sheet and the backsheet. Wetness bridging between the first and second electrode traces may be detectable by the passive RFID tag in response to the passive RFID tag being excited by external energy.

In some embodiments, the first layer may comprise a low density polyethylene (LDPE) film. The backsheet may include a second layer which may comprise a polypropylene spunbond nonwoven layer to which the LDPE film may be adhered. In some embodiments, the LDPE film has a weight of about 18 grams per square meter (gsm). In some embodiments, the polypropylene spunbond nonwoven layer may have a weight of about 22 gsm. The LDPE film may be adhered to the polypropylene spunbond nonwoven layer with hot melt adhesive that may coat substantially an entirety of adjacent surfaces of the LDPE film and the polypropylene spunbond nonwoven layer. In some embodiments, a laminate formed by the first and second layers of the backsheet has a weight of about 48 to about 55 gsm.

In some embodiments, a minimum perpendicular distance between centerlines of straight line segment portions of the first electrode trace and the second electrode trace may be about 190 millimeters (mm). Alternatively or additionally, a centerline of a first straight line segment portion of the first electrode trace may be spaced by a perpendicular distance from a second straight line segment portion of the second electrode trace by a distance of about 200 mm. In some embodiments, a space between the first straight line segment portion and the second straight line segment portion may lack any further electrode trace portions such that small amounts of fluid deposited in between the first and second straight line portions may not bridge the space between the first and second straight line segments unless the amount of fluid exceeds about 120 milliliters (mL).

In some embodiments, the first electrode trace may have first and second straight line segment portions that may be oriented in a machine direction of the incontinence detection pad and the second electrode trace may have third and fourth straight line segment portions that may be oriented in the machine direction of the incontinence detection pad. A first wicking rate of fluid in the machine direction may be greater than a second wicking rate of fluid in a cross direction of the incontinence detection pad. The first straight line segment portion of the first trace and the third straight line segment portion of the second trace may extend all the way to a first peripheral edge of the backsheet.

In some embodiments, the conductive ink pattern may include a sacrificial trace segment from a second, next adjacent incontinence detection pad that was attached to incontinence detection pad during a manufacturing process prior to the incontinence detection pad being detached from the second, next adjacent incontinence detection pad. The sacrificial trace segment may have a pair of ends terminating at a second peripheral edge of the of the backsheet. The second peripheral edge may be spaced from and parallel with the first peripheral edge. The sacrificial trace segment may be somewhat U-shaped.

If desired, a tag footprint may be printed on the first layer of the backsheet to indicate a boundary within which location of the passive RFID may be assured to result in electrical coupling between the electrical contacts of the passive RFID tag and the respective ends of the first and second electrode traces. In some embodiments, the passive RFID tag may be generally rectangular and the tag footprint may be generally rectangular in shape. A foam pad may be situated between the passive RFID tag and the absorbent core and the foam pad may be sized to fit within the tag footprint. The foam pad may be adhered to the passive RFID tag with hot melt adhesive.

In some embodiments, the backsheet may be generally rectangular and the first and second electrode traces may have rounded corner portions spaced from diagonally opposite corners of the backsheet. A radius defined by a rounded centerline of the rounded corner portions of the first and second electrode traces may be about 190 mm. In some embodiments, the LDPE film is corona treated prior to the conductive ink pattern being printed on the LDPE film. The absorbent core may comprise an airlaid material. Optionally, the airlaid material may have a weight of about 135 gsm.

The backsheet may be rectangular in shape and the absorbent core may be rectangular in shape with the absorbent core having a smaller surface area than the backsheet such that peripheral portions of the backsheet may extend beyond the absorbent core around a periphery of the absorbent core. For example, end edges of the absorbent core may be spaced inwardly from end edges of the backsheet by about 55 mm+/−about 10 mm and wherein side edges of the absorbent core may be spaced inwardly from side edges of the backsheet by about 45 mm+/−about 10 mm.

In some embodiments, the backsheet may contain a registration mark that is used during manufacturing. Optionally, the absorbent core may be adhered to the top sheet but not to the backsheet. For example, the absorbent core may be adhered to the top sheet with hot melt adhesive that may coat substantially an entirety of adjacent surfaces of the absorbent core and the top sheet.

In some embodiments, the top sheet may be approximately the same size as the backsheet and may be adhered to the backsheet at peripheral regions of the top sheet and backsheet. The top sheet and backsheet may each be rectangular in shape. The peripheral regions at the ends of the top sheet and backsheet may be adhered by hot melt adhesive that may be slot coated onto the backsheet. The peripheral regions at the sides of the top sheet and backsheet may be adhered by hot melt adhesive that may be sprayed onto the backsheet. In some embodiments, the top sheet may comprise a polypropylene spunbond nonwoven material. A weight of the polypropylene spunbond nonwoven material may be about 17 gsm, for example.

In some embodiments, the top sheet may be generally quadrilateral in shape and the top sheet may have first indicia indicating that a first edge of the quadrilateral should be oriented toward a head of a patient under which the incontinence detection pad may be located. Alternatively or additionally, the top sheet may have second indicia indicating that a second edge of the quadrilateral, opposite the first edge, should be oriented toward feet of the patient. Thus, the top sheet may be generally quadrilateral in shape and the top sheet may have first indicia indicating that a first edge of the quadrilateral should be oriented toward feet of a patient under which the incontinence detection pad is located.

In some embodiments, the conductive ink pattern may be printed on the backsheet and then cured in line during manufacture of the incontinence detection pad. In some embodiments, additional reinforcement strips may be attached to the backsheet adjacent to sides or ends or both thereof. Alternatively or additionally, additional reinforcement strips may be attached to the top sheet adjacent to sides or ends or both thereof. In some embodiments, portions of the backsheet and top sheet adjacent to sides or ends or both of the incontinence detection pad may be folded over and adhered to the backsheet to create double thickness reinforced regions of the incontinence detection pad. In other embodiments, portions of the backsheet and top sheet adjacent to sides or ends or both of the incontinence detection pad may be folded over and adhered to the top sheet to create double thickness reinforced regions of the incontinence detection pad.

According to another aspect of the present disclosure, a method of manufacturing an incontinence detection pad is provided. The method may include unrolling a continuous roll of backsheet material that may have a series of electrode traces printed thereon. Each electrode trace on the continuous roll may have a sacrificial trace portion. The method may further include attaching an RFID tag to a pair of terminal ends of a first trace electrode of the series of electrode traces and testing the first electrode trace by exciting the RFID tag with energy to confirm that the first electrode trace forms a completed short circuit between the terminal ends of the first electrode trace. The method also may include cutting the backsheet material at a location which severs the sacrificial trace portion from the rest of the first electrode trace, thereby leaving a pair of spaced moisture detection electrode traces on a first backsheet for a first incontinence detection pad and leaving the sacrificial trace portion behind on a trailing, second backsheet for a second incontinence detection pad.

In some embodiments, the method further includes laminating an absorbent core to a top sheet to form a laminate and attaching the laminate to the backsheet to sandwich the absorbent core between the top sheet and the backsheet. The laminate may be attached to the backsheet after testing the first electrode trace by exciting the RFID tag with energy. Alternatively, the laminate may be attached to the backsheet before testing the first electrode trace by exciting the RFID tag with energy. In some embodiments, attaching the RFID tag to the pair of terminal ends of the first trace electrode of the series of electrode traces may include removing the RFID tag from a roll of material carrying a series of RFID tags and adhering the RFID tag to the backsheet material. In some embodiments, laminating the absorbent core to the top sheet may include using a lined, combed, slot coating process to deposit glue in substantially parallel rows on the top sheet. For example, the substantially parallel rows of glue deposited on the top sheet may each be about 1 mm wide with a spacing between the parallel rows of about 4 mm.

In some embodiments, the method may include storing an identifier of the RFID tag of any incontinence pad for which the first electrode trace does not form a completed short circuit between the terminal ends of the first electrode trace as determined by the testing, whereby the identifier may indicate a rejected incontinence detection pad. The method may further include exciting the RFID tag with energy a second time to read the identifier of the rejected incontinence detection pad and scrapping the rejected incontinence detection pad by removing it from a manufacturing line.

In some embodiments, the method further include folding the backsheet, the absorbent core, and the top sheet before exciting the RFID tag with energy the second time. Cutting the backsheet material at the location which severs the sacrificial trace portion from the rest of the first electrode trace may occur after the backsheet, absorbent core, and top sheet are folded and before exciting the RFID tag with energy the second time.

In some embodiments, the method may include adding a mark to any incontinence pad for which the first electrode trace does not form a completed short circuit between the terminal ends of the first electrode trace as determined by the testing, whereby the mark indicates a rejected incontinence detection pad. For example, the mark may become visible when exposed to ultraviolet (UV) light.

According to still another aspect of the present disclosure, an incontinence detection pad may include a substrate and a conductive electrode on the substrate. The electrode may have a pair of spaced and parallel elongated trace portions and a plurality of angled trace portions that may bridge the space between the pair of spaced and parallel elongated trace portions. The angled trace portions each may be non-parallel with and non-perpendicular to either of the pair of spaced and parallel elongated trace portions.

In some embodiments, spaces between adjacent pairs of the plurality of angled traces may be shaped as rhomboids. Optionally, the spaced and parallel elongated trace portions and the angled trace portions may have substantially equal widths. For example, the widths of the elongated trace portions and the angled trace portions each may be about 1 mm. A distance between outside boundaries of the parallel elongated trace portions may be about 3 mm.

In some embodiments, an RFID tag may be attached to the substrate and an electrical contact of the RFID tag electrically may couple with a terminal end of the electrode. If desired, the incontinence detection pad may further have a second electrode that may have a second pair of spaced and parallel elongated trace portions and a second plurality of angled trace portions that may bridge the space between the second pair of spaced and parallel elongated trace portions. The second angled trace portions each may be non-parallel with and non-perpendicular to either of the second pair of spaced and parallel elongated trace portions. The RFID tag may have a second electrical contact that may electrically couple with a second terminal end of the second conductive trace.

The substrate may comprise a sheet or film of polyethylene and the conductive electrode may be printed on the sheet or film of polyethylene. The substrate may further comprise a layer of nonwoven material adhered to the sheet or film of polyethylene.

According to yet another aspect of the present disclosure, an incontinence detection pad may include a substrate, a first electrode on the substrate and a second electrode on the substrate. The first electrode may be spaced from the second electrode. A first RFID chip may be coupled to respective terminal ends of the first and second electrodes. The first RFID chip may sense an open circuit between the first and second electrodes in the absence of any fluid bridging a space between the first and second electrodes. The incontinence pad may have a sentinel electrode on the substrate and routed alongside the first and second conductive electrodes in close proximity thereto. A second RFID chip coupled to first and second ends of the sentinel electrode, the sentinel electrode may form a continuous loop between the first and second ends. The second RFID chip may sense that the sentinel electrode forms a closed circuit. If the sentinel trace becomes broken, the second RFID chip may sense an open circuit in the sentinel electrode and a signal may be sent by the second RFID chip to indicate that the incontinence pad should not be used because of the likelihood that at least one of the first and second conductive electrodes is also broken.

In some embodiments, the first and second RFID chips may be located on the substrate in side-by-side relation. The first and second RFID chips may be mounted on a common inlay which may permit the first and second RFID chips to be mounted to the substrate substantially simultaneously. The common piece of material may comprise a piece of foam, for example. The inlay may include a first pair of electrical contacts and a first antenna that may be coupled electrically to the first RFID chip and a second pair of electrical contacts and a second antenna that may be coupled electrically to the second RFID chip.

In some embodiments, the first and second antennae may be located on the inlay in a space defined between the first and second pairs of electrical contacts. Alternatively, the first and second pairs of electrical contacts may be located on the inlay in a space defined between the first and second antennae. In another variant, only one pair of the first and second pair of electrical contacts may be located on the inlay in a space defined between the first and second antennae. In some embodiments, the first pair of electrical contacts may couple to the terminal ends of the first and second electrodes and the second pair of electrical contacts may couple to the first and second ends of the sentinel electrode.

According to yet a further aspect of the pressing disclosure, a dressing for attachment to a patient having a wound is provided. The dressing may include a base sheet that may be made of fluid impermeable material. The base sheet may have a first surface and a second surface facing away from the first surface. A first moisture detection sensor may be provided on the first surface of the base sheet and a second moisture detection sensor may be provided on the second surface of the base sheet. A first fluid permeable cover sheet may cover the first moisture detection sensor and may be attached to the first surface of the base sheet. A second fluid permeable cover sheet may cover the second moisture detection sensor and may be attached to the second surface of the base sheet. A first layer of absorbent material may be sandwiched between the first surface and the first cover sheet. A second layer of absorbent material may be sandwiched between the second surface and the second cover sheet. The base sheet may be attachable to a patient such that the first surface faces toward the wound of the patient. The first moisture detection sensor may transmit a first signal if the first moisture detection sensor detects moisture from the wound. The second moisture detection sensor may transmit a second signal if the second moisture detection sensor detects incontinence from the patient.

In some embodiments, the base sheet may comprise polyethylene. If desired, the base sheet may be triangular in shape. A periphery of the base sheet may have adhesive for attachment of the dressing to the patient. Optionally, a peripheral region of the base sheet may extend beyond boundaries of the first and second cover sheets.

In some embodiments, the first moisture detection sensor may include a pair of spaced apart first electrodes and a first RFID tag that may be coupled to respective first ends of the first electrodes. The second moisture detection sensor may include a pair of spaced apart second electrodes and a second RFID tag that may be coupled to respective first ends of the second electrodes. The first RFID tag and the second RFID tag may have random delay times in connection with transmission of data in response to being excited with energy. At least one of the first and second RFID tags may be configured to receive a wireless message that may command the respective first or second RFID tag not to transmit any data in response to a next excitation of energy.

In some embodiments, the first electrodes and the second electrodes comprise conductive ink that may be printed on the respective first and second surfaces of the base sheet. A first peripheral region of the first cover sheet may extend beyond a first outer periphery of the first layer of absorbent material and a second peripheral region of the second cover sheet may extend beyond a second outer periphery of the second layer of absorbent material. The base sheet may be sized and configured to cover a sacral region of the patient.

In some embodiments, the base sheet may include a first base sheet layer and a second base sheet layer that may be removably coupled to the first base sheet layer. The first base sheet layer may carry the first moisture detection sensor, the first layer of absorbent material, and the first cover sheet. The second base sheet layer may carry the second moisture detection sensor, the second layer of absorbent material, and the second cover sheet. The first base sheet layer along with the first moisture detection sensor, the first layer of absorbent material, and the first cover sheet may be removable from the second base sheet layer to permit replacement of the first base sheet layer along with the first moisture detection sensor, the first layer of absorbent material, and the first cover sheet after an incontinence event without the need to replace the second base sheet layer carrying the second moisture detection sensor, the second layer of absorbent material, and the second cover sheet.

According to still a further aspect of the present disclosure, a method may include providing reconfigurable devices in a plurality of patient rooms, configuring a portable computer as a WiFi hotspot, programming the portable computer to transmit a service set identifier (SSID), transporting the portable computer into communicative proximity of a first reconfigurable device so that the reconfigurable device may be able to detect the SSID included in a transmission from the portable computer, detecting the SSID in the first reconfigurable device, ceasing communications, in the first reconfigurable device, with a network of a healthcare facility, using the portable computer to establish a secure shell (SSH) connection with the first reconfigurable device, and reconfiguring the reconfigurable device via the SSH connection.

In some embodiments, the method may further include checking, in the reconfigurable device, to determine if a signal strength of the transmission from the portable computer having the SSID meets a threshold signal strength prior to ceasing communications with the network of the healthcare facility. Alternatively or additionally, the method may further include transporting the portable computer out of communicative proximity of the first reconfigurable device and, in response, the first reconfigurable device may automatically reconnect to the network of the healthcare facility. For example, automatically reconnecting to the network may occur only after a threshold amount of time has passed after the portable computer is transported out of communicative proximity of the first reconfigurable device. The threshold amount of time may be about ten seconds in some embodiments.

In some embodiments, the portable computer and the first reconfigurable device may communicate via wireless transmissions. The portable computer and the first reconfigurable device may communicate according to the TCP/IP protocol. Alternatively or additionally, the first reconfigurable device may communicate via wireless transmissions with the network of the healthcare facility. The plurality of reconfigurable devices may include hospital beds. Alternatively or additionally, the plurality of reconfigurable devices may include incontinence detection systems.

Additional features, which alone or in combination with any other feature(s), such as those listed above and/or those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The foregoing and other features of the various embodiments of the methods and apparatuses described herein will become more apparent from the following detailed description and the accompanying drawings in which:

FIG. 30 is an exploded perspective view of the visual indicator of FIGS. 11-15;

FIG. 32 is an exploded end elevation view of the back sheet showing, from bottom to top, a polypropylene spunbond nonwoven layer, a layer of hot melt adhesive, a high density polyethylene (LDPE) layer, and conductive ink which forms the electrode traces on the LDPE layer;

FIG. 33 is a top view showing an absorbent core adhered to a top sheet such that perimetral portions of the top sheet extend outwardly from a perimeter of the absorbent core;

FIG. 34A is a top view of the backsheet of FIG. 31 showing strips at first and second ends of the backsheet where hot melt adhesive is slot coated onto the backsheet prior to attachment of the top sheet and absorbent core to the backsheet;

FIG. 34B is a top view of the backsheet of FIG. 31, similar to FIG. 34A, showing strips at first and second sides of the backsheet where hot melt adhesive is spray coated onto the backsheet prior to attachment of the top sheet and absorbent core to the backsheet;

FIG. 37 is a top plan view of an alternative embodiment of an incontinence detection pad;

FIG. 38 is an exploded end view of the incontinence detection pad of FIG. 37 showing, from top to bottom, a polypropylene spunbond nonwoven top sheet, a layer of intermittent hot melt adhesive, an absorbent core of airlaid material, hot melt adhesive spray coated at the sides of the incontinence detection pad, hot melt adhesive slot coated along the length of the incontinence detection pad but with an uncovered strip along the length of the pad, the RFID tag situated beneath the uncovered strip of slot coated hot melt adhesive, and a backsheet;

FIG. 39 is a top view of the backsheet of FIG. 38 showing the adhesive patterns and showing the electrode trace patterns of the incontinence detection pad and showing an enlarged bubble with the RFID tag on the backsheet and ends of the electrodes terminating at electrical contacts of the RFID tag;

FIG. 50 is an exploded perspective view showing components of a dressing that has a central base sheet with electrode traces on opposite surfaces for detecting wound moisture and for detecting incontinence;

FIG. 51 is an exploded side view of the dressing of FIG. 50 showing, from top to bottom, a first fluid permeable cover sheet, a first layer of absorbent material, the base sheet having RFID tags on top and bottom surfaces thereof for electrical connection to respective electrodes on the top and bottom surfaces, a second layer of absorbent material, and a second fluid permeable cover sheet;

FIG. 69F is a digital photo of a bottom plan view of the incontinence detection pad of FIG. 69A;

FIG. 69G is a digital photo of a portion of the incontinence detection pad of FIG. 69F showing an RFID tag having an antenna pattern visible through a backsheet of the incontinence detection pad;

FIG. 69H is a digital photo of a portion of the incontinence detection pad of FIG. 69F showing a junction between substantially perpendicular line segments of an electrode trace of the incontinence detection pad;

FIG. 69I is a digital photo showing an isometric view of the upper surface of the incontinence pad of FIG. 69A;

FIG. 69J is a digital photo showing an isometric view of the bottom surface of the incontinence pad of FIG. 69F;

FIG. 69K is a digital photo showing a side elevation view of the incontinence detection pad of FIG. 69A;

FIG. 69L is a digital photo showing an end elevation view of the incontinence detection pad of FIG. 69A; and FIG. 70 is a top plan view of an incontinence detection pad having the series of head indicia and the series of foot indicia extending across a portion of the pad containing an absorbent core.

DETAILED DESCRIPTION

The present disclosure relates to systems and methods for detecting incontinence or other moisture caused events associated with a person being monitored. Thus, it should be appreciated that the systems described herein are able to detect biofluids such as blood, urine, fecal matter, interstitial fluid, saline, or any other fluid having a large concentration of ions that easily conduct electricity. The term "inconti-nence" as used herein is intended to cover all of these biofluids. The present disclosure further describes systems and methods for reporting detected incontinence events to hospital caregivers, a nurse call system, or an EMR (electronic medical record) system to allow patients to be quickly removed from the soiled environment.

Figure 1A:
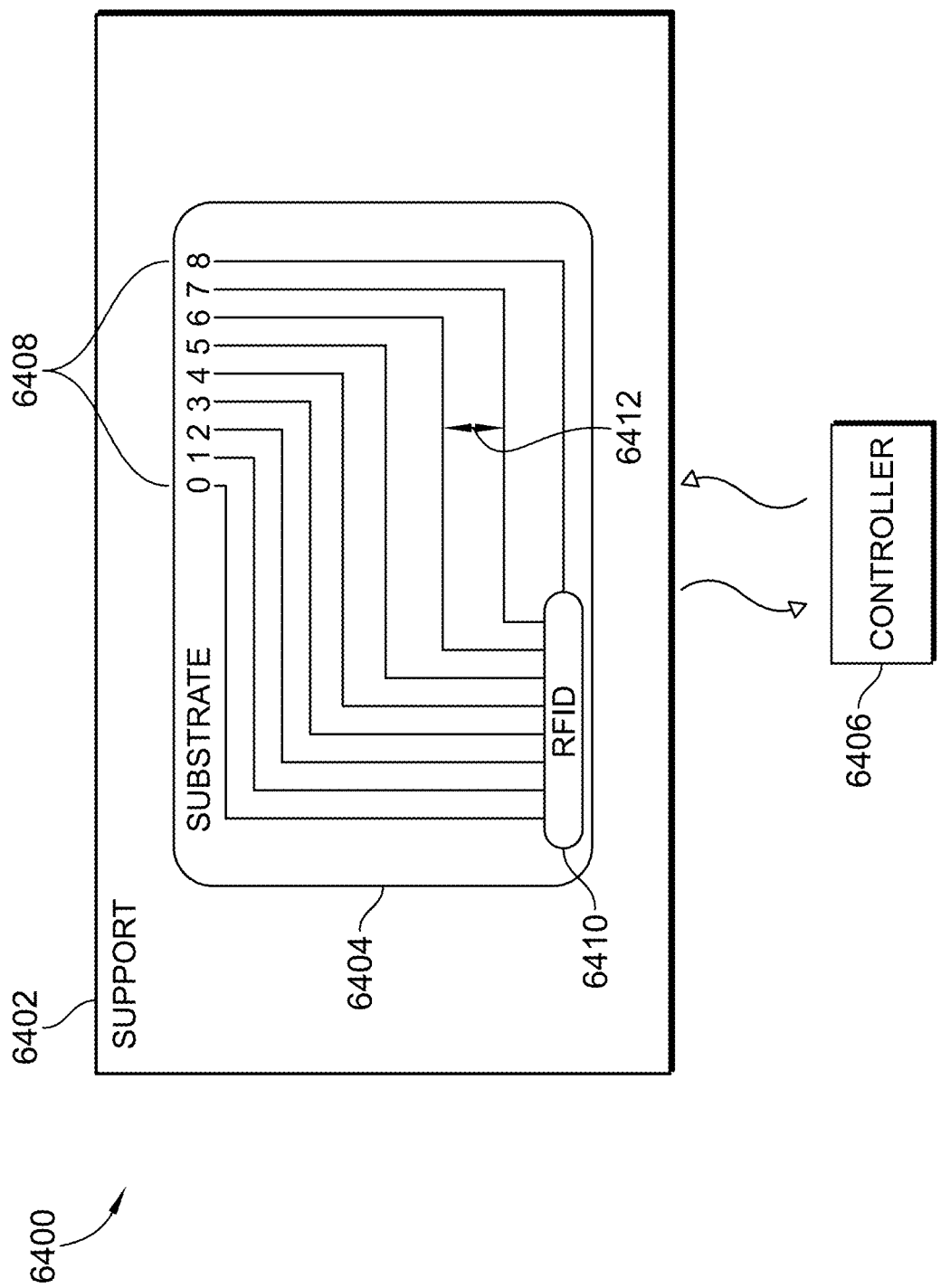
FIG. 1A is a schematic view of an embodiment of a sensor pad for detecting moisture presence and moisture volume.
Figure 1B:
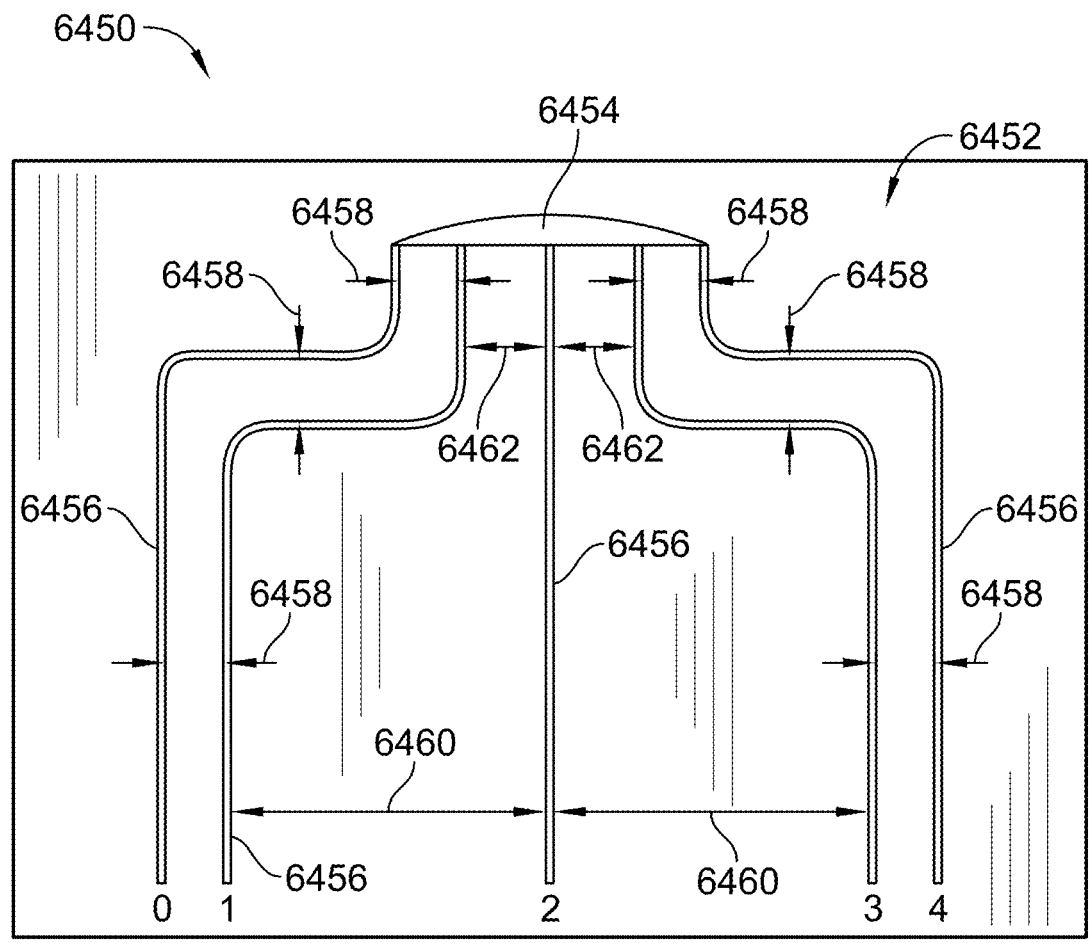
FIG. 1B is a schematic view of an alternative embodiment of a sensor pad for detecting moisture presence and moisture volume.
Figure 2:
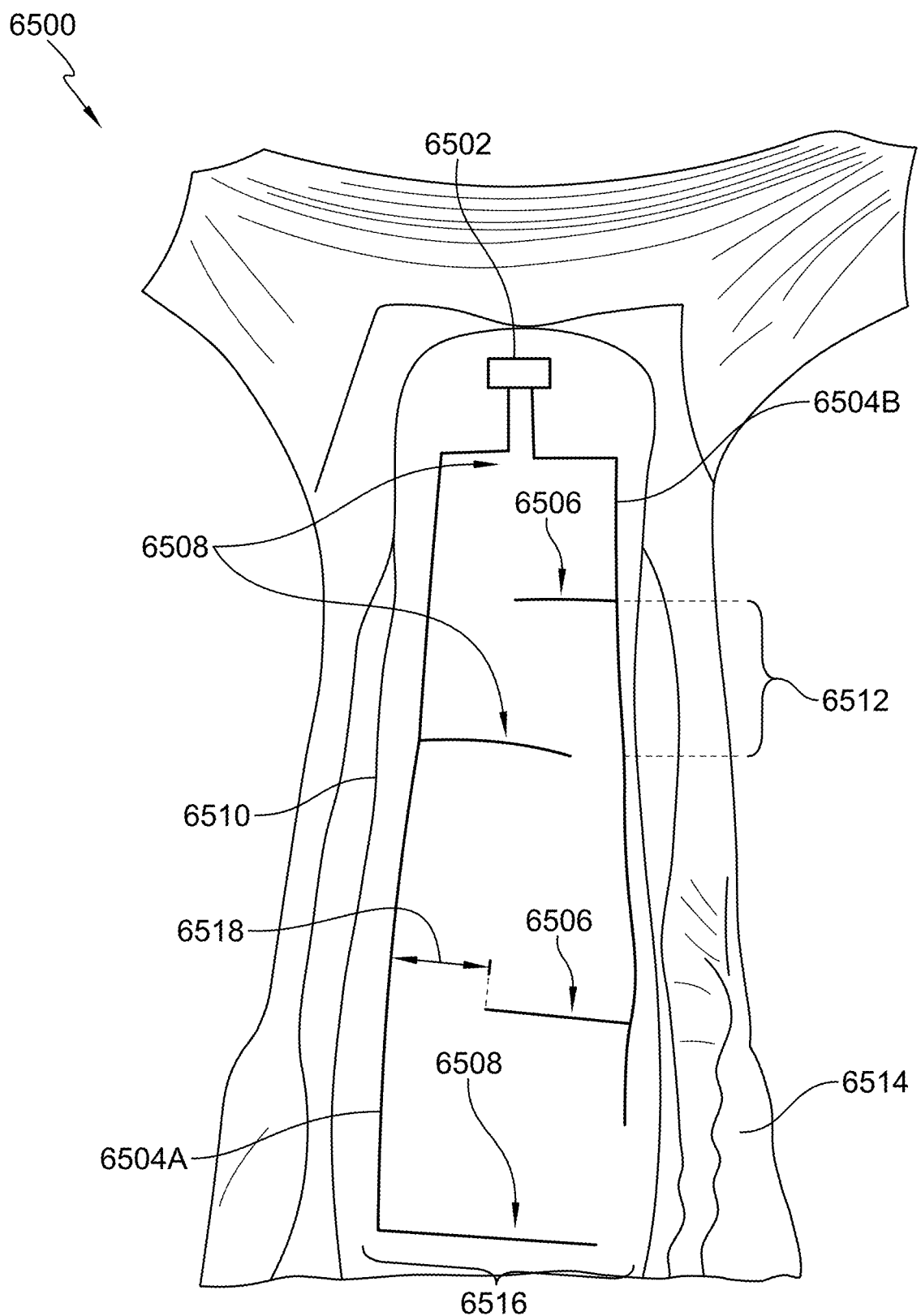
FIG. 2 is a plan view of a wearable sensor pad for detecting moisture presence above a minimum volume.

FIGS. 1A, 1B and 2 schematically show three embodiments of a sensor system 6400, 6450, 6500 that detects a volume of incontinence or other moisture. System 6400 includes an occupant support 6402 that is embodied as, for example, a hospital bed, a residential bed, a chair, a wheelchair, a mattress, a stretcher, a patient transport device, or any other type of person support apparatus. A substrate, or incontinence pad 6404, rests on the occupant support 6402, such as a mattress, in an area or zone in which it is desired to conduct surveillance for unwanted moisture or other moisture related abnormalities. In other embodiments, the pad 6404 is integrated into the support 6402, such as a mattress. In still other embodiments, the pad 6404 is integrated within an undergarment or other article of clothing or the pad 6404 itself is a diaper or disposable undergarment.

The illustrative system 6400 for detecting a volume of moisture on the occupant support 6402 includes a plurality of sensor traces 6408. The plurality of sensor traces 6408 in the illustrative example includes sensing traces 0-8. It is contemplated that there are more or fewer sensor traces in other embodiments. The sensor traces are placed at predetermined distances 6412 from one another and portions or segments of the traces lie in parallel. It should be understood, however, that while the segments (e.g., 0, 1, 2, 3, 4, 5, 6, 7 and 8) are shown in FIG. 1 as linear segments, any suitable spatial arrangement of the sensing traces 6408 that maintains the desired spacing 6412 between the sensing traces 6408 work sufficiently according to this disclosure.

In the illustrative example, sensor traces 0-7 are generally Z-shaped, each with a first end segment coupled to an RFID tag 6410, a second end segment spaced from the first segment and generally parallel therewith, and a middle segment interconnecting the end segments and oriented in substantially perpendicular relation with the end segments. The first segments of traces 0-7 are of decreasing length from trace 0 (i.e., the longest first segment) to trace 7 (i.e., the shortest first segment). The second segments of traces 0-7 are of increasing length from trace 0 (i.e., the shortest second segment) to trace 7 (i.e., the longest second segment). The middle segment of each trace 0-7 is approximately the same length as each of the other middle segments of each of the other traces 0-7. Trace 8 is generally L-shaped in the illustrative example having a first segment coupled to the RFID circuit in substantially parallel relation with the middle segments of traces 0-7 and a second segment that is substantially perpendicular to the first segment of trace 8 and substantially parallel with the first and second end segments of traces 0-7. The length of the first segment of trace 8 is approximately equal to the lengths of the middle segments of traces 0-7.

In some embodiments, the distance 6412 between each of the adjacent traces 0-8 is the same for each segment of each trace 0-8. In other embodiments, the distance 6412 between each of the sensor traces 0-8 is different. It is also contemplated by this disclosure that, in some embodiments, the distance 6412 between middle segments of traces 0-7 and between the middle segment of trace 7 and the first segment of trace 8 is different than the distance 6412 between respective first end segments of traces 0-7, respective second end segments of traces 0-7, and the second segment of trace 8 and the second end segment of trace 7 of other traces. The distance 6412 between each sensor trace is defined by one or more moisture management criteria, for example.

The moisture management criterion includes a moisture-related property of the substrate pad 6404 in some instances. For example, a moisture management criterion may be a moisture-related property of the moisture absorbent material of the incontinence pad (such as, for example, a wicking or absorption property).

In an illustrative example, the distance 6412 is in the range of about 4 inches, based on a desired moisture sensitivity in the range of about 50 milliliters (e.g., 6412 is the distance that 50 ml of liquid travels in the specified type of material forming the substrate 6404 or a layer of an incontinence pad in which the substrate 6404 is integrated). Thus, a notification is issued by a notification device as described elsewhere herein, when the sensor traces 6-7 are exposed to moisture indicating an amount of moisture in the range of about 50 milliliters (i.e., enough moisture to bridge two adjacent traces 6408). In another illustrative example, if moisture is exposed to sensing traces 6, 7, 8, a signal is generated indicating an amount of moisture in the range of 100 milliliters (i.e., enough moisture to bridge three adjacent traces 6408). Likewise, if sensing traces 5, 6, 7, 8 are exposed to moisture, a signal is generated indicating an amount of moisture in the range of 150 milliliters (i.e., enough moisture to bridge four adjacent traces). Thus, system 6400 is a high resolution incontinence detection system in that it is able to determine how much biofluid is being sensed by traces 6408. The sensor traces 6408 are connected to a passive RFID tag 6410 in the illustrative example. RFID tag 6410 is excited by a controller 6406 which transmits an electromagnetic signal and receives the response from the RFID tag 6410.

Referring now to FIG. 1B, sensor system 6450 includes an incontinence detection pad 6452 having an RFID tag 6454 and a series of electrode traces 6456 extending from RFID tag 6454. In the illustrative example, traces 6456 are labeled as traces 0-4. The traces 6456 labeled 0, 1, 3 and 4 are generally Z-shaped whereas the trace 6456 labeled 2 is formed as a generally straight line. Traces 6456 labeled 0 and 1 are spaced apart by a first distance 6458 and so too are the traces 6456 labeled 3 and 4. A distance 6460 between the trace 6456 labeled 2 and respective lower straight portions of traces 6456 labeled 1 and 3 is about four times that of distance 6458. Thus, a larger amount of moisture or fluid is needed in the central region of pad 6452 to electrically interconnect or short out the trace 6456 labeled 2 with the trace 6456 labeled 1 or the trace 6456 labeled 3 than is need to electrically interconnect or short out the trace 6456 labeled 0 with the trace 6456 labeled 1 or the trace 6456 labeled 3 with the trace 6456 labeled 4. A distance 6462 between the trace 6456 labeled 2 and respective upper straight portions of traces 6456 labeled 1 and 3 is about 1.5 times that of distance 6458.

According to some embodiments of the present disclosure, RFID tags 6410, 6454 or the controllers, such as controller 6406, that read these tags 6410, 6454, are programmable such that subsets of traces 0-8 of FIG. 1A and subsets of traces 6456 labeled 0-4 of FIG. 1B are considered active traces for purposes of detecting moisture or fluid and others of the traces are ignored. As such, a fluid volume threshold is variable among a plurality of fluid volume thresholds so that the RFID tag 6410, 6454 or associated controller 6406, such as that of a reader, generates an alarm if the fluid volume exceeds a selected fluid volume threshold and so that the controller does not generate the alarm if the fluid volume is below the selected fluid volume threshold.

The plurality of electrically conductive traces of systems 6400, 6450 are, therefore, laid out in a grid pattern to define a plurality of sensing blocks (e.g., the spaces between the traces). The fluid volume being sensed by systems 6400, 6450 is estimated by the RFID tag 6410, 6454 and/or the associated controller 6406 based on how many sensing blocks of the plurality of sensing blocks have been exposed to fluid. In some embodiments, the selected fluid volume threshold is selected automatically by the controller 6406 based on information (e.g., a patient's Braden score) received from a remote computer relating to a condition of a patient. For example, the selected fluid volume threshold is smaller if the condition of the patient indicates that the patient is at risk of developing pressure ulcers than if the condition of the patient indicates that the patient is not at risk of developing pressure ulcers.

In some embodiments of systems 6400, 6450, as well as in other embodiments disclose herein, first and second fluid volume thresholds are selectable from among more than two fluid volume thresholds. The system controller 6406, such as a controller of a reader, generates a first alarm if the first fluid volume threshold is sensed by the respective incontinence detection pad, such as pad 6404 or pad 6452, and the controller 6406 generates a second alarm if the second fluid volume threshold is sensed. The first alarm is different than the second alarm in some embodiments. For example, the first alarm may be a visual alarm and the second alarm may be an audible alarm. As another example, the first alarm may be an audible alarm at a first volume of loudness and the second alarm may be an audible alarm at a second volume of loudness that is different than the first volume. Alternatively of additionally, at least one of the first alarm and the second alarm may include a transmission to a nurse call system. Further alternatively or additionally, the first alarm may include a first textual message presented on a display and the second alarm may include a second textual message presented on the display. Thus, the first alarm may include a first visual alarm and the second alarm may include a second visual alarm.

Referring now to FIG. 2, system 6500 is incorporated into a wearable substrate such as a diaper or other wearable pad 6514. In this embodiment, connector traces 6504A, 6504B extend from passive RFID tag 6502 and extend longitudinally in substantially parallel relation along the outer edges of a moisture zone 6516 of the diaper or wearable pad 6514. Shielding material or a shield 6510 coat or otherwise overlie each of the connector traces 6504A, 6504B to prevent the connector traces from being exposed to moisture. Alternatively or additionally, connector traces 6504A, 6504B lie outside moisture zone 6516 in some embodiments so as to inhibit any chance for exposure to moisture that is present within zone 6516. In some embodiments therefore, shields 6510 are not needed for covering traces 6504A, 65-4B and are omitted.

First and second sets of sensor traces 6506, 6508 extend from respective connector traces 6504A, 6504B in a direction substantially perpendicular to traces 6504A, 6504B. Traces 6506, 6508 extend across the moisture zone 6516 but terminate prior to reaching the opposite trace 6504A, 6504B. Thus, in the illustrative example, traces 6506 each extend from trace 6504B and terminal ends of traces 6506 are spaced from trace 6504A. Similarly, traces 6508 each extend from trace 6504A and terminal ends of traces 6508 are spaced from trace 6504B. A distance 6518 (shown in FIG. 2) between the terminal end of one of traces 6506 and trace 6504A) is provided between each terminal end of traces 6506, 6508 and the trace 6504A, 6504B spaced therefrom.

The first 6506 and second traces 6508 are arranged in an alternating pattern along the length of the diaper 6514. Thus, trace 6504 and its accompany traces 6508 form a first comb-like pattern and trace 6506 and its accompanying traces 6506 form a second comb-like pattern. The comb-like patterns are arranged to that traces 6506 are interdigitated with traces 6508. The spacing distance 6518 is smaller than a spacing 6512 between adjacent traces 6506, 6508. Because of the shielding 6510 covering traces 6504A, 6504B, moisture that would otherwise make an electrical connection between terminal ends of traces 6506, 6508 and the traces 6504A, 6504B spaced therefrom by distance 6518, is unable to do so. Instead, an electrical connection is made between only when sufficient moisture is present to expose a first and second sensor trace 6506, 6508 to moisture across distance 6512. For example, in some embodiments contemplated herein, distance 6512 between first and second sensor traces 6506, 6508 requires that 150 milliliters (ml) of moisture be present within moisture zone 6516 before an electrical connection is made between adjacent traces 6506, 6508. Thus, the distance 6512 is selected in the illustrative example so that a signal from RFID tag 6502 is generated in response to moisture contacting one first sensing trace 6506 and one second sensing trace 6508 which occurs when about 150 milliliters (ml) of moisture is present in the moisture zone 6516.

By shielding connecting traces 6504A, 6504B with moisture resistant layers (not shown) that comprise shields 6510, oversensitivity may be avoided such that a signal may only be generated when a prescribed fluid volume is present in the moisture zone 6516. This prevents, for example, incontinence signals being sent by RFID tag 6502 in response to perspiration or other moisture that bridges across any of spaces 6518. Alternatively, connecting traces 6504A, 6504B are positioned outside of moisture zone 6516 as mentioned above to achieve a similar result. The first sensing traces 6506 and second sensing traces 6508 are spaced apart by a predetermined distance 6512 that is based on a desired moisture sensitivity which also takes into account the wicking and absorbency properties of the diaper or other wearable pad 6514 within zone 6516. According to the present disclosure, shielded connector traces, similar to traces 6504A, 6504B, and unshielded sensor traces, similar to traces 6506, 6508, also may be used in non-wearable pad embodiments, such each of the other pad embodiments disclosed herein.

Figure 3:
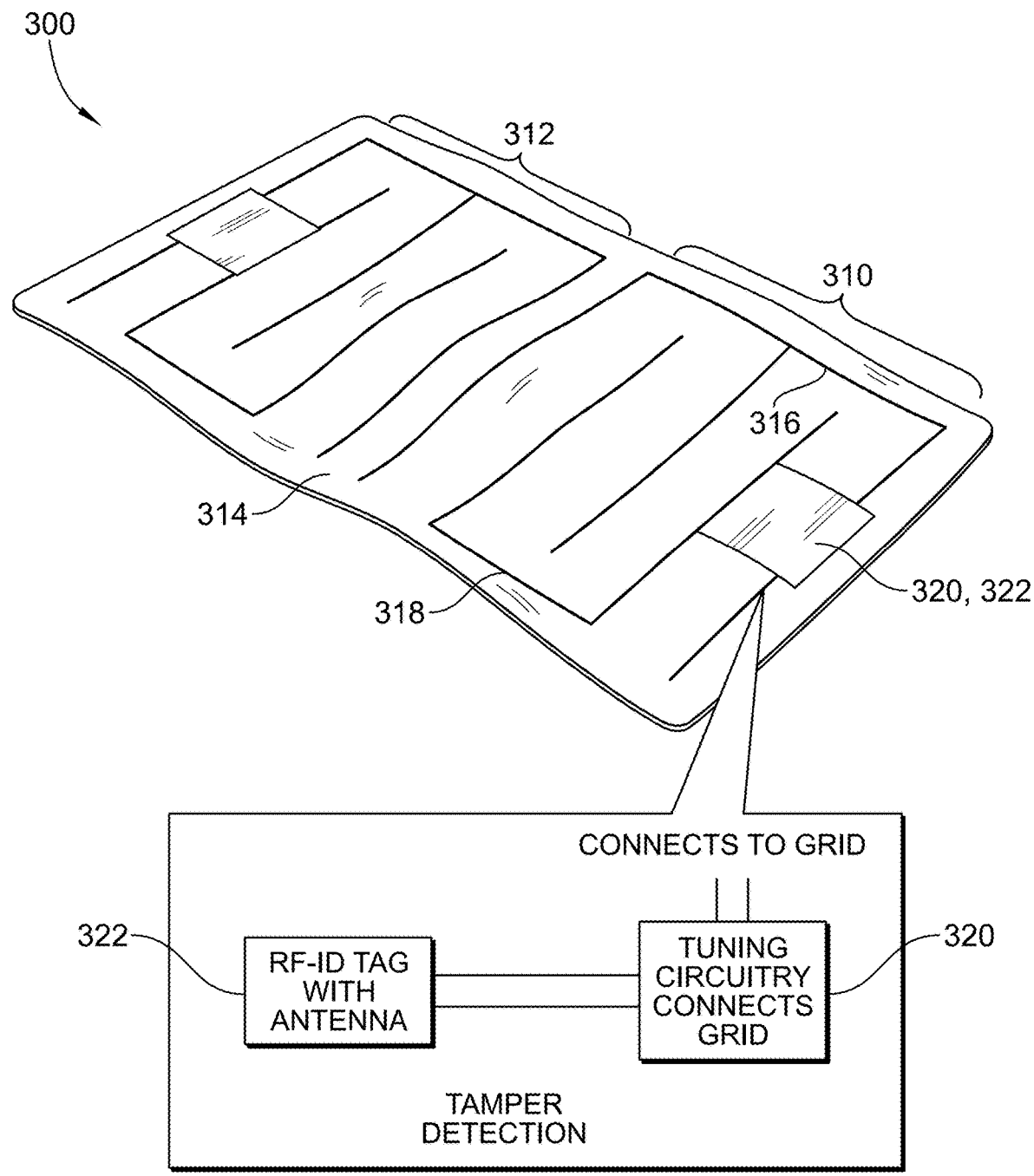
FIG. 3 is partly a perspective view and partly a diagrammatic view of an embodiment of a sensor pad for detecting moisture presence above a minimum volume showing two RFID sensors each connected to a respective sensor trace grid.
Figure 9:
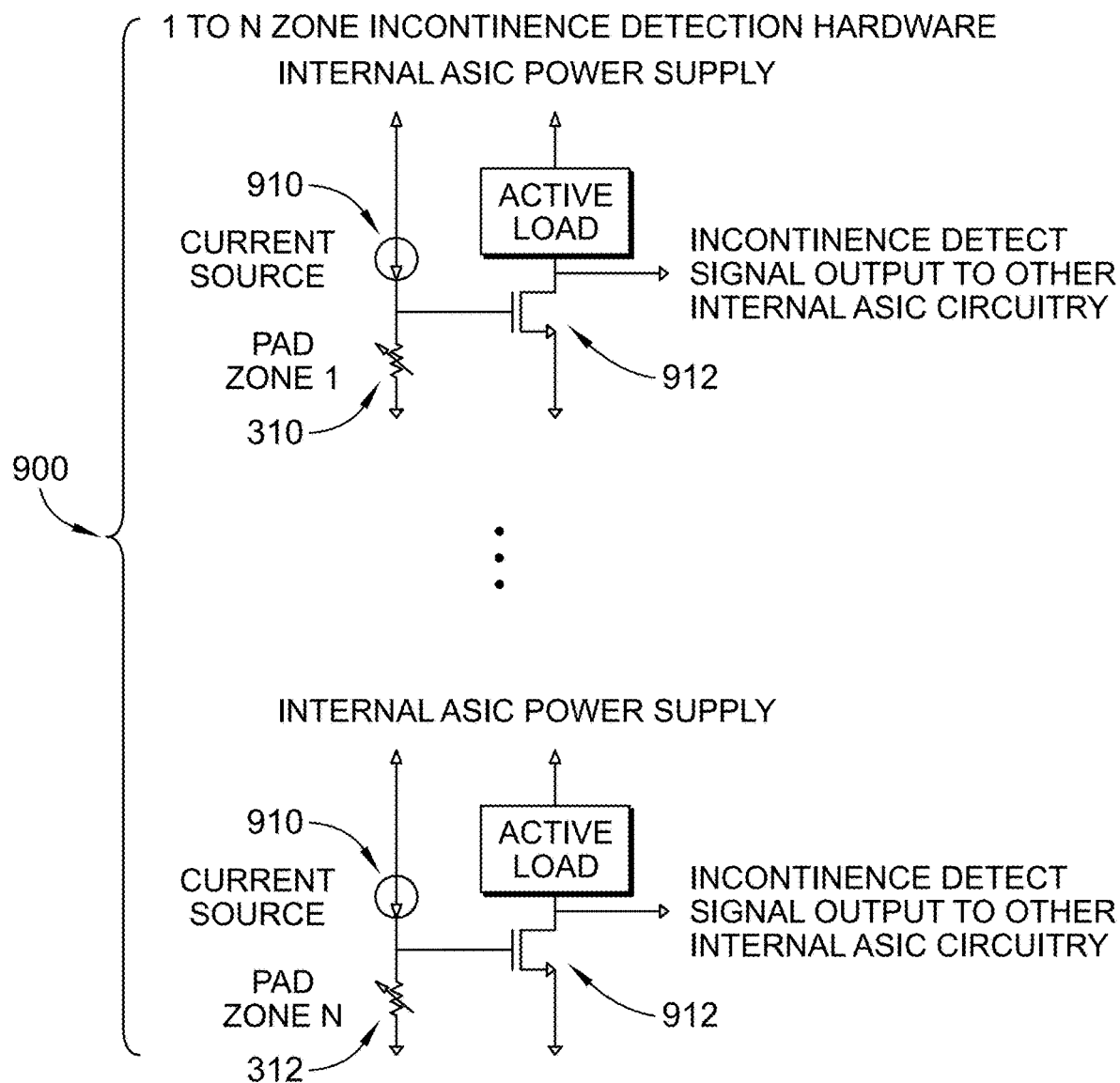
FIG. 9 is an electrical schematic showing an example of analog circuitry configured to sense moisture in the incontinence pads disclosed herein.

FIG. 3 discloses another embodiment of an RFID implemented moisture detection sensor system 300 employing a pair of sensors 310, 312 on a substrate such as a patient support or pad 314. The discussion below of sensor 310 is equally applicable to sensor 312. That is sensor 310 and sensor 312 are substantially the same although, the illustrative example, sensor 312 is a mirror image of sensor 310. Sensor 310 includes first and second trace grids 316, 318 that are spaced apart and form a somewhat serpentine pattern on the bed. Trace 318 is generally U-shaped and trace 316 is generally M-shaped or W-shaped depending upon the direction at which trace 316 is viewed. The U-shaped pattern of trace 318 is interdigitated with the M-shaped pattern of trace 316. Thus, traces 316, 318 form a comb-like pattern. Moisture detection takes place at the sensor 310 by way of a tuning circuit 320 connected to an RFID tag 322. When moisture bridges any of the spaces between trace 316 and trace 318, tuning circuitry 320 outputs a signal to RFID tag 322 which, in turn, emits a wireless signal indicating that moisture is present According to this disclosure, tuning circuit 320 on sensor 310 may determine moisture presence by analog, digital or hybrid mechanisms. In one method of analog operation, as shown in FIG. 9, an ultralow power ASIC 900 includes a current source 910 to the open (dry) circuit of sensor traces 316, 318 of respective sensors 310, 312. As suggested in FIG. 9, the incontinence may have 1 to n zones for incontinence detection. Thus, pads having only one zone or two zones or more than two zones are contemplated by this disclosure. The current source 910 may be implemented using two transistors and one or more resistors, for example, as is known in the art. The current source 910 attempts to force current through the traces 316, 318 and a resulting voltage is either sufficient or insufficient to allow a transistor 912 to be turned on. The resulting digital bit at the output of the transistor 912 indicates whether or not the detection zone contains a sufficient amount of conductive moisture to bridge between traces 316, 318.

The current source 910 may be configured to selectively test the various trace pairs 316, 318 and/or multiple sources current 910 may be connected to multiple trace pairs 316, 318 in order to determine the reach of the conductive moisture. FIG. 9 represents just one example of an incontinence detection circuit that is implemented with very few transistors and very little current (which is in short supply in a passive RFID tag). Many other analog circuit examples are possible, all following this same "ohmmeter" (relative resistance) detection scheme. The basic idea is to force a test current of very small magnitude into the pad (large resistance in pristine state) and monitor the resulting voltage to detect the presence of a biofluid.

In another approach, a completely digital implementation is used to determine the resistance, and therefore the amount of biofluid spilled, using a resistive voltage divider and a MOSFET coupled at the gate of a transistor to the center of a voltage divider. The output of the MOSFET indicates WET or DRY. The MOSFET may further be used as an active load and negate the need for the external voltage divider resistor to couple to adjacent conductive traces. An alternative digital implementation may include a standard cell analog to digital converter relying on the fluid signal not changing quickly or often. A low resolution ADC (6 bit or less) could be implemented as a resistive divider ladder on the ASIC die. Rudimentary comparators may be used to determine the value of the digital bit outputs. Still further, the sensor may be implemented as a switch.

In still another approach a hybrid circuit implementation, such as a coulomb meter, is used. The coulomb meter is used to estimate resistance by integrating the charge using a capacitor or other charge storage element that passes through the conductive strips embedded in the incontinence device (e.g., pad, brief, diaper, etc.) in a given time interval, and regularly resetting the charge on the capacitor and determining whether the voltage on the capacitor meets or exceeds a specific threshold. The voltage on the capacitor relates to the charge as Q=CV, where Q is in Coulombs, V is in Volts and C is in Farads.

Further according to this disclosure, it is desirable to know when an incontinence detection conductor (e.g., trace 316 or trace 318) has been broken, usually through mechanical forces. This broken wire or trace detection may be accomplished by measuring the voltage at the end of all of the incontinence traces on the device and ensuring they are at ground potential. These traces may be connected to inputs on the ASIC and the voltage determined using any of the methods outlined above (analog comparator, etc). Any trace that measures above ground potential can be assumed to be broken. A broken trace signal or data can be communicated to the ASIC and over the RF channel of the RFID chip.

According to some embodiments contemplated herein, RFID chip 322 operates at about 915 MegaHertz (MHz) and has a tamper evident, binary input into the RFID chip 322 which is normally (e.g., in other applications) used to detect if a package has been opened, but in the incontinence detection systems contemplated herein, this tamper detection input is used instead to report the "switch closure" caused by an incontinence event. In some embodiments, including those disclosed herein, the RFID chips used in the incontinence pads are passive chips that communicate with an associated reader by using the electromagnetic field generated by the reader to power the chip and communicate via so-called "backscatter" techniques. In other embodiments, semi-passive or active RFID chips are used.

Upon moisture detection, the tamper evident input of the RFID chip has an electrical signal applied thereto which sets a status bit in the RFID chip. When the RFID chip is interrogated by the associated reader, the RFID chip sends stored data including the status bit state (e.g., logic 1 or logic 0). The reader or other processing circuitry determines whether the incontinence pad is wet or dry by evaluating the tamper evident status bit that has been received by the reader. Discrete circuit components are used to match the impedance of the sensor traces and the RFID chip in some embodiments. Other embodiments may use RFID chips operating at high frequency (HF) (13.56 MHz), ultra high frequency (UHF)(800 MHz-1 Giga Hertz (GHz)) or microwave (2.4 GHz-5 GHz).

Figure 10:
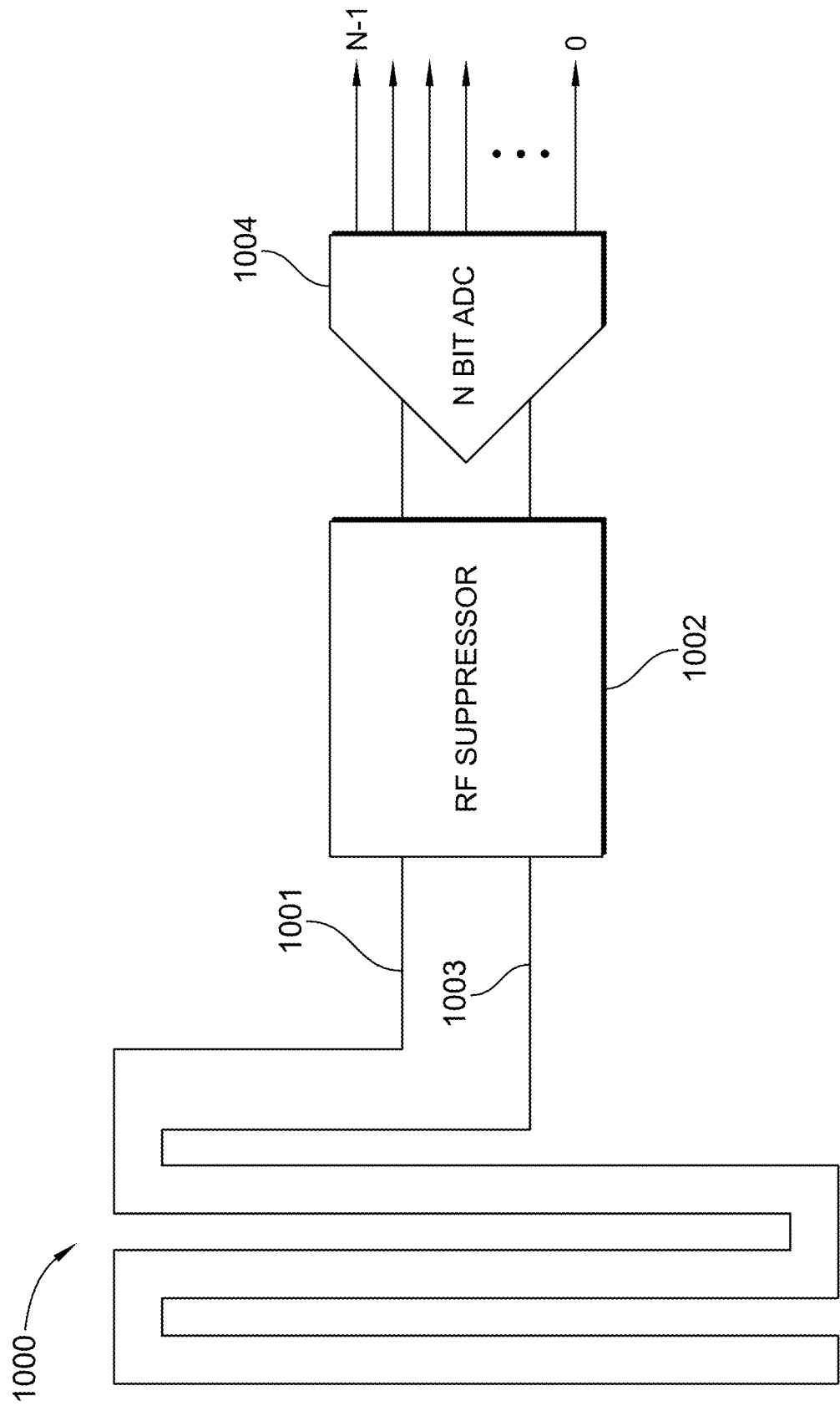
FIG. 10 is an electrical schematic showing an incontinence sensor being provided by an uninterrupted, serpentine-shaped trace forming a loop that is coupled to an RF suppressor and showing the RF suppressor coupled to an n bit analog-to-digital converter (ADC)

Referring now to FIG. 10, an incontinence sensor 1000 includes an uninterrupted, serpentine-shaped trace forming a loop that terminates at leads 1001, 1003 that, in turn, couple to a radio frequency (RF) suppressor 1002. RF suppressor 1002 is coupled to an n bit analog-to-digital converter (ADC) 1004 by conductors 1006, 1008. In some embodiments, ADC 1004 is included in an application specific integrated circuit (ASIC) such as ASIC 900 mentioned above. ADC 1004 is a low power ASIC in some embodiments.

Sensor 1000 is illustratively a detection grid that is fashioned from a conductive ink which has several kilo Ohms (kΩ)/meter (m) resistance. Because sensor 1000 forms a complete loop, it is possible to detect a broken detection grid while still being able to sense conductive fluids introduced into the associated incontinence pad of which sensor 1000 is a part. When sensor 1000 is broken, an open circuit results and the resistance is effectively infinite. When moisture or liquid is present on sensor 1000, the wet part of the sensor 1000 is essentially a short circuit having zero resistance and the dry portion of sensor 100 is the only portion that contributes to the overall resistance of the sensor 1000. Thus, the sensor 1000 or detection grid divides into two parts, the wet part and the dry part. As such, the resistance of the loop of sensor 1000 changes depending upon an amount and location of moisture on the loop. The ADC 1004 has an output that correlates to the resistance of the loop of sensor 1000.

The RF suppressor 1002 located between sensor 1000 and ADC 1004 is a feature that is either printed on the associated incontinence pad or is on a circuit inlay. The RF suppressor 1002 excludes the RF voltage at the tamper evident input (see above discussion) of the associated RFID tag or chip. There is a limit for RF voltage that most RFID tags at their input terminals, such as the tamper evident input, which could be exceeded with the sensor 1000 detection grid and level of electromagnetic fields that may be generated by the associated antenna/reader combination with the expected power output on the order of 1 Watt (W) and antenna gain. The RF suppressor can take a number of forms such as a common mode choke formed by having serpentine lines right at the input terminals for the RFID inlay or, alternatively, by having tuned stubs to create an RF short and reflect the incident RF energy back into the sensor 1000 detection grid while still providing DC connectivity for conductive liquid detection.

Figure 4:
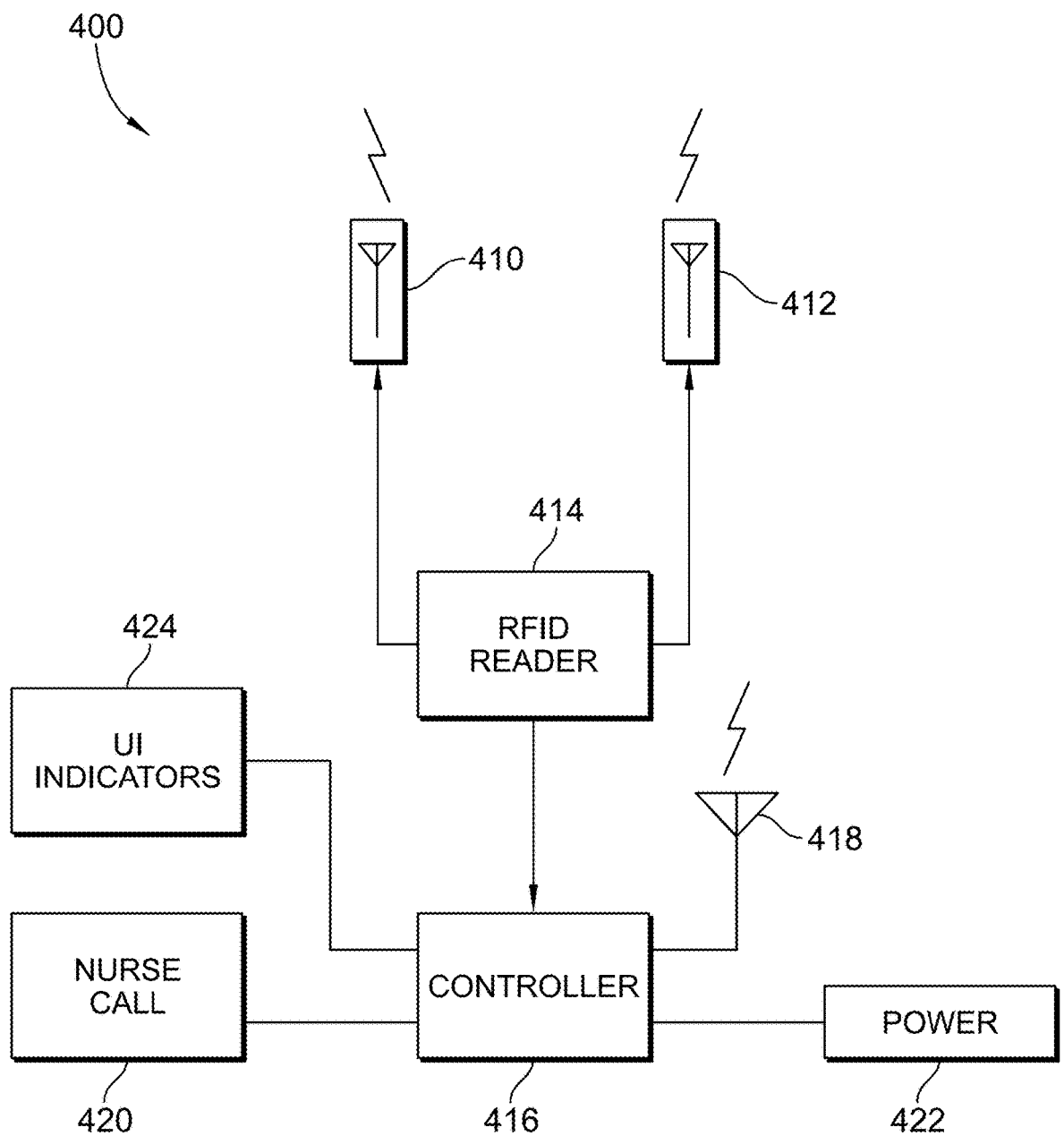
FIG. 4 is a block diagram of an embodiment of a moisture detection and alert system having a pair of receiving antennae, an RFID reader coupled to the receiving antennae, a controller coupled to the RFID reader, and the controller being coupled to a nurse call system, UI indicators and power.

Referring now to FIG. 4, a communications system 400 is configured to communicate with the sensor system 300. An RFID reader 414 employs a pair of antennas 410, 412 that are signaled by reader 414 to poll sensors 310, 312 to report that switch closure of the sensors, i.e. an incontinence event, has occurred. Energy from antennas 410, 412 is used by the passive RFID tags 322 to power them to return incontinence detection information to antennas 410, 412. The detected event is relayed to a controller 416 which is configured with software to communicate the incontinence detection information to an appropriate caregiver or system as described in further detail below with respect to FIG. 5. In the illustrative FIG. 4 example, the controller 416 is connected with a nurse call system 420, a power source 422, and a wireless communications device, such as a Wi-Fi antenna 418, in order to communicate the sensed incontinence event with other associated systems. Controller 416 is also coupled to user interface (UI) indicators, such as lights or a graphical display on a patient bed or on a room wall or other piece of nearby equipment, to indicate locally whether the incontinence pad 300 is wet or dry.

Figure 5:
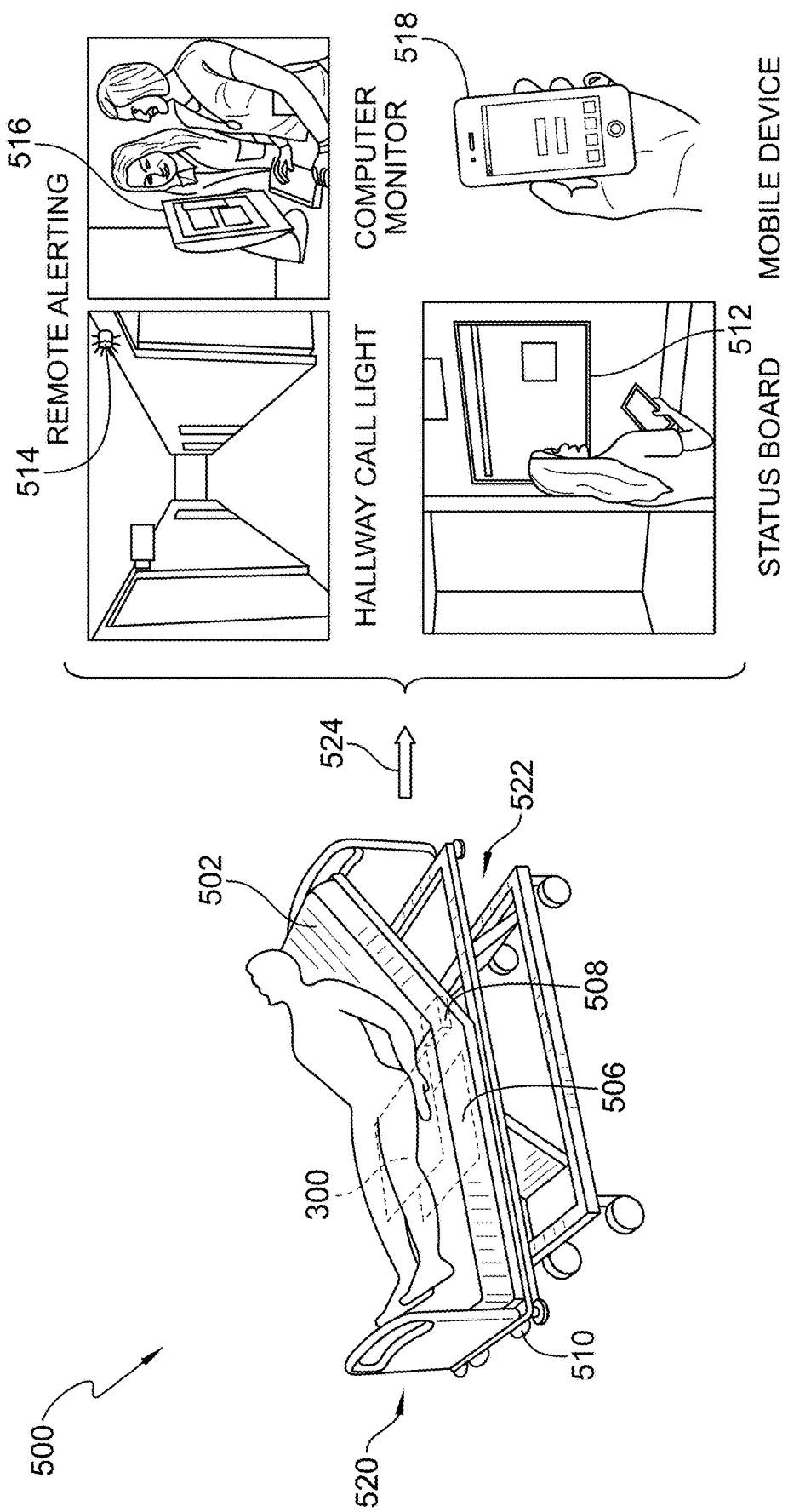
FIG. 5 is a schematic view of a moisture detection and alert system showing an incontinence detection pad (in phantom) beneath a patient, a receiving antenna pad (in phantom) beneath the incontinence detection pad, and a controller (in phantom) coupled to the receiving antenna pad and configured to communicate one or more signals regarding incontinence detection to a hallway call light alert, a remote computer for display on a computer monitor, a status board, and a mobile device as indicated diagrammatically by the arrow.

In some embodiments, the sensor system or incontinence pad 300 and communication system 400 are implemented as part of a remote alert system 500 as shown in FIG. 5. In particular, the incontinence pad 300 is placed between a patient and an underlying mattress 502 of a patient bed 520 beneath the patient's pelvic area. In some embodiments, pad 300 is integrated into mattress 502 to form a part thereof, but is removable for replacement with a clean pad after an incontinence event occurs. The antenna 410, 412 of communications system 400 are included in a substrate 506 mounted to a frame 522 of bed 520. A housing 508 contains RFID reader 414 and controller 416 therein in the illustrative example. In other embodiments, separate housings contain these elements. Housing 508 is also coupled to frame 522 of bed 520 in the illustrative example. Thus, the antennas 410, 412 of substrate 506 are in communication with reader 414 and with controller 416 located in housing 508 and these components operate in the manner described above in connection with FIGS. 3 and 4.

Upon detection of a moisture event the controller 416 in housing 508 communicates with circuitry of bed 520 to activate one or more in-room alerts such as indicators or illuminating devices 510 that are located on bed 520 and that are easily viewed by a caregiver. Additionally or alternatively, the controller 416 communicates the event to devices for remote alerting such as a status board 512 or other visual display of a hospital information system, a hallway call light 514 such as a light in a dome light or alert light assembly, a computer monitor 516 of a nurse call system and/or an electronic medical records (EMR) system, or even a caregiver's mobile device 518.

The controller 416 communicates the moisture event via Wi-Fi antenna 418 or other known wireless communication equipment and protocols in some embodiments. Alternatively or additionally, controller 416 communicates the moisture event via a wired connection, such as a 37-pin nurse call cable. It will be appreciated that a healthcare facilities' network infrastructure, represented diagrammatically by arrow 524 in FIG. 5, serves as an intermediary between system 500 and the one or more remote alerting devices 512, 514, 516, 518 with which system 500 communicates. Thus, wireless access points, gateways, routers, cabling, connection ports, jacks, and the like are the type of equipment represented by arrow 524 in FIG. 5.

In some embodiments, information indicating that the pad is dry or that no moisture event has occurred is communicated by controller 416 to one or more remote computer devices, such as an EMR computer, for storage in a patient's EMR. Such information is communicated at pre-set intervals, such as every hour or every half hour or more or less frequently, for example. The interval for communicating such information is programmable by caregivers in some embodiments. Further alternatively or additionally, a caregiver selects a user input such as an icon on a graphical display of a patient bed or at remote computer to command the reader to poll the incontinence pad to obtain information regarding the wet/dry status of the pad. By permitting the caregiver to determine when the incontinence pad status information is received, alert fatigue is avoided because the caregiver receives the information when the caregiver is able to act on it.

Figure 6:
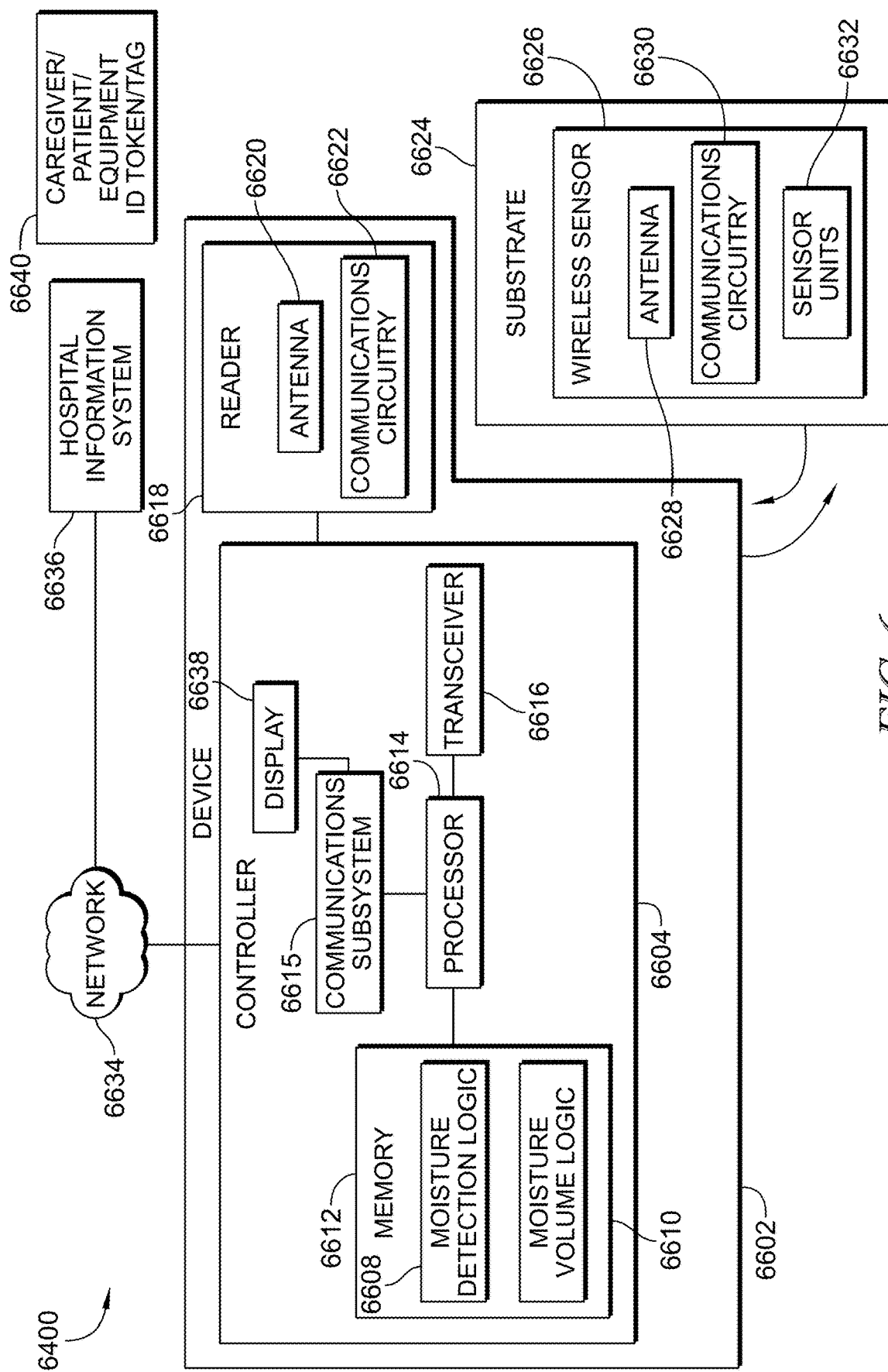
FIG. 6 is a block diagram of a sensor event detection system showing a device having a controller and a reader to read wireless signals transmitted by a wireless sensor on a substrate.

Referring now to FIG. 6, an "on demand" system 6400 is shown and is configured for requesting of moisture status from an incontinence detection apparatus such as those discussed above in connection with FIGS. 1-5. In the illustrative example, the system 6400 includes a wireless sensor 6626 on a substrate 6624 in communication with a device 6602 including a controller 6604. Device 6602 is a patient bed in some embodiments but may just as well be another piece of equipment or a portable handheld device. Controller 6604 is configured to power the wireless sensor 6626 via a transceiver 6616. More specifically, processor 6614 controls the interrogation of the wireless sensor 6626 by the transceiver 6616. Antenna 6628 of the wireless sensor 6626 is configured to receive signals from the transceiver 6616. Sensor traces, similar to those discussed elsewhere herein, of sensor units 6632 that are exposed to moisture affect the signal sent back to the transceiver 6616 via communications circuitry 6630. Transceiver 6616, therefore, is configured to receive communications from the wireless sensor 6626. Processor 6614 is in communication with memory 6612, having embodied therein, a software module, routine, or instructions executable by the processor 6614 to analyze the signals received by the transceiver 6616 and apply moisture detection logic 6608 and moisture volume logic 6610 thereto, to determine if a moisture event has occurred and the volume of the moisture event.

In some embodiments such as the illustrative embodiment, the processor 6614 of controller 6604 is communicatively coupled to one or more other computing systems, such as a hospital information system 6636 (e.g., a nurse call system and/or an electronic medical records (EMR) system), by one or more networks 6634 or other communication links. As such, occurrences of moisture detection events detected by the processor 6614 executing the moisture detection logic 6608 is communicated to one or more other electronic devices, as described above.

Memory 6612 may be pre-programmed with instructions for the processor to generate specific alerts based on one or more of moisture detection and a particular threshold of a volume of moisture being detected. For instance, the alerts illuminate one or more indicators that are color coded to indicate different levels of volume. In some examples, a first color, such as green, is used to indicate the substrate is dry; yellow indicates slight moisture or low severity notification such as 50 milliliters to 100 milliliters range; and red indicates a large amount of moisture such as greater than 150 milliliters which corresponds to the substrate 6624 being soaked and needing to be changed. The alerts can be further customized to individual patients depending on time of day, activity/mobility, age, weight, and type of incontinence. For instance, at nighttime the threshold for a severe alert may be higher so as to not unnecessarily disturb a patient's sleep.

As an alternative to continuously monitoring and instant notification of the moisture state of the patient, device 6602 can be handheld and incorporated in a mobile device such that a caregiver can "spot check" the patient while making patient rounds or while otherwise in the patient's room. This cuts down on the amount that system 6400 is continuously monitoring for events and reduces the amount of continuously generated data for system 6400 to handle. The terms "continuously monitoring" and "continuously generated" as used herein is intended to mean multiple times per second (e.g., every 50 milliseconds or every 200 milliseconds) or multiple times per minute if the polling cycle from transceiver 6616 is longer than one second, as well as including polling cycles that are longer than one minute. The term "instant notification" is intended to mean as soon as the system 6400 is able to process the information and activate a notification (e.g., turn on a light, display information on a screen, send a message to a mobile device, etc.) during its normal operation and so is intended to account for the inherent processing time in the system 6400.

For example, in the illustrative embodiment, device 6602 includes a reader 6618 with an antenna 6620 and communications circuitry 6622. Reader 6618 may be a barcode scanner in some embodiments. The caregiver carrying device 6602 uses the reader 6618 to scan a tag or token 6640 having a barcode or other ID information associated with a patient (such as a hospital ID bracelet) or associated with medical equipment used by the patient (such as a bed) or associated with the caregiver (e.g., the caregiver's own ID tag). In response to this scanning of ID information, the reader 6618 sends a signal to the processor 6614 via communications subsystem 6615 and, in turn, processor 6614 triggers the transceiver 6616 to interrogate the wireless sensor 6626 of the patient. If an incontinence event has occurred, as determined by processor 6614 based on the information sent back to transceiver 6616 from wireless sensor 6626, an alert is then shown on a display 6638 on the handheld device 6602 so that the caregiver can take appropriate actions while present with the patient.

As mentioned above, in some embodiments, device 6602 is attached to or coupled to patient equipment, such as a bed or chair on which the patient is supported. In such embodiments, the reader 6618 may activate the system 6400 to interrogate the sensor 6626 automatically in response to detection of the caregiver. For example, in some embodiments, the reader 6618 senses the presence of a caregiver tag 6640 using RFID or infrared (IR) technology when the caregiver is within reception range of reader 6618 which generally corresponds to the caregiver being within proximity of the patient on device 6602. If there has been an incontinence event, then the associated alert is shown on display 6638 of device 6602 so that the caregiver can take appropriate actions while present with the patient.

Figure 7:
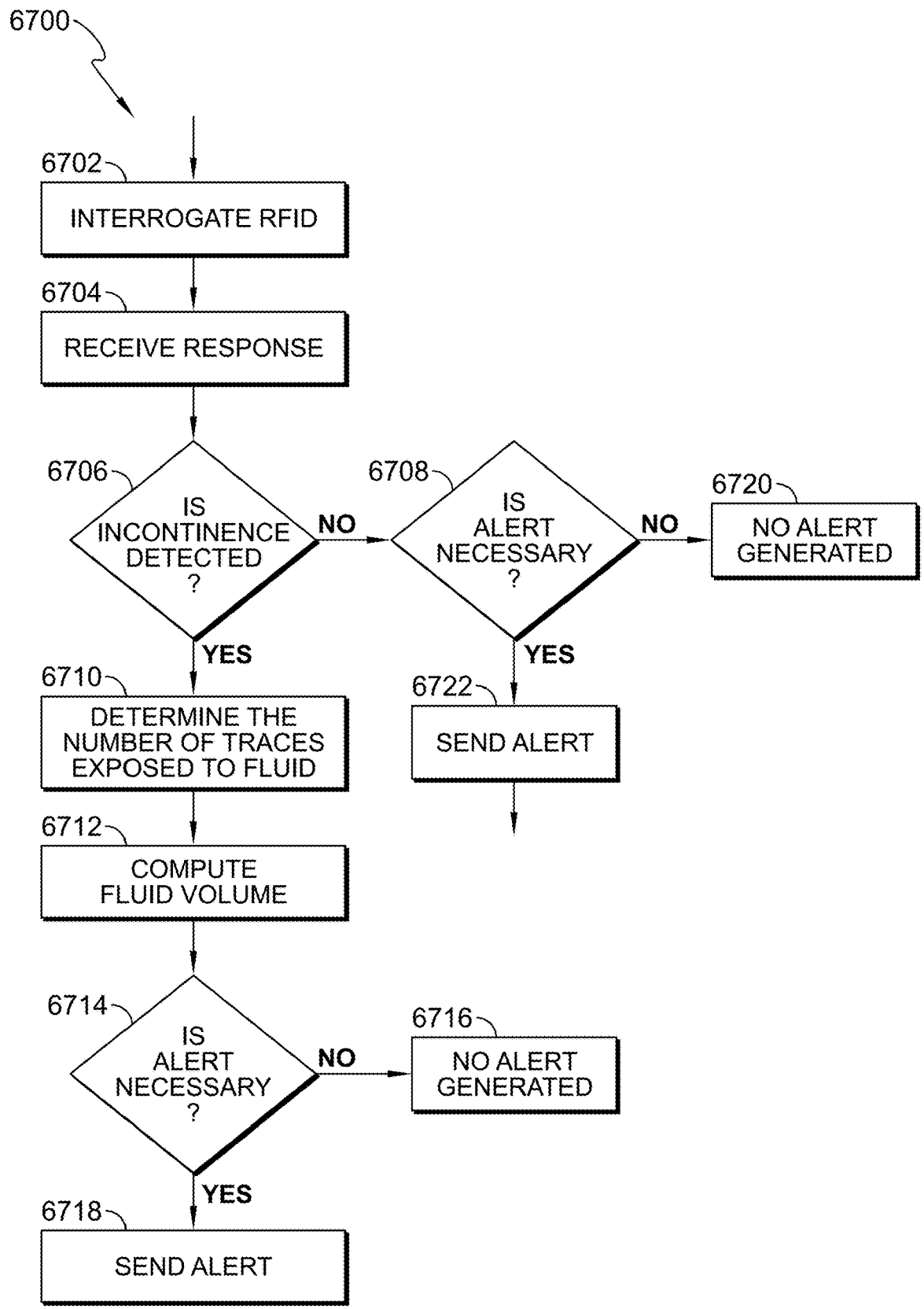
FIG. 7 is a flow diagram of a sensor detection algorithm in which incontinence is detected and a fluid volume is computed.

Referring now to FIG. 7, a method or algorithm 6700 implemented by system 6400 is shown. According to algorithm 6700, the controller 6604 interrogates an RFID tag in wireless sensor 6626 as indicated at block 6702. Controller 6604 then receives a response from the interrogation as indicated at block 6704. Controller 6604 determines based on the received signal if incontinence or other fluid is present as indicated at block 6706. If there is no incontinence detected, controller 6604 determines whether an alert should be generated as indicated at block 6708 (i.e. "green" meaning okay/no moisture) and generates an alert signal as indicated at block 6722. If the controller 6604 only generates alerts for moisture, no alert is generated as indicated at block 6720.

If incontinence is detected at block 6706 of algorithm 6700, the controller 6604 determines the number of traces exposed to fluid as indicated at block 6710. Based on the number of traces exposed to fluid, a predetermined distance between the traces, and the wicking properties of a substrate that holds the traces, the controller 6604 then computes a fluid volume detected as indicated at block 6712. The volume is compared to predefined alert thresholds by controller 6604 to determine if an alert (e.g., yellow for medium amount of fluid; red for a larger amount of fluid) is necessary as indicated at 6714 and, if so, the corresponding coded alert message is sent to display 6638 by processor 6614 of controller 6604 as indicated at block 6718. If the fluid volume detected does not meet any of the predefined alert thresholds, no alert may be generated as indicated at block 6716.

Figure 8A:
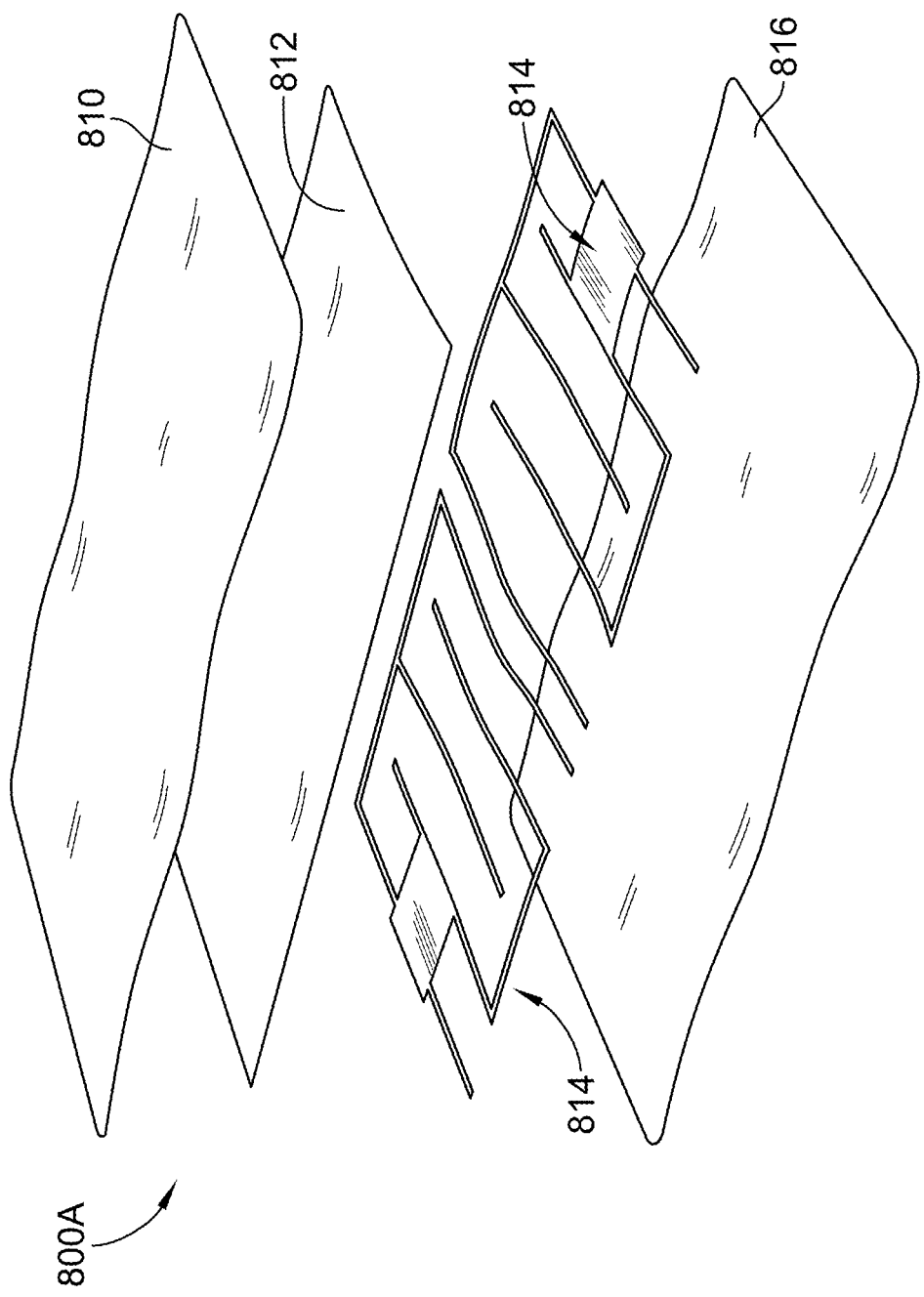
FIGS. 8A-D are exploded views of sensor pads having a sensing grid layer including two RFID sensors and associated sensor traces.

Referring now to FIGS. 8A-8D, illustrative embodiments showing how a pair of sensors or sensing grids 814 for detecting moisture can be incorporated into respective pads 800A-D are shown. Each of the pads 800A-D is configured to support a patient on a top surface and is typically used with a patient support, frame, or bed. In a first embodiment pad 800A, as shown in FIG. 8A, a top surface consists of a non-woven layer 810, in contact with an absorbent layer 812, and the sensing grids 814 are printed directly onto barrier layer 816 which defines the bottom surface of pad 800A. The non-woven top layer 810 typically is a polymer-based material and is made from bonded fibers and/or filaments. The non-woven top layer 810 provides comfort and softness for a patient on the pad 800A. Absorbent layer 812 provides a core material of the pad to hold moisture and may include, for example, wood pulp and/or extruded polymer fibers. The fibers can be loose or bonded into a web of material at the option of the pad designer.

Sensing grids 814 include conductive ink traces as well as an RFID chip or tag as described above in connection with the embodiments of FIGS. 1-6. Suitable conductive inks include, for example, carbon, silver, copper, zinc and graphene. Barrier layer 816 is typically polyethylene (PE) which provides a barrier to prevent moisture penetration to a support surface or frame beneath pad 800A. Polypropylene (PP) sheets and/or polyurethane (PU) sheets are also acceptable to be used as barrier layer 816. The barrier layer 816 may or may not be breathable. In some embodiments, barrier layer 816 is substantially waterproof. In a prototype system which was found to work acceptably, silver ink was printed on a sheet of PE material that was inserted into a pad that, itself, had a bottom substantially waterproof layer. The layer of PE material with silver ink was situated between the bottom layer and an overlying layer of absorbent material.

Figure 8B:
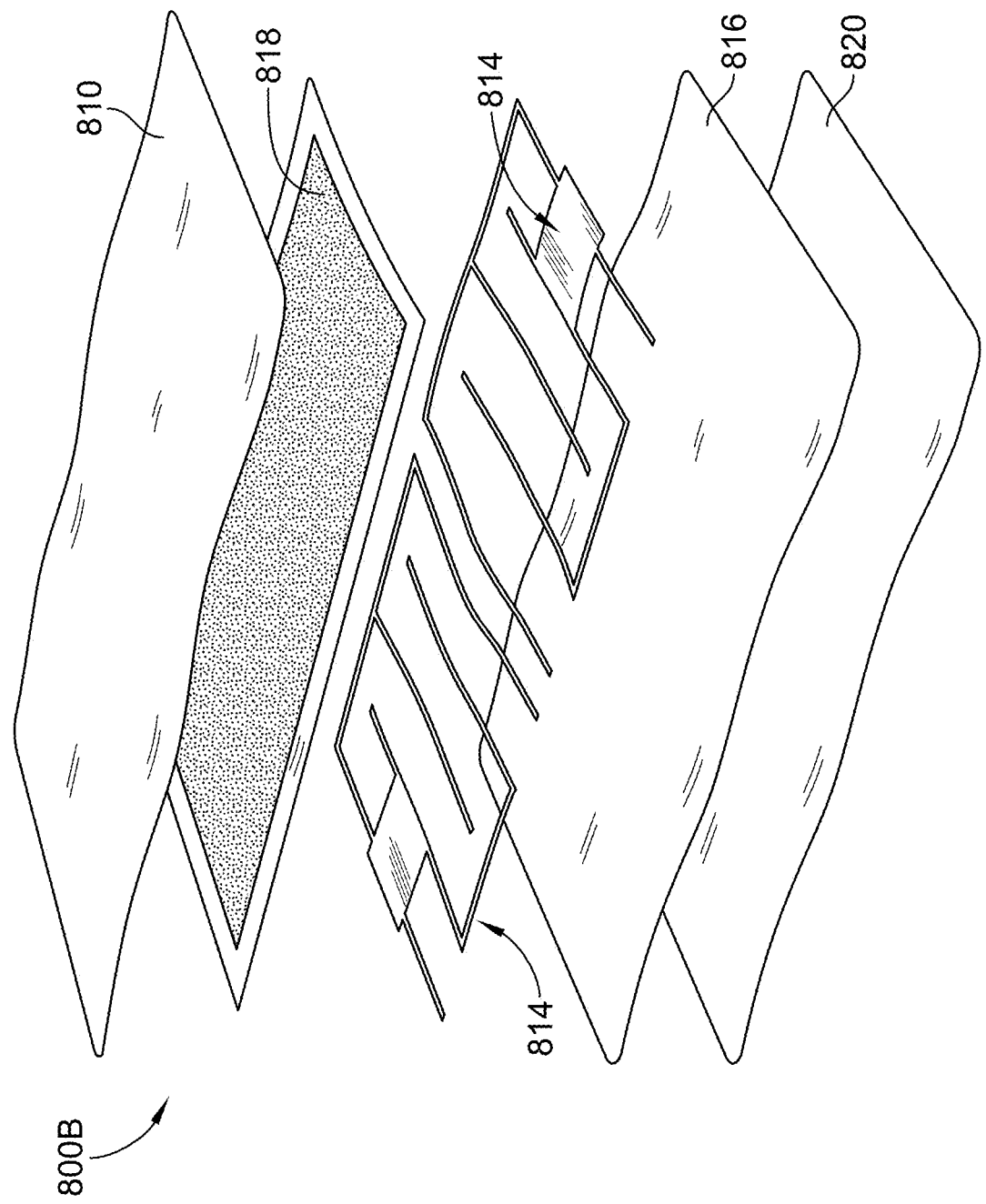

In another exemplary embodiment pad 800B, as shown in FIG. 8B, a top surface non-woven layer 810 is provided in contact with an absorbent layer 818 with super absorbent polymer beneath it. Sensing grids 814 are printed directly on barrier layer 816 and a non-woven layer 820 is provided beneath the barrier layer 816 to contact a patient support or frame. In this embodiment, an absorbent layer with super absorbent polymer 818 is provided. The super absorbent polymer (SAP) provides 3-5 times more moisture absorption than the wood pulp absorbent layer 812 of pad 800A of FIG. 8A. The SAP will typically be incorporated into absorbent layer 818 as powder but can be fibers if desired. An example of a SAP that may be used in absorbent layer 818 is sodium polyacrylate. Alternatively or additionally, the SAP may be impregnated into layer 818 or be situated on top of layer 818 in other embodiments. The non-woven bottom layer 820 is optional and may be added to provide friction to prevent sliding with respect to a patient support or frame. The non-woven bottom layer 820 may also be added to provide grip when moving the pad 800B and to provide increased tensile strength for moving patients.

Figure 8C:
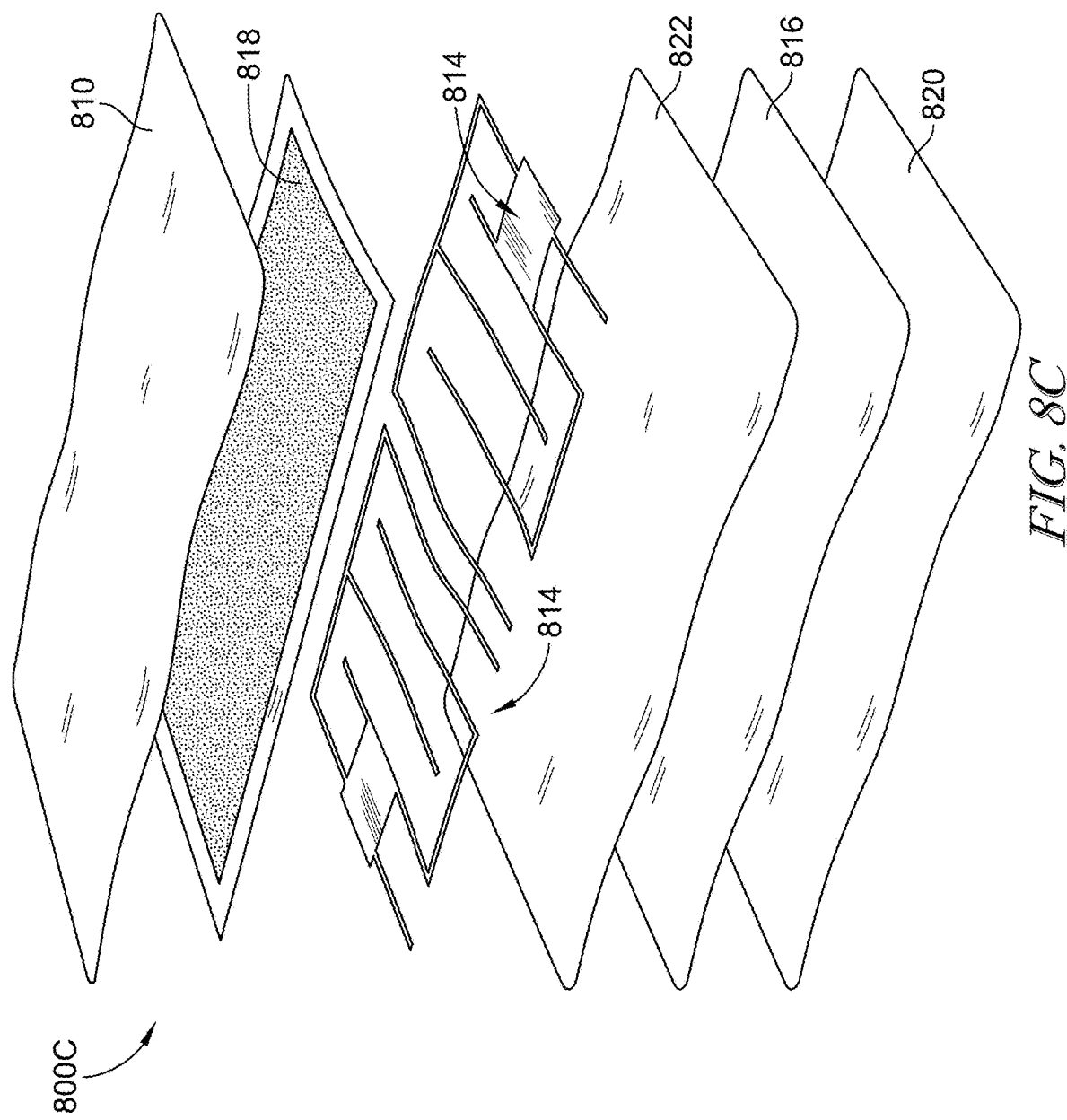

In another exemplary embodiment pad 800C, as shown in FIG. 8C, pad 800 includes a non-woven layer 810 at the top surface, an absorbent layer with SAP 818, sensing grid layers 814 printed on a top surface of a non-woven substrate 822 between the absorbent layer with SAP 818 and the bottom of the non-woven substrate 822, barrier layer 816 and non-woven layer 820 at the bottom. In this embodiment, non-woven substrate 822 of pad 800C provides an alternative to printing on the barrier sheet 816 if, for example, the barrier sheet 816 is made of a material that is not capable of surviving the print curing process required to print the conductive ink traces onto the barrier layer 816. The non-woven substrate 822 may also provide additional tensile strength thereby preventing electrode and/or pad rupture and stretching. In a variant of pad 800C of FIG. 8C, the sensing grids 814 are printed on a bottom surface of the non-woven substrate 822 that faces the barrier layer 816. This provides an extra layer that moisture from a patient on the top surface must wick through. This may prevent false positives for incontinence detection caused by perspiration or other undesirable moisture detection, for example.

Figure 8D:
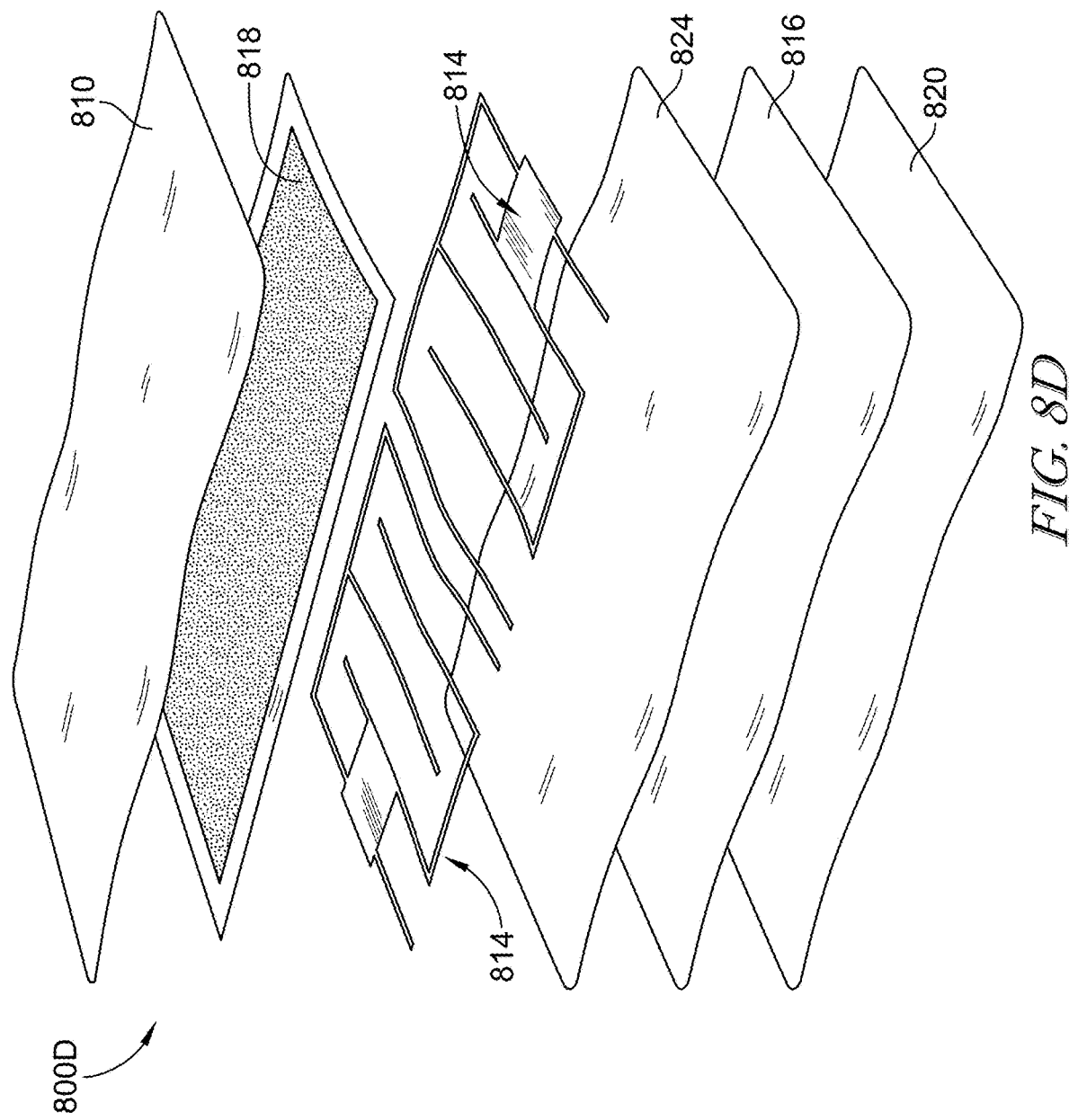

In another exemplary embodiment, as shown in FIG. 8D, pad 800D includes a non-woven top layer 810, an absorbent layer with SAP 818, sensing grids 814 printed onto film substrate 824 which is a co-laminate with the barrier layer 816, and non-woven layer 820. Absorbent layer 812 and absorbent layer with SAP 818 may be alternatively used in any of the embodiments depending on the desired level of moisture retention. Similarly non-woven layer 820 may be optionally provided or removed from any of the embodiments depending on the desirability of the features it provides.

In the illustrative examples of pads 800A-800D, each of layers 810, 812 816, 818, 820, 822, 824, to the extent present, are generally rectangular in shape. However, layers 812, 818 are slightly smaller in length and width dimensions than layers 810, 816, 820, 822, 824. The larger-sized layers 810, 816, 820, 822, 824 are attached at their peripheries (again, to the extent present in any particular pad 800A-D) such as by sewing, sonic or RF welding, adhesive or other laminating technique. Thus, the periphery of the absorbent material layers 812, 818 is inset by a small amount from the overall periphery of pads 800A-D. The sensing grids 814 are within the periphery of the absorbent layers 812, 818 and so are also inset from the overall periphery of pads 800A-D. In other embodiments, the layers 810, 812 816, 818, 820, 822, 824 are attached to each other across their entire widths and not just at the peripheries.

In the illustrative examples, incontinence pad 300 includes two sensors 310, 312 and incontinence pads 800A-D each include two sensors 814. However, it is within the scope of the present disclosure for only a single sensor, with a single RFID tag or chip, to be used in pads that are generally the same size as pads 300, 800A-D or even larger.

The use of two sensors in the illustrative examples was dictated by the equipment available to screen print the traces (e.g., traces 316, 318) of the sensors. Thus, use of larger screen printing equipment permits the traces to be made larger and therefore, permits a single-sensor pad to be manufactured.

In a prototype embodiment, the sensor traces were printed using a standard screen printer. Individual sheets of PE were manually placed on the printer. After printing, the individual PE sheets were manually placed on a rack to separate each sheet. The rack of sensors was placed into an oven and the ink (silver in the prototype) of the sensors was thermally cured. An RFID label that used an existing RFID chip from Convergence Systems Limited of Hong Kong was then attached to PE sheet having the cured traces. The RFID label was printed and cured on an existing high volume roll-to-roll system. An adhesive was applied to the RFID label and the label was manually attached to the printed sensor. Copper rivets were then use to electrically attach the label to the sensor traces. The pad of the prototype was a standard pad available from Principle Business Enterprises, Inc. (PBE) of Bowling Green, Ohio. The pad was slit along one of its edges. Adhesive was applied to the back of each sensor. Two sensors were then manually inserted between the middle absorbent layer and the bottom PP layer of the pad. The slit through which the sensors were inserted was then glued shut.

The present disclosure contemplates systems that are able to estimate the type of biofluid present on the incontinence pads, the quantity of biofluid released onto the pads, and the integrity of the interdigitated conductive fingers (or other patterns of traces). Biofluid volume estimation is accomplished, for example, using multiple sensors in multiple zones with outputs from the sensors feeding into multiple inputs of an RFID chip. The volume is estimated based on the number of inputs into the RFID chip that are active.

Another way to estimate biofluid volume is to provide a current source with the RFID chip, along with an Analog to Digital Converter (ADC). The current source forces current to the conductive traces and when biofluid is present between them, the current flowing between the traces produces a voltage that is read by the ADC. By using calibration data, the volume and fluid type may be estimated based on the measured voltage. The time rate of change in the voltage produced also can be used to estimate the rate at which fluid is being introduced onto the incontinence pad.

Various alerts are generated based on type of biofluid on the pad and/or volume of biofluid on the pad and/or the rate at which the biofluid was delivered to the pad. Thus, variable alarm thresholds are contemplated by this disclosure. For example, an alert is generated for a lower volume of blood than it may take for an alert to be generated for urine. As another example, if the rate of biofluid delivery is too high, an alert may be generated.

The type of biofluid present on the pad can be estimated using methods such as sensing the conductivity and/or resistance of the biofluid on the pad. Urine is relatively conductive (in the range of 0.06 to 0.1 siemens per meter (S/m)) but blood is much more conductive (in the range of 1.18 to 3.35 S/m). So, even for small amounts of blood, it is able to be distinguished from urine based on a conductivity measurement. Fecal conductivity is typically much lower, but more variable depending upon ion content. Values of 0.06 S/m are typical. Measurement of the actual value of conductivity of the biofluid is not necessary. Instead, the relative or indicated conductivity is suitable for measurement. In some embodiments, other types of fluids found in a healthcare environment may be detected in a similar manner, such as indicating that a patient has spilled a drink or meal on the bed.

Determining conductivity of a biofluid may be accomplished by having a current source with the RFID tag, and forcing a current between the two traces or electrodes, and then estimating the voltage drop across the two electrodes. This may be accomplished by an ADC or a series of comparators effectively operating as an ADC. Measuring across successive pairs of conductors may yield an estimate of the volume or biofluid and provide an indication as to the type of biofluid.

Figure 11:
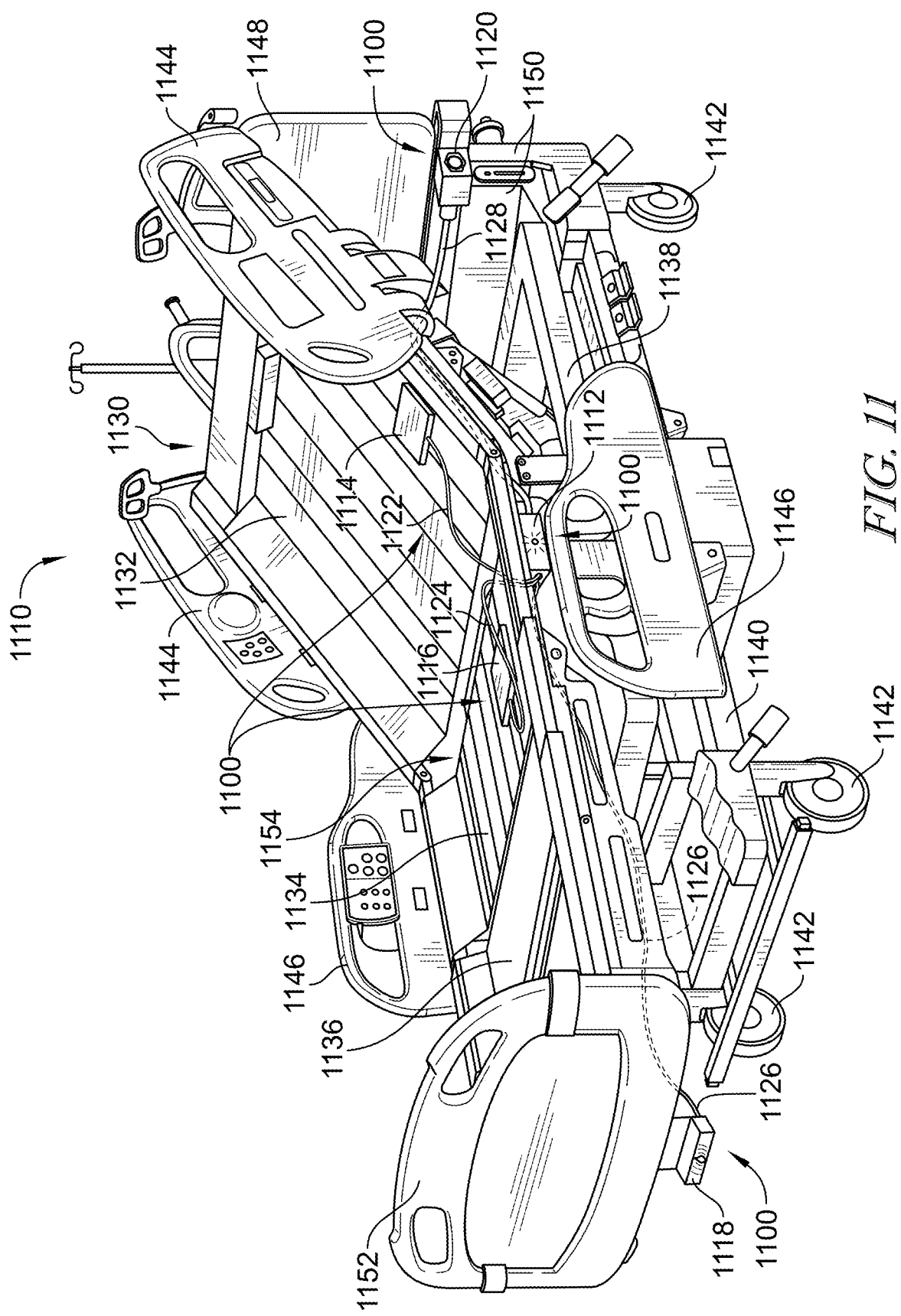
FIG. 11 is a perspective view showing a pair of antenna, a reader, a visual indicator, and an output port of an incontinence detection system retrofitted on a first embodiment of a hospital bed with a first antenna of the pair being coupled to a head section of a stepped deck of the hospital bed and a second antenna of the pair being coupled to a thigh section of the stepped deck.
Figure 12:
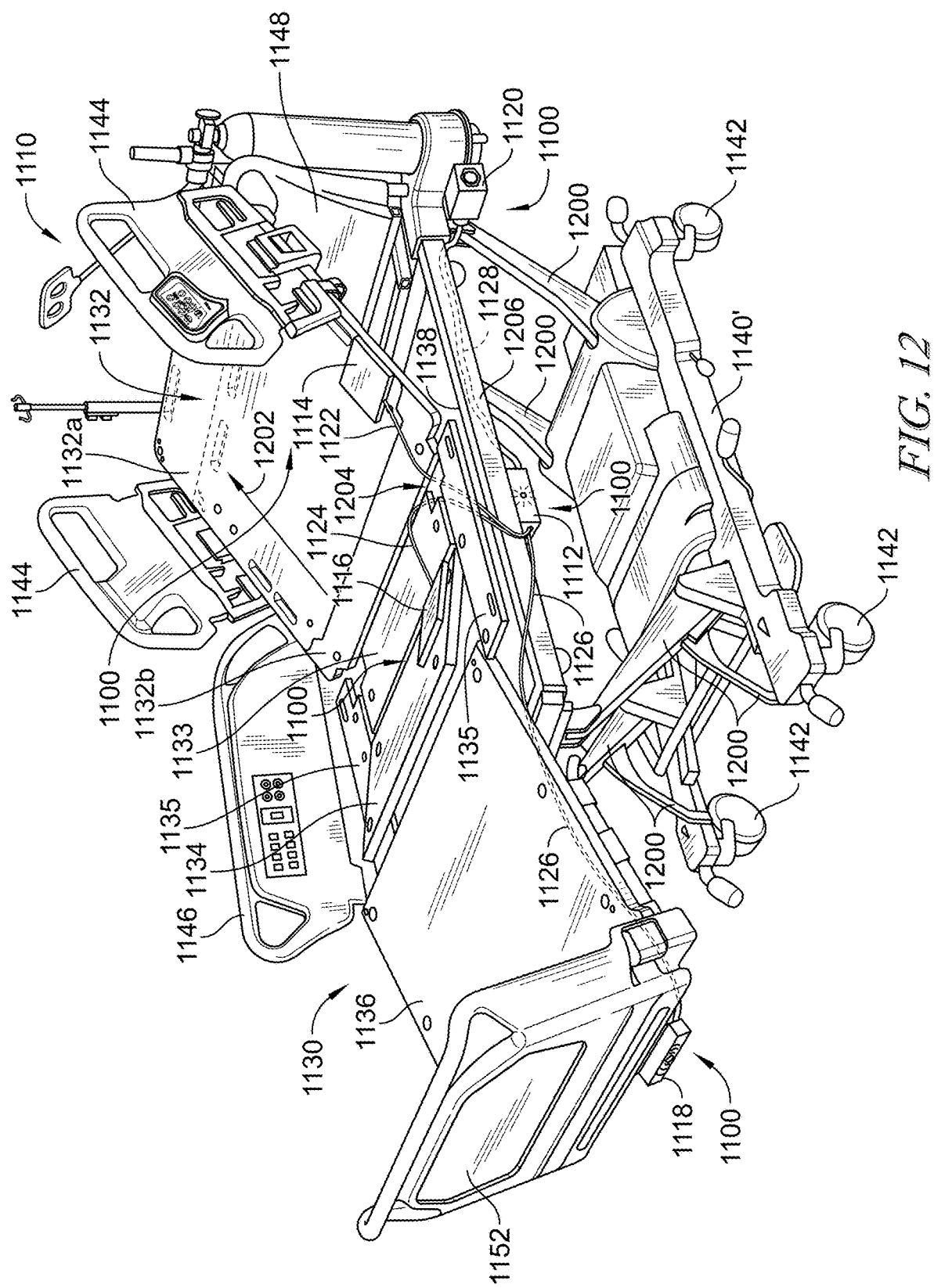
FIG. 12 is a perspective view, similar to FIG. 11, showing the pair of antenna, the reader, the visual indicator, and the output port of the incontinence detection system retrofitted on a second embodiment of a hospital bed with the first antenna being coupled to a slideable panel of a head section of the hospital bed and the second antenna coupled to a thigh section of the hospital bed.
Figure 13:
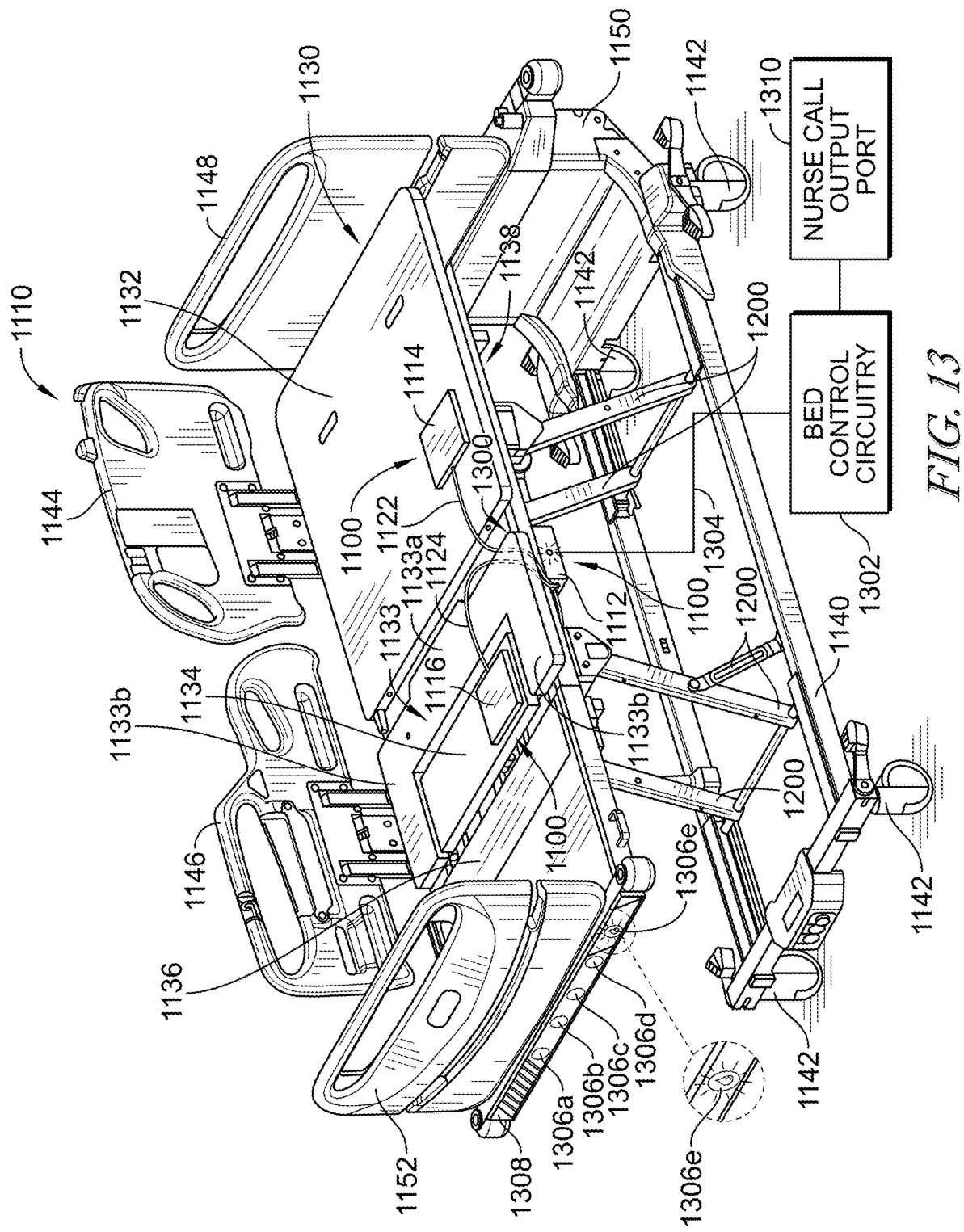
FIG. 13 is a perspective view, similar to FIGS. 11 and 12, showing the pair of antenna, the reader, and the visual indicator of the incontinence detection system installed on a third embodiment of a hospital bed with the first antenna being coupled to a head section of the hospital bed and the second antenna coupled to a thigh section of the hospital bed and showing, diagrammatically, the reader being coupled electrically to bed control circuitry to send incontinence detection data via the bed control circuitry to a nurse call output port of the hospital bed.
Figure 14:
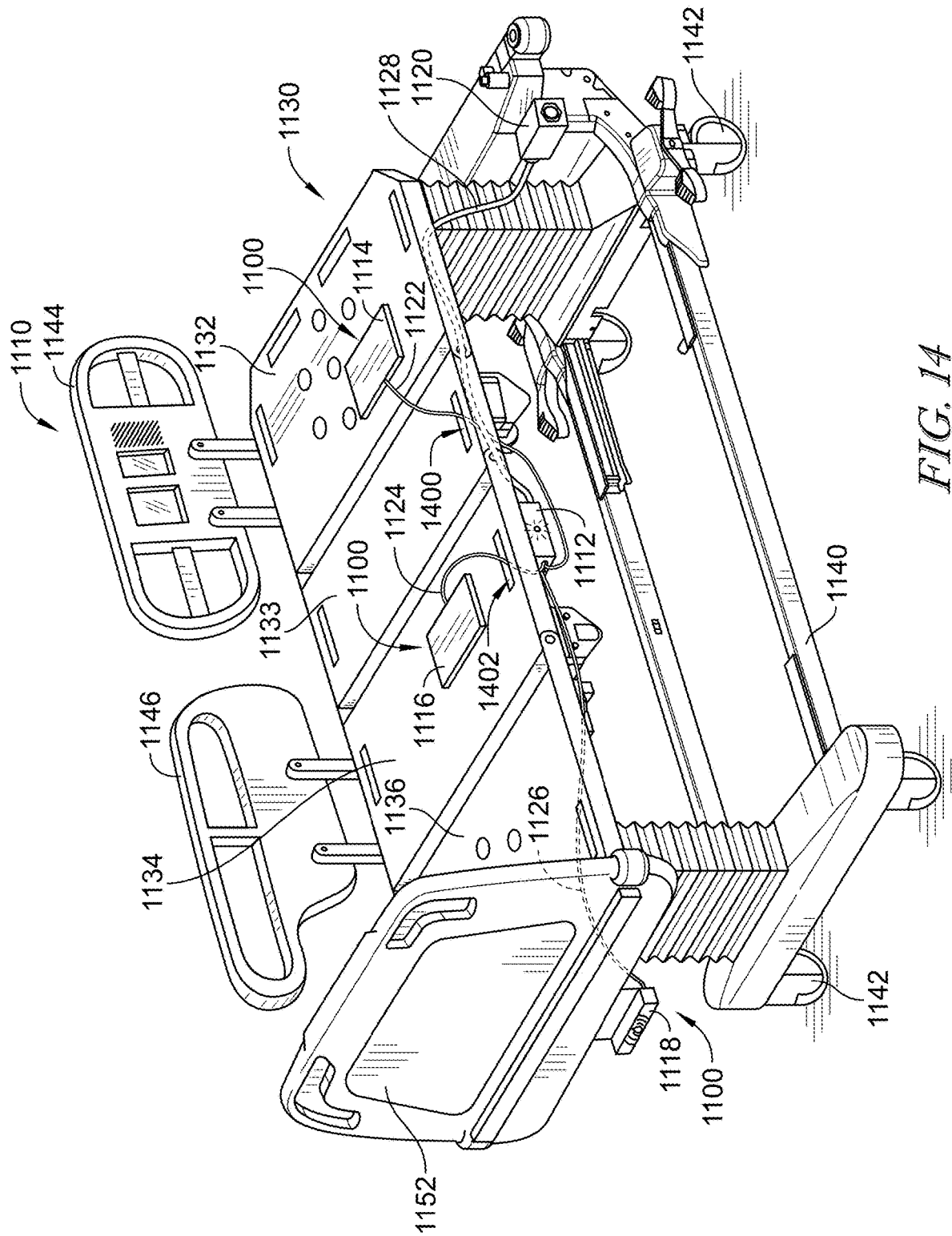
FIG. 14 is a perspective view, similar to FIGS. 11-13, showing the pair of antenna, the reader, the visual indicator, and the output port of the incontinence detection system retrofitted on a fourth embodiment of a hospital bed with the first antenna being coupled to a head section of the hospital bed and the second antenna coupled to a thigh section of the hospital bed and showing cables from the antenna to the reader being routed through holes formed in a seat section and the thigh section of the hospital bed.
Figure 15:
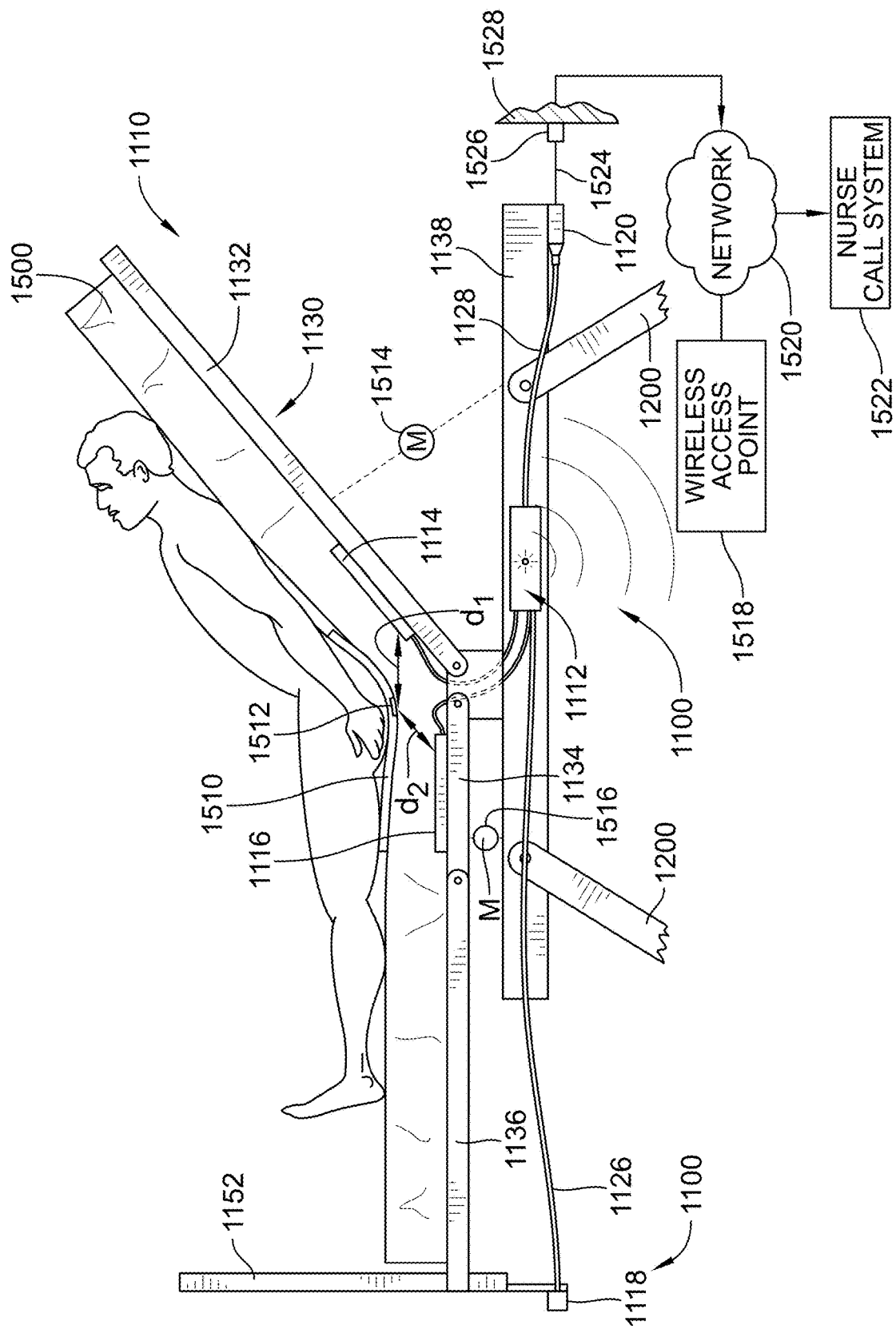
FIG. 15 is a diagrammatic view showing distances between the first and second antennae of the incontinence detection system and an RFID tag of an incontinence detection pad situated between a patient and an upper surface of a mattress of a hospital bed and showing the reader communicating with a network via wired and wireless datalinks.

Referring now to FIGS. 11-15, an incontinence detection system 1100 is attached to different types of hospital beds 1110. The bed 1110 of FIG. 11 is illustrative of the VERSACARE® bed available from Hill-Rom Company, Inc. The bed 1110 of FIG. 12 is illustrative of the PROGRESSA® bed available from Hill-Rom Company, Inc. The bed 1110 of FIG. 13 is a bed currently in development for sale by Hill-Rom Company, Inc. Details of bed 1110 of FIG. 13 can be found in International Patent Application No. PCT/US2016/034908, which was filed May 29, 2016, and which is hereby incorporated by reference herein in its entirety. The bed 1110 of FIG. 14 is similar to the Secure II bed available from Stryker Corporation. The bed 1110 of FIG. 15 is a generic bed which is shown diagrammatically.

With the exception of bed 1110 of FIG. 13 which will be discussed below, the incontinence detection system 1100 includes a reader 1112, first and second antennae 1114, 1116, a visual indicator 1118, and an output port 1120 as shown in FIGS. 11, 12, 14 and 15. A first cable 1122 electrically couples antenna 1114 to reader 1112. A second cable 1124 electrically couples antenna 1116 to reader 1112. A third cable 1126 electrically couples reader 1112 to visual indicator 1118. A fourth cable 1128 electrically couples reader 1112 to output port 1120.

Bed 1110 of FIG. 11 has a mattress support deck 1130 with a dished head section 1132, a dished thigh section 1134, and an extendable and retractable foot section 1136. A seat section in the form of a smaller dished panel is situated in the space between head section 1132 and thigh section 1134 but cannot be seen in FIG. 11. Bed 1110 of FIG. 11 has an upper frame 1138 upon which sections 1132, 1134, 1136 of deck 1130 are supported for pivoting or articulating movement. Seat section (not shown) is stationary relative to upper frame 1138 in bed 1110 of FIG. 11. Deck 1130 is sometimes referred to as a step deck in the art due to the dished shape of some or all of the deck sections 1132, 1134, 1136 and the seat section.

Bed 1110 of FIG. 11 also has a base frame 1140 which is supported on a floor by a set of four casters 1142, three of which can be seen in FIG. 11. Bed 1110 has a lift system to raise, lower and tilt upper frame 1138 relative to base frame 1140 as is known in the art. The lift system is in the form of linkages and motorized linear actuators in some embodiments. Bed 1110 of FIG. 11 has a pair of head end siderails (sometimes referred to as head rails) 1144 that are mounted to and move with head section 1132 as it is pivotably raised and lowered relative to upper frame 1138, a pair of foot end siderails 1146 (sometimes referred to as foot rails) that are mounted to upper frame 1138, a headboard 1148 removably coupled to an upstanding portion 1150 of base frame 1140, and a footboard 1152 removably coupled to a foot end portion of foot section 1136 which is the extendable and retractable portion of foot section 1136. Additional details of the VERSACARE® bed 1110 shown in FIG. 11 can be found in Service Manual, VersaCare® Bed, from Hill-Rom, Product P3200/P3201, ® 2008 by Hill-Rom Services, Inc. and in U.S. Pat. No. 7,533,429, each of which is hereby incorporated by reference herein for all that it teaches.

Still referring to FIG. 11, reader 1112 is shown mounted to an underside of a frame member of thigh section 1134. Thus, in the illustrative example, reader 1112 articulates with thigh section 1134 as thigh section 1134 pivots relative to upper frame 1138. In other embodiments, reader 1112 is mounted to upper frame 1138. Reader 1112 may become blocked from view in the illustrative example when the adjacent siderail 1146 is moved from the illustrative lowered position up to a raised position. It should be appreciated that each of siderails 1144, 1146 is movable between raised and lowered positions relative to their respective support structure (e.g., head section 1132 in the case of siderails 1144 and upper frame 1138 in the case of siderails 1146).

Antenna 1114 is mounted to head section 1132 closer to the left side of bed 1110 than to the right side. Similarly, antenna 1124 is mounted to thigh section 1134 closer to the left side of bed 1110 than to the right side. The left and right sides of bed 1110 correspond to left and right sides of a patient lying in bed 1110 in a supine position. Due to the dished shape of deck sections 1132, 1134, the angled side walls of the deck sections 1132, 1134 that angle upwardly from the bottom panel of deck sections 1132, 1134 limit how close to the left side of bed 1110 antennae 1114, 1116 can be placed. Suffice it to say that antennae 1114, 1116 are located on the bottom panels of respective sections 1132, 1134 as close to the angled sidewalls of deck sections 1132, 1134 on the left side of bed 1110 as is practical. In some embodiments, strips of hook and loop fasteners (not shown) are used to hold antennae 1114, 1116 in place on the respective deck sections 1132, 1134.

The reason for locating antennae 1114, 1116 closer to the left side of bed is twofold. First, the thickness of each antenna 1114, 1116 is in the range of about one inch, give or take a ½ inch or so, and therefore, by placing the antennae 1114, 1116 closer to the left side of deck 1130, a patient positioned on a mattress supported by deck 1130 is less likely to "feel" the antennae 1114, 1116 through the mattress. Second, incontinence detection pads contemplated by this disclosure have RFID tags situated near the left side of the pads. Thus, the antennae 1114, 1116 which emit or radiate energy to power the RFID tags and to read the data sent or reflected back from the RFID tags operate more efficiently when they are closer to the RFID tags. Accordingly, it should be appreciated that, in alternative embodiments of incontinence detection system 1100, antennae 1114, 1116 may be located closer to the right side of bed 1110 if the incontinence pads of such alternative embodiments have their respective RFID tags situated near the right sides of the pads rather than the left sides. Alternatively or additionally, deck sections 1132, 1134 may be formed with recesses in which respective antennae 1114, 1116 are received so that upper surfaces of antennae 1114, 1116 are generally flush with upper surfaces of the bottom panel of deck sections 1132, 1134.

Cables 1122, 1124 are routed from respective antennae 1114, 1116 to reader 1112 through a gap or space 1154 defined between a foot end of head section 1132 and a head end of thigh section 1134. The manner in which cables 1122, 1124 are routed in the illustrative FIG. 11 example suggests that they both are routed through a space between a foot end of the seat section (not shown) and the head end of the thigh section 1134. However, one or both of cables 1122, 1124 may just as well be routed through a space between a foot end of the head section 1132 and a head end of the seat section (not shown). Regardless of the exact routing path, cables 1122, 1124 are provided with sufficient slack to permit head section 1132 and thigh section 1134 to pivot through their full ranges of movement relative to upper frame 1138.

Cable 1126 is routed from reader 1112 to visual indicator 1118 along an underside of thigh section 1134 and foot section 1136. Because visual indicator 1118 is mounted to the portion of foot section 1136 that extends and retracts, cable 1126 is provided with sufficient slack to permit the extension and retraction of foot section 1136 through its full range of movement. Cable 1128 is routed from reader 1112 to output port 1120 along portions of deck 1130 and frames 1138, 1140 as desired. Because output port 1120 is mounted to upstanding portion 1150 of base frame 1140 and because reader 1112 is mounted to deck 1130 or frame 1138, as the case may be, which are able to be raised, lowered and tilted relative to base frame 1140, cable 1128 is provided with sufficient slack to permit the upper frame 1138, along with deck 1130, to be raised, lowered and tilted relative to base frame 1140 through its full range of movement.

Suitable cable management devices such as zip ties, hooks, clips, straps, bands, and the like are provided in some embodiments to attach cables 1122, 1124, 1126, 1128 to portions of bed 1110 at various locations to prevent unwanted sagging or movement of cables 1122, 1124, 1126, 1128. However, as suggested above, some portions of cables 1122, 1124, 1126, 1128 should be sufficiently slack to permit movement of the various portions of bed 1110 without stretching, pinching or binding the respective cable 1122, 1124, 1126, 1128.

Referring now to FIG. 12, the illustrative PROGRESSA® bed 1110 shown therein has similar features as the illustrative VERSACARE® bed 1110 of FIG. 11. Thus, like reference numbers are used to denote like portions of these beds 1110 and the description above is equally applicable except where noted below in the discussion of bed 1110 of FIG. 12. In FIG. 12, the foot rail 1146 at the left side of the bed 1110 has been removed so that certain aspects of mattress support deck 1130 are more readily visible. Bed 1110 of FIG. 12 has a base 1140' that includes a shroud and the metal frame members of the base frame covered by the shroud. The arms or links 1200 of the lift system of bed 1110 of FIG. 12 can also be seen, although the linear actuators that are operated to move arms 1200 to raise, lower and tilt upper frame 1138 relative to base 1140' are covered by the shroud of base 1140'.

Deck 1130 of FIG. 12 has flat panels for its various sections and so is not a step deck. Deck 1130 of FIG. 12 has a first head section portion or panel 1132a and a second head section portion or panel 1132b that are included in head section 1132 of bed 1110 of FIG. 12. As head section is pivotably raised relative to upper frame 1138, deck panel 1132a translates in parallel relation with deck panel 1132b in a direction indicated by arrow 1202. As head section is pivotably lowered relative to upper frame 1138, deck panel 1132a translates in parallel relation with deck panel 1132b in a direction opposite of arrow 1202. First antenna 1114 of incontinence detection system 1100 of FIG. 12 is coupled to the movable deck panel 1132a in a lower left side corner region thereof. Thus, antenna 1114 translates with head section portion 1132a relative to head section portion 1132b. Cable 1122 that extends from antenna 1114 to reader 1112 includes sufficient slack to accommodate this movement of antenna 1114.

In some embodiments, a pivot axis about which head section 1132 of bed 1110 of FIG. 12 pivots relative to upper frame 1138 translates toward the head end of upper frame 1138 when head section 1132 is raised and translates toward the foot end of upper frame 1138 when head section 1132 is lowered. Such movement of the head section pivot axis during raising of head section 1132 further increases a distance between antenna 1114 and reader 1112 which also is accommodated by slack in cable 1122. Additional details of a suitable mechanism for translating head section portion 1132*a* relative to head section portion 1132*b* and for translating the head section pivot axis relative to upper frame 1138 can be found in U.S. Pat. No. 8,516,634 which is hereby incorporated by reference herein in its entirety. Further details of bed 1110 of FIG. 12 can also be found in Service Manual, Progressa™ Bed, From Hill-Rom, Product No. P7500, ©2013 by Hill-Rom Services, Inc.

A seat section 1133 of deck 1130 of bed 1110 can be seen in FIG. 12. Seat section 1133 is situated longitudinally between the foot end of portion 1132*b* of head section 1132 and the head end of thigh section 1134. Deck 1130 of FIG. 12 includes a pair of side panels 1135, each of which is situated laterally outboard of seat section 1133 and thigh section 1134. Thus, one of panels 1135 is located to the right of deck sections 1133, 1134 and the other of panels 1135 is located to the left of deck sections 1133, 1135. Panels 1135 and seat section 1133 are fixed relative to upper frame 1138 in the illustrative embodiment. Thus, in the lateral dimension of bed 1110 of FIG. 12, seat and thigh sections 1133, 1134 are not as wide as head and foot sections 1132, 1136. Accordingly, antenna 1116 mounted to thigh section 1134 of FIG. 12 is located further from the left side of bed 1110 than is antenna 1114. That is antennae 1114, 1116 are located at different distances from the left side of bed 1110 (or the left side of deck 1130) of FIG. 12.

In alternative embodiments, antenna 1116 is mounted to seat section 1133 near the left edge thereof. In other embodiments, antenna 1116 is mounted such that a portion of antenna 1116 is supported by the panel 1135 and another portion of antenna 1116 is supported by seat section 1133. In still other embodiments, antenna 1114 is mounted to seat section 1133 or to a combination of panel 1135 and seat section 1133 as just described. In further embodiments, antennae 1114, 1116 are mounted at these various locations on the right side of deck 1130 rather than the illustrative left side.

In the illustrative FIG. 12 example, cables 1122, 1124 are routed from respective antennae 1114, 1116 to reader 1112 through a space or gap 1204 formed adjacent to a junction between the panel 1135 at the left side of bed 1110, a left head end corner region of seat section 1133, and a left foot end corner region of panel 1132*b* of head section 1132. In the illustrative FIG. 12 example, reader 112 is mounted to an undersurface of a longitudinal frame member 1206 of upper frame 1138. In other embodiments, reader 1112 is mounted to a side surface of frame member 1206. The side surface of frame member 1206 in such embodiments may be the inwardly facing side surface (i.e., the one facing toward a center of bed 1110) or the outwardly facing side surface (i.e., the one that can be seen in FIG. 12 facing away from the center of bed 1110).

Foot section 1136 of bed 1110 of FIG. 12 is also extendable and retractable. Thus, cable 1126 of FIG. 12 has sufficient slack to accommodate the extension and retraction of foot section 1136. Output port 1120 of FIG. 12 is mounted to upper frame 1138 to be raised, lowered, and tilted therewith. Thus, extra slack does not need to be provided in that cable 1128 of FIG. 12 that extends between reader 1112 and output port 1120. Thus, in FIG. 12, cable 1128 is shown as being situated against the inwardly facing side surface of upper frame member 1206 along a majority of its length.

Referring now to FIG. 13, the illustrative bed 1110 is similar to those of FIGS. 11 and 12 such that like reference numbers are used to denote like components of these beds. The descriptions above of beds 1110 of FIGS. 11 and 12 is equally applicable to bed 1110 of FIG. 13 except where noted in the description that follows. Also, in the FIG. 13 example, the head rail 1144 and the foot rail 1146 at the left side of bed 1110 have been removed. In FIG. 13, head section 1132 includes a single flat panel and antenna 1114 is mounted thereto in the left, foot end corner region.

Seat section 1133 of FIG. 13 includes a U-shaped panel with a main portion 1133*a* and side portions 1133*b* extending toward a foot end of bed 1110 from the main portion. Thigh section 1134 nests within the U-shape of seat section 1133 when in a lowered position as shown in FIG. 13. Antenna 1116 is coupled to thigh section 1116 near the left edge thereof. In alternative embodiments, one or the other of antennae 1114, 1116 is coupled to seat section 1133 near the left edge thereof. In further alternative embodiments, antennae 1114, 1116 are coupled to deck 1130 closer to the right side thereof.

In the illustrative FIG. 13 example, cables 1122, 1124 are routed from respective antennae 1114, 1116 to reader 1112 through a space or gap 1300 formed between a foot end of head section 1132 and a head end of seat section 1133. One key difference between the incontinence detection system 1100 of FIG. 13 and those of FIGS. 11 and 12 is that visual indicator 1118, output port 1120, and cables 1126, 1128 are omitted in the FIG. 13 system 1100. Instead, reader 1112 is electrically coupled to bed control circuitry 1302 via a suitable cable 1304 as shown diagrammatically in FIG. 13.

Bed 1110 of FIG. 13 has a series of alert lights 1306*a*, 1306*b*, 1306*c*, 1306*d*, 1306*e* that are included in a foot end frame member 1308 of foot section 1136 and that are controlled by bed control circuitry 1302. Alert lights 1306*a*-*e* are similar to those shown and described in International Patent Application No. PCT/US2016/034908 which is already incorporated by reference herein (see particularly, FIG. 97 along with the related discussion of that document). For purposes of this disclosure, alert light 1306*e* is the one that is illuminated in connection with the incontinence detection system 1100 of bed 1110 of FIG. 13. Circuitry 1302 of bed 1110 commands alert light 1306*e* to shine or illuminate white light when reader 1112 is turned on but no incontinence detection pad is detected. Circuitry 1302 of bed 1110 commands alert light 1306*e* to shine green light when reader 1112 is turned on and is communicating with an incontinence detection pad that is dry, or at least not sufficiently wet to be sensed by the pad. Circuitry 1302 of bed 1110 commands alert light 1306*e* to shine yellow (aka amber) light, and to flash in some embodiment, when reader 1112 is turned on and is communicating with an incontinence detection pad that is wet.

Bed circuitry 1302 is operable to output bed data, including data detected by the incontinence detection system 1100, through a nurse call output port 1310 shown diagrammatically in FIG. 13. Port 1310 is a 37-pin connector in some embodiments, for example. Such 37-pin connectors are known connectors which are sometimes used on hospital beds for communication with a nurse call system of a healthcare facility. In some embodiments, the incontinence detection information or data, such as data including information regarding whether the incontinence detection pad has detected wetness, is transmitted from bed 1110 by circuitry 1302 via port 1310 in one or more data packets that also include the other bed data. In other embodiments, the incontinence detection information is transmitted in one or more data packets that do not include the bed data. That is the incontinence detection data can be transmitted in the same data packets as the bed data or in separate packets.

Referring now to FIG. 14, the illustrative bed 1110 has some features similar to those of FIGS. 11-13 such that like reference numbers are used to denote like components of these beds. The key difference between bed 1110 of FIG. 14 and the beds of FIGS. 11-13 is the routing of cables 1122, 1124 between respective antennae 1114, 1116 and reader 1112. In the illustrative FIG. 14 example, cable 1122 is routed from antenna 1114, which is coupled to head section 1132, to reader 1112 through a hole 1400 formed in seat section 1133. Also in the illustrative example, cable 1124 is routed from antenna 1116, which is coupled to thigh section 1134, to reader 1112 through a hole 1402 formed in thigh section 1134. The general concept depicted in FIG. 14, therefore, is that cables 1122, 1124 can be routed through holes formed in any of deck sections 1132, 1133, 1134, 1136 of deck 1130, as desired, rather than being routed through the spaces that exist between the various deck sections 1132, 1133, 1134, 136. Embodiments having one of cables 1122, 1124 routed through a space between deck sections 1132, 1133, 1134, 1136 and the other of cables 1122, 1124 routed through a hole provided in any of deck sections 1132, 1133, 1134, 1136 are also contemplated by this disclosure.

Referring now to FIG. 15, a diagrammatic view of bed 1110 and incontinence detection system 1100 is provided. Bed 1110 of FIG. 15 has a mattress 1500 (aka a patient support surface or just a surface) supported on deck sections 1132, 1134, 1136 of deck 1130. No seat section is depicted in FIG. 15 but, of course, one is present in some embodiments. An incontinence detection pad 1510 having an RFID tag 1512 is situated between a patient and mattress 1500. Pad 1510 is generally located beneath the patient's buttocks and upper thighs so as to increase the likelihood of absorbing and detecting incontinence expelled by the patient.

A head section motor 1514 for pivotably raising and lowering head section 1132 and a thigh section motor 1516 for pivotably raising and lowering thigh section 1134, such as through flanges, brackets, and/or linkages attached to frame 1138 and sections 1132, 1134, are shown diagrammatically in FIG. 15. Motors 1514, 1516 are included in respective linear actuators in some embodiments of bed 1110. Bed control circuitry 1302 commands operation of motors 1514, 1516 in response to user inputs on bed as is known in the art.

As indicated diagrammatically in FIG. 15, antenna 1114 is located a first distance $d_1$ away from RFID tag 1512 and antenna 1116 is located a second distance $d_2$ away from RFID tag 1512. Antennae 1114, 1116 are controlled by reader 1112 to emit energy through mattress 1500 to RFID tag 1512 and tag 1512 responds with its data back to one or both of antennae 1114, 116 through mattress 1500. Reader 1112 is also able to write data to RFID tag 1512 via antennae 1114, 1116. Thus, once pad 1510 becomes wet a particular bit of data is set in memory of RFID tag 1512 (more particularly, an RFID chip of tag 1512) and when reader processes the data received from RFID tag 1512, it is able to determine whether the pad 1510 is wet or not wet (more particularly, not sufficiently wet to cause the particular bit to get set).

If reader 1112 determines that pad 1510 is wet, a second bit (aka a kill bit) is set in RFID tag 1512 by reader 1112 via one or both of antennae 1114, 1116. Once the kill bit is set in RFID tag 1512, it remains unchanged thereafter. If pad 1510 dries out after having been wet, reader 1512 will see that the kill bit is still set when it receives subsequent data from RFID tag 1512 such that the particular pad 1510 should not be re-used. In some embodiments, reader 1512 sends an alert to indicate that the pad is a "bad" pad that should not be used because it has been previously soiled with wetness. In other embodiments, reader 1112 simply causes visual indicator 1118 to emit white light indicating that a "good" pad is not being read by the reader.

In some embodiments, reader 1112 energizes antennae 1114, 1116 to scan for RFID tag 1512 using a linear frequency hopping scheme that cycles through fifty frequencies between a lower frequency limit and an upper frequency limit via one of antennae 1114, 1116 and then cycles through the fifty different frequencies between the lower frequency limit and the upper frequency limit via the other of antennae 1114, 1116. The frequency hopping scheme is non-consecutive and the hops are arranged near the bottom of the frequency band and hop in approximately 5 Megahertz (MHz) jumps to near the top of the frequency band, then the hops go back near the bottom of the frequency band until all fifty frequencies are used.

In some embodiments, the lower frequency limit is about 902 Megahertz (MHz) and the upper frequency limit is about 928 MHz. Each antenna 1114, 1116 is used for a limited number of frequency transmissions, typically nine in some instances but could be fifteen or more in other instances. Thus, one of antenna 1114, 1116 is used for a set of frequency transmissions and then the sequence continues using the other antenna 1114, 1116. Thus, after a block set of scans using one of antenna 1114, 1116, the next block of scans is emitted from the other of antenna 1114, 1116. Thus, the block of scans alternate back and forth between antennae 1114, 1116.

The frequency transmissions are of different classes which, in some embodiments, comprise filter transmissions of about 8 milliseconds, inventory transmissions of about 37 milliseconds, select transmissions of about 15 milliseconds and read tag transmissions of about 15 milliseconds. The transmission timing is variable and can be adjusted depending upon the circumstances and conditions in the field. In some embodiments, there is a delay period of about 185 milliseconds between every pair of transmissions, resulting in a more uniform duty cycle and a total pause of two seconds for each complete cycle on one antenna.

To give one example, the block scans may include five frequencies that are spread out over a wide range between the upper and lower frequency limits. For example, if a first scan is at 902 MHz, the next successive scans in the block of five scans may increment by 20%, 40%, 60%, and 80% of the 26 MHz spread between the upper and lower limits. Thus, each successive scan is at an additional increment of 5.2 MHz as compared to the previous scan. Thus, the last scan in the block of five scans is 20.8 MHz larger than the first scan in the block of five scans. The next block of five scans, from the other one of antennae 1114, 1116 which was dormant during the first scan, uses a different starting frequency such as 902.52 MHz and then proceeds with 20%, 40%, 60%, 80% incrementing scheme from that starting frequency. To have 50 frequencies scanned between the limits 902 MHz and 928 MHz, inclusive thereof, the increment is 0.52 (i.e., 928 MHz-902 MHz=26 Hz/50=0.52 MHz). Each of the 50 different frequencies are required by regulations to be scanned before a scanning frequency may be repeated, as noted above.

By providing a delay period, such as 185 milliseconds in the illustrative example, and only scanning a limited number of frequencies in succession at a time, heating of the patient's tissue is avoided and is kept within U.S. Federal Communications Commission (FCC) maximum permissible exposure (MPE) limits. The MPE limits specified by the FCC are dependent upon frequency and power density limits which are specified as an average value over a six minute period. In the 902 MHz-928 MHz frequency band, the power density limit is 0.601 milliWatts (mW)/cm$^2$ over any six minute period of time. In some embodiments, the duty cycle of frequency transmissions is 11.5% and so, with the 185 millisecond delay, each cycle of transmissions and delay is about two seconds in length.

As further indicated diagrammatically in FIG. 15, reader 1112 has wireless communication capability. In the illustrative example, reader 1112 communicates wirelessly with a wireless access point 1518. The wireless communication between reader 1112 and wireless access point 1518 is bidirectional in some embodiments. That is, wireless messages can be sent and received by reader 1112 and by wireless access point 1518. Wireless access point 1518 is coupled to a network 1520 so that messages from reader 1112 received by wireless access point 1519 are ultimately able to be transmitted through network 1520 to other computer devices of other systems. For example, messages from reader 1112 are communicated to a nurse call system 1522 in the illustrative example. The block 1522 labeled nurse call system in FIG. 15 is intended to represent the various servers, computers, room stations, staff stations, and master nurse stations as well as any additional associated infrastructure associated with a nurse call system. Such nurse call systems and associated infrastructure are shown and described, for example, in U.S. Pat. Nos. 9,411,934 and 8,598,995 which are hereby incorporated by reference herein.

As shown diagrammatically in FIG. 15, output port 1120 is electrically coupled via a wired connection 1524 to an input port 1526 located on a wall 1528 in a hospital room. In some embodiments, wall 1528 may comprise a room wall of a healthcare facility. In other embodiments, wall 1528 may comprise a panel of a piece of architectural equipment such as a headwall unit, a bed locator unit, a column, an arm, a service chase or the like that are installed in a hospital room. Input port 1526 is coupled to network 1520 via suitable infrastructure such as cabling, routers, gateways, and the like. Thus, data from reader 1112 of system 1100 communicated to port 1526 from port 1120 also can be received by computer devices of other systems such as nurse call system 1522. Thus, in the illustrative example, reader 1112 is able to communicate data from system 1100 via a wired datalink 1524 and a wireless datalink between reader 1112 and wireless access point 1518.

In some embodiments, such as the illustrative embodiments of FIGS. 11, 12 and 14, output port 1120 comprises a female ¼ inch receptacle which is configured for receipt of a male ¼ inch jack (sometimes referred to as a phono jack). Input port 1526 is also a female ¼ inch receptacle that receives a male ¼ inch jack. In such embodiments, the data communicated via such ¼ inch receptacles and ¼ inch jacks are binary in nature to indicate simply whether incontinence detection pad 1510 is wet or not wet. Such binary signals are sometimes referred to as contact closures because, when in a high state (e.g., logic level 1), they close a relay coupled to port 1526 which, in turn, sends a signal to nurse call system 1522. In some embodiments, the closure of the relay occurs at the low state (e.g., logic level 0) rather than the high state depending upon the relay design. In either case, the signal to nurse call system 1522 is a simple on/off or binary signal. In some embodiments, the relays are wired directly into the nurse call system 1522 without involving network 1520. If desired, a more sophisticated output port 1120 and input port 1526 may be used. For example, RJ-45 connectors, 37-pin connectors, RS-232 connectors and the like (e.g., multi-pin/multi-port or multi-contact) devices may be used as ports 1120, 1526 in some embodiments according to this disclosure.

Figure 16A:
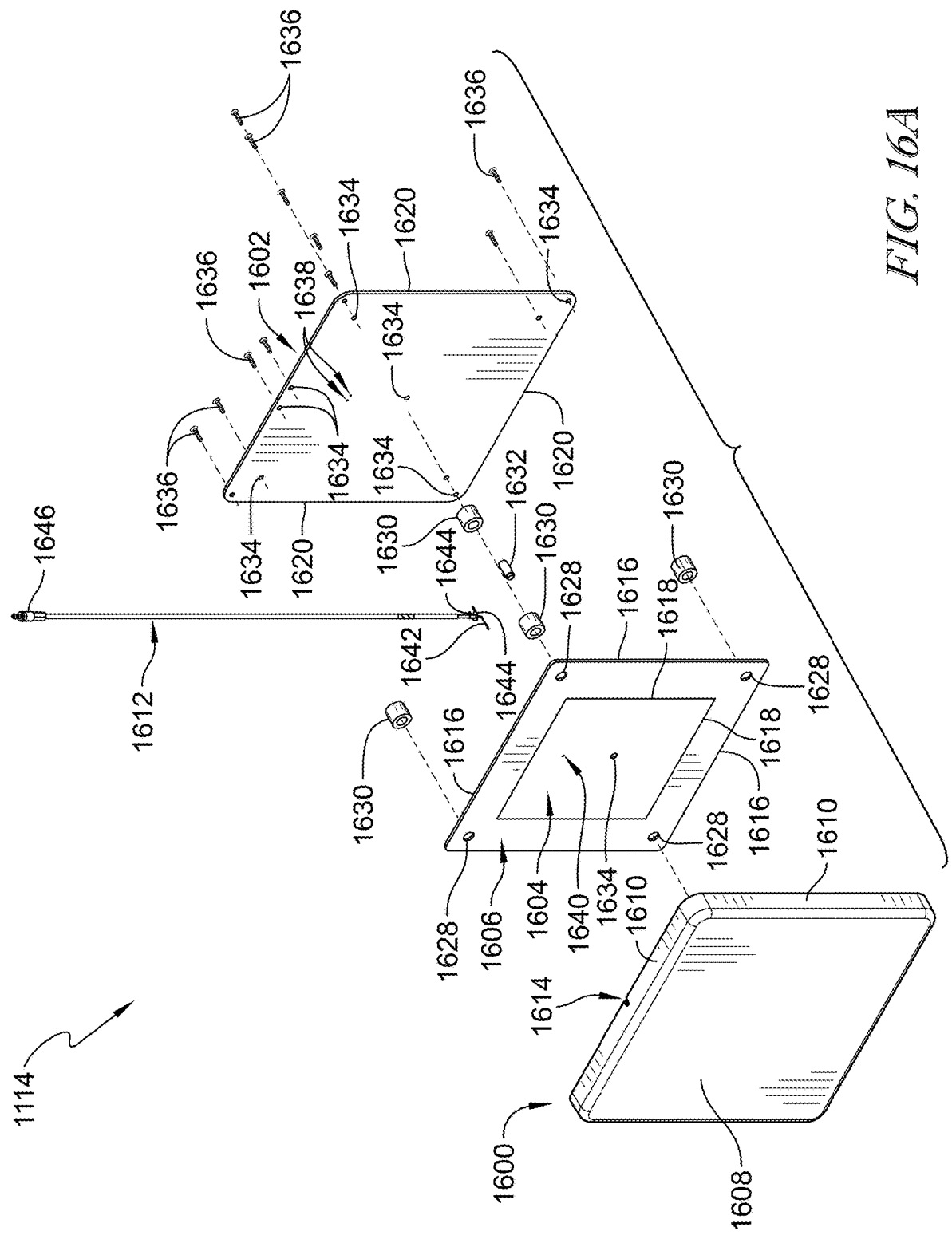
FIG. 16A is an exploded perspective view showing components of one antenna of the pair of antennae of the incontinence detection system of FIGS. 11-15.

Referring now to FIG. 16A, an exploded view of antenna 1114 is shown. It should be appreciated that antenna 1116 is constructed from the same components as antenna 1114 and therefore, the following description of antenna 1114 shown in FIG. 16A is equally applicable to antenna 1116. Antenna 1114 includes a housing or cover 1600, a ground plate 1602, and an antenna plate 1604 carried on a printed circuit board (PCB) 1606. Housing 1600 is square shaped and, in some embodiments, is about 207.5 mm in length on each side. Housing 1600 has a generally flat top wall 1608 and a perimetral side wall 1610 that extends away from top wall 1608 toward ground plate 1602.

In the illustrative embodiment, a distance between a plane defined by the upper surface of top wall 1608 and a plane defined by the bottom edge of perimetral side wall 1610 (e.g., the height of housing 1600 when supported on a horizontal deck section 1132, 1334, for example) is about 19.0 mm. The junction between top wall 1608 and perimetral side wall 1610 is rounded and in some embodiments the rounding is radiused at about 5.0 mm. Top wall 1608 and side walls 1610 each have thicknesses of about 3.0 mm. The rounding at corner regions defined by the junction of adjacent side walls 1610 is about 13.4 mm in some embodiments.

Antenna 1114 includes a coaxial cable 1612 that extends through side wall 1610 and enters into a space defined between ground plate 1602 and PCB 1606. Sidewall 1610 is formed to include a notch 1614 that receives cable 1612 therein. In the illustrative embodiment, PCB 1606 is an FR-4 printed circuit board which is made of a composite material composed of woven fiberglass cloth with an epoxy resin binder that is flame resistant. Also in the illustrative embodiment, antenna plate 1606 comprises a ½ ounce (oz.) copper cladding on PCB 1606. Such ½ oz. copper cladding is about 17.5 μm (or 0.7 mils) thick according to industry standards.

A perimetral edge 1616 of PCB 1606 defines the overall square shape of PCB 1606 and antenna plate 1604 is also square shaped, but with a smaller length dimension than PCT 1606. Antenna plate 1604 is centered on PCB 1606 such that edges 1618 of plate 1604 are parallel with associated edges 1616 of PCB 1606. In the illustrative embodiment, PCB 1606 has a length of about 184.2 mm per side and antenna plate 1604 has a length of about 117.0 mm per side. Thus, perimetral portions of PCB 1606 defined between edges 1618 of plate 1604 and edges 1616 of the PCB 1606 extend beyond the perimeter of the antenna plate 1604 defined by edges 1618.

Ground plate 1602 also comprises an FR-4 printed circuit board and has ½ oz. copper cladding thereon which extends over the entire surface that faces toward PCB 1606. PCB 1606 and the PCB of ground plate 1602 serve as nonconductive substrates on which the conductive copper cladding is carried. A perimetral edge 1620 of ground plate 1602 defines the overall square shape of plate 1602. In the illustrative example, plate 1602 has a length of about 203.2 mm per side.

As shown in FIG. 6B, in an interior region of housing 1600, four connection bosses 1622 are formed integrally with inside corner regions of perimetral sidewall 1610. An additional set of four connection bosses 1624 are formed integrally with an inside surface of top wall 1608 and extend from top wall 1608 in substantially perpendicular relation therewith. Bosses 1624 are generally cylindrical in shape. A further set of two connection bosses 1626 are provided in the interior region of housing 1600 adjacent to an inner surface of one of side walls 1610 with notch 1614 being situated about midway therebetween. Each of bosses 1622, 1624, 1626 has a threaded bore. As measured between centerlines of the respective threaded bores, bosses 1622 are arranged in a square having sides with a length of about 189.0 mm and bosses 1624 are arranged in a square having sides with a length of about 156.0 mm. Housing 1114 of antenna is made from a suitable plastics material such as, for example, Ashai XYRON™ 240Z-U5026 material.

As shown in FIG. 16A, PCB 1606 as four boss-receiving holes 1628 through which bosses 1624 extend when PCB 1606 and antenna plate 1604 are installed in housing 1600. Thus, centers of holes 1628 define a square having sides with a length of about 156.0 mm which matches the spacing of respective bosses 1624. When installed, antenna plate 1604 abuts the inner surface of top wall 1608. Antenna 1114 includes a set of four spacers 1630 which each mount over a respective boss 1624 after PCB 1606 and antenna plate 1604 are installed on bosses 1624. Spacers 1630 are cylindrically tubular elements made of a suitable plastics material such as DELRIN® material, for example. In the illustrative example, spacers 1630 have a length of about 12.0 mm, an outside diameter of about 14.0 mm, and an inside diameter of about 7.7 mm. Bosses 1624 have an outside diameter of about 8.0 mm in the illustrative example. Thus, spacers 1630 are press fit onto bosses 1624.

Antenna 1114 also has a ground spacer 1632 which extends between a center of ground plate 1602 and a center of PCB 1606. Spacer 1632 has includes a cylindrical main body portion having an outside diameter of about 6.0 mm and a cylindrical stepped down end portion which has an outside diameter of about 4.5 mm. PCB 1606 and antenna plate 1604 have a central hole 1634 formed therethrough which receives the stepped down end portion of spacer 1632 therein. The main body portion of spacer 1632 is about 12.0 mm in length, which matches the length of spacers 1630, and the stepped down end portion has a length of about 2.0 mm. Thus, PCB 1606 rests upon an annular shoulder of spacer 1632, the annular shoulder being defined as the surface extending between the stepped down end portion and the main body portion of spacer 1632. Spacer has a threaded bore extending axially therethrough. In the illustrative example, spacer 1632 is made from a suitable metal material such as AISI 1018 cold drawn steel, for example.

Ground plate 1602 nests within a bottom region of perimetral side wall 1610 of housing 1600 such that the surface of ground plate 1602 having the copper cladding abuts some or all of bosses 1622, 1624, 1626 and spacers 1630, 1632. Ground plate 1602 has a set of bolt-receiving apertures 1634 (not all of which are numbered in FIG. 16A) that are aligned with the bores of respective bosses 1622, 1624, 1626 and spacers 1630, 1632. Antenna 1114 has a set of bolts or screws 1636 (not all of which are numbered in FIG. 16A) that extend through apertures 1634 and thread into the threaded bores of respective bosses 1622, 1624, 1626 with the exception of one bolt 1636 which threads into ground spacer 1632. When ground plate 1602 is fastened in place relative to housing 1600 by bolts 1636, an outer surface of ground plate 1602 is generally coplanar with a bottom edge of side wall 1610 in some embodiments.

Ground plate 1602 has a pair of spaced ground wire through holes 1638 and PCB 1606 and antenna plate 1604 has a coax wire through hole 1640. The copper cladding on ground plate 1602 and antenna plate 1604 coats the respective through holes 1638, 1640. An end of coaxial cable 1612 extends through perimetral side wall 1610 of housing 1600 and into the gap between PCB 1606 and ground plate 1602 in substantially parallel relation with ground plate 1602 and PCB 1606. Cable 1612 has at its terminal end a first conductor 1642 (e.g., a coax wire) that is routed so as to be coupled to antenna plate 1604 carried by PCB 1606 and a pair of second conductors (e.g., ground wires from the sheathing of coaxial cable 1612) that are routed so as to be coupled to ground plate 1602. In the illustrative embodiments, first conductor 1642 is inserted into through hole 1640 and soldered in place and second conductors 1644 are inserted into respective through holes 1638 and soldered in place.

In the illustrative example, at one terminal end of cable 1612, conductors 1642, 1644 are generally perpendicular to ground plate 1602 and PCB 1606, as well as antenna plate 1604 carried by PCB 1606. At an end of cable 1612 opposite of the end having conductors 1642, 1644, a coax connector 1646 that couples to circuitry of reader 1112 or to an extension cable that, in turn, couples to the circuitry of reader 1112. The extension cable (not shown) is used if cable 1612 does not have sufficient length to reach reader 1112 from the location at which antenna 1114 is mounted to the respective hospital bed 1110.

Figure 17:
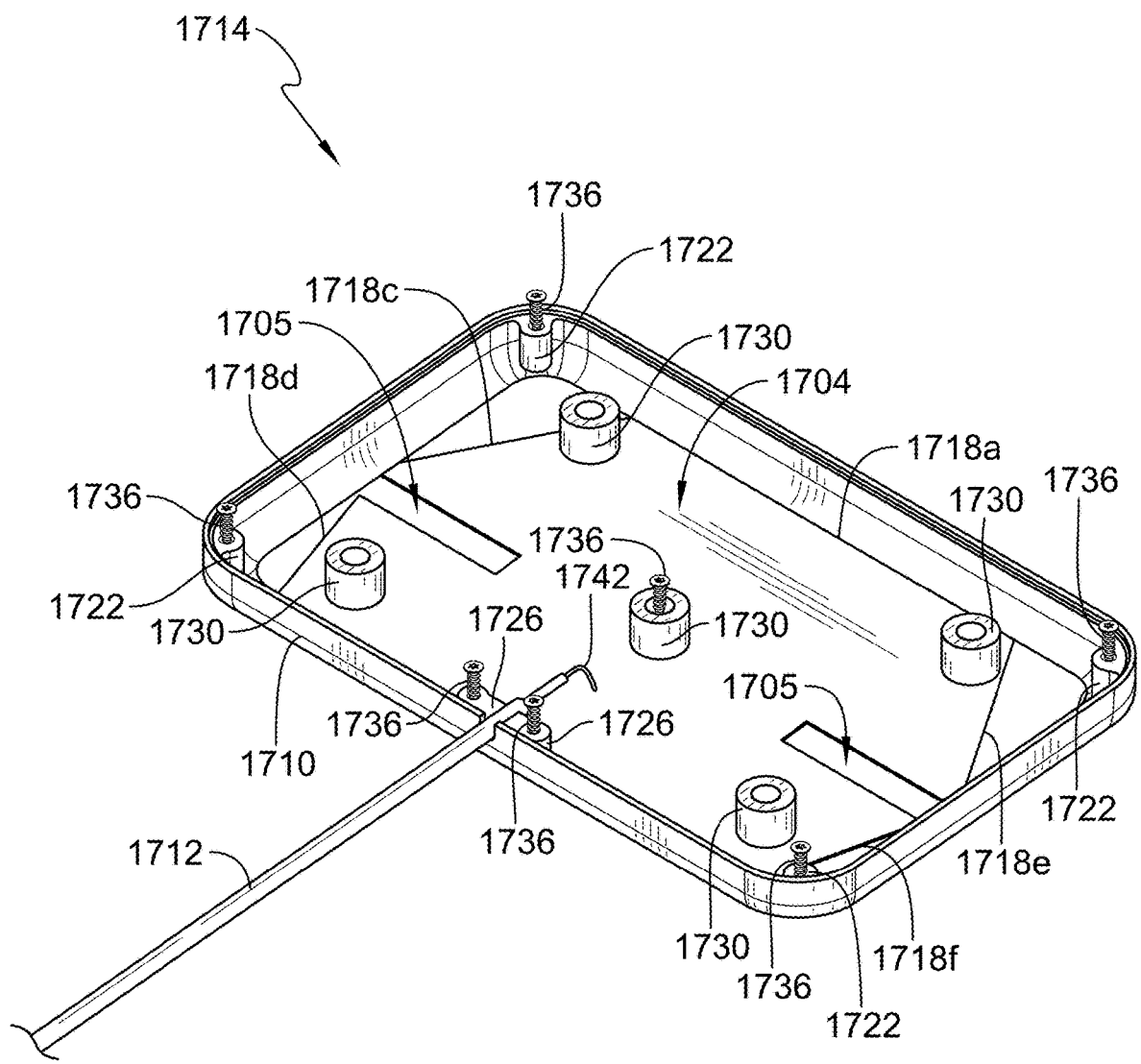
FIG. 17 is a perspective view showing an alternative embodiment of an antenna having an antenna plate shaped has an elongated hexagon with notches formed at the ends of the elongated hexagon.
Figure 18:
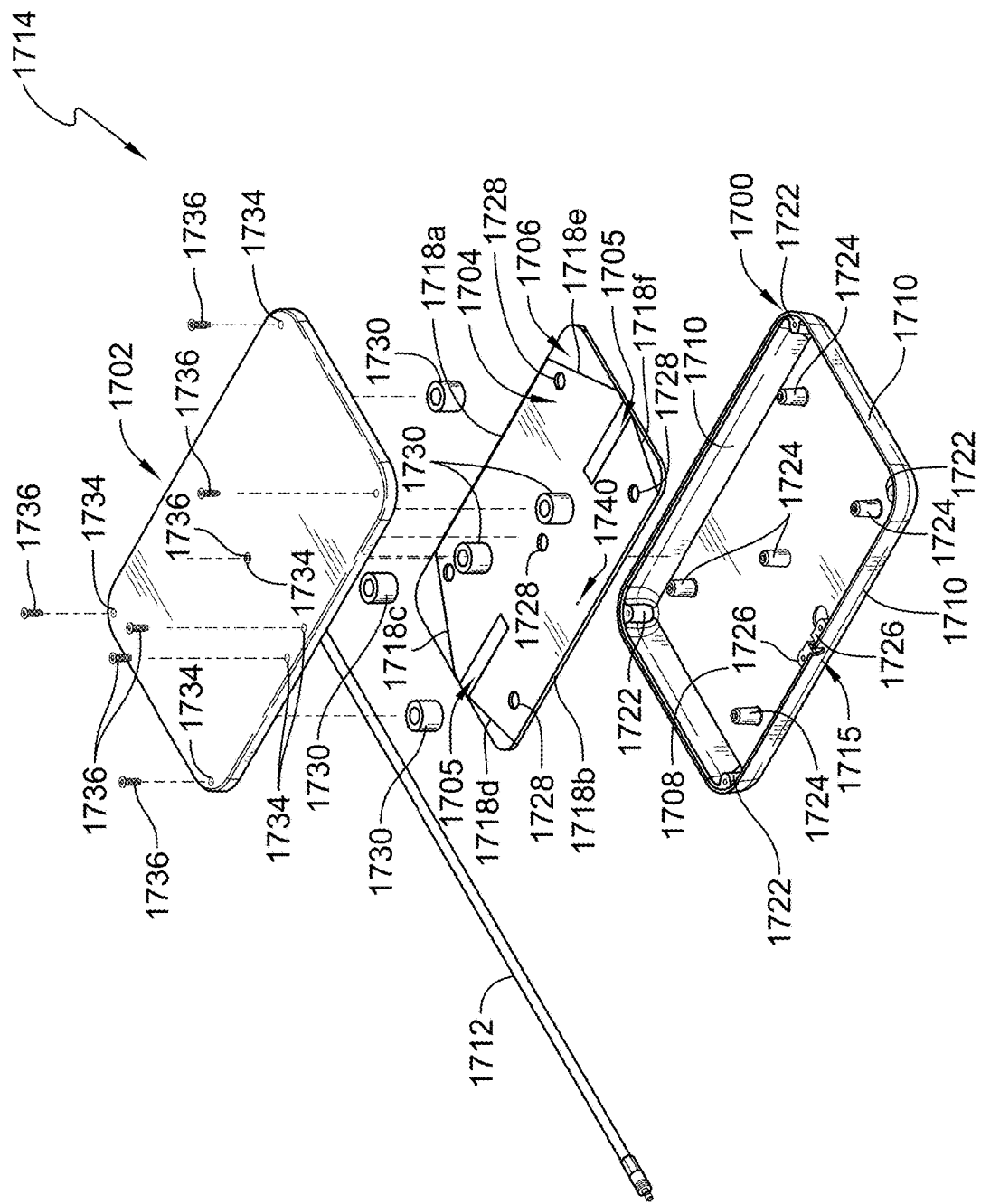
FIG. 18 is an exploded perspective view showing components of the antenna of FIG. 17.
Figure 19:
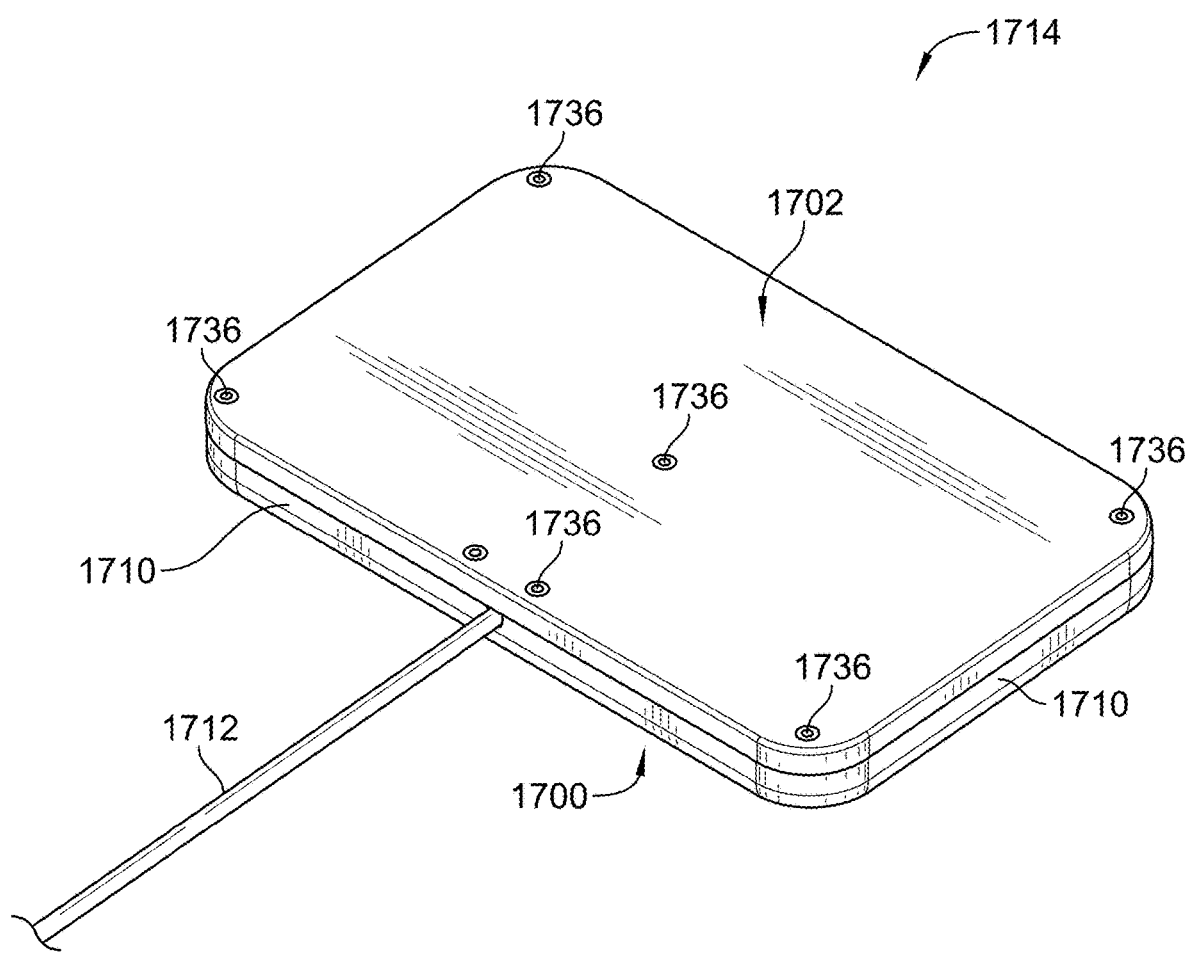
FIG. 19 is a perspective view of the antenna of FIGS. 17 and 18 showing a ground plate attached to a housing of the antenna.

Referring now to FIGS. 17-19, an alternative embodiment of an antenna 1714 includes a cover or housing 1700, a ground plate 1702, and an antenna plate 1704 carried on a printed circuit board (PCB) 1706. Housing 1700 is rectangular in shape in the illustrative example. Antenna plate 1704 is shaped as an elongated hexagon with first and second notches 1705 formed at the respective ends of the elongated hexagon. Thus, a perimeter of the antenna plate 1704 has first and second spaced apart side edges 1718a, 1718b that are substantially parallel and that are longer than four end edges 1718c, 1718d, 1718e, 1718f of the elongated hexagon as shown in FIGS. 17 and 18. Opposite pairs of the end edges 1718c, 1718d, 1718e, 1718f defining opposite ends of the elongated hexagon. Thus, edges 1718c, 1718d form one end of the elongated hexagon and edges 1718e, 1718f form the other end of the elongate hexagon.

The first and second elongated notches 1705 that extend from the end edges 1718c, 1718d, 1718e, 1718f of the elongated hexagon toward a central region of the antenna plate 1704. In the illustrative example, notches 1705 are substantially parallel with the first and second spaced apart side edges 1718a, 1718b of the elongated hexagon. Notches 1705 are open at the end edges 1718c, 1718d, 1718e, 1718f of the elongated hexagon about midway between the first and second spaced apart side edges 1718a, 1718b. According to the present disclosure, the first and second notches 1705 act as an electronic band gap.

As shown in FIG. 18, housing 1700 has a generally flat top wall 1708 and a perimetral side wall 1710 that extends away from top wall 1708 toward ground plate 1702. Housing 1700 also has four corner bosses 1722 and a set of five cylindrical bosses 1724. One of bosses 1724 extends from a central region of top wall 1708 and the other four bosses 1724 are situated at corners of an imaginary rectangle that is smaller than an imaginary rectangle formed by the location of bosses 1722. A notch 1715 is formed in side wall 1710 between a pair of bosses 1726 of housing 1700. Antenna 1714 has a coaxial cable 1712 that extends through notch 1715 into an interior region of housing 1700 between antenna plate 1704 and ground plate 1702. Antenna plate 1704 and PCB 1706 have a set of five holes 1728 formed therethrough. Bosses 1724 extend through respective holes 1728 when PCB 1706 and antenna plate 1704 are installed in housing 1700.

Antenna 1714 has a set of five cylindrical spacers 1730 that mount over portions of respective bosses 1724 that project from holes 1728 beyond antenna plate 1704. Ground plate 1702 includes a set of bolt-receiving apertures 1734 that receive respective screws or bolts 1736. Bolts 1736 extend through apertures 1734 of ground plate 1702 and thread into respective threaded bores of bosses 1722, 1724, 1726 thereby to couple ground plate 1702 to housing 1700. Ground plate 1702 includes a nonconductive substrate with a metallic plate or cladding carried by the substrate. A first conductor 1742, such as a coax wire shown in FIG. 17, and one more ground conductors (not shown but similar to ground wires 1644 of FIG. 16A) attach to respective antenna plate 1704 and ground plate 1702. Thus, in the illustrative example, antenna plate 1704 has a through hole 1740 into which conductor 1742 is inserted. Ground plate 1702 includes one or more similar through holes for insertion of the respective ground wires.

Figure 16B:
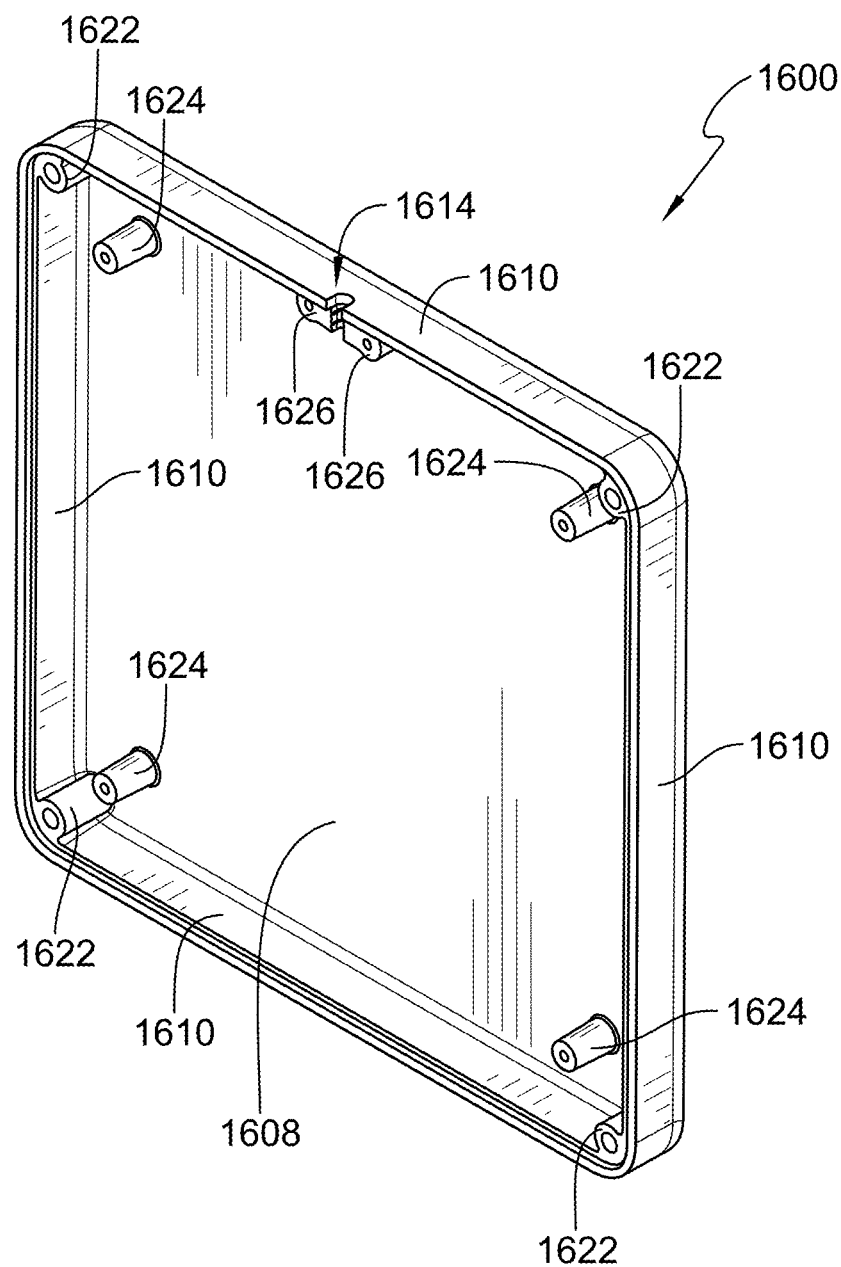
FIG. 16B is a perspective view showing an inside of a cover or housing of the antennae of FIG. 16A.

If desired, the various components of antenna 1714 are made from the same type of materials described above in connection with the various like components of antenna 1114 shown in FIGS. 16A and 16B. It should be appreciated that antenna 1714 can be used in incontinence detection system 1100, as well as in any other incontinence detection shown or described herein, in lieu of or in addition to one or both of antenna 1114, 1116.

Figure 20:
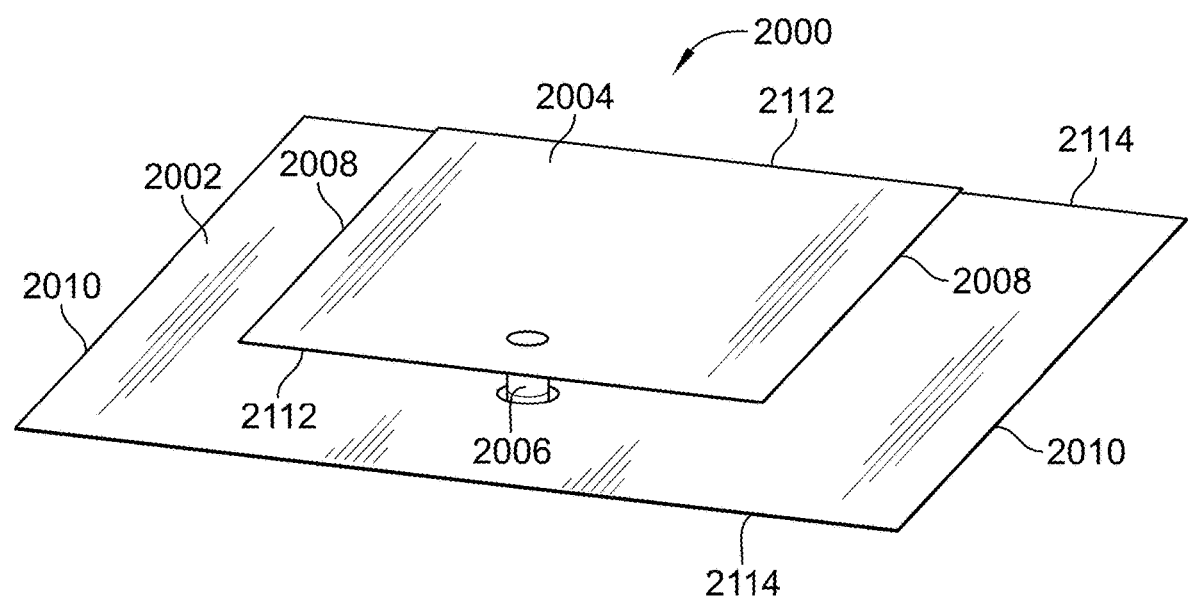
FIG. 20 is a perspective view of an antenna, similar to the antenna of FIGS. 11-16, showing a rectangular ground plate and a rectangular antenna plate supported above the ground plate in parallel spaced relation therewith.

Referring now to FIG. 20, an antenna 2000, similar to the antenna 1114, 1116 of FIGS. 11-16B, includes a rectangular ground plate 2002 and a rectangular antenna plate 2004 supported above the ground plate 2002 by a post 2006. Plate 2004 is supported in substantially parallel spaced relation with plate 2002. The length and width of plate 2004 are both smaller than the length and width of plate 2002. In some embodiments, plate 2004 is centered with respect to plate 2002. Plate 2004 is oriented so that its end edges 2008 are substantially parallel with end edges 2010 of plate 2002 and so that its side edges 2112 are substantially parallel with side edges 2114 of plate 2002. Antenna 2000 is sometimes referred to as a patch antenna with antenna plate 2004 being fed by a center conductor of a coaxial cable adjacent to one of edges 2008, 2112. The shield or sheath of coaxial cable is attached to ground plate 2002 (aka a ground plane).

Figure 21:
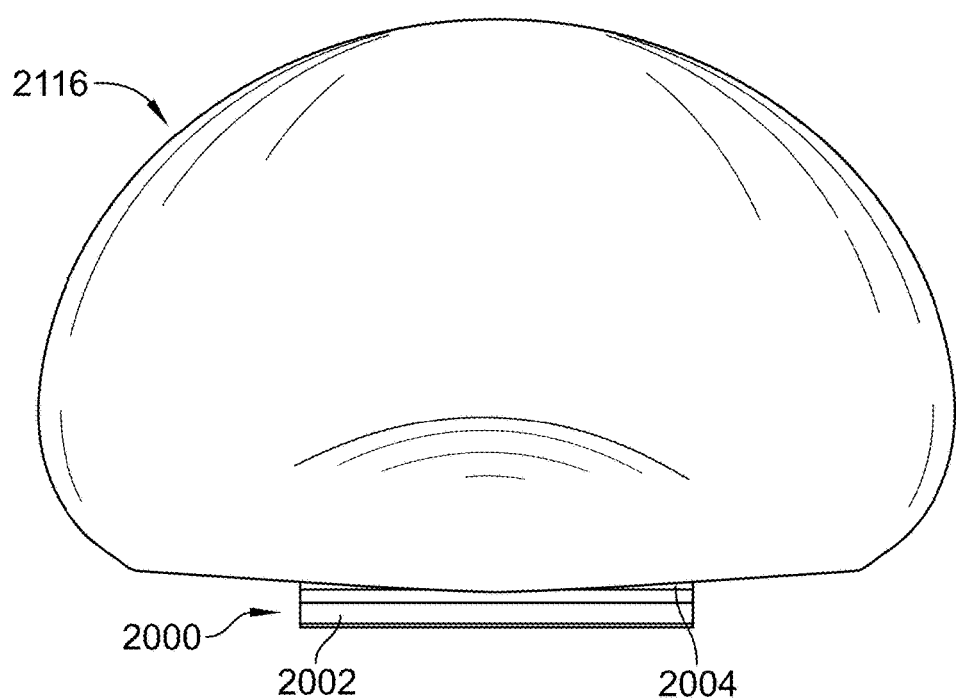
FIG. 21 is a side elevation view of the antenna of FIG. 20 showing a radiation pattern of the antenna.
Figure 22:
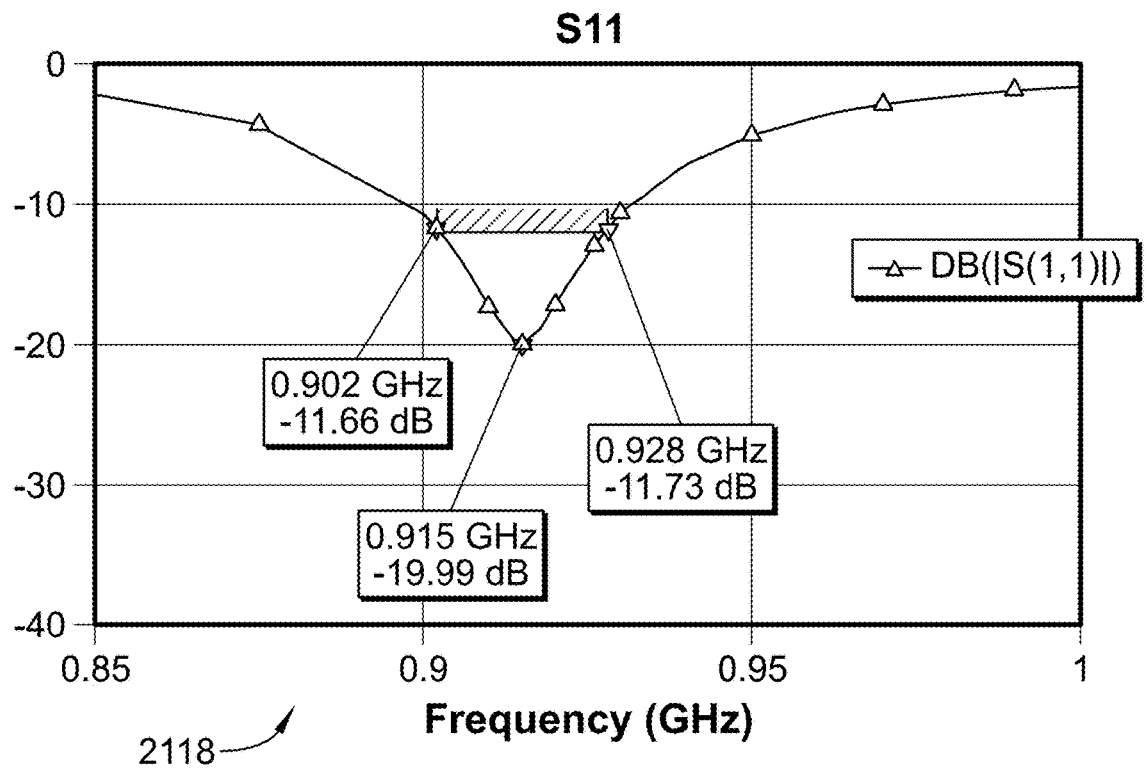
FIG. 22 is a graph showing the reflection S-parameter of the antenna of FIG. 20 with the y-axis units being decibels (dB) and x-axis units being frequency in Gigahertz (GHz)

Referring now to FIG. 21, a side elevation view of the antenna 2000 is shown along with a radiation pattern 2116 of antenna 2000. FIG. 22 has a graph 2118 of the reflected power of antenna 2000 and, more particularly, shows the reflection S-parameter of antenna 2000 of FIG. 20 with the y-axis units being decibels (dB) and x-axis units being frequency in Gigahertz (GHz). S-parameters are sometimes referred to as scattering parameters. It is generally desirable to have minimal reflected power over the whole band of interest, in this case 902 MHz-928 MHz (indicated as 0.902 GHz-0.928 GHz in graph 2118). In general, S11 represents how much power is reflected from the antenna, and is sometimes referred to as the reflection coefficient. FIG. 22 indicates that antenna 2000 reflects best at 915 MHz (indicated as 0.915 GHz in graph 2118). The bandwidth of any given antenna is considered to be range over which the S-parameter, S11, is −6 dB or lower (i.e., more negative).

Figure 23:
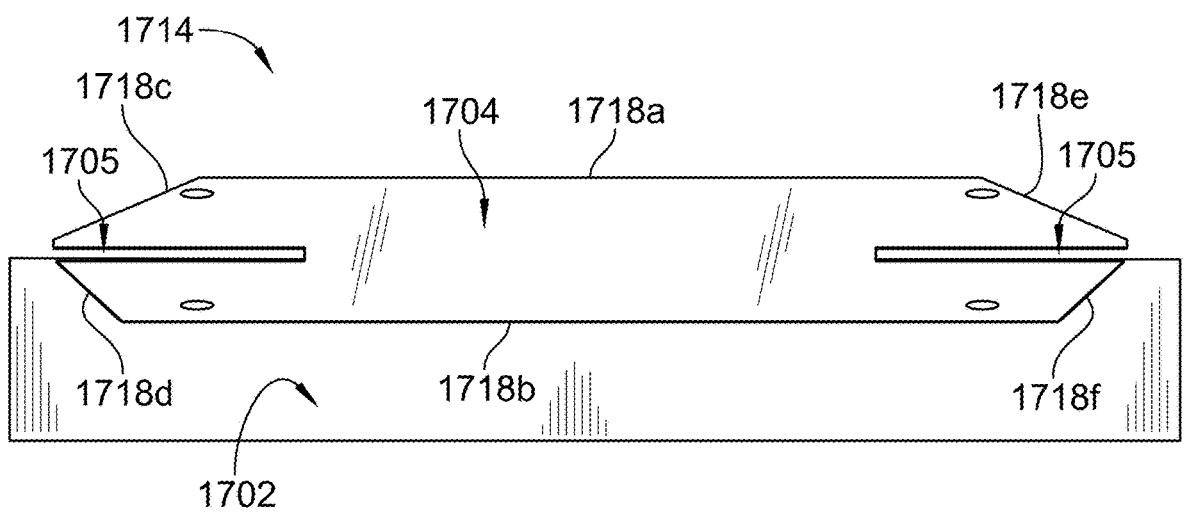
FIG. 23 is a perspective view of an antenna, similar to the antenna of FIGS. 17-19, showing a rectangular ground plate and an antenna plate shaped as an elongated hexagon with notches supported above the ground plate in parallel spaced relation therewith.
Figure 24:
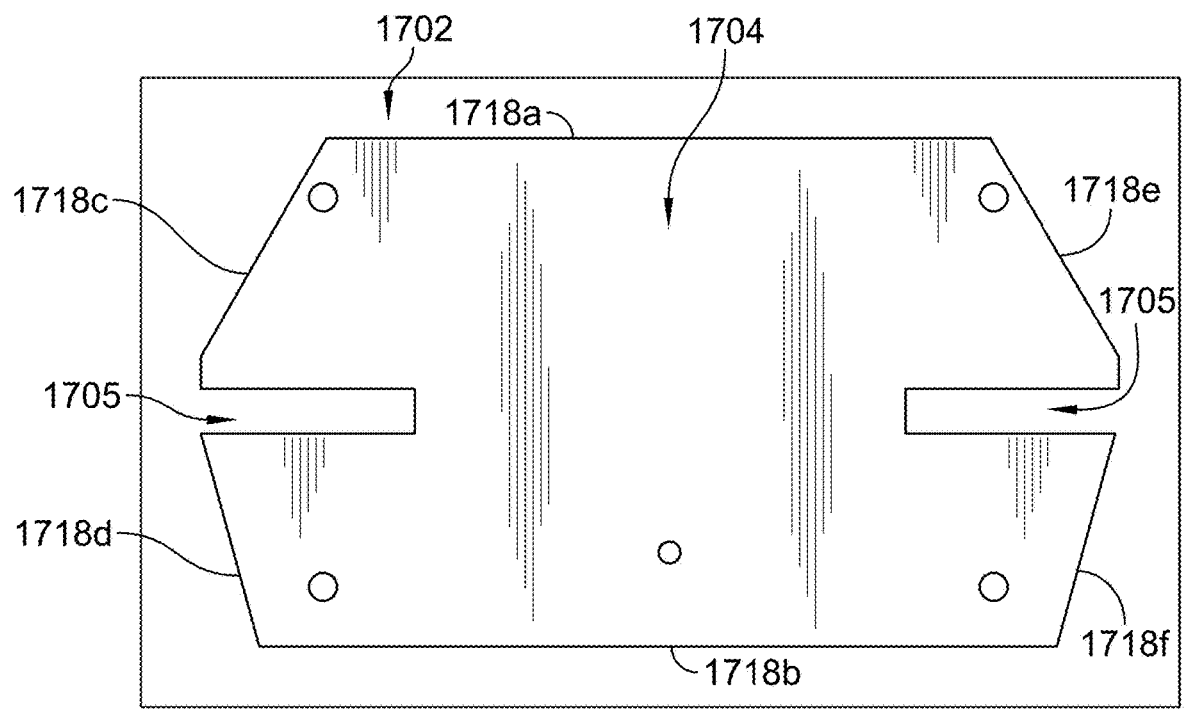
FIG. 24 is a top view of the antenna of FIG. 23.

Referring now to FIGS. 23 and 24 an antenna, similar to the antenna 1714 of FIGS. 17-19, is shown. Thus, like reference numbers are used in FIGS. 23 and 24 to denote the various portions of antenna 1714. Antenna 1714, therefore, has rectangular ground plate 1702 and antenna plate 1704 shaped as an elongated hexagon with notches 1705. Antenna plate 1704 is supported above the ground plate 1702 in parallel spaced relation therewith.

Figure 25:
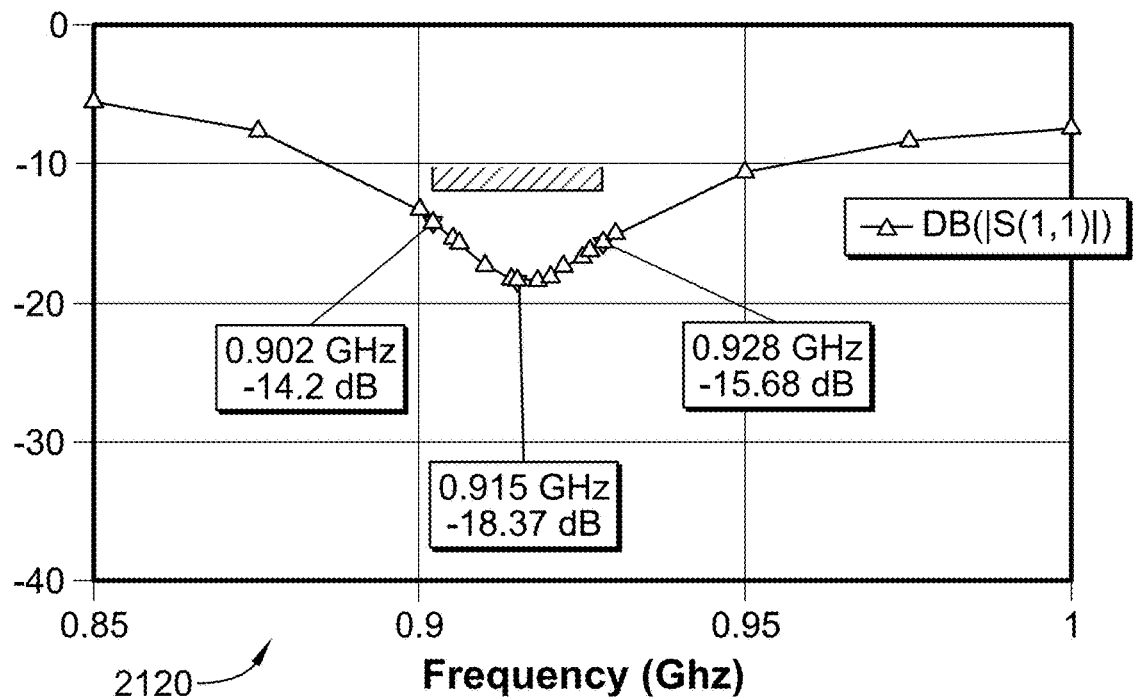
FIG. 25 is a graph showing the reflection S-parameter of the antenna of FIGS. 23 and 24 with the y-axis units being decibels (dB) and x-axis units being frequency in Gigahertz (GHz)
Figure 26:
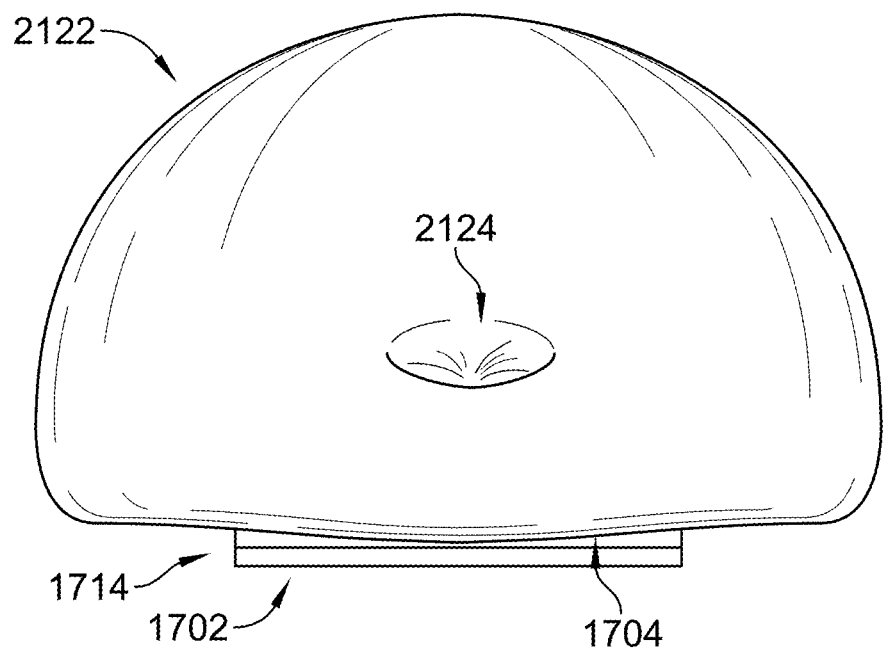
FIG. 26 is a side elevation view of the antenna of FIG. 23 showing a radiation pattern of the antenna.
Figure 27:
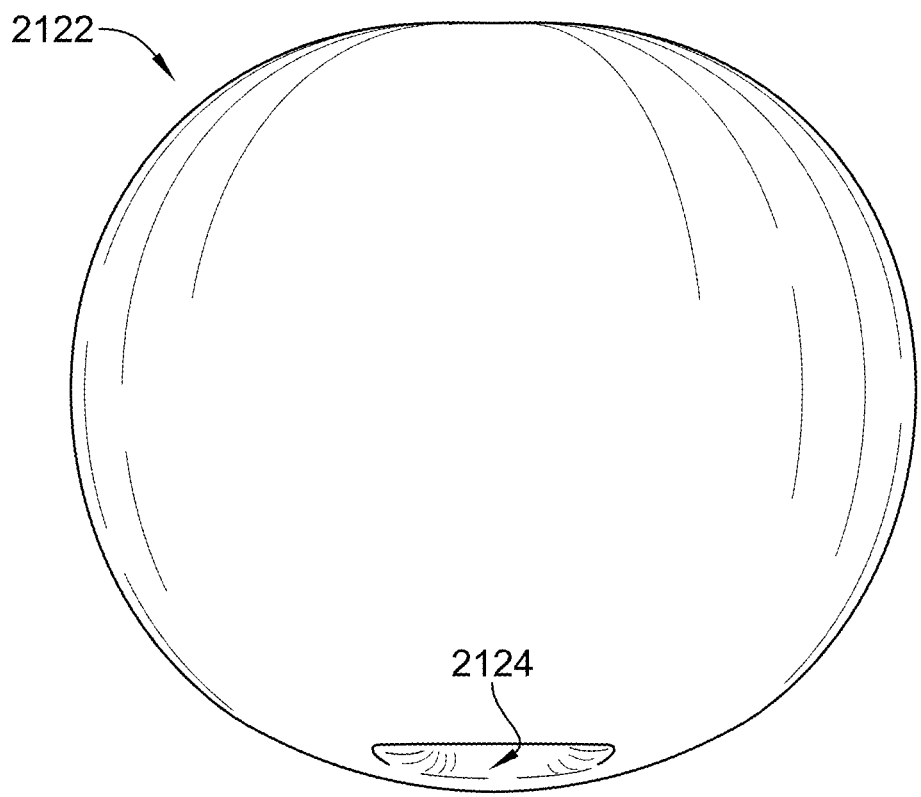
FIG. 27 is a top plan view of the radiation pattern of FIG. 26.

Referring now to FIG. 25, a graph 2120 shows the reflected power and more particularly, the reflection S-parameter of the antenna of FIGS. 23 and 24 with the y-axis units being decibels (dB) and x-axis units being frequency in Gigahertz (GHz). FIG. 26 shows a side elevation view of a radiation pattern 2122 of the antenna 1714 of FIGS. 23 and 24 and FIG. 27 shows a top plan view of the radiation pattern 2122 of FIG. 26. Pattern 2122 has a minimum point 2124, akin to a dimple, which represents a less visible reflection area in that region. However, because multiple antennae 1714 are used in system 1100, the minimum 2124 the overall coverage area is acceptable.

As compared to antenna 2000 of FIG. 20, antenna 1714 has a larger bandwidth or wider frequency coverage and the S-parameter curve has lower (i.e., more negative) S-parameter values at the upper and lower frequency limits, 902 MHz and 928 MHz, respectively than antenna 2000. Thus, at the upper and lower frequency limits of interest, antenna 1714 of FIGS. 23 and 24 reflects better than antenna 2000. The tradeoff is that around the center frequencies, roughly 915 MHz in the illustrative graph 2120, antenna 1714 of FIGS. 23 and 24 does not reflect quite as well as antenna 2000. However, the flatter S11 numbers over the entire operational frequency range of interest is considered a net positive. Also, antenna 1714 is able to operate acceptably in light of manufacturing tolerances if the tuning points shift slightly as compared to antenna 2000. This is because the bandwidth of antenna 1714 is wider than the bandwidth of antenna 2000.

The shape of antenna 1714 contributes to its enhanced performance, as compared to antenna 2000, in a couple of ways. First, the tapered shape of edges 1718c, 1718d, 1718e, 1718f allows a range of wavelengths to resonate at various points along these edges 1718c, 1718d, 1718e, 1718f. This helps broaden the frequency range of antenna 1714 but does not reduce the intensity of the resonance, which is why the reflection S-parameter, S11, is broader but somewhat shallower in the center. Second, notches 1705 at each end of antenna 1714 acts as an electronic band gap structure of a simple type, which allows lower frequencies for the same distance. This allows the vertical spacing between ground plate 1702 and antenna plate 1704 of antenna 1714 to be less than the vertical spacing between ground plate 2002 and antenna plate 2004 of antenna 2000 for comparable performance in the frequency range of interest.

Figure 28:
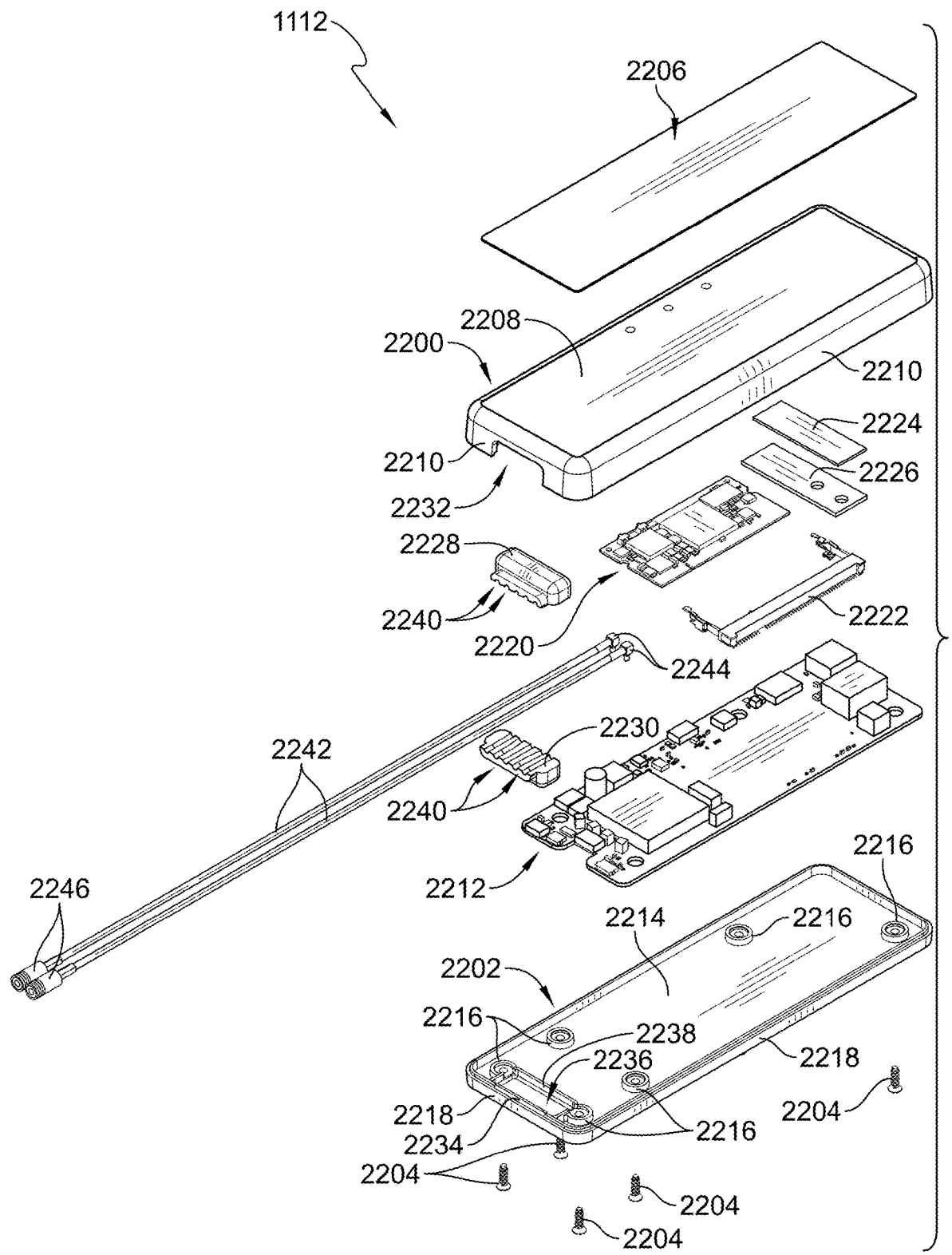
FIG. 28 is an exploded perspective view of the reader of FIGS. 11-15.

Referring now to FIG. 28, reader 1112 includes a front cover 2200 and a back cover 2202 which couple together with suitable fasteners, such as illustrative bolts 2204, to house the electrical circuitry of reader 1112 therein. A rectangular label 2206 covers a substantially rectangular top surface 2208 of front cover 2202. Top surface 2208 is recessed by an amount that is substantially equivalent to a thickness of label 2206. Cover 2200 has a perimetral side wall 2210 extending from top wall 2208 toward back cover 2202. Reader 1112 has a first printed circuit board (PCB) assembly 2212 which is supported relative to a generally rectangular bottom wall 2214 of back cover 2202 by cylindrical bosses or pedestals 2216 that are formed integrally with cover 2202. Cover 2202 has a perimetral side wall 2218 extending from bottom wall 2208 toward front cover 2200.

Reader 1112 includes a second printed circuit board (PCB) assembly 2220, which in the illustrative embodiment comprises a Variscite System on Module (SOM), model no. VAR-SOM-AM43, available from Variscite Ltd. of Lod, Israel. Reader 1112 further has an electrical connector 2222 which electrically interconnects PCB assembly 2212 and PCB assembly 2220. In some embodiments, connector 2222 is an EMBOSS TAPE DDR3 204P 5.2H STDR connector available from TE Connectivity Ltd. of Schaffhausen, Switzerland as part number 2-2013289-1. Reader 1112 further includes a patch 2224 of double sided tape which is used to couple an antenna plate 2226 to an interior surface of top wall 2208. Antenna 2226 is coupled to one or both of PCB assemblies 2212, 2220 and is used for bidirectional wireless communications, such as WiFi communications, with external devices, such as wireless access point 1518, shown diagrammatically in FIG. 15.

Still referring to FIG. 28, reader 1112 has a first cable gasket 2228 and a second cable gasket 2230. First gasket 2228 nests within cover 2200 and has a portion that extends through a notch 2232 formed in side wall 2210. Second gasket 2230 nests within cover 2202 and a portion that extends above an edge 2234 of side wall 2218. Cover 2202 has a pocket 2236 defined by a portion of side wall 2218 and a set of internal walls 2238. A portion of second gasket 2230 is received within pocket 2236. Cover 2200 has a similar type of pocket (not shown) in some embodiments for receipt of a portion of first gasket 2228 therein. Gaskets 2228, 2230 each have a set of five grooves or channels 2240. When gaskets 2228, 2230 are clamped together due to coupling of covers 2200, 2202 together, the grooves 2240 of gasket 2228 cooperate with the grooves 2240 of gasket 2230 to form cable-receiving openings.

In the illustrative FIG. 28 example, two antenna cables 2242 are shown. Antenna cables 2242 are included in first and second cables 1122, 1124 of FIGS. 11-15 in some embodiments. Antenna cables 2242 have first connectors 2244 at one end that couple to respective ports of first PCB assembly 2212 and second connectors 2246 at an opposite end that couple to respective connectors 1646 (see FIG. 16A) of antennae 1114, 1116. Cables 1126, 1128 are also routed through respective openings of gaskets 2228, 2230 and are electrically coupled to PCB assembly 2212 or PCB assembly 2220 of reader 1112. The fifth opening, formed by one set of mating grooves 2240 of gaskets 2228, 2230 is used for a power cable such as cable 1304 (see FIG. 13) of reader 1112. Thus, the power cable couples to bed control circuitry 1302 of beds 1110 in some embodiments. In other embodiments, the power cable has a standard AC plug for plugging into standard AC outlets such as those provided on a room wall or those provided as auxiliary power outlets on beds 1110. In other embodiments, the power cable may have a connector configured to plug into an Ethernet port to receive power over Ethernet (PoE).

Figure 29A:
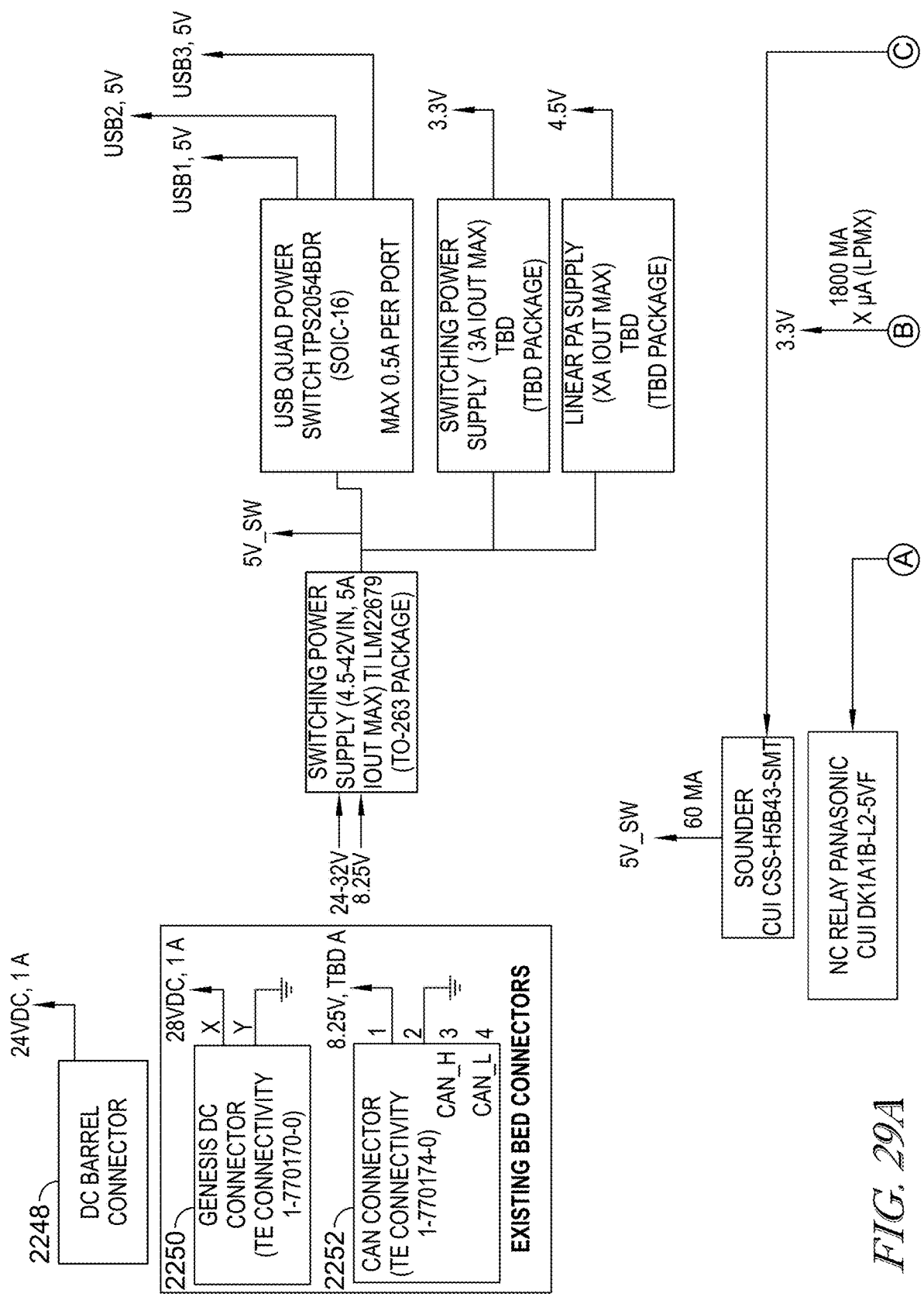
FIGS. 29A, 29B and 29C together form a block diagram of the reader of FIG. 28.
Figure 29B:
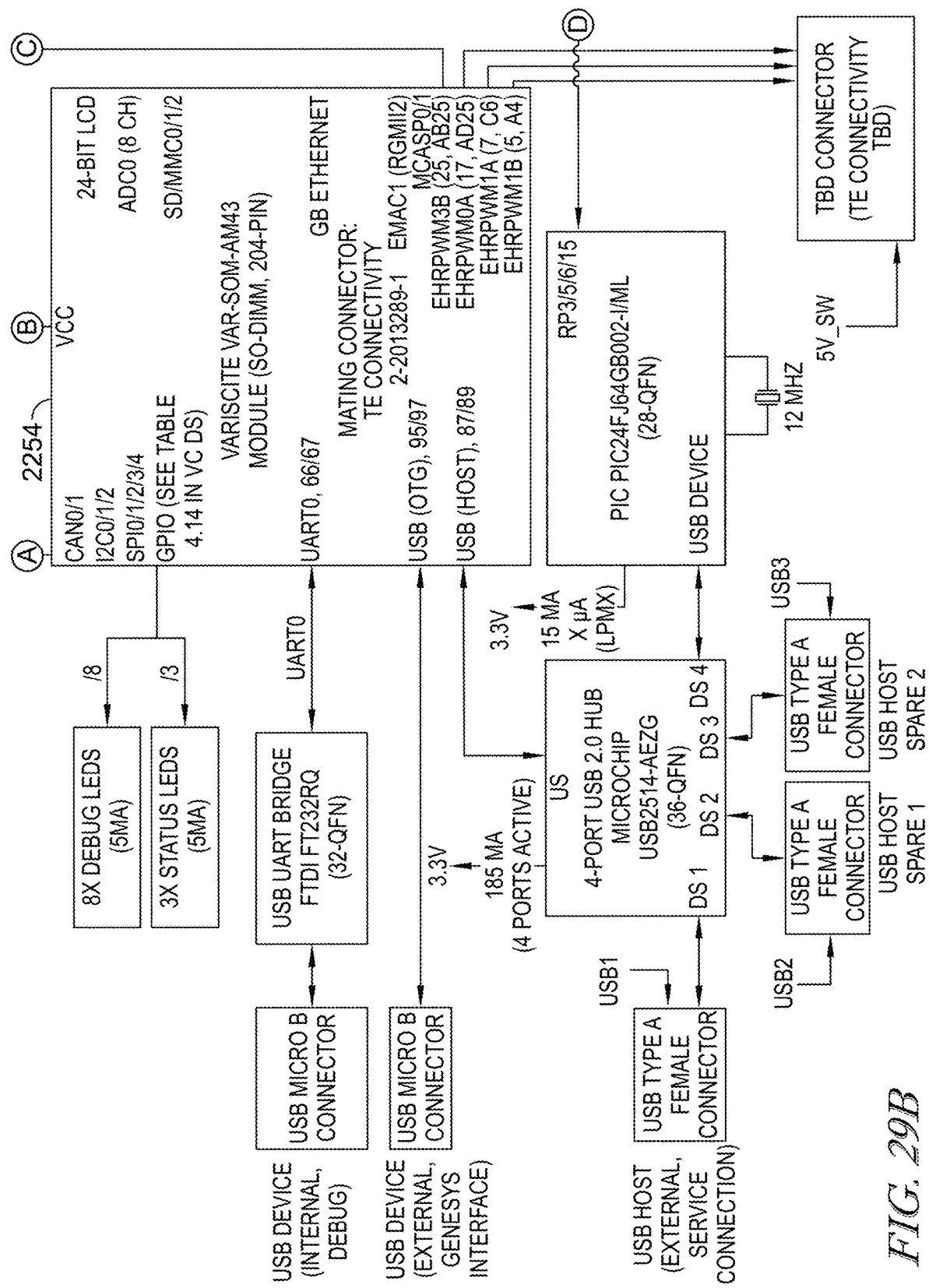
Figure 29C:
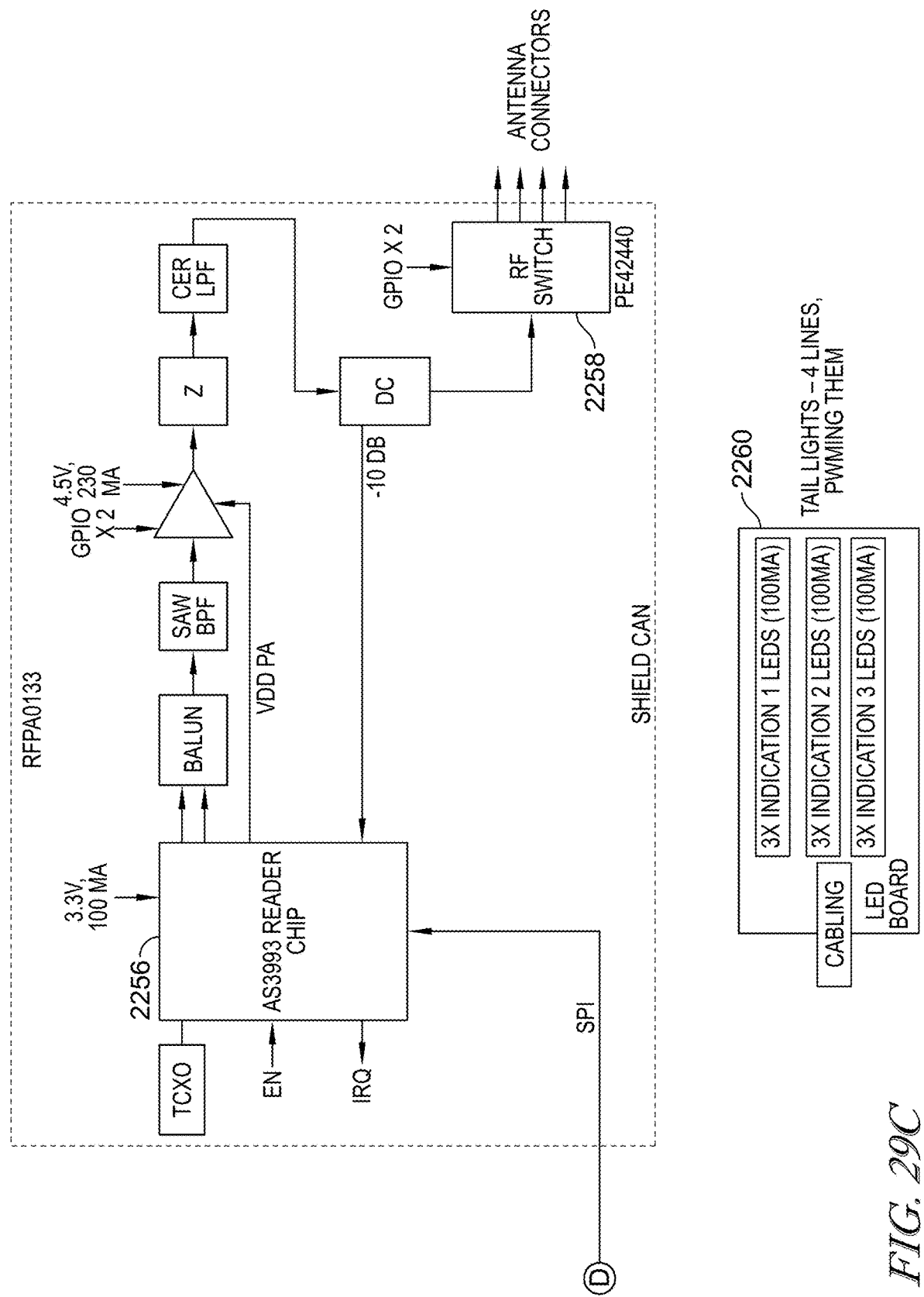

A block diagram of the circuitry of PCB assemblies 2212, 2220 is shown in FIGS. 29A, 29B and 29C which connect together to form the overall block diagram of the electrical circuitry of reader 1112. The various blocks of FIGS. 29A, 29B, 29C are labeled to indicate their functions and/or part numbers. Thus, FIGS. 29A, 29B, 29C speak for themselves such that a detailed description of each block is not required. However, certain notable blocks of FIGS. 29A, 29B, 29C will be pointed out and briefly discussed below.

As shown in FIG. 29A, the circuitry of reader 1112 includes a DC barrel connector 2248 for connection to 24 Volt DC power if such power is available. A first connector 2250 for coupling the reader circuitry to bed control circuitry 1302 of bed 1110 of FIG. 13 via cable 1304 is also shown in FIG. 29A. A second connector 2252 for coupling the reader circuitry to beds 1110 or other devices that communicate according to the controller area network (CAN) protocol is also shown in FIG. 29A. As shown in FIG. 29B, block 2254 comprises the Variscite SOM mentioned above in connection with PCB assembly 2220. As shown in FIG. 29C, the reader circuitry includes an AS3993 reader chip 2256 available from AMS AG of Premstätten, Austria. As also shown in FIG. 29C, the reader circuitry further includes a PE42440 RF switch 2258 available from Peregrine Semiconductor Corporation of San Diego, Calif. RF switch applies the scanning frequencies to antenna 1114, 1116 in some embodiments. FIG. 29 also has a block 2260 which corresponds to the visual indicator 1118 of FIGS. 11, 12, 14 and 15. Thus, block 2260 is technically not part of the circuitry of reader 1112.

Referring now to FIG. 30, the visual indicator 1118 of FIGS. 11, 12, 14 and 15 includes a bracket 3000 having a top wall 3002 and a back wall 3004 extending downwardly from a rear edge 3006 of top wall 3002. When viewed from the side, an edge 3008 of top wall 3002 and an edge of 3010 of back wall 3004 cooperate to form an upside down L-shape. Top wall 3002 of bracket attaches to a frame member of bed 1110, such as a frame member of foot section 1136 or a frame member of upper frame 1138. For example, hook-and-loop fastener strips or adhesive or double sided tape may be used to attach bracket 3000 of visual indicator 1118 to the frame of bed 1110.

Visual indicator 1118 further includes a gasket 3012 that abuts back wall 3004 of bracket 3000, a circuit board 3014 that couples to a pedestal 3016 of gasket 3012, a cover 3018 having a back edge 3020 that is received in a groove 3022 of gasket 3012, and a transparent or translucent label or lens 3024 that covers an opening 3026 of a front wall 3028 of cover 3018. In some embodiments, indicia such as any of those shown in FIGS. 63A-D and 64A-D are printed on lens 3024. Circuit board 3014 has one or more light emitting diodes (LED's) that are operated to shine white, green, or amber (and to flash amber in some embodiments) depending upon the conditions of system 1100 as discussed above.

Back wall 3004 has a pair of holes 3028 and gasket 3012 has a pair of holes 3030, only one of which can be seen in FIG. 30. A pair of bolts or screws 3032 extends through the pair of holes 3028 of back wall 3004 and through the pair of holes 3030 of gasket 3012 and thread into threaded bores of bosses formed in the interior region of cover 3018. Back wall 3004 also has a notch 3034 formed along a bottom edge 3036 thereof. Notch 3034 is sized to permit an electrical connector 3038 provided at the end of cable 1126 to connect to an electrical connector of circuit board 3014.

Figure 31:
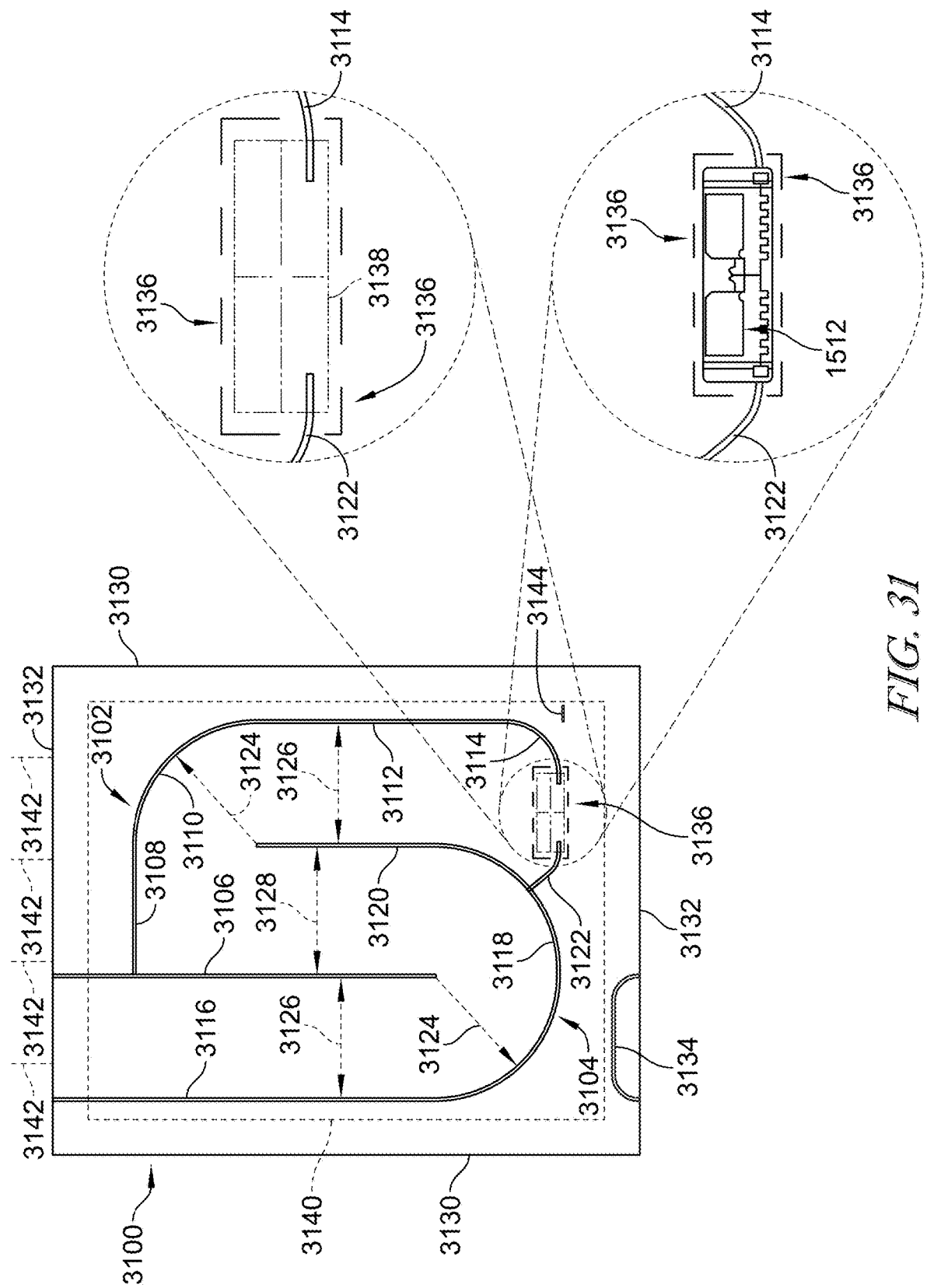
FIG. 31 is a top plan view of a first embodiment of a backsheet of an incontinence detection pad of the incontinence detection system showing a pair of electrodes with respective ends terminating within a rectangular tag footprint printed on the backsheet, showing a first enlarged bubble without an RFID tag present, and a second enlarged bubble with the RFID tag attached to the backsheet within the rectangular tag footprint.

Referring now to FIG. 31, a backsheet 3100 of an incontinence detection pad that is suitable for use with incontinence detection system 1100 and other such systems disclosed herein is shown. Backsheet 3100 is rectangular in shape and has first and second electrode traces 3102, 3104 printed thereon. Electrode traces 3102, 3104 are sometimes referred to herein as electrodes 3102, 3104. Electrode 3102 has a first straight line segment portion 3106, a second straight line segment portion 3108 that is substantially perpendicular to portion 3106, a first rounded portion 3110, a third straight line segment portion 3112 that is substantially parallel with portion 3106, and a second rounded portion 3114. Electrode 3104 has a first straight line segment portion 3116, a rounded portion 3118, and a second straight line segment portion 3120. Electrode 3104 also includes a curved extension portion 3122.

Portion 3120 of trace 3104 is substantially parallel with, and situated between, portions 3106, 3112 of trace 3102. Rounded portion 3110 of trace 3102 interconnects portions 3108 and 3112 and extends over an arc of about 90°. Rounded portion 3118 of trace 3104 interconnects portions 3116, 3120 and extends over an arc of about 180°. Electrodes 3102, 3104 are printed on backsheet 3100 and comprise a conductive ink such as carbon ink, silver ink, or the like. In some embodiments, the thickness of traces 3102, 3104 is about 3.0 mm+/−0.5 mm. Rounded portions 3110, 3118 have radii 3124 of about 190.0 mm in the illustrative example. The radius 3124 of portion 3110 of electrode 3102 is centered on a terminal end of portion 3120 of electrode 3104. The radius 3124 of portion 3118 is centered on a terminal end of portion 3106 of electrode 3102.

Perpendicular distances 3126 between portion 3106 of electrode 3102 and portion 3116 of electrode 3104 and between portion 3112 of electrode 3102 and portion 3120 of electrode 3104 is about 190.0 mm in the illustrative example. A perpendicular distance 3128 between portion 3106 of electrode 3102 and portion 3120 of electrode 3104 is about 200.0 mm in the illustrative example. Radii 3124 and distances 3126, 3128 are measured based on centerlines of the respective traces 3102, 3104. Side edges 3130 of backsheet 3100 have lengths of about 900.0 mm and end edges 3132 have lengths of about 750.0 mm in the illustrative example. The long dimension of backsheet 3130 is sometimes referred to as the machine direction (MD) and the short dimension of backsheet 3100 is sometimes referred to as the cross direction (CD).

Backsheet 3100 includes a sacrificial trace 3134 in an end region adjacent to one of edges 3132. Sacrificial trace 3134 is left over from an electrode trace of a next adjacent backsheet 3100 during a manufacturing process as will be described below in further detail in connection with FIG. 36. Sacrificial trace 3134 is somewhat U-shaped or C-shaped. An RFID tag foot print 3136 in the form of a dashed rectangle is printed on backsheet 3100 as shown in FIG. 31. Portion 3114 of electrode 3102 and portion 3122 of electrode 3104 have terminal ends located within foot print 3136. Foot print 3136 delineates an alignment zone or region of backsheet 3100 within which RFID tag 1512 (see FIG. 15) can be placed and form proper electrical contacts with portions 3114, 3122 of electrodes 3102, 3104. In FIG. 31, a first enlarged bubble at the top right region of the page shows foot print 3136 prior to attachment of RFID tag 1512. A phantom box 3138 in the first enlarged bubble indicates one example of a space that RFID tag 1512 may occupy within foot print 3136. A second enlarged bubble of FIG. 31 shows RFID tag installed on backsheet 3100 within the foot print 3136.

Still referring to FIG. 31, a substantially rectangular phantom box 3140 is shown on backsheet 3100 to delineate the general location of a perimeter of an absorbent core of an incontinence detection pad in which backsheet 3100 is included. A set of dashed lines 3142 adjacent one of edges 3132 indicates the locations at which the incontinence detection pad having backsheet 3100 is folded in the machine direction. It should be noted that the two fold lines on the right side of backsheet 3100 pass to the right and left of foot print 3138 and the RFID tag 1512 contained therein. Thus, the machine direction folds are oriented so that the RFID tag 1512 is not folded when the associated incontinence detection pad is folded. Backsheet 3100 also has an additional registration mark 3144 that is used during the manufacture of the incontinence detection pad in which backsheet 3100 is included.

Referring now to FIG. 32, an exploded end elevation view of the backsheet 3100 is shown. In the illustrative embodiment, backsheet 3100 includes a polypropylene spunbond nonwoven layer 3146, a layer of hot melt adhesive 3148, a high density polyethylene (LDPE) layer 3150, and conductive ink 3152 which forms the electrode traces 3102, 3104 on the LDPE layer 3150. Thus, layers 3146, 3150 form a laminate as the overall structure of backsheet 3100. In some embodiments, layer 3150 has a weight of about 18 grams per square meter (gsm) and layer 3146 has a weight of about 22 gsm. In some embodiments, layer 3150 is corona treated with ultraviolet (UV) light prior to printing the conductive ink 3152 thereon. Such corona treatment temporarily renders layer 3150 hydrophilic to increase to the adhesion of ink 3152 to layer 5150. With hot melt adhesive being about 2 gsm, the overall weight of backsheet 3100 is about 42 gsm (18+22+2). However, it should be appreciated that other weights for backsheet 3100 and various material that comprise backsheet 3100 are within the scope of this disclosure.

Referring now to FIG. 33, an absorbent core 3154 is shown adhered to a top sheet 3156. Top sheet 3156 is rectangular in shape and has substantially the same length and width dimensions as backsheet 3100. Thus, the same reference numbers used in connection with the edges 3130, 3132 of backsheet 3100 are used to denote the side edges 3130 and end edges 3132 of top sheet 3156. Absorbent core 3154 is also rectangular in shape but its overall dimensions are smaller than top sheet 3156 and backsheet 3100. Thus, perimetral portions 3158 of top sheet 3156 extend outwardly from a perimeter of the absorbent core 3154. Absorbent core has side edges 3160 that are about 790 mm+/−10 mm in length and end edges 3162 that are about 660+/−10 mm in length. Thus, because absorbent core 3154 is centered on top sheet 3156, a distance from each side edge 3160 of core 3154 to the adjacent side edge 3130 of top sheet 3156 is about 45 mm and a distance from each end edge 3162 of core 3154 to the adjacent end edge 3132 of top sheet 3156 is about 55 mm.

Absorbent core 3154 is adhered to top sheet 3156 and the perimetral edge portions of top sheet 3156 are adhered to edge regions of backsheet 3100. As shown in FIG. 34A, prior to attachment of top sheet 3156 and absorbent core 3154 to backsheet 3100, strips 3164 of hot melt adhesive are slot coated onto backsheet 3100 at first and second ends of backsheet 3100 adjacent to end edges 3132. As shown in FIG. 34B, prior to attachment of top sheet 3156 and absorbent core 3154 to backsheet 3100, strips 3166 of hot melt adhesive are spray coated to backsheet 3100 at first and second sides of backsheet 3100 adjacent to side edges 3130. The width of strips 3164 is about 45 mm and the width of strips 3166 is about 39.5 mm in some embodiments. After strips 3164, 3166 of adhesive are applied to backsheet 3100, top sheet 3156 and absorbent core 3154 are mated with backsheet 3100 with edges 3130, 3132 of top sheet 3156 substantially aligned with edges 3130, 3132 of back sheet.

Figure 35:
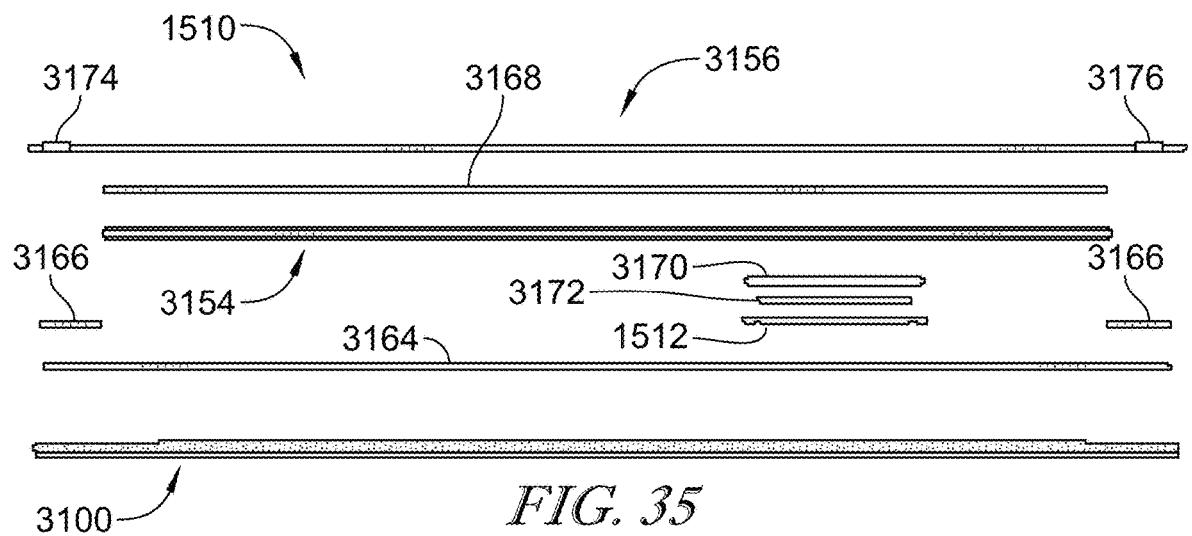
FIG. 35 is an exploded end elevation view of the incontinence detection pad showing from top to bottom a polypropylene spunbond nonwoven top sheet, a layer of hot melt adhesive, an absorbent core made of airlaid material, a foam spacer of the RFID tag, foam adhesive, the RFID tag inlay, the spray coated adhesive spaced on opposite sides of the RFID tag inlay, the slot coated adhesive, and the backsheet.

Referring now to FIG. 35, an exploded end elevation view of the incontinence detection pad 1510 is shown. In the illustrative embodiment, pad 1510 comprises a polypropylene spunbond nonwoven layer top sheet 3156, a layer 3168 of hot melt adhesive, absorbent core 3154 made of airlaid material, a foam spacer 3170 of the RFID tag, foam adhesive 3172, the RFID tag or inlay 1512, the spray coated adhesive strips 3166, one of the slot coated adhesive strips 3164, and the backsheet 3100. Top sheet 3156 has a weight of about 15 gsm to about 17 gsm in some embodiments. According to this disclosure, a series of foot indicia or graphics 3174 and a series of head indicia or graphics 3176 is printed near edges 3130 of top sheet 3156. Such graphics are shown, for example, in FIGS. 59A-62D, 65A-69D, and 70.

Layer 3168 of adhesive has a weight of 2 gsm in some embodiments. Layer 3168 is a lined, combed, slot coated layer having adhesive applied in rows along the machine direction of top sheet 3156 that are about 1 mm wide and that are spaced apart by about 4 mm. Such lined, combed, slot coating of adhesive 3168 results in incontinence detection pad 1510 having a ribbed or furrowed upper surface texture. This texture can be seen in the digital photos of FIGS. 69A-69E. The ribbed texture serves to trap any fluid, such as urinary incontinence, on pad 1510 and to reduce the chances that the fluid will run off pad 1510. In other embodiments, a different combed, slot coating may be used such as for example, 1 mm glue strips with 1 mm gaps for 50% coverage or 2 mm glue strips with 10 mm gaps for 17% coverage. Strips 3164 may be similarly slot coated in any of these manners in some embodiments. Adhesive strips 3166 have a weight of about 2 gsm and adhesive trips 3164 have a weight of about 6 gsm in some embodiments. Absorbent core 3154 has a weight of about 135 gsm and comprises Fitesa B871M135S30 airlaid material in some embodiments.

Figure 36:
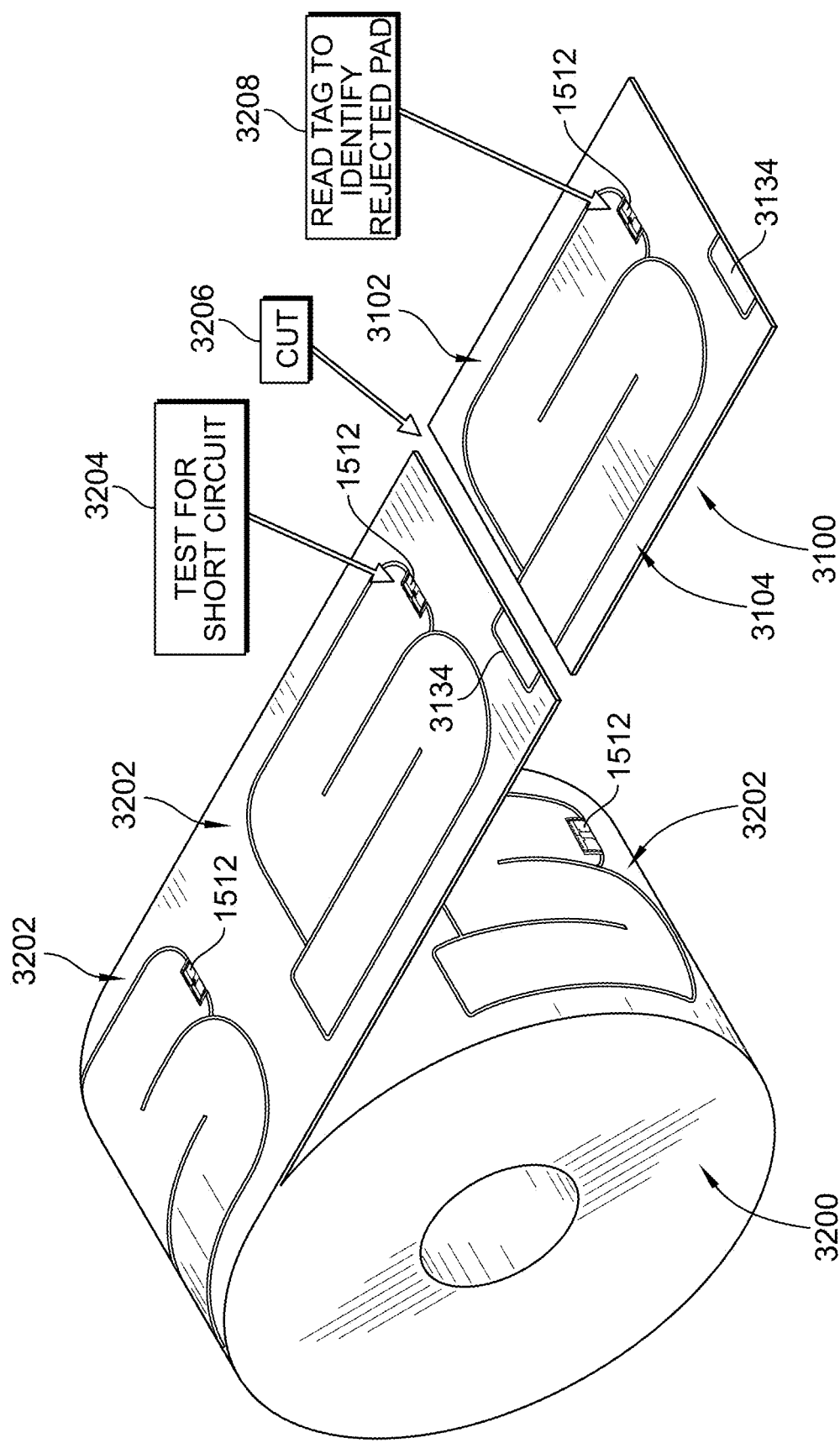
FIG. 36 is a diagrammatic view of a manufacturing process in which a roll of backsheet material has an electrode trace forming a closed circuit between contacts of the RFID tag, a test for short circuit being performed to read the RFID tag to confirm that no breaks exist in the electrode trace, the material being cut at a location that severs a sacrificial trace portion from the rest of the trace, and the tag is read to identify any rejected pads having a broken electrode trace.

Referring now to FIG. 36, a diagrammatic view of a manufacturing process is shown in which a roll 3200 of backsheet material has a series of single electrode traces 3202 forming a closed circuit between contacts of the associated RFID tags 1512. As indicated diagrammatically at block 3204 in FIG. 36, a test for short circuit is performed to read the RFID tag 1512 to confirm that no breaks exist in the associated electrode trace 1512. If the short circuit test is failed, a serial number of an RFID chip of RFID tag 1512 is stored in memory of a computer device on the manufacturing line for later use.

After the short circuit test of block 3204 is conducted, the roll of material 3200 is cut at a location that severs sacrificial trace portion 3134 from the rest of the associated trace 3202 as indicated diagrammatically at block 3206. After the cut, a single backsheet 3100 is formed with spaced apart traces 3102, 3104 thereon. The sacrificial trace portion 3134 associated with the cut backsheet 3100 is left behind on the next adjacent backsheet 3100 which has not yet been cut. The backsheet 3100 is cut at the leading end of roll 3200. In some embodiments, material 3200 is folded in the machine direction along one or more of the fold lines 3142 shown in FIG. 31 prior to the cutting operation of block 3206.

Later in the manufacturing process, the tag 1512 of each incontinence detection pad 1510 is read again, as indicated at block 3208 in FIG. 36, to identify any rejected pads 1510 that failed the test at block 3204 due to having a broken electrode trace 3202. The identification is accomplished by comparing the serial number read from tag 1512 with the serial number(s) of rejected pads that are stored in memory. The rejected pads, once identified, are removed from the manufacturing line. In some embodiments, a mark is added to any incontinence pad 1510 for which the first electrode trace does not form a completed short circuit between the terminal ends of the first electrode trace as determined by the testing 3204. Therefore, the mark indicates a rejected incontinence detection pad 1510. For example, the mark may become visible when exposed to ultraviolet (UV) light.

In some embodiments, when RFID tag 1512 is read at block 3208, data from tag 1512 is analyzed to confirm that traces 3102, 3104 form an open circuit. This open circuit test is performed to confirm that sacrificial trace portion 3134 has successfully been severed from the associated electrode traces 3102, 3104. If the roll of material 3200 becomes out of registry with the manufacturing equipment doing the cutting, it would be possible for the cut to miss the sacrificial trace portion 3134 and leave a short circuit electrode trace 3202 on the backsheet 3100 after the cutting operation. Thus, the open circuit test at block 3208 monitors for this out of registry situation.

It should be appreciated that, in some embodiments, the tests at one or both of blocks 3204, 3208 are performed after the absorbent core 3154 and top sheet 3156 are attached to backsheet 3100. The cutting operation 3206 is performed after such attachment of the core 3154 and top sheet 3156 to the backsheet material of roll 3200 in some embodiments. In such embodiments, the short circuit test at block 3204 can be performed before or after the attachment of core 3154 and top sheet 3156 to the leading end material of roll 3200.

Referring now to FIGS. 37-39, an alternative embodiment of an incontinence detection pad 3210 is shown. Pad 3210 is similar to pad 1510 and so the same reference numbers are used to denote like portions of pads 1510, 3210. As shown in FIG. 38, pad 3210 includes polypropylene spunbond nonwoven top sheet 3156 having indicia 3174, 3176, layer of intermittent hot melt adhesive 3168, absorbent core 3154 of airlaid material, hot melt adhesive 3166 spray coated at the sides of the incontinence detection pad 3210, hot melt adhesive 3164 slot coated along the length of the incontinence detection pad 3210 but with an uncovered strip or region 3214 along the length of the pad 3210, an alternative embodiment of an RFID tag 3212 situated beneath the uncovered strip 3214 of slot coated hot melt adhesive 3164, and backsheet 3100. Thus, adhesive covers more area of backsheet 3100 of pad 3210 than pad 1510. The uncovered region 3214 prevents the adhesive from fouling RFID tag 3212.

Referring now to FIG. 39, the detail of first and second electrode traces 3102, 3104 on backsheet 3100 of pad 3210 can be seen. Electrode 3102 includes a first straight trace portion 3216 which extends in the machine direction of pad 3210 and first and second straight trace portions 3218, 3220 which extend in the cross direction of pad 3210. Trace portions 3218, 3220 are substantially perpendicular to trace portion 3216 and extend therefrom toward electrode 3104. Electrode 3210 also has a second straight trace portion 3222 extending from trace portion 3220 in the machine direction of pad 3210 and terminating at an electrical contact 3224 of RFID tag 3212. Electrode 3104 includes a first straight trace portion 3226 which extends in the machine direction of pad 3210 and first, second, and third straight trace portions 3228, 3230 which extend in the cross direction of pad 3210. Trace portions 3228, 3230, 3232 are substantially perpendicular to trace portion 3226 and extend therefrom toward electrode 3102. Trace portion 3232 terminates at an electrical contact 3234 of RFID tag 3212. The termination of trace portions 3222, 3232 at respective electrical contacts 3224, 3234 of RFID tag 3212 are shown best in the enlarged bubble of FIG. 39.

Figure 40:
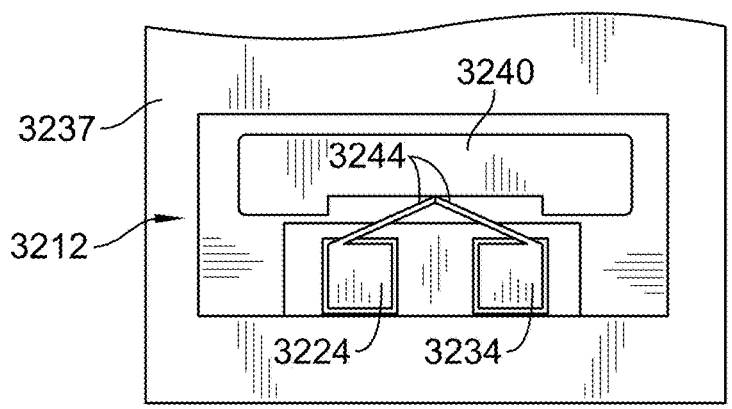
FIG. 40 is a top view of an alternative embodiment of an RFID tag on a release liner prior to the RFID tag being attached to the backsheet showing a substantially rectangular layer of non-conductive adhesive, a pair of electrical contacts on an inlay film near the bottom of the non-conductive adhesive, an aluminum antenna near the top of the non-conductive adhesive.
Figure 41:
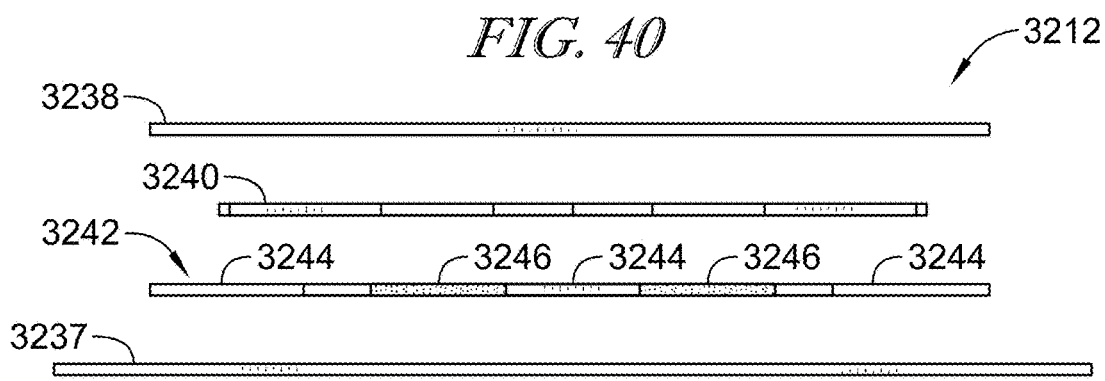
FIG. 41 is an exploded side view of the RFID tag of FIG. 40 showing, top to bottom, an inlay film, an inlay antenna, a layer of adhesive including non-conductive portions and conductive portions, and a release liner.
Figure 42:
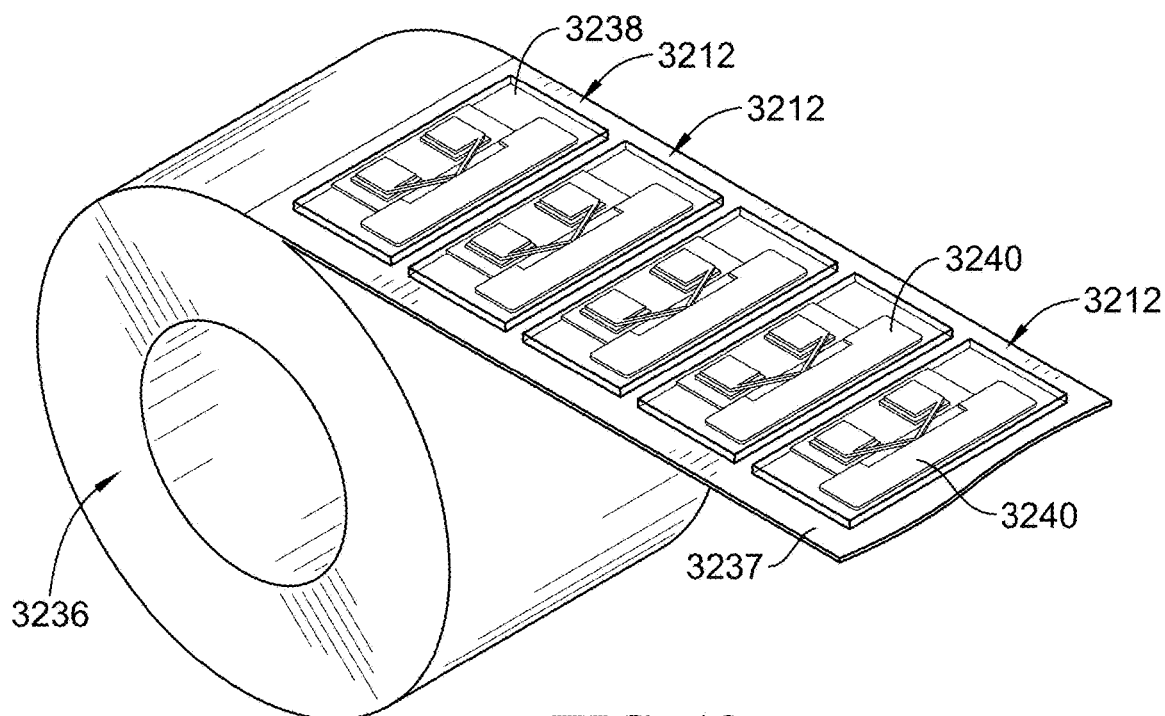
FIG. 42 is a perspective view of a roll of release liner carrying a plurality of RFID tags.

Referring now to FIGS. 40-42, a series of RFID tags 3212 are shown provided on a roll 3236 of release liner 3237. During the manufacture of pads 3210, tags 3212 are removed from roll 3236 and attached to the backsheet 3100. Each tag 3212 has an inlay film 3238, an inlay antenna 3240, and a layer of adhesive 3242 including non-conductive portions 3244 and conductive portions 3246 as shown in FIG. 41. The release liner 3237 is also shown in FIG. 41. Electrical contacts 3224, 3234 are included as part of inlay film 3238. In some embodiments, antenna 3240 is made of aluminum. A pair of inclined arms 3242 interconnects electrical contacts 3224, 3234 with an RFID chip of tag 3212.

Figure 57:
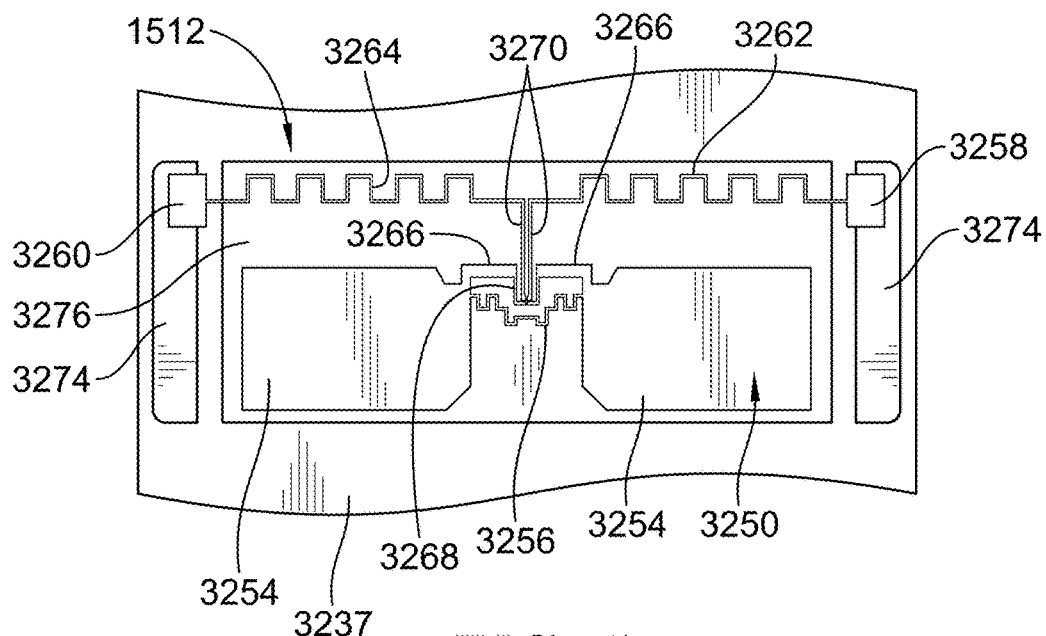
FIG. 57 is a top plan view of the antenna of FIG. 56B installed on an RFID tag carried on a release liner.

It should be appreciated that RFID tags 1512 of pads 1510 also are provided on rolls 3236 of release liner 3237 for manufacture. One such RFID tag 1512 on release liner 3237 is shown in FIG. 57. RFID tag 1512 has an antenna and electrical contact inlay 3250. In some embodiments, inlay 3250 is made of aluminum. Inlay 3250 includes a pair of large antenna patches 3254, a first undulated trace 3256 interconnecting patches 3254, a first electrical contact 3258, a second electrical contact 3260, a second undulated trace 3262 extending from contact 3258 toward contact 3260, and a third undulated trace 3264 extending from contact 3260 toward contact 3258. A pair of arms 3266 extends from patches 3254 and a U-shaped trace 3268 interconnects arms 3266. Pair of straight traces 3270 extends from respective undulated traces 3262, 3264 and terminate in U-shaped trace 3268.

RFID tag 1512 includes an RFID chip which is very small and that electrically couples to traces 3268, 3270. One suitable RFID chip is a model no. SL3S1003_1013 UCODE G2iM 2015 chip available from NXP Semiconductors N.V. of Eindhoven, Netherlands. The dimensions of this RFID chip are 1 mm by 1.45 mm by 0.5 mm. This RFID chip used in RFID tag 1512 has memory with a tamper evident status bit that is used to indicate with the pad is wet or not wet and a kill bit to indicate whether the pad has been wet previously. The tamper evident status bit and the kill bit have already been discussed herein.

Figure 58:
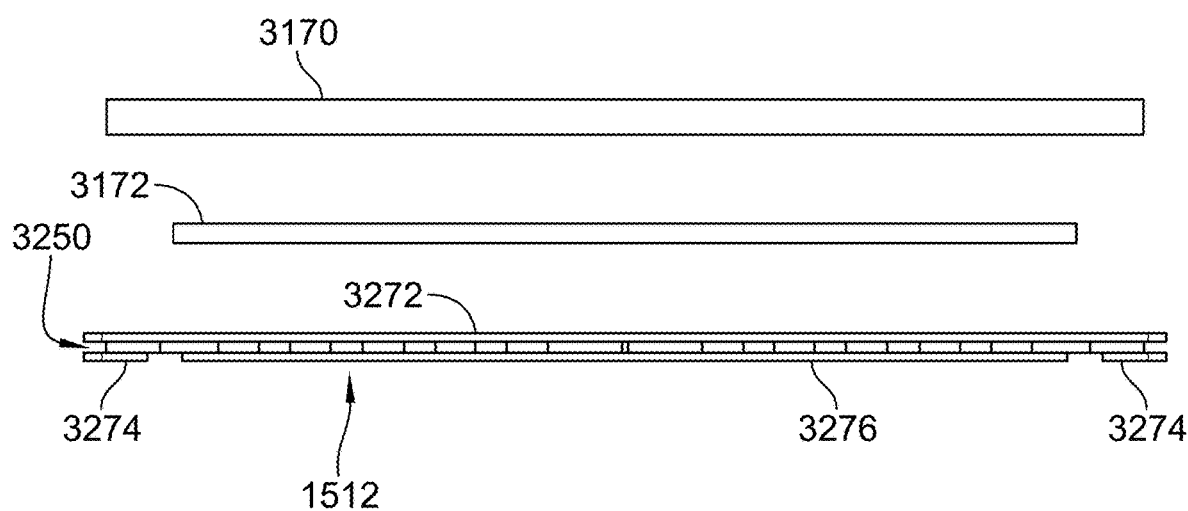
FIG. 58 is an exploded side view of the RFID tag of FIG. 57 showing, from top to bottom, a foam tag cover, a layer of hot melt adhesive, and the RFID tag inlay.
Figure 59A:
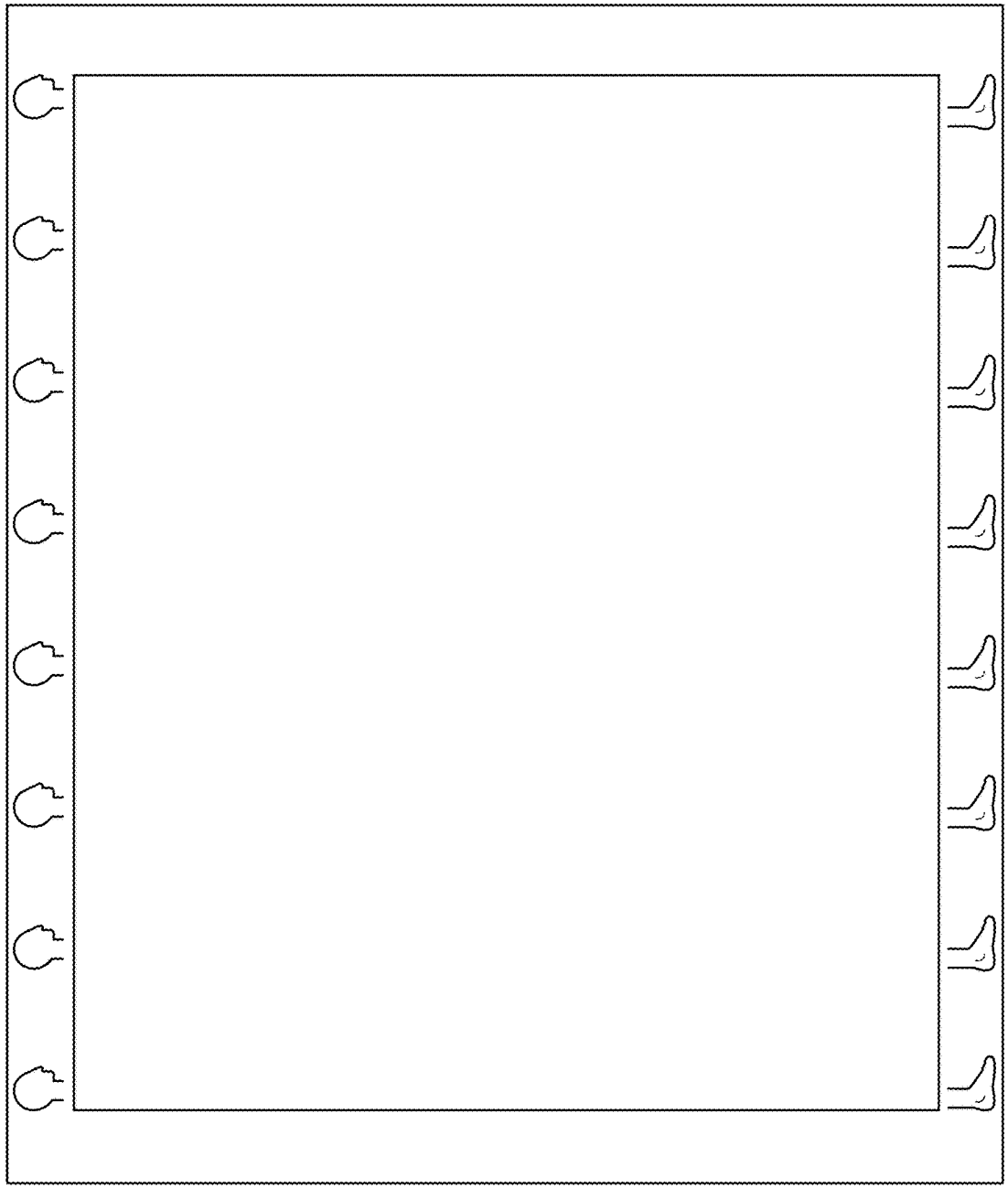
FIG. 59A is a top plan view of an incontinence detection pad showing a substantially rectangular outline of an absorbent core occupying a central region of the incontinence detection pad, a series of head indicia located between a first perimeter edge of the pad and the outline of the absorbent core, and showing a series of foot indicia located between a second perimeter edge of the pad and the outline of the absorbent core.
Figure 59B:
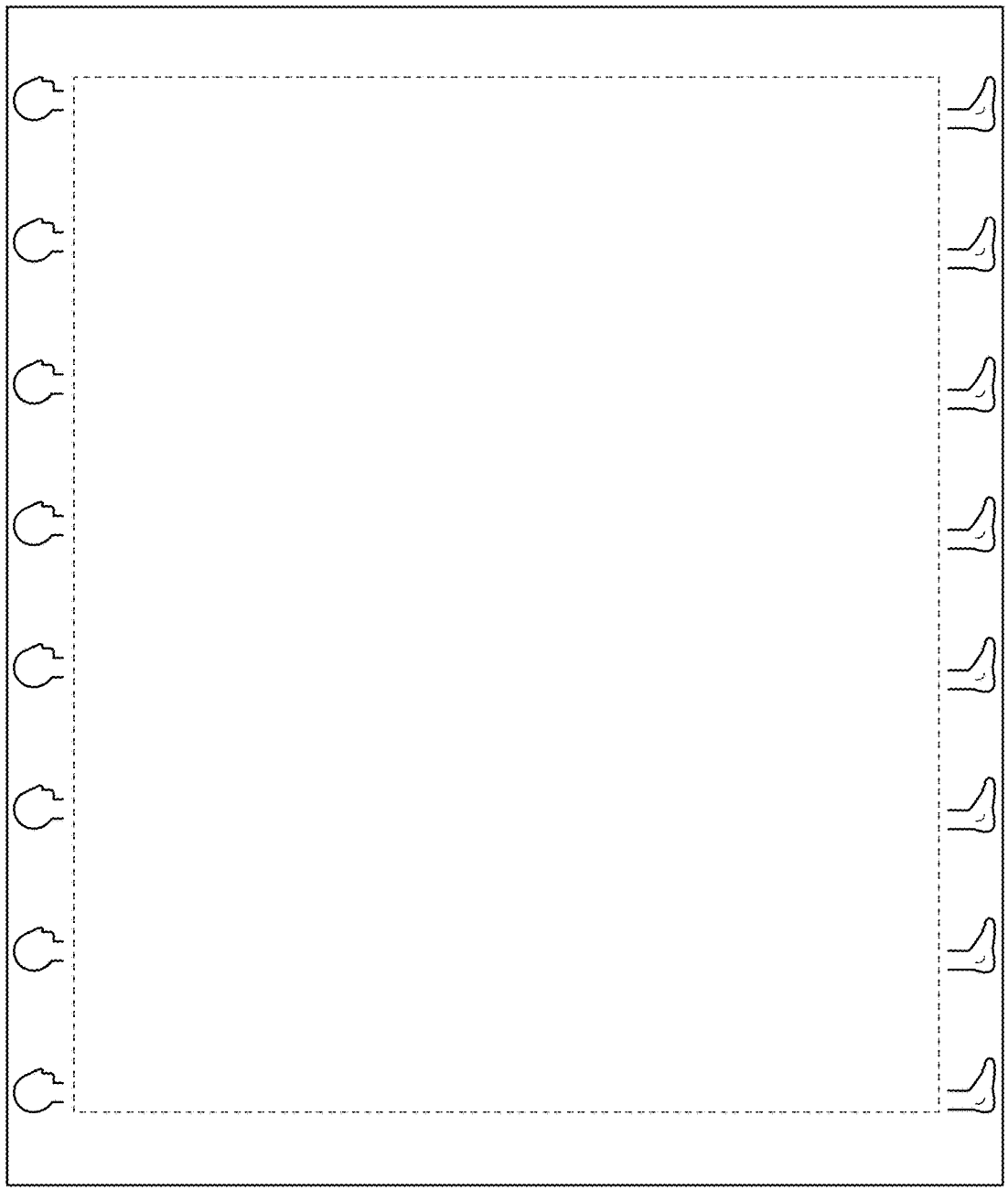
FIG. 59B is a top plan view of the incontinence detection pad, similar to FIG. 59A, showing the substantially rectangular outline of the absorbent core dotted out.
Figure 59C:
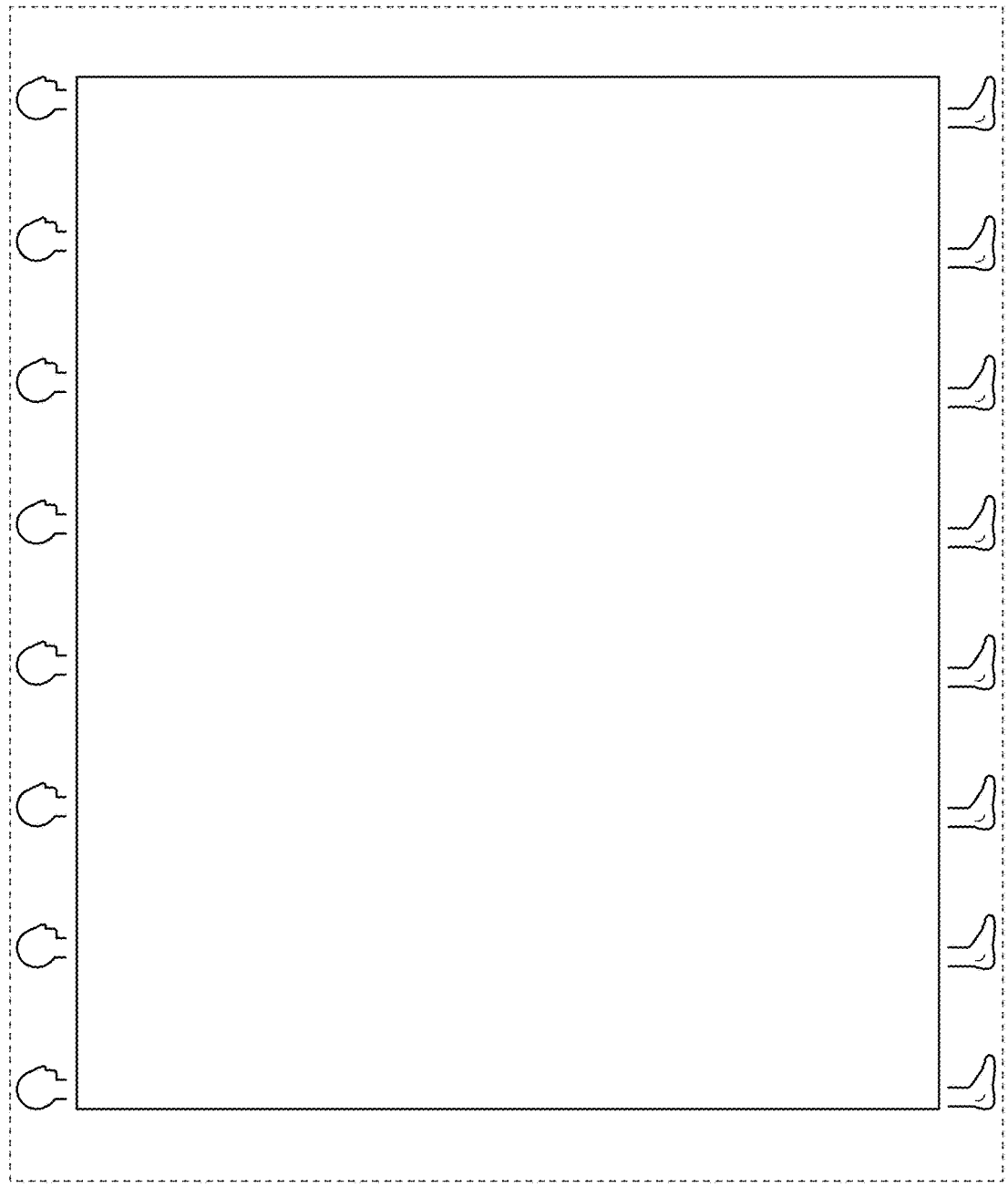
FIG. 59C is a top plan view of the incontinence detection pad, similar to FIG. 59A, showing an outer perimeter of the incontinence detection pad doted out.
Figure 59D:
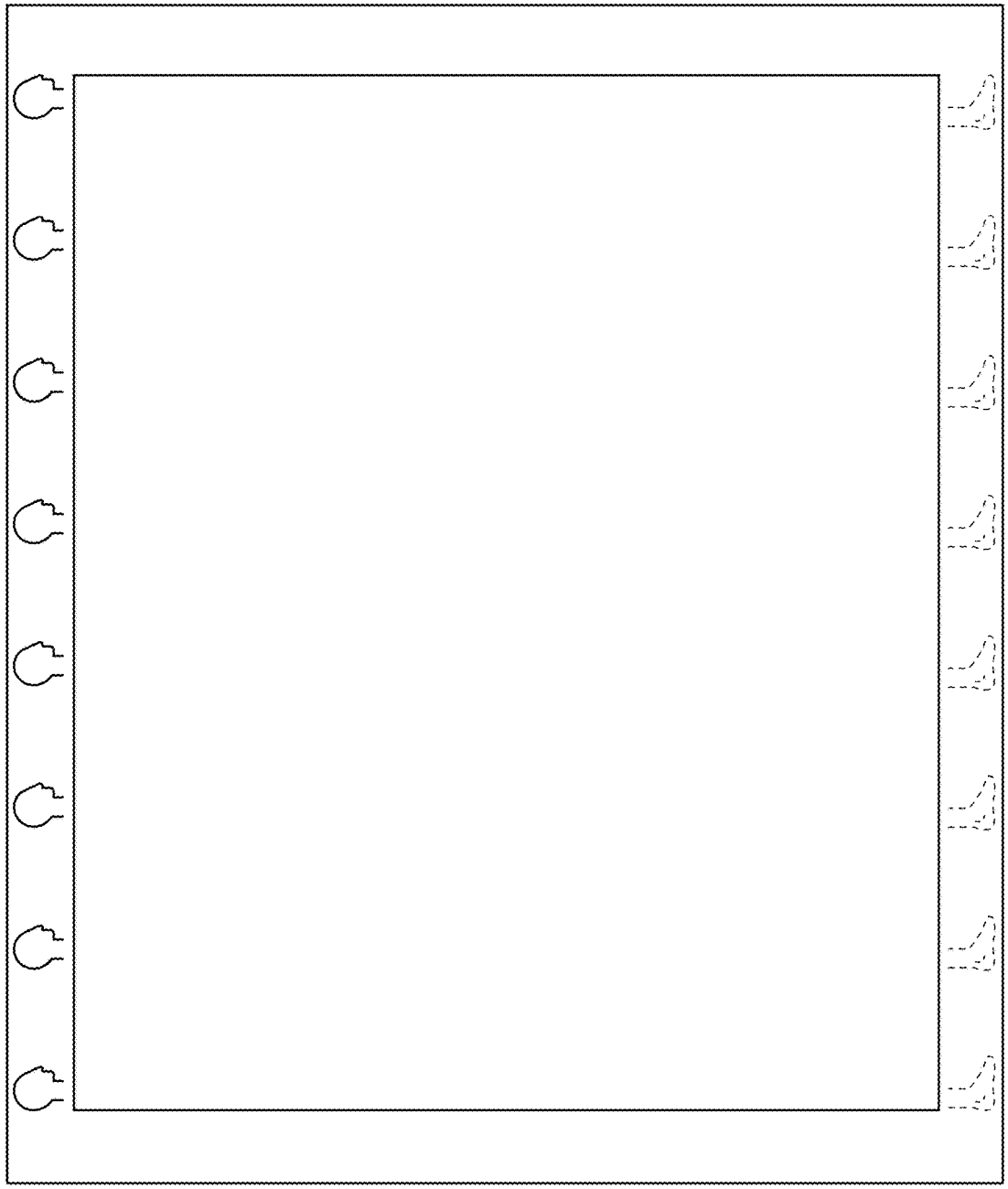
FIG. 59D is a top plan view of the incontinence detection pad, similar to FIG. 59A, showing the series of foot indicia dotted out.
Figure 59E:
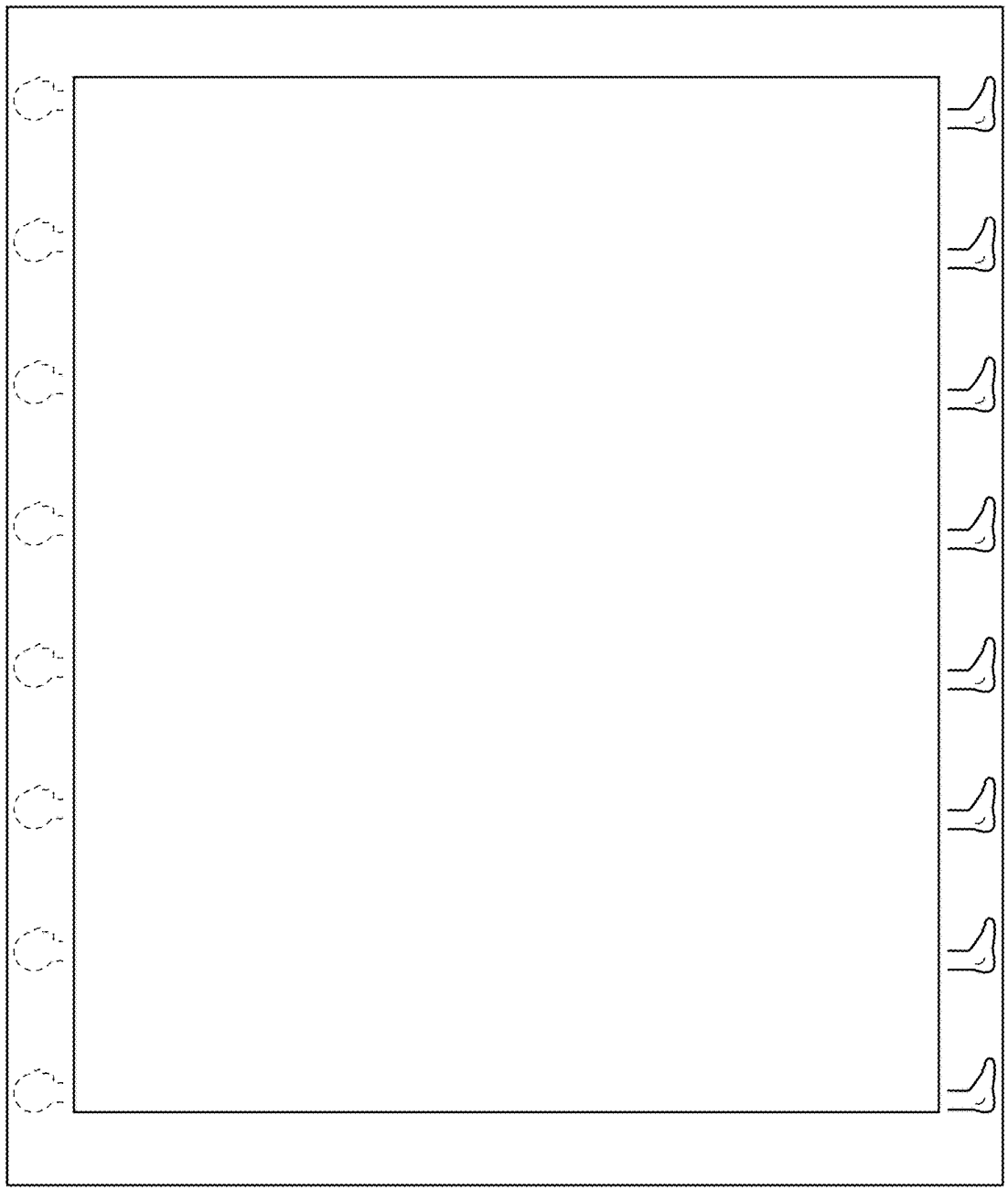
FIG. 59E is a top plan view of the incontinence detection pad, similar to FIG. 59A, showing the series of head indicia dotted out.
Figure 59F:
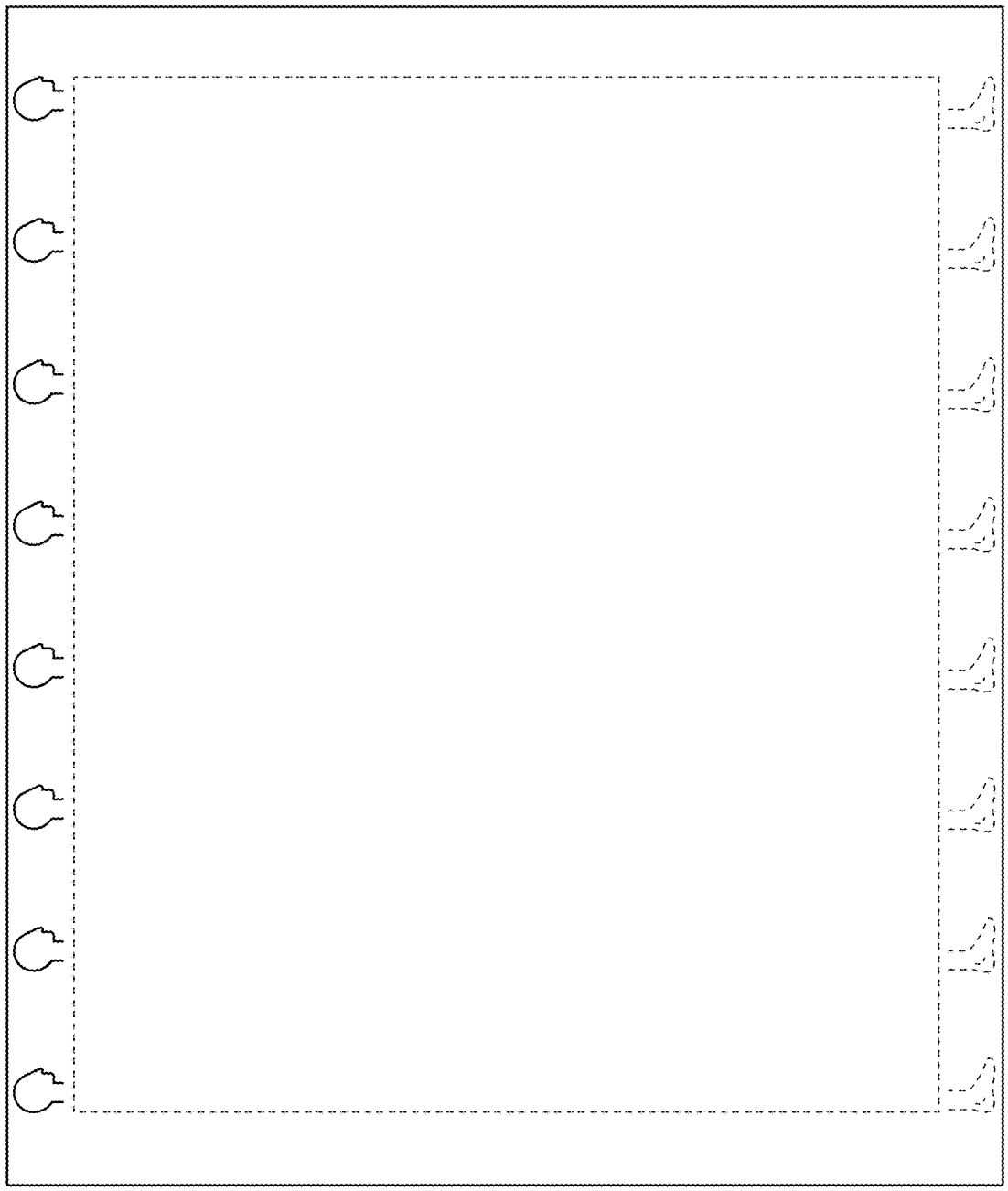
FIG. 59F is a top plan view of the incontinence detection pad, similar to FIG. 59A, showing the substantially rectangular outline of the absorbent core dotted out and showing the series of foot indicia dotted out.
Figure 59G:
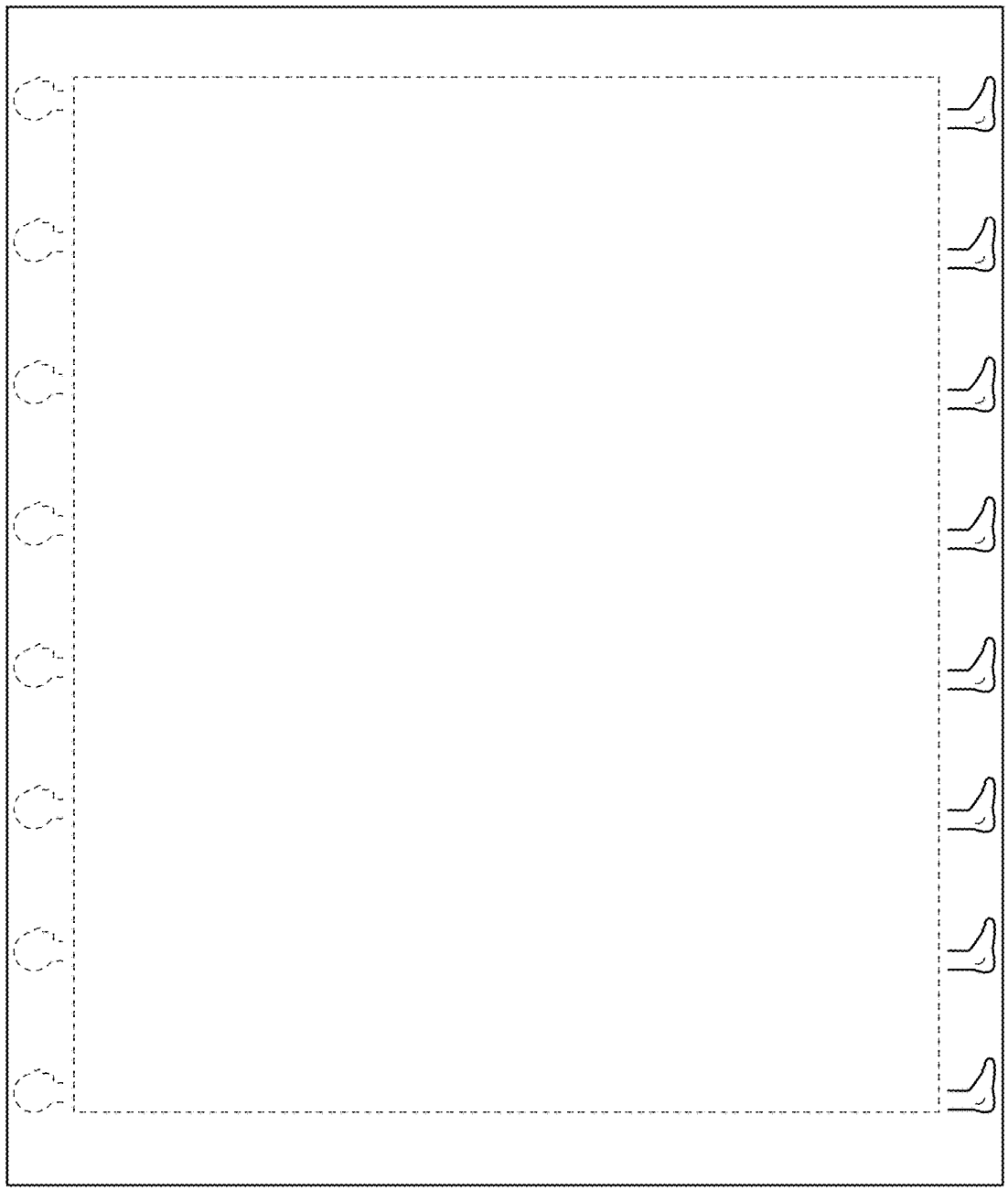
FIG. 59G is a top plan view of the incontinence detection pad, similar to FIG. 59A, showing the substantially rectangular outline of the absorbent core dotted out and showing the series of head indicia dotted out.
Figure 60A:
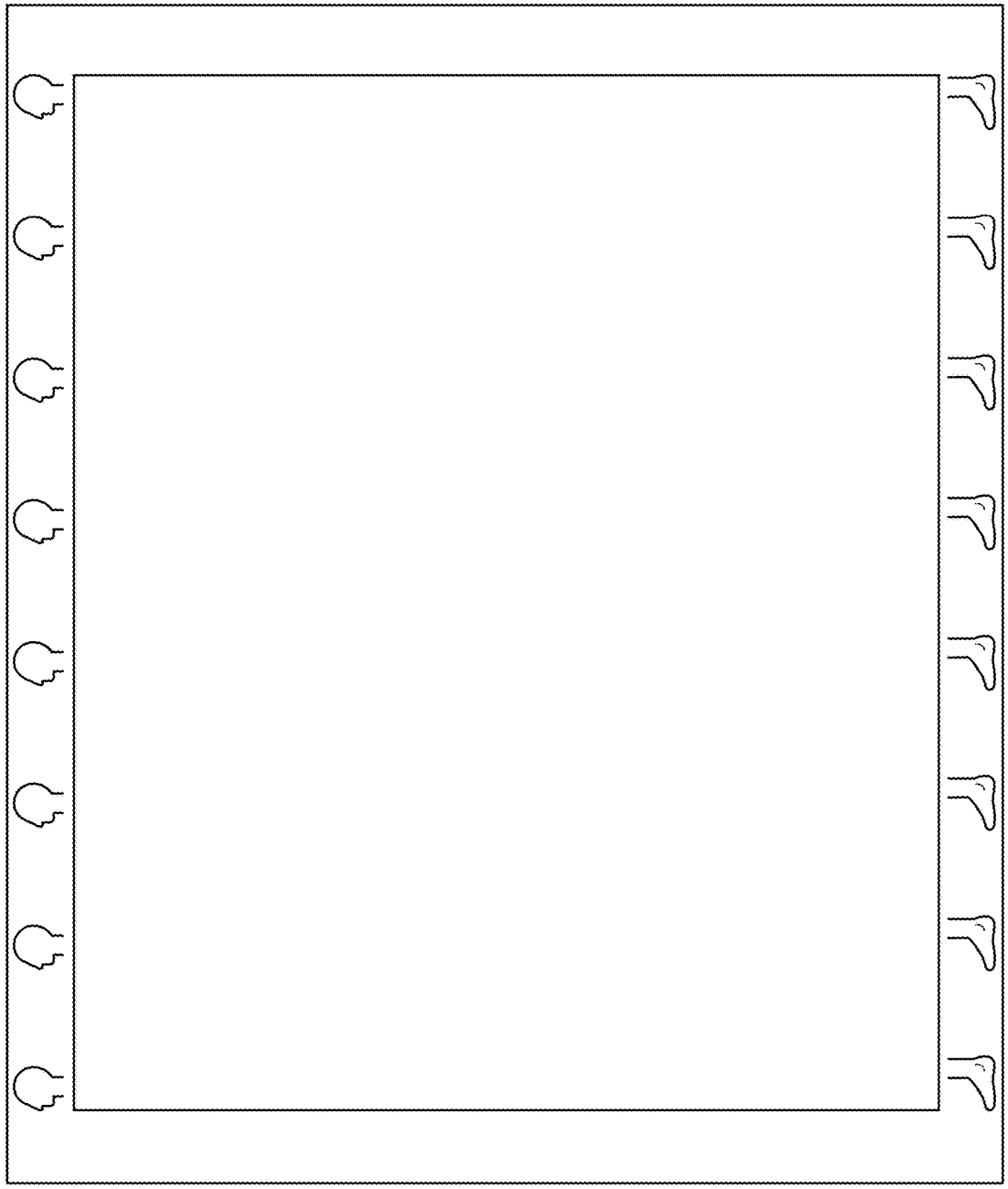
FIG. 60A is a top plan view of an incontinence detection pad, similar to FIG. 59A, but showing the head indicia and foot indicia facing to the left instead of to the right.
Figure 60B:
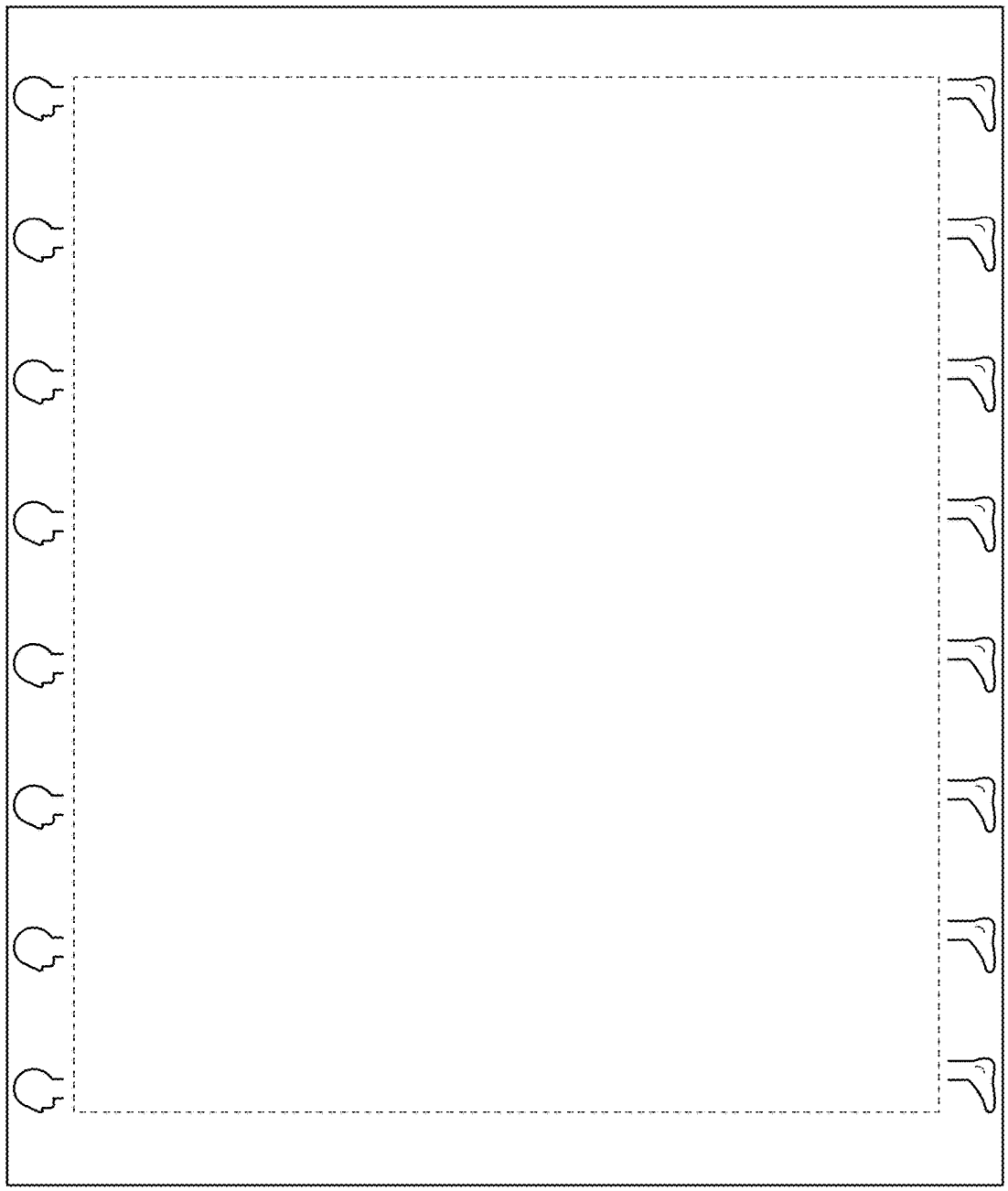
FIG. 60B is a top plan view of the incontinence detection pad, similar to FIG. 60A, showing the substantially rectangular outline of the absorbent core dotted out.
Figure 60C:
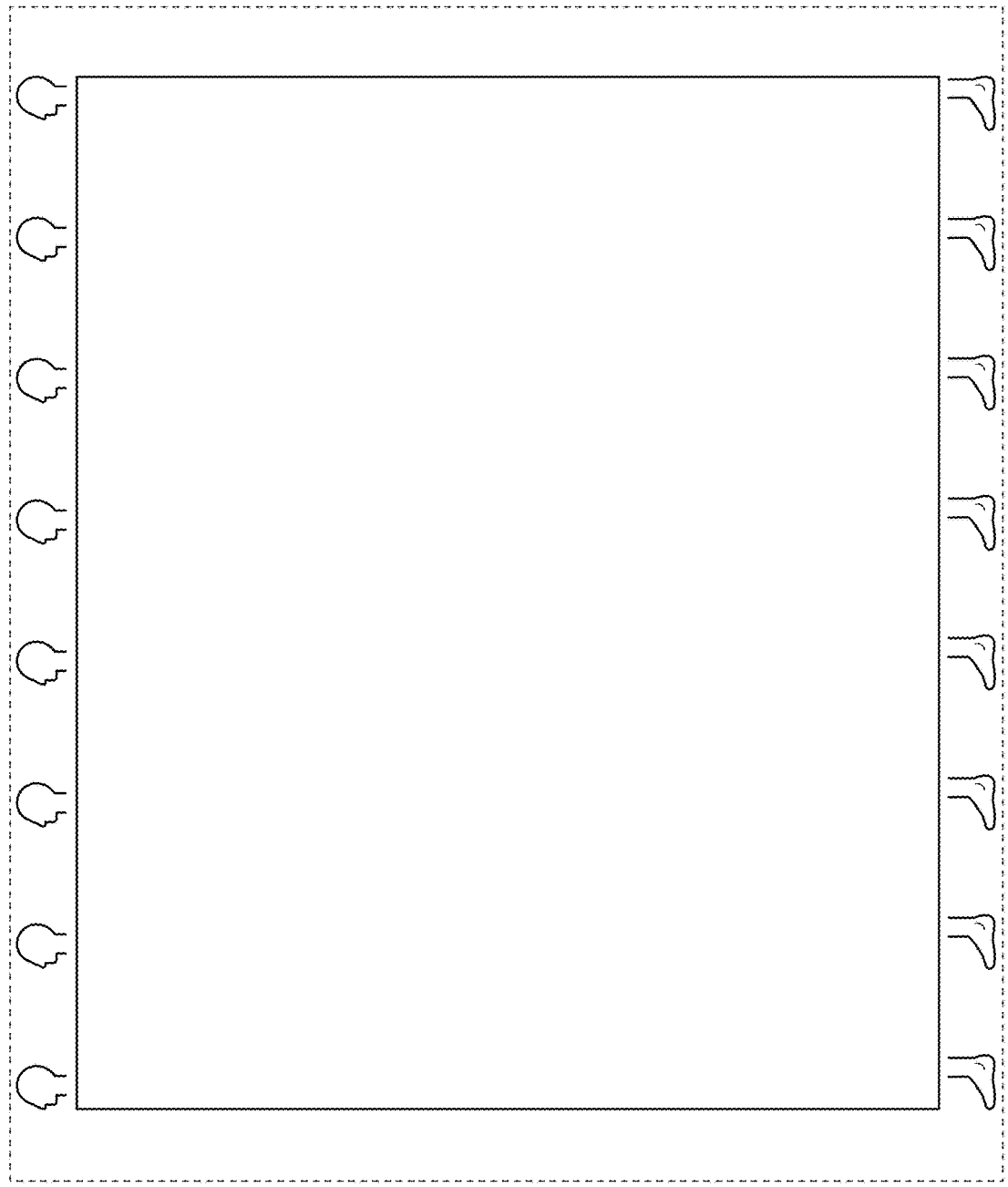
FIG. 60C is a top plan view of the incontinence detection pad, similar to FIG. 60A, showing an outer perimeter of the incontinence detection pad doted out.
Figure 60D:
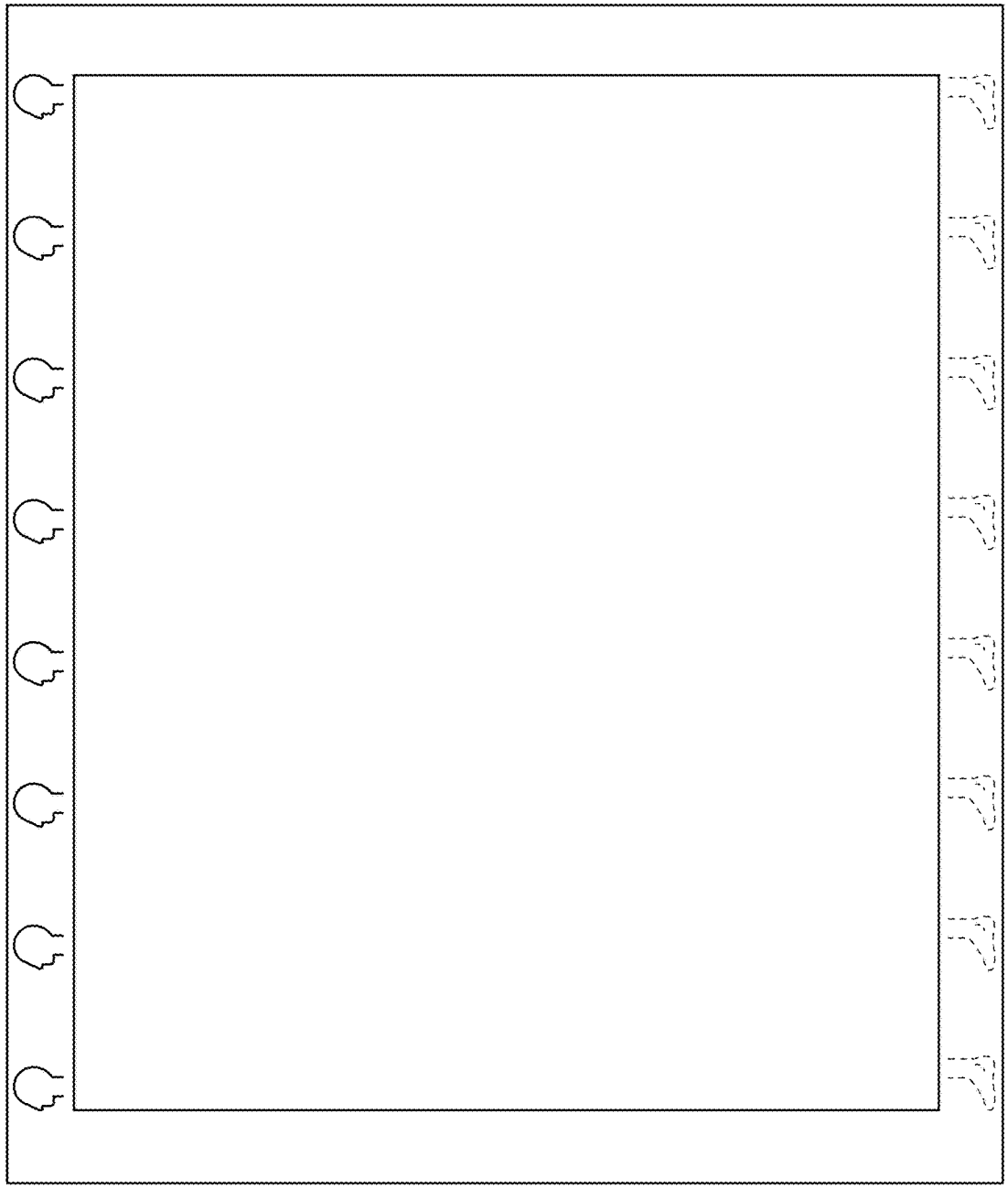
FIG. 60D is a top plan view of the incontinence detection pad, similar to FIG. 60A, showing the series of foot indicia dotted out.
Figure 60E:
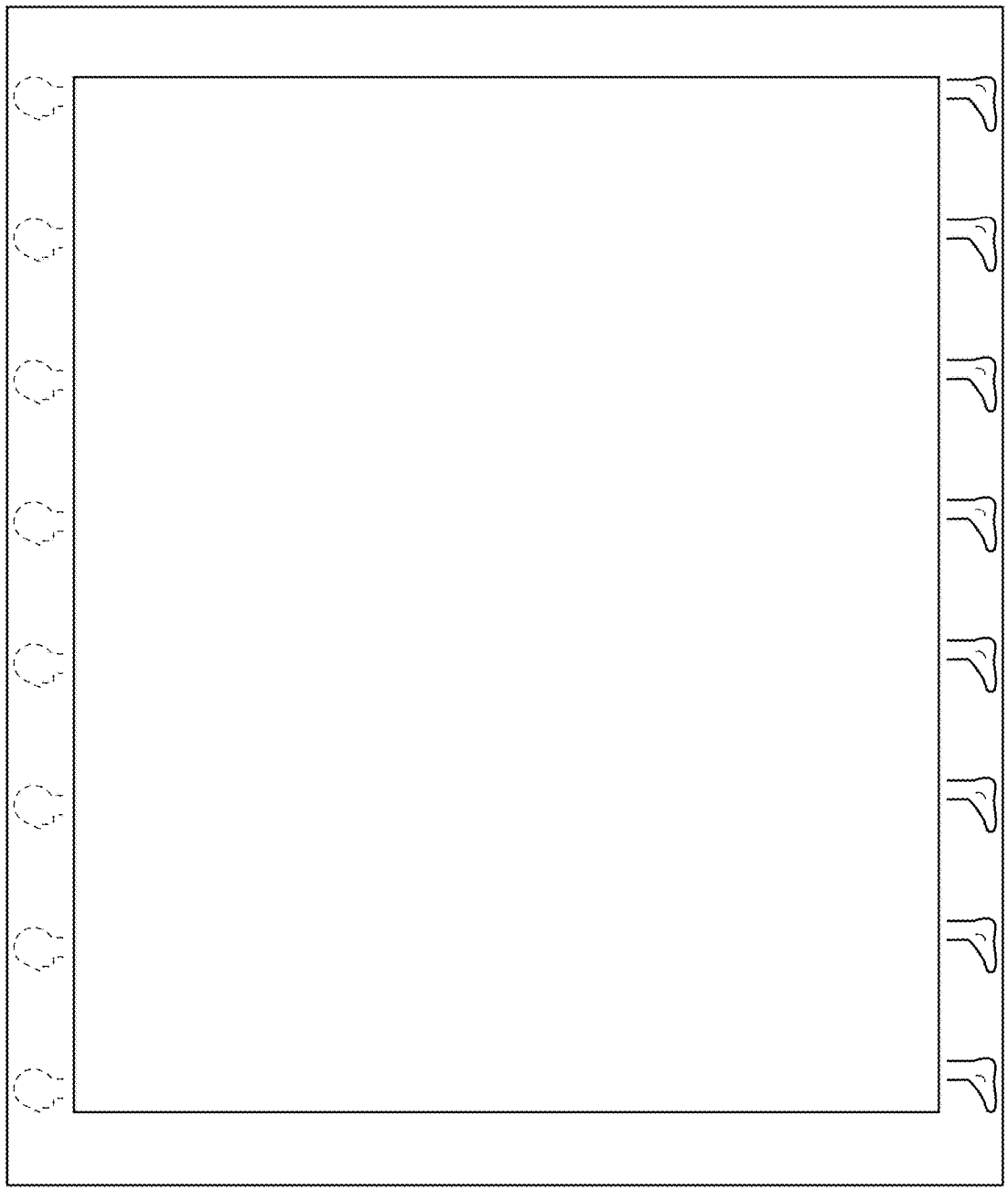
FIG. 60E is a top plan view of the incontinence detection pad, similar to FIG. 60A, showing the series of head indicia dotted out.
Figure 60F:
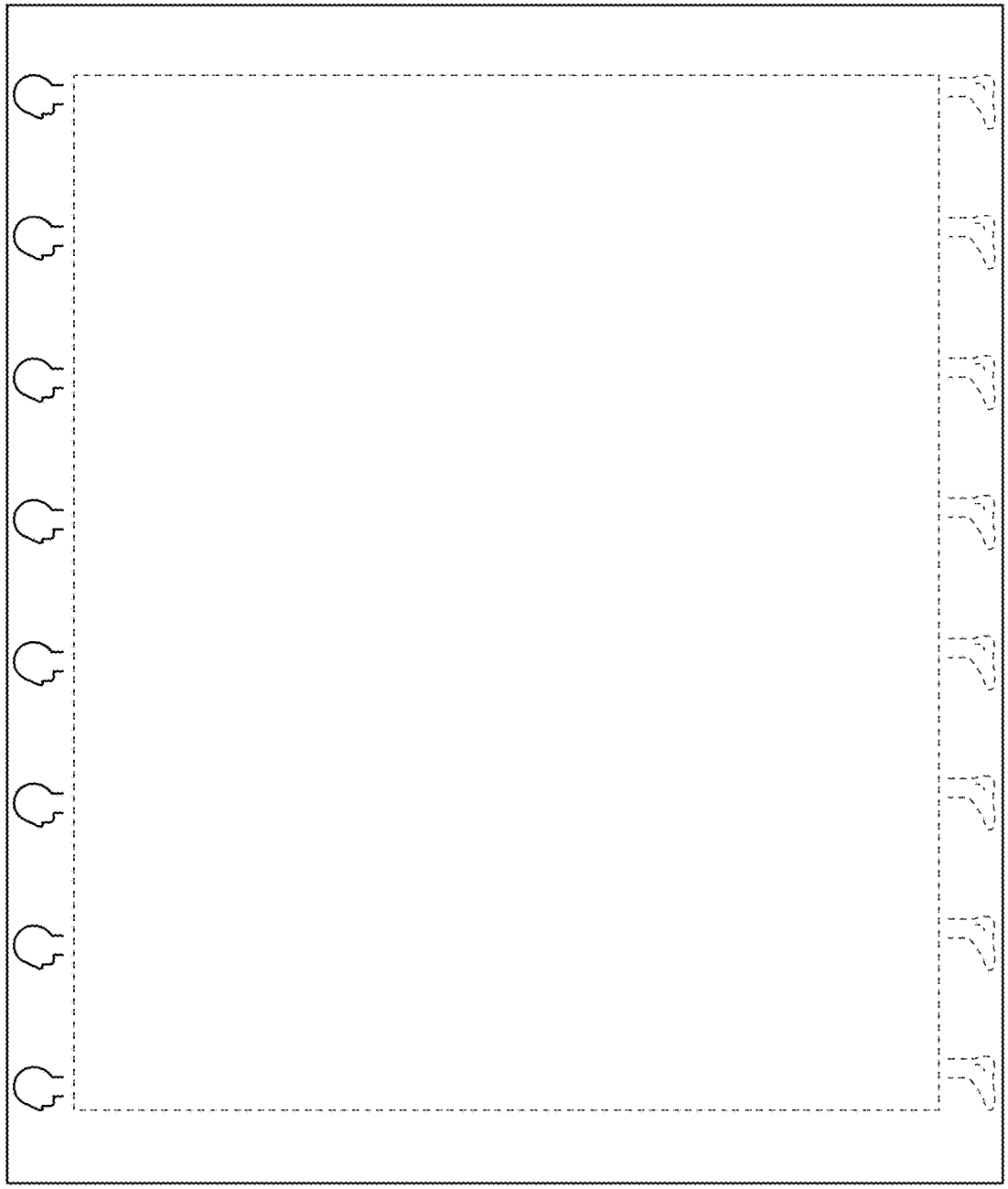
FIG. 60F is a top plan view of the incontinence detection pad, similar to FIG. 60A, showing the substantially rectangular outline of the absorbent core dotted out and showing the series of foot indicia dotted out.
Figure 60G:
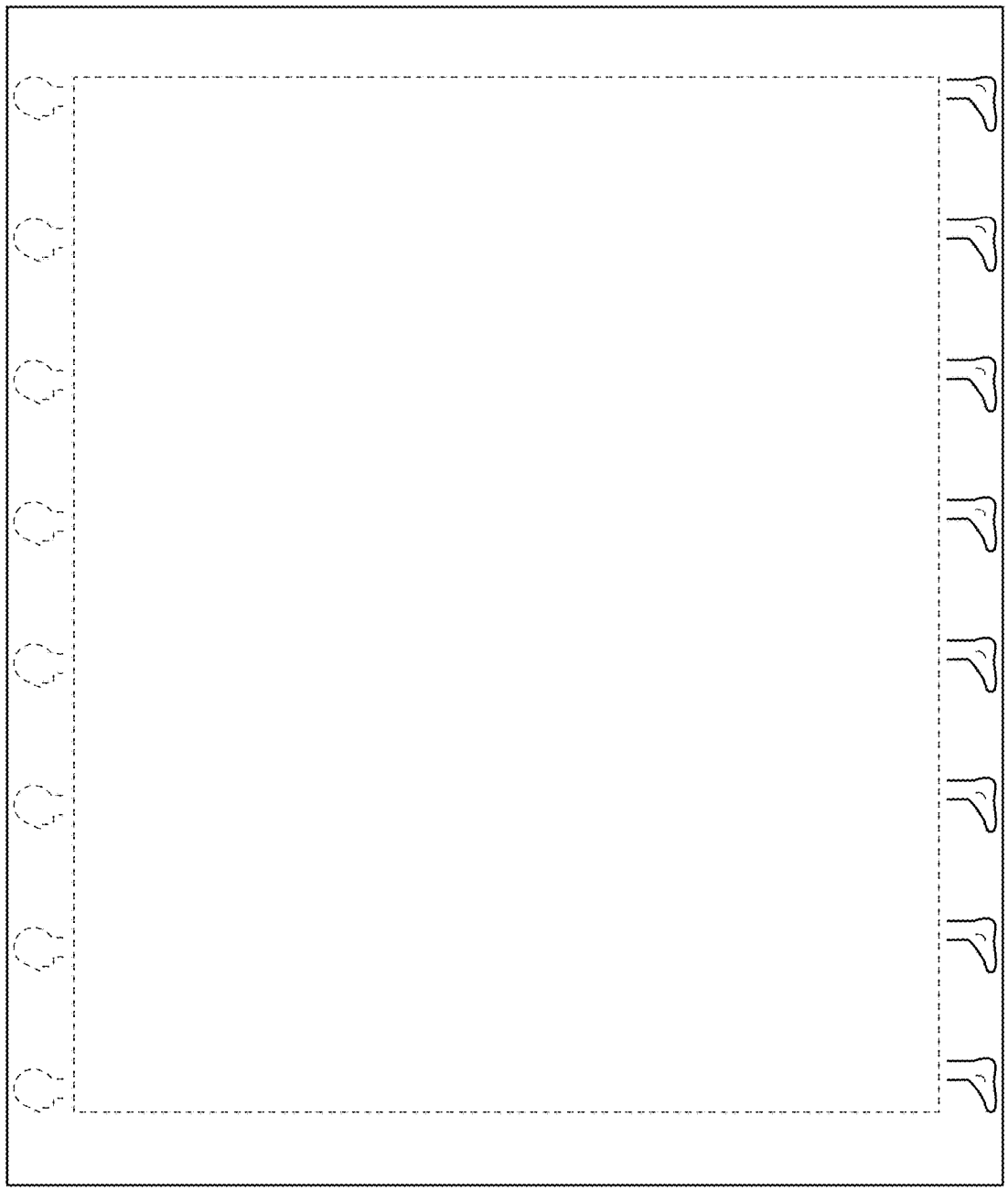
FIG. 60G is a top plan view of the incontinence detection pad, similar to FIG. 60A, showing the substantially rectangular outline of the absorbent core dotted out and showing the series of head indicia dotted out.
Figure 61A:
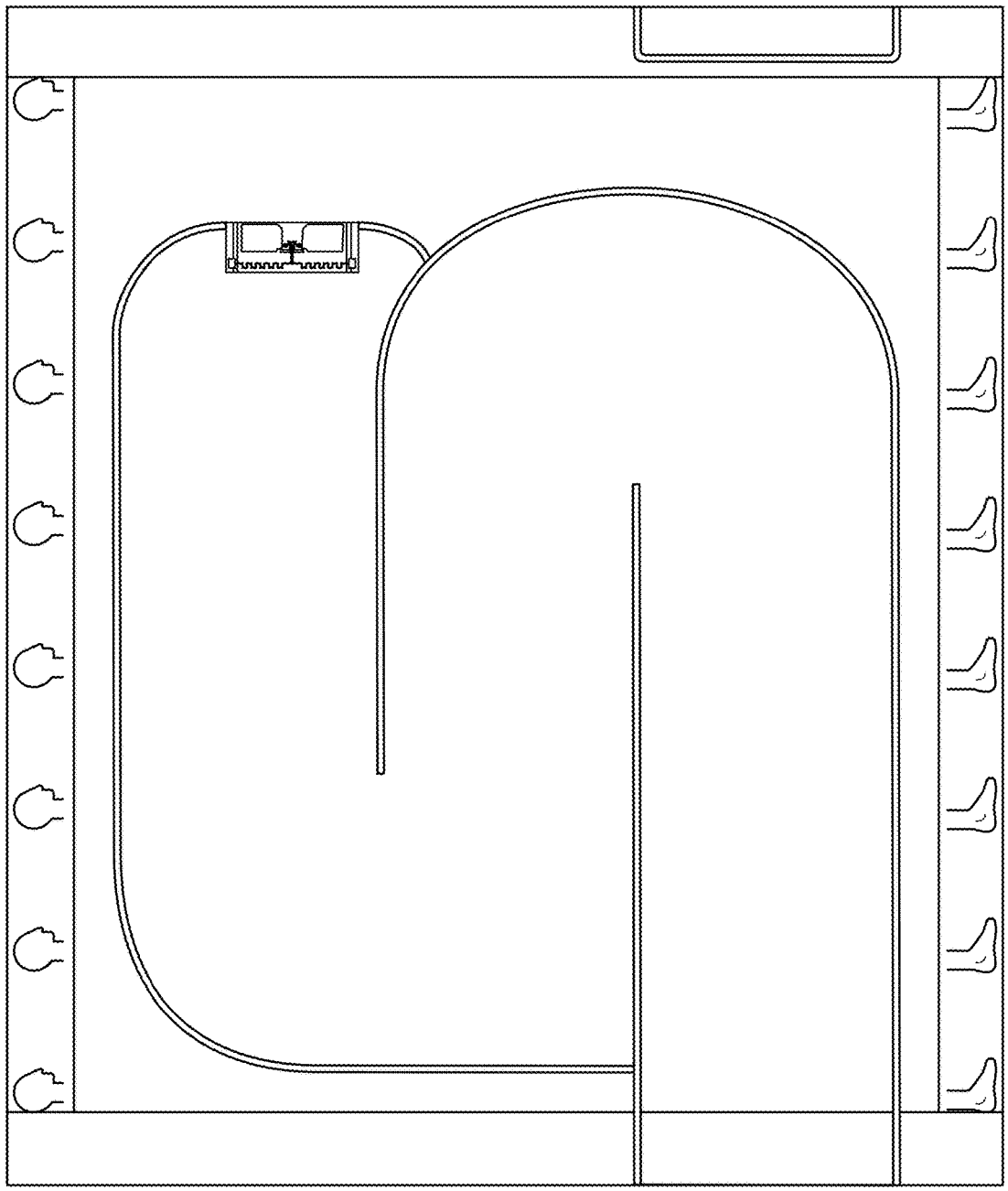
FIG. 61A is a top plan view of the incontinence detection pad, similar to FIG. 59A, but additionally showing the outline of the electrode traces, the RFID tag, the sacrificial trace and end adhesive strips.
Figure 61B:
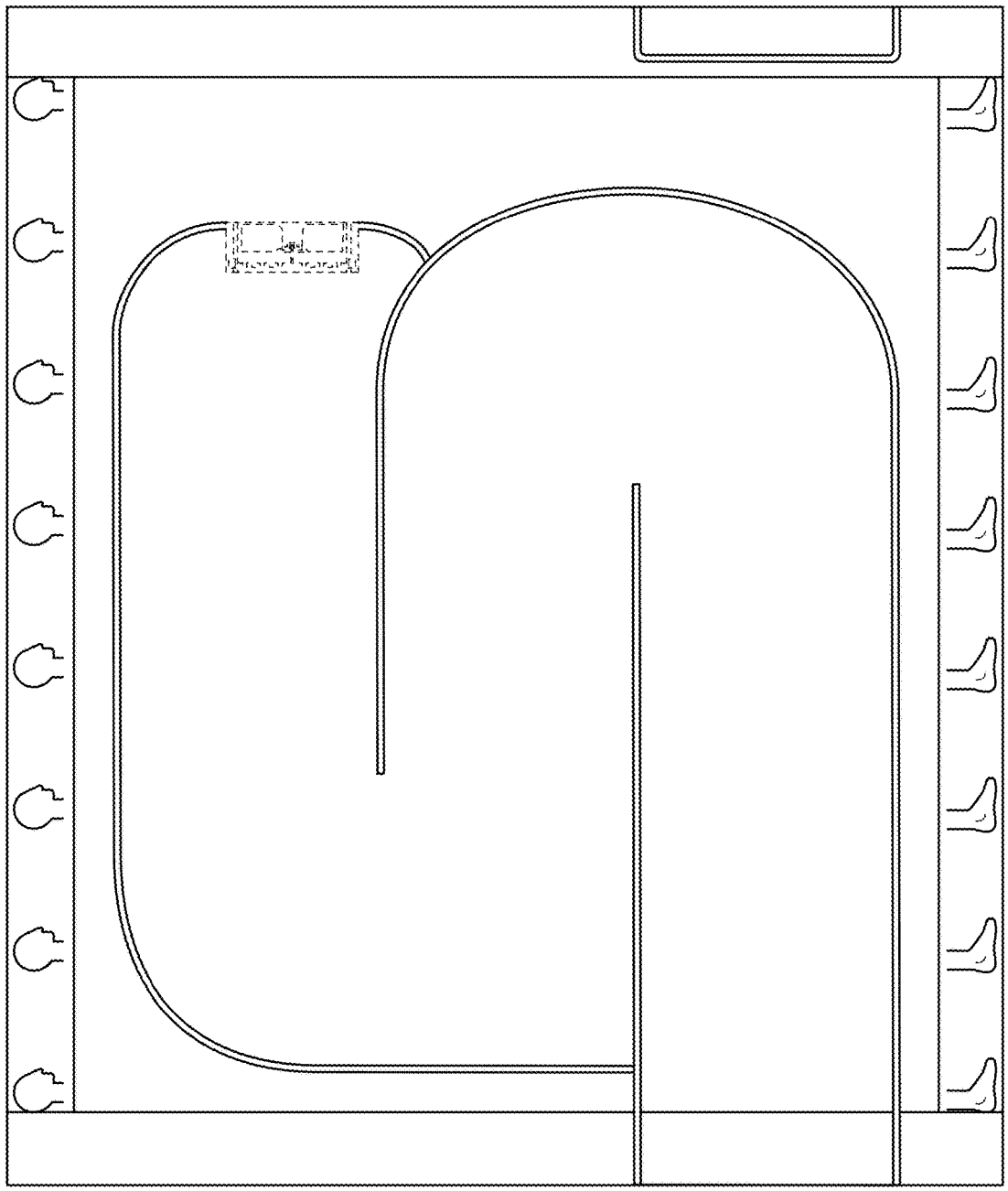
FIG. 61B is a top plan view of the incontinence detection pad, similar to FIG. 61A, showing the RFID tag dotted out.
Figure 61C:
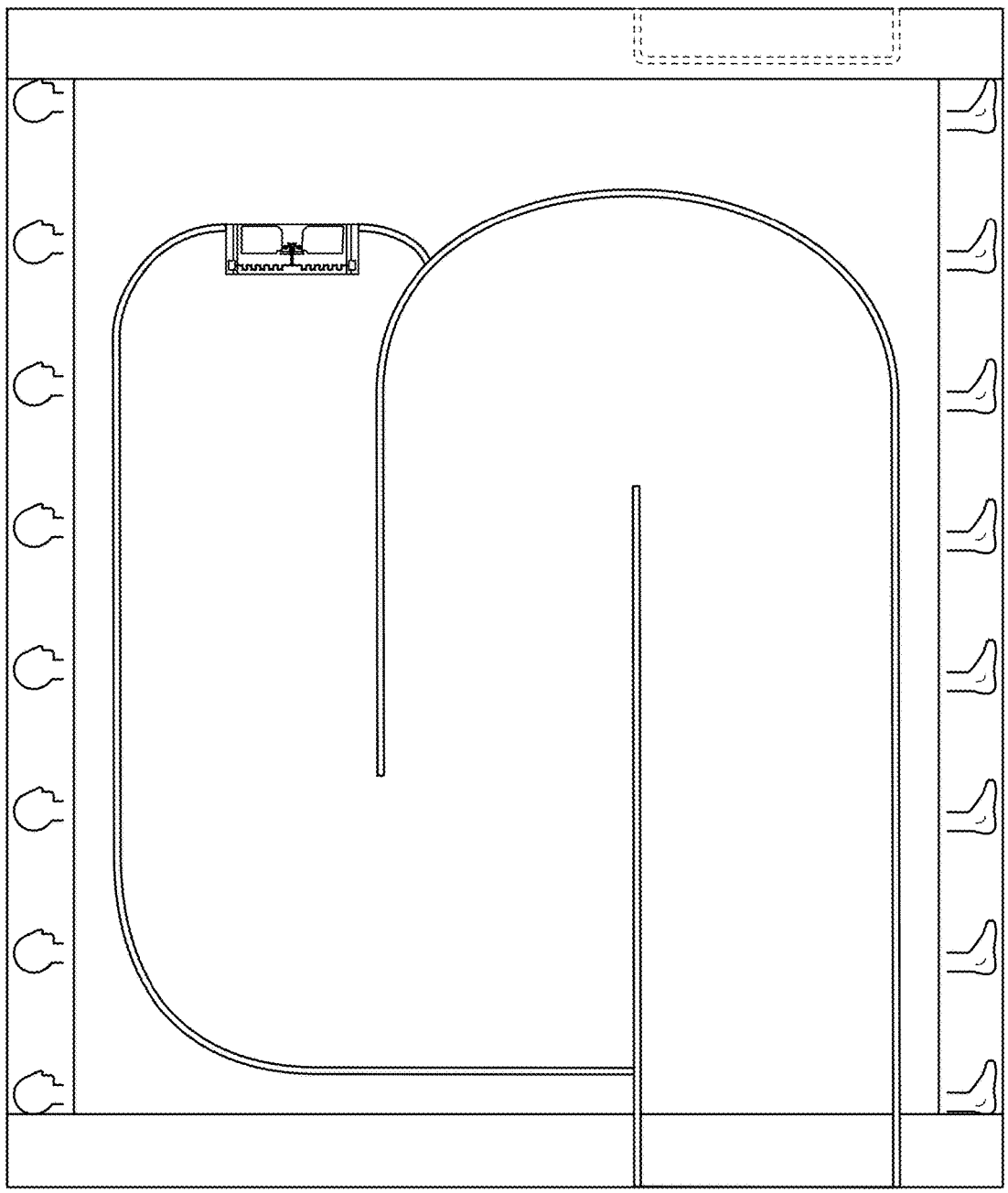
FIG. 61C is a top plan view of the incontinence detection pad, similar to FIG. 61A, showing the sacrificial trace dotted out.
Figure 61D:
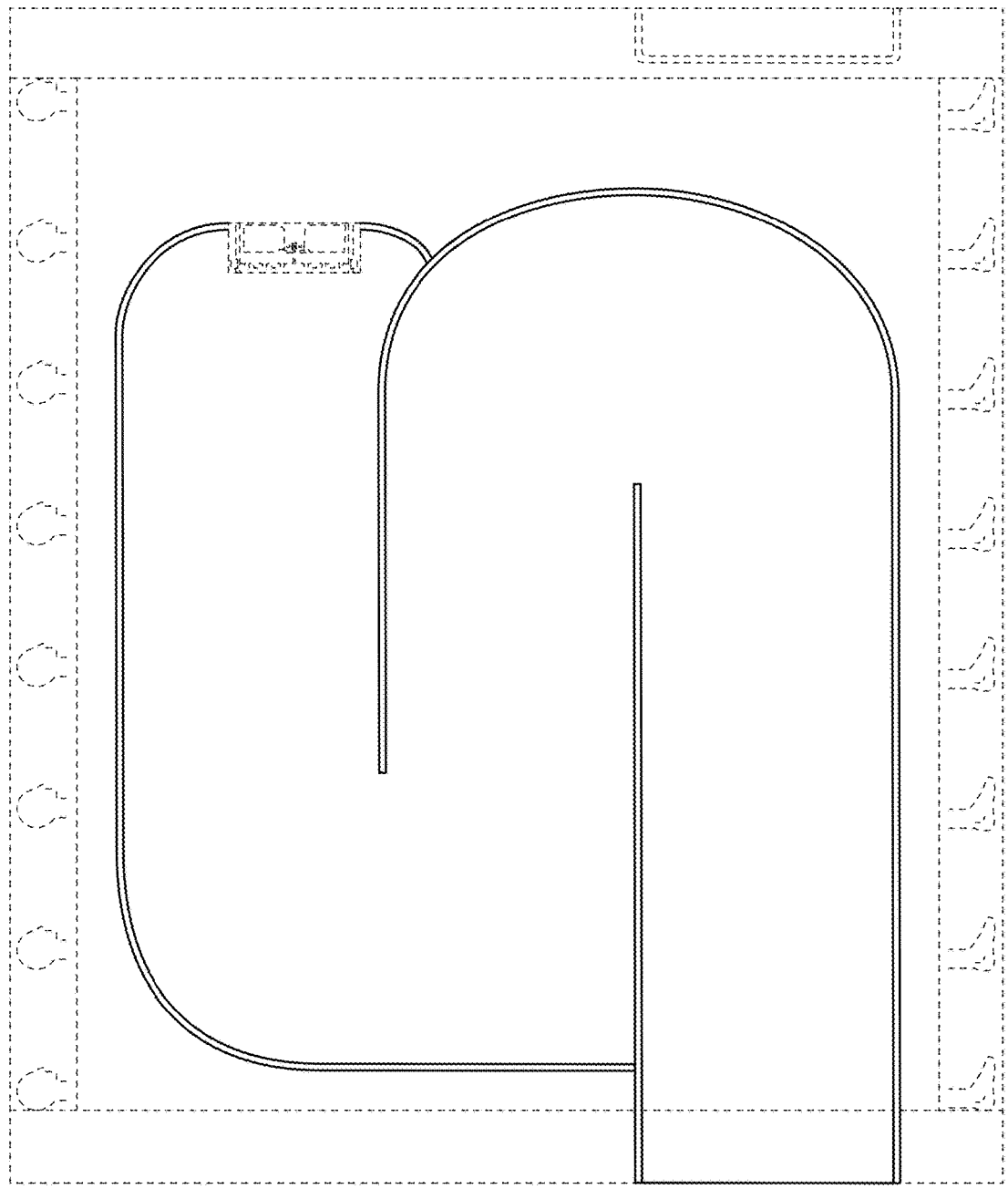
FIG. 61D is a top plan view of the incontinence detection pad, similar to FIG. 61A, showing the electrode traces in solid and everything else dotted out.
Figure 61E:
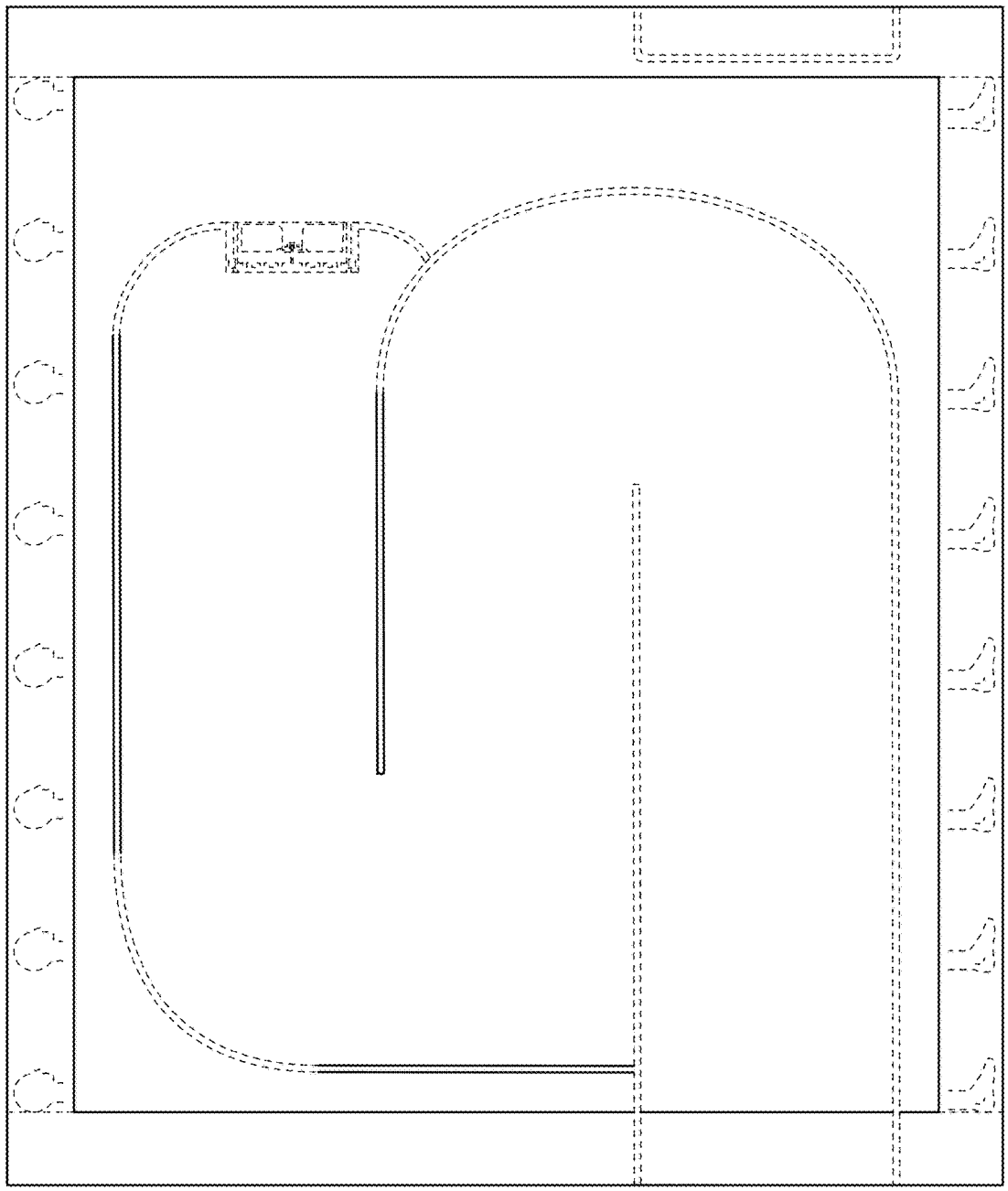
FIG. 61E is a top plan view of the incontinence detection pad, similar to FIG. 61A, showing the RFID tag, the sacrificial trace, the head and foot indicia, and portions of the electrode traces dotted out.
Figure 62A:
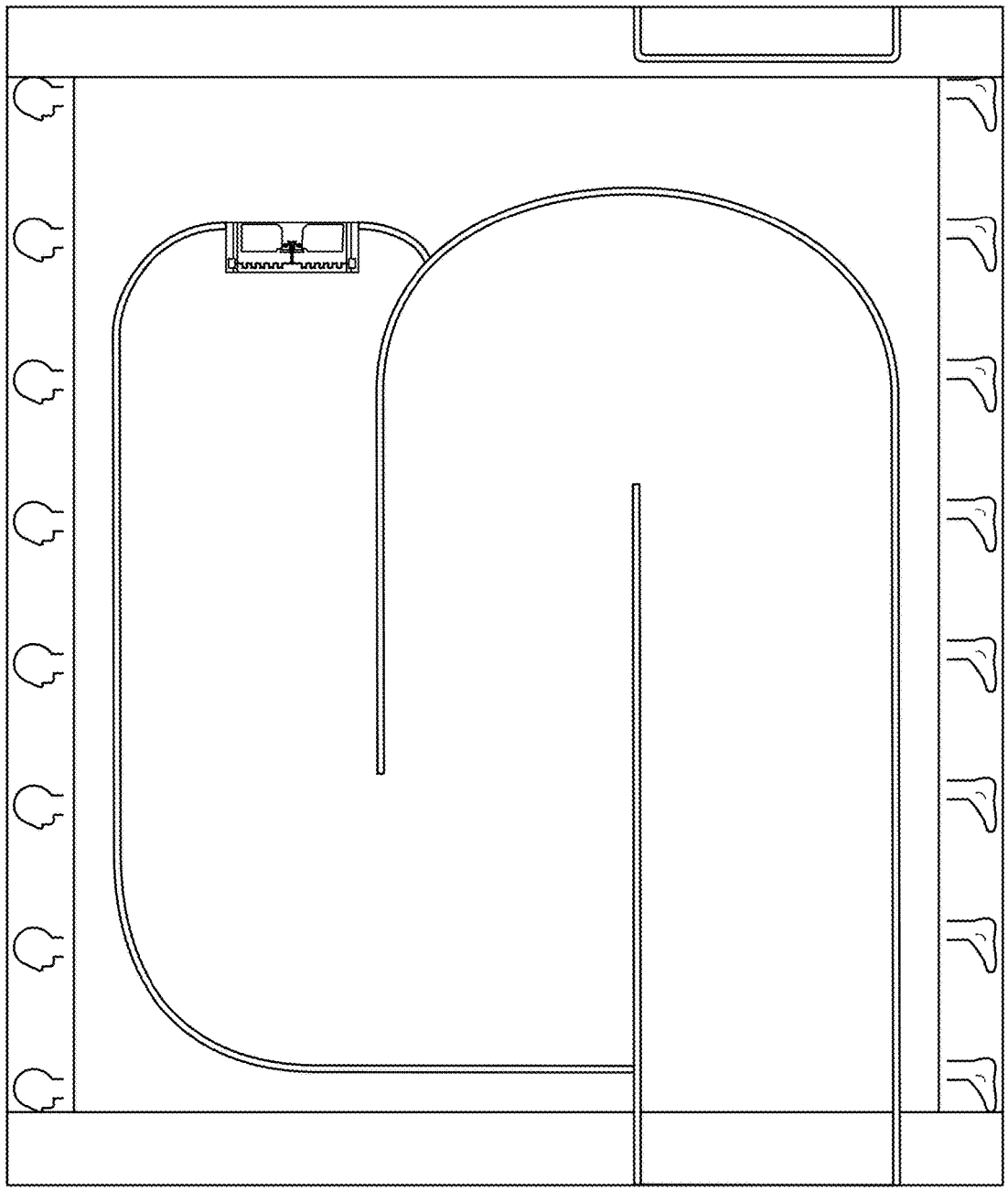
FIG. 62A is a top plan view of the incontinence detection pad, similar to FIG. 61A, but showing the head indicia and foot indicia facing to the left instead of to the right.
Figure 62B:
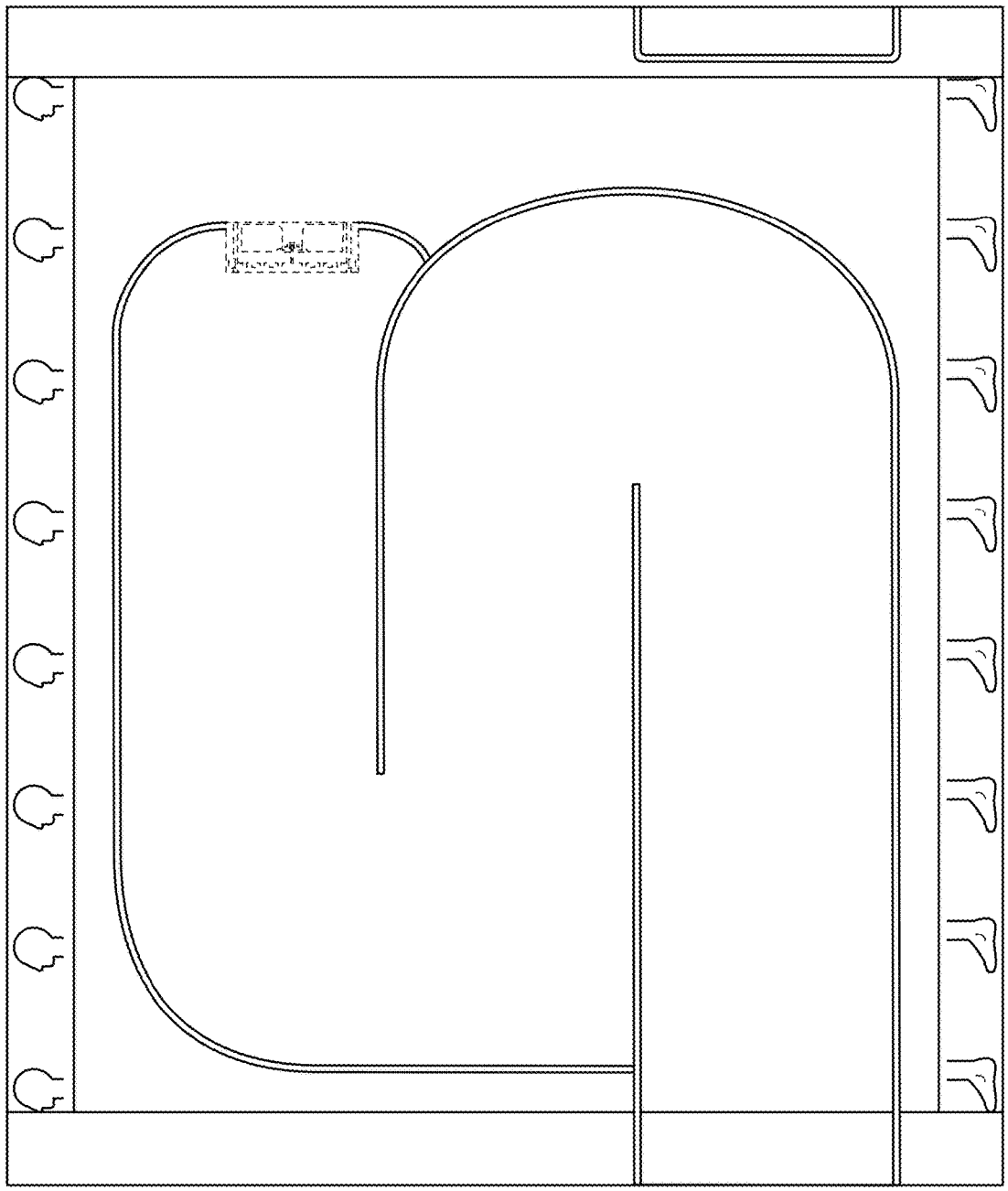
FIG. 62B is a top plan view of the incontinence detection pad, similar to FIG. 62A, showing the RFID tag dotted out.
Figure 62C:
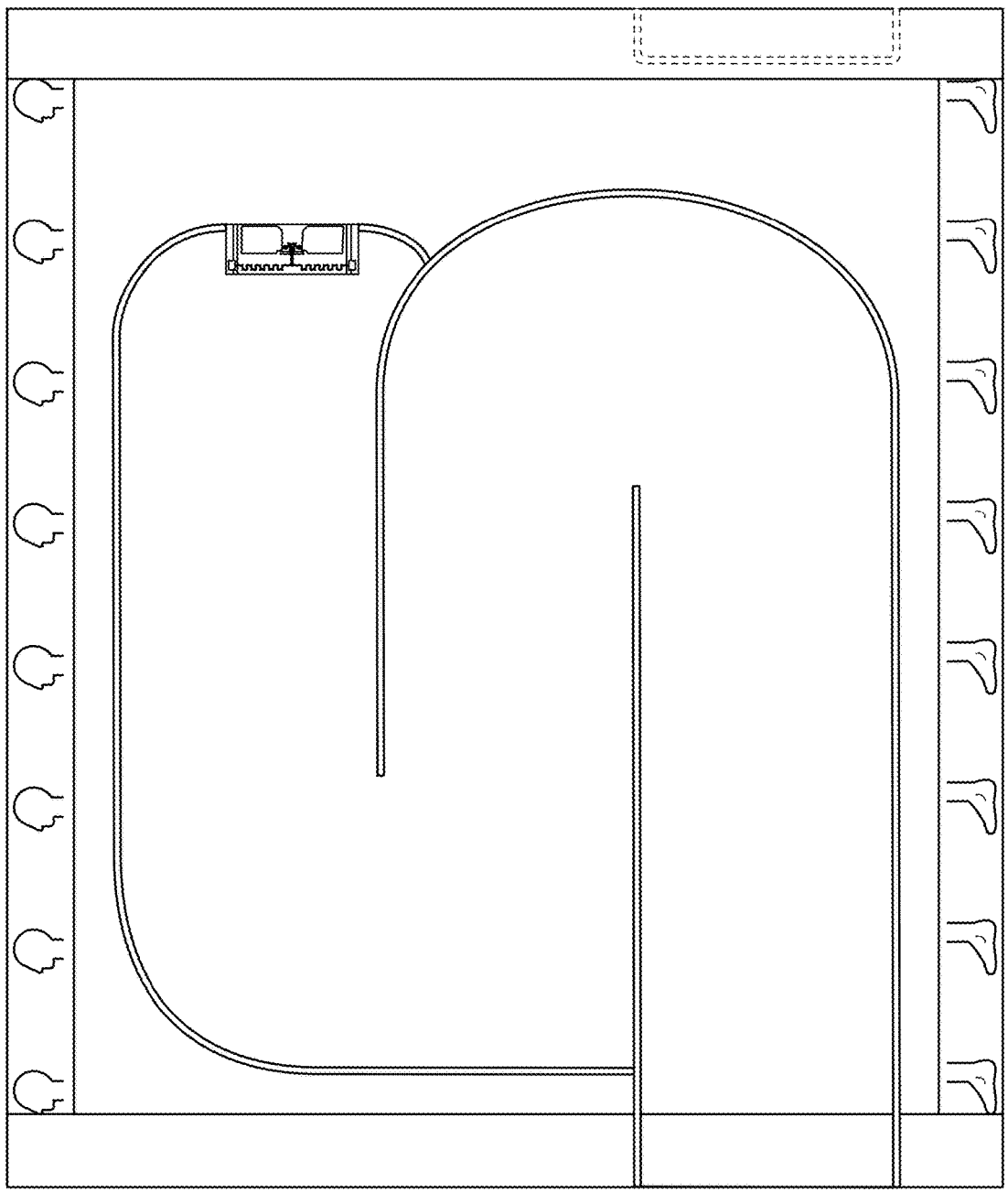
FIG. 62C is a top plan view of the incontinence detection pad, similar to FIG. 62A, showing the sacrificial trace dotted out.
Figure 62D:
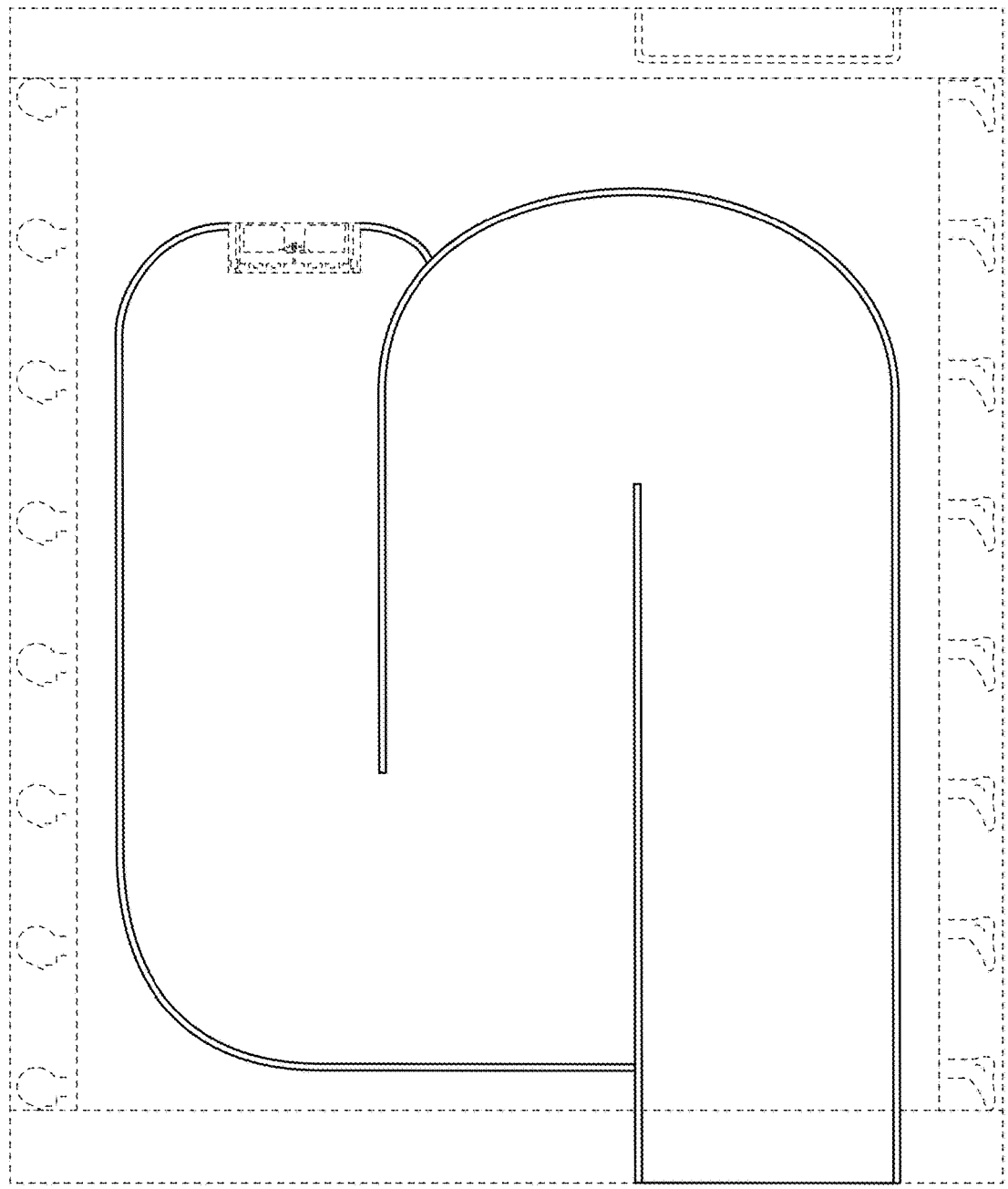
FIG. 62D is a top plan view of the incontinence detection pad, similar to FIG. 62A, showing the electrode traces in solid and everything else dotted out.
Figure 63A:
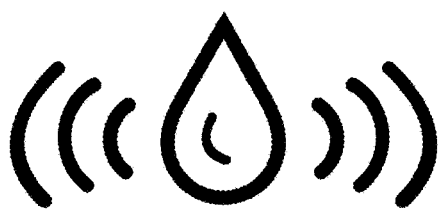
FIG. 63A is a front view of a first style of a water droplet icon.
Figure 63B:
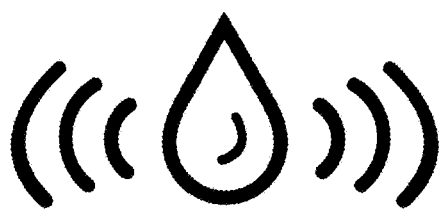
FIG. 63B is a front view of the first style of water droplet icon but showing a shading curve inside the water droplet on the right instead of the left.
Figure 63C:
FIG. 63C is a front view of the first style of water droplet icon of FIG. 63A showing curved lines outside the water droplet to the left and to the right dotted out.
Figure 63D:
FIG. 63D is a front view of the first style of water droplet icon of FIG. 63B showing curved lines outside the water droplet to the left and to the right dotted out.
Figure 64A:
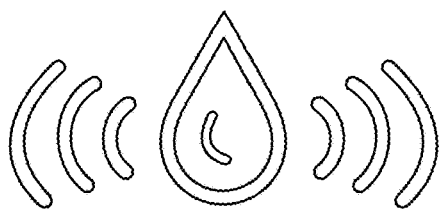
FIG. 64A is a front view of a second style of a water droplet icon.
Figure 64B:
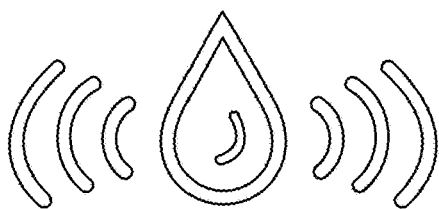
FIG. 64B is a front view of the second style of water droplet icon but showing a shading curve inside the water droplet on the right instead of the left.
Figure 64C:
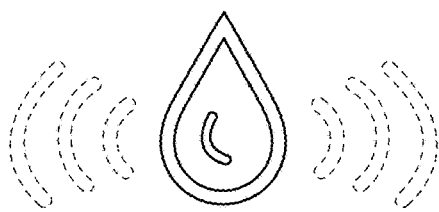
FIG. 64C is a front view of the second style of water droplet icon of FIG. 64A showing curved lines outside the water droplet to the left and to the right dotted out.
Figure 64D:
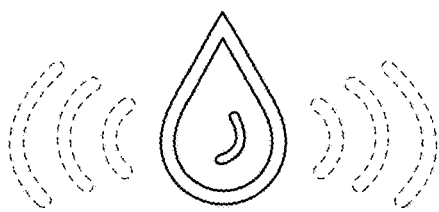
FIG. 64D is a front view of the second style of water droplet icon of FIG. 64B showing curved lines outside the water droplet to the left and to the right dotted out.
Figure 65A:
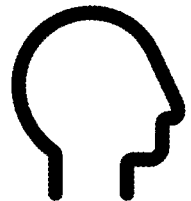
FIG. 65A is a front view of a first style of one of the head indicia of FIGS. 59A and 61A.
Figure 65B:
FIG. 65B is a front view, similar to FIG. 65A, but showing the first style of the head indicia facing left instead of right.
Figure 66A:
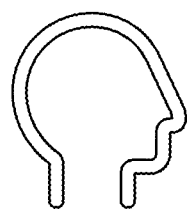
FIG. 66A is a front view of a second style of one of the head indicia of FIGS. 59A and 61A.
Figure 66B:
FIG. 66B is a front view, similar to FIG. 66A, but showing the second style of the head indicia facing left instead of right.
Figure 67A:
FIG. 67A is a front view of a first style of one of the foot indicia of FIGS. 59A and 61A.
Figure 67B:
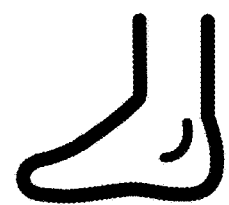
FIG. 67B is a front view, similar to FIG. 67A, but showing the first style of the foot indicia facing left instead of right.
Figure 67C:
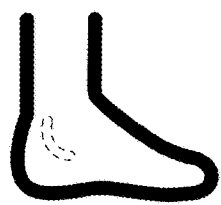
FIG. 67C is a front view, similar to FIG. 67A, but showing an ankle curve dotted out.
Figure 67D:
FIG. 67D is a front view, similar to FIG. 67B, but showing an ankle curve dotted out.
Figure 68A:
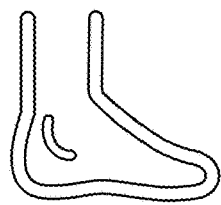
FIG. 68A is a front view of a second style of one of the foot indicia of FIGS. 59A and 61A.
Figure 68B:
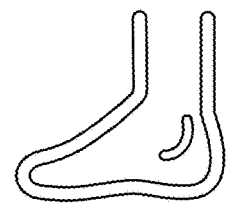
FIG. 68B is a front view, similar to FIG. 68A, but showing the second style of the foot indicia facing left instead of right.
Figure 68C:
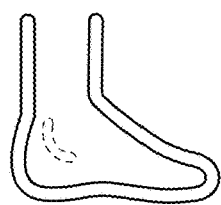
FIG. 68C is a front view, similar to FIG. 68A, but showing an ankle curve dotted out.
Figure 68D:
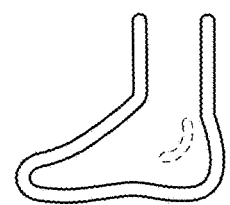
FIG. 68D is a front view, similar to FIG. 68B, but showing an ankle curve dotted out.
Figure 69A:
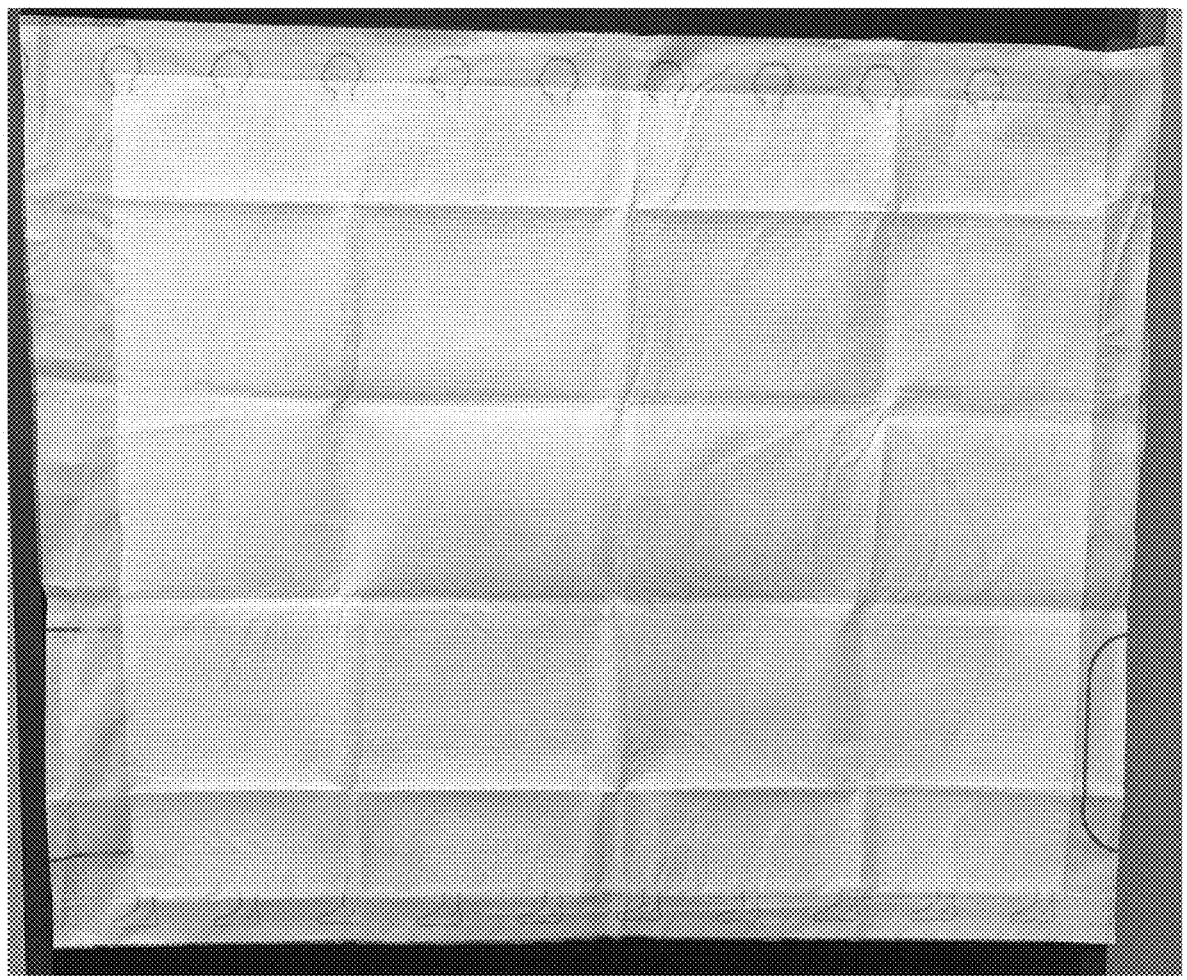
FIG. 69A is a digital photo of a top plan view of an incontinence detection pad.
Figure 69B:
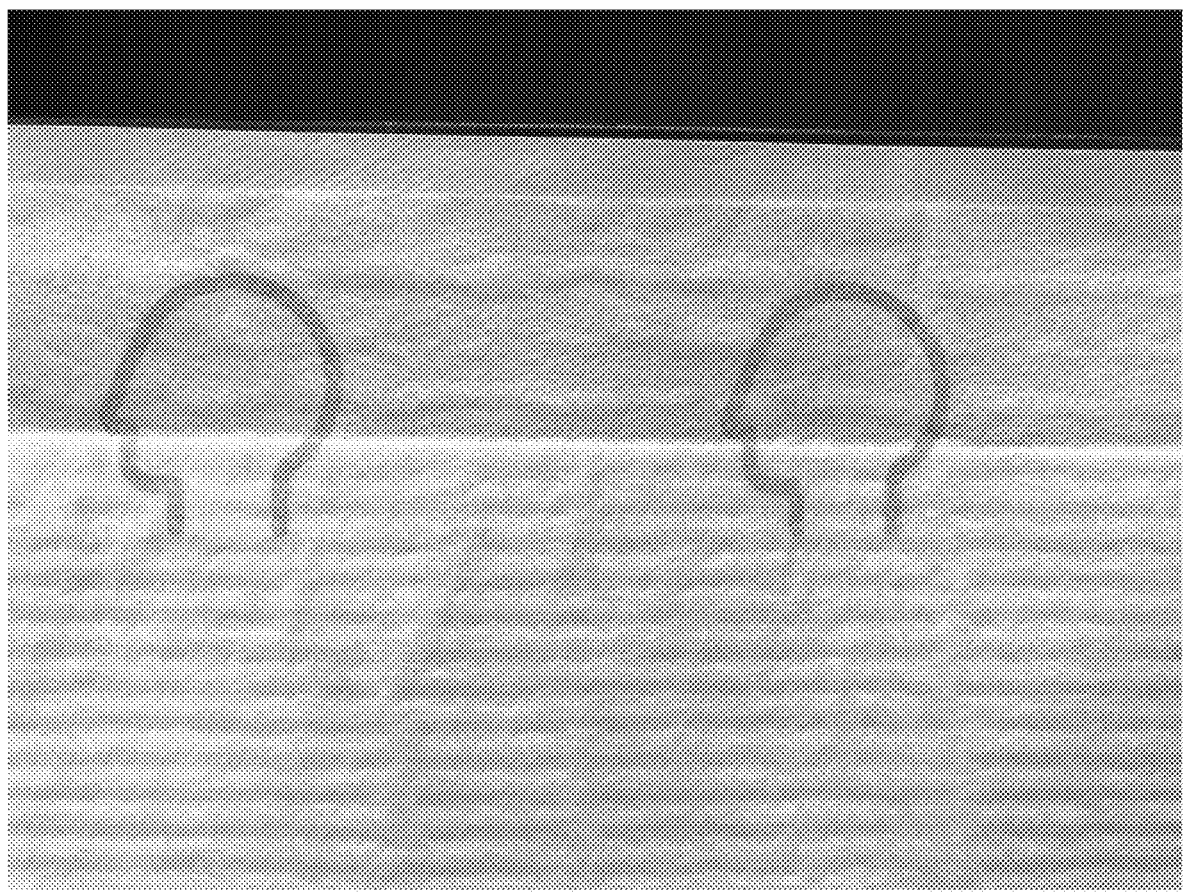
FIG. 69B is a digital photo of a portion of the incontinence detection pad of FIG. 69A showing head indicia.
Figure 69C:
FIG. 69C is a digital photo of a portion of the incontinence detection pad of FIG. 69A showing a sacrificial trace to the right in the photo and a series of foot indicia at a bottom of the photo.
Figure 69D:
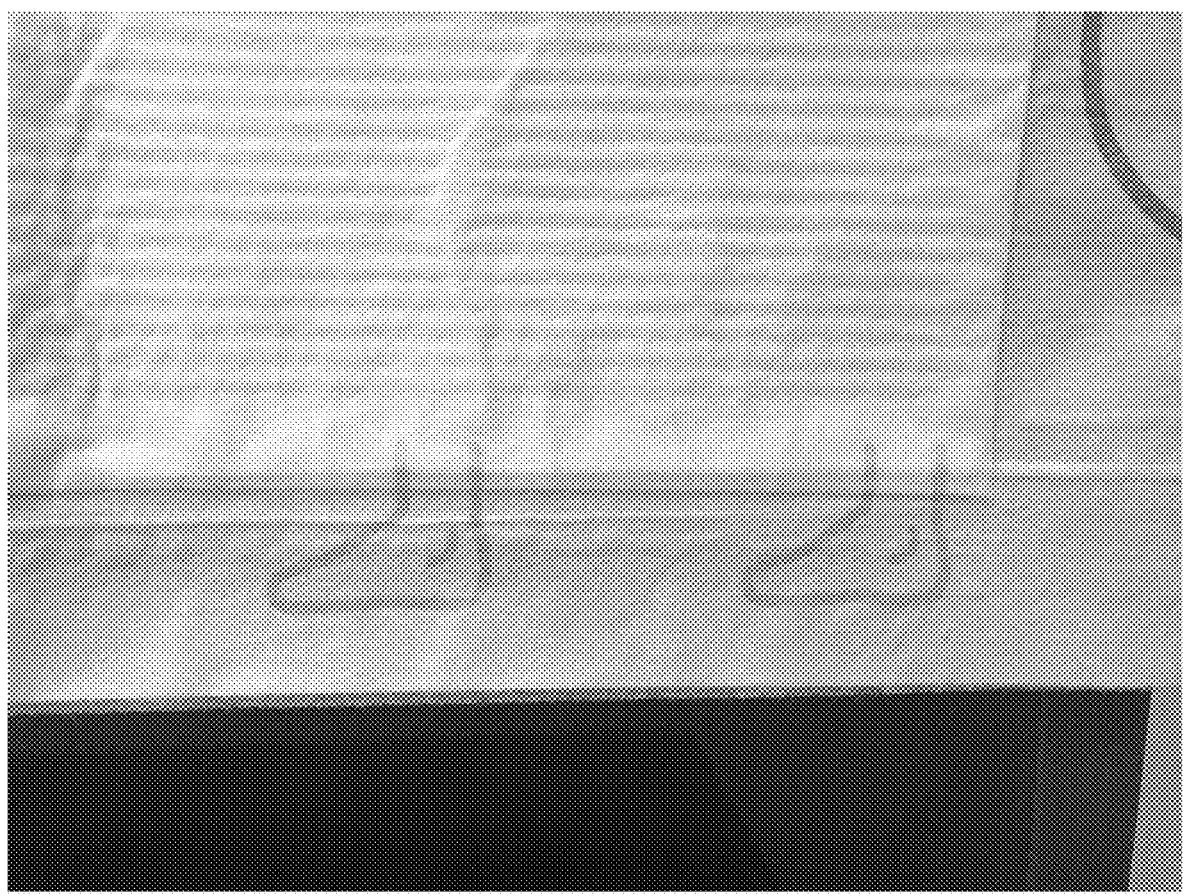
FIG. 69D is a digital photo of a portion of the incontinence detection pad of FIG. 69A showing a pair of foot inidicia.
Figure 69E:
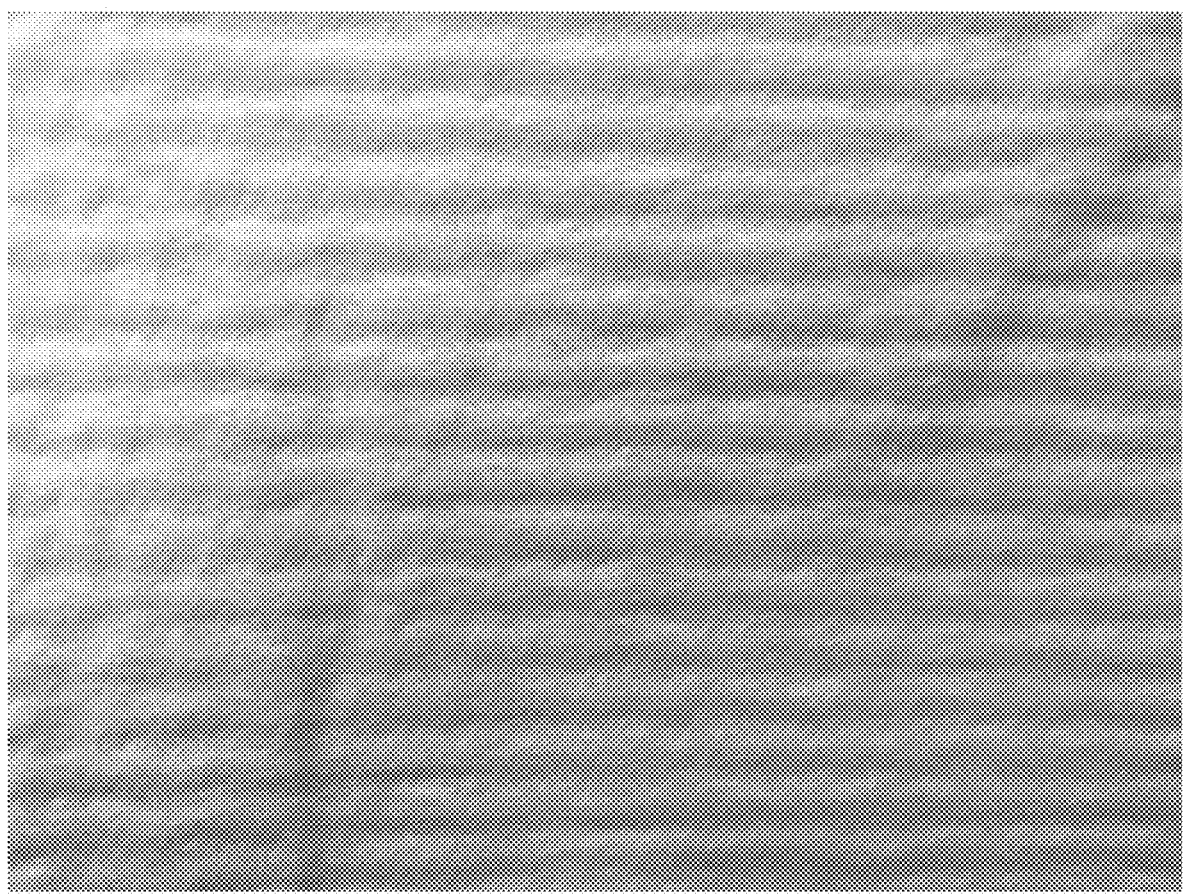
FIG. 69E is a digital photo of a portion of the incontinence detection pad of FIG. 69A showing a close up of a ridge pattern of an upper surface of the incontinence detection pad.
Figure 69F:
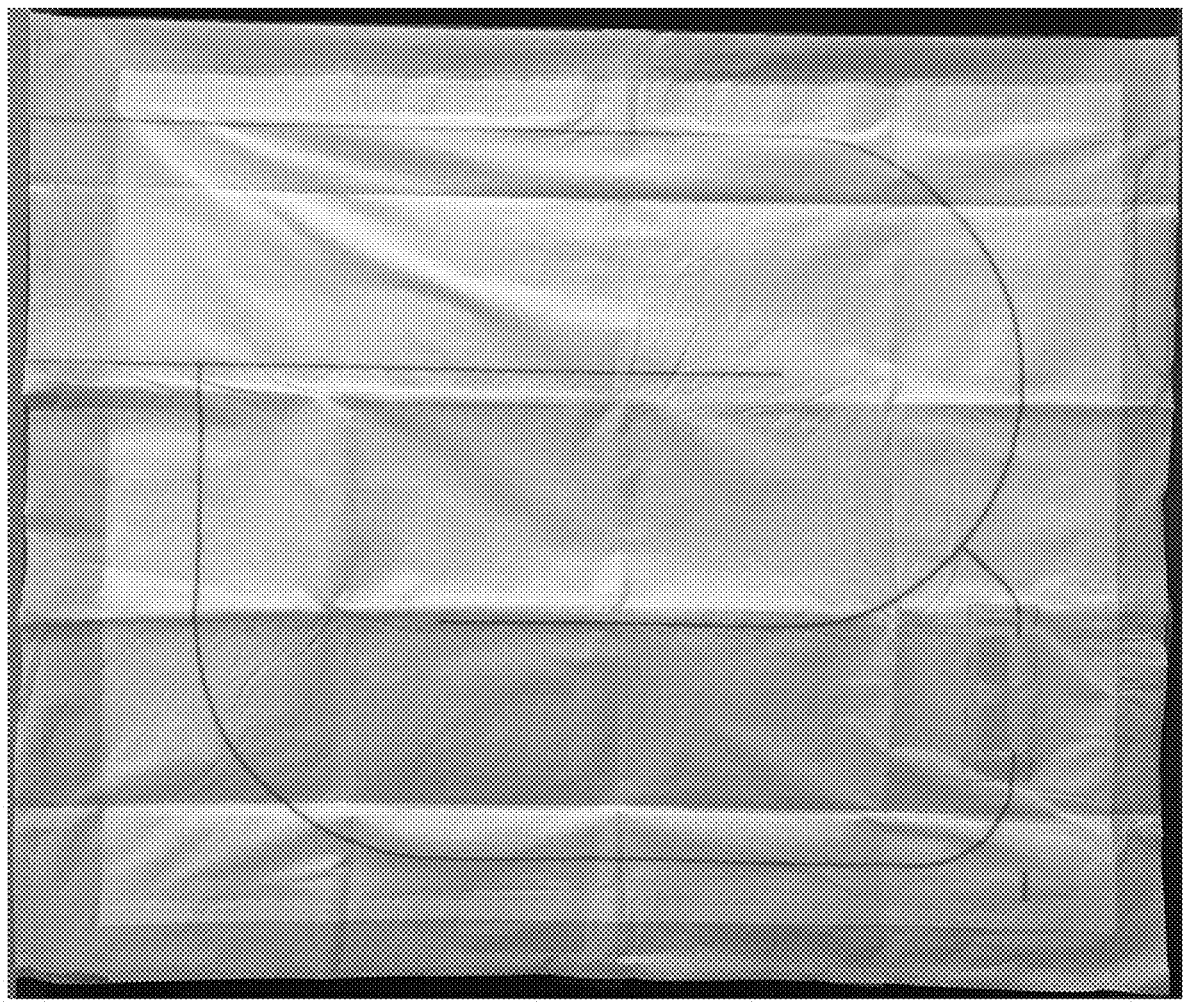
Figure 69G:
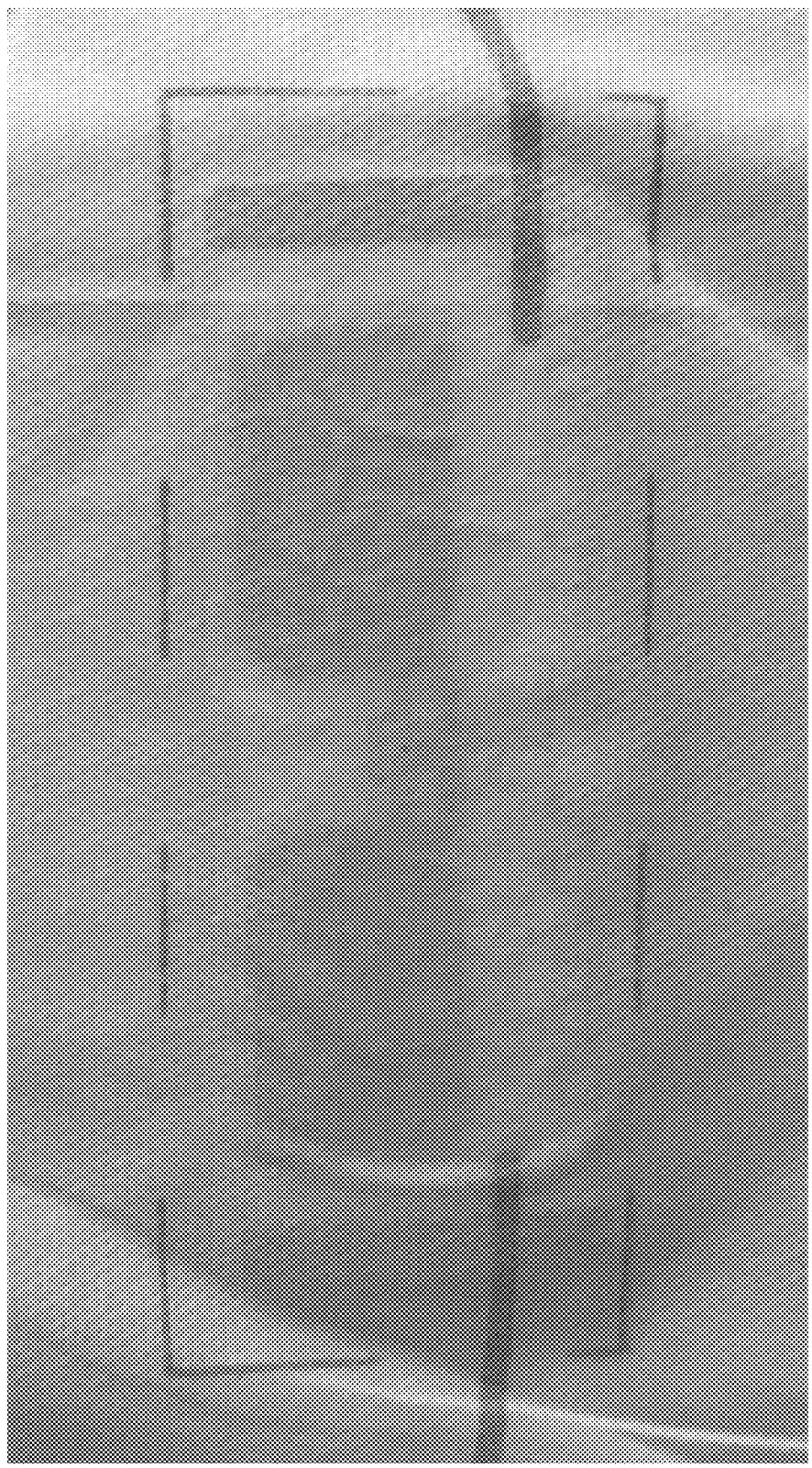
Figure 69H:
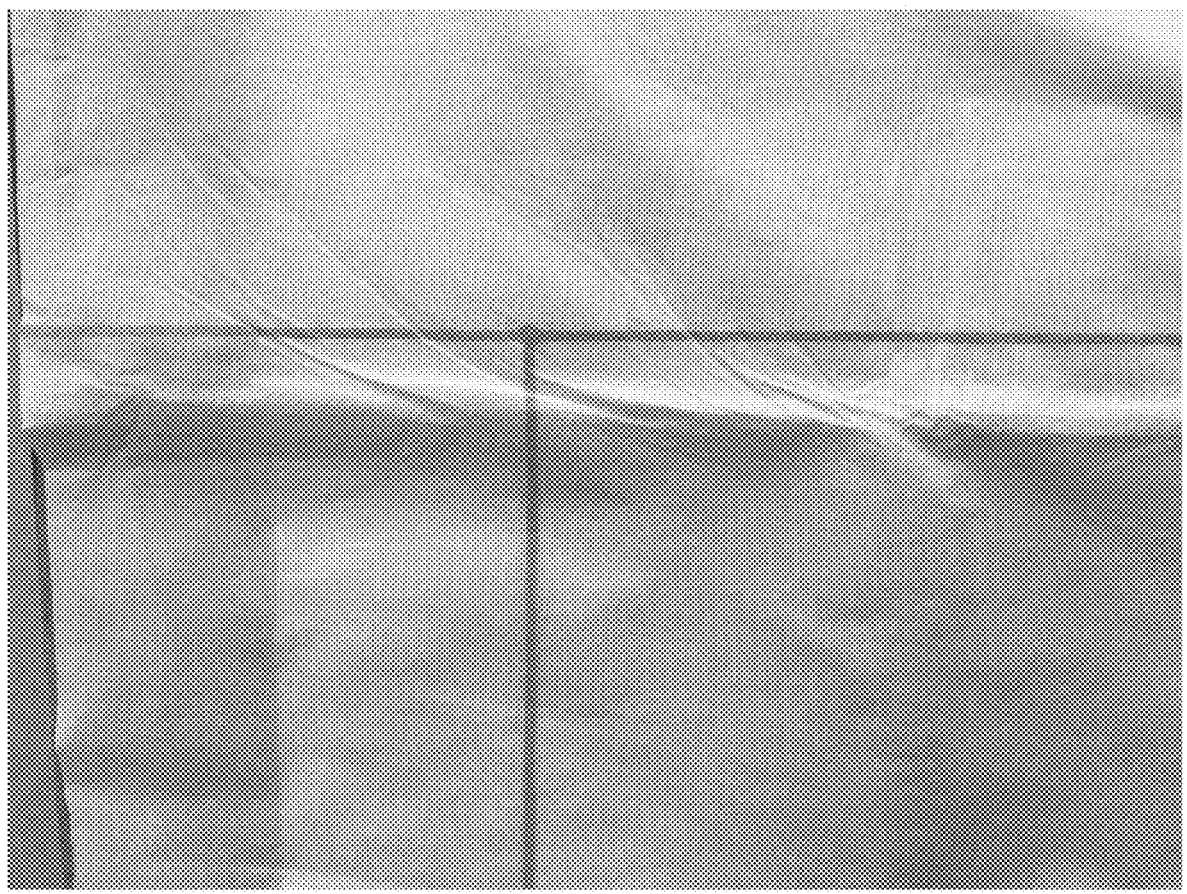
Figure 69I:
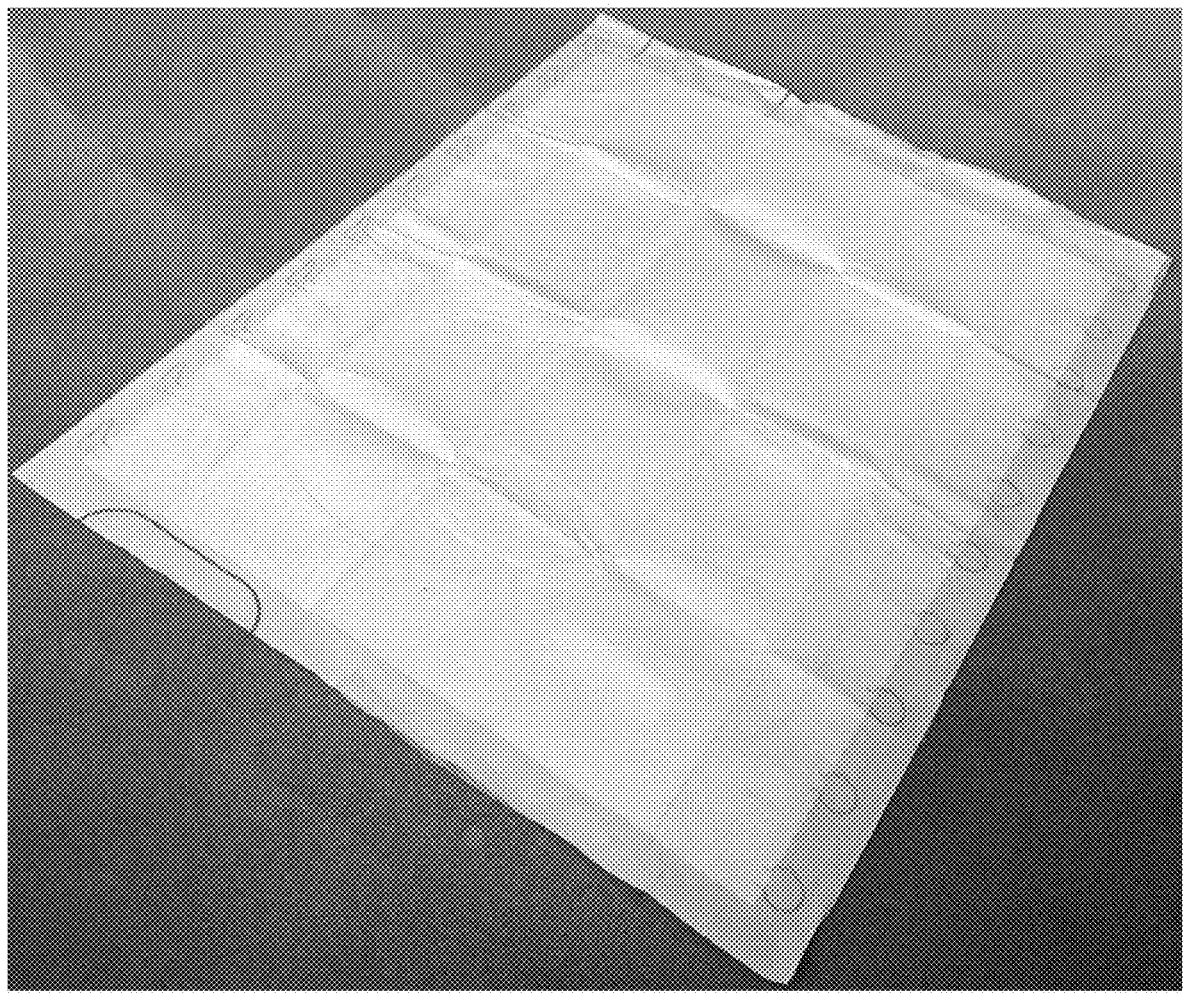
Figure 69J:
Figure 69K:
Figure 69L:
Figure 70:
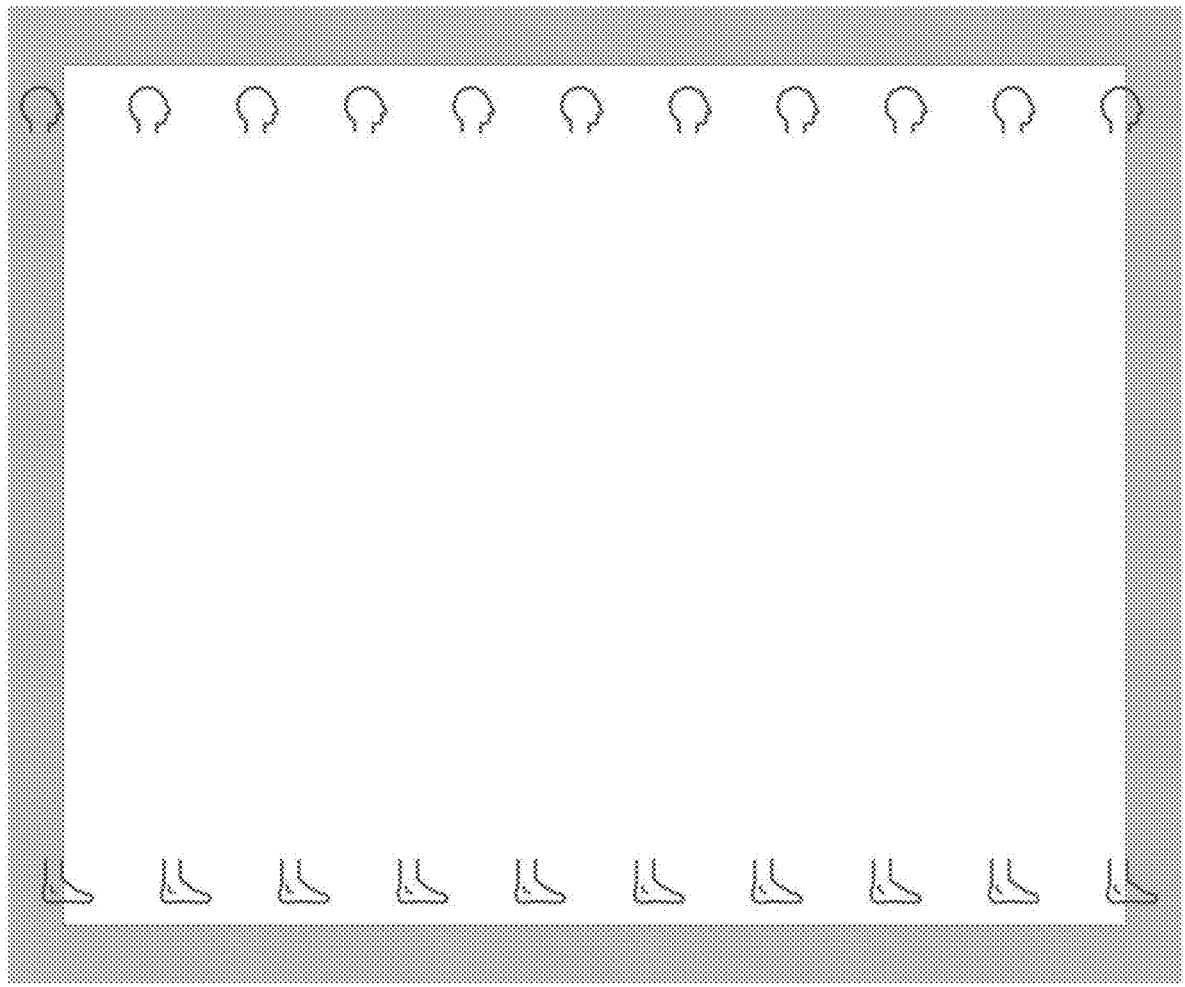

As shown in FIG. 58, foam tag cover 3170 is attached to RFID tag with layer 3172 of hot melt adhesive. As also shown in FIG. 58, RFID tag 1512 includes a tag inlay film 3272 over antenna and electrical contact inlay 3250, patches 3274 of conductive adhesive beneath ends of inlay 3250, and a layer of nonconductive adhesive 3276 in the central region of inlay 3250 The patches 3274 of conductive adhesive are larger than electrical contacts 3258, 3260 and it is these larger patches 3274 that electrically couple to electrodes 3102, 3104 of backsheet 3100 of pad 1510. This can be seen in the digital photos of FIGS. 69F and 69G, for example.

Figure 43:
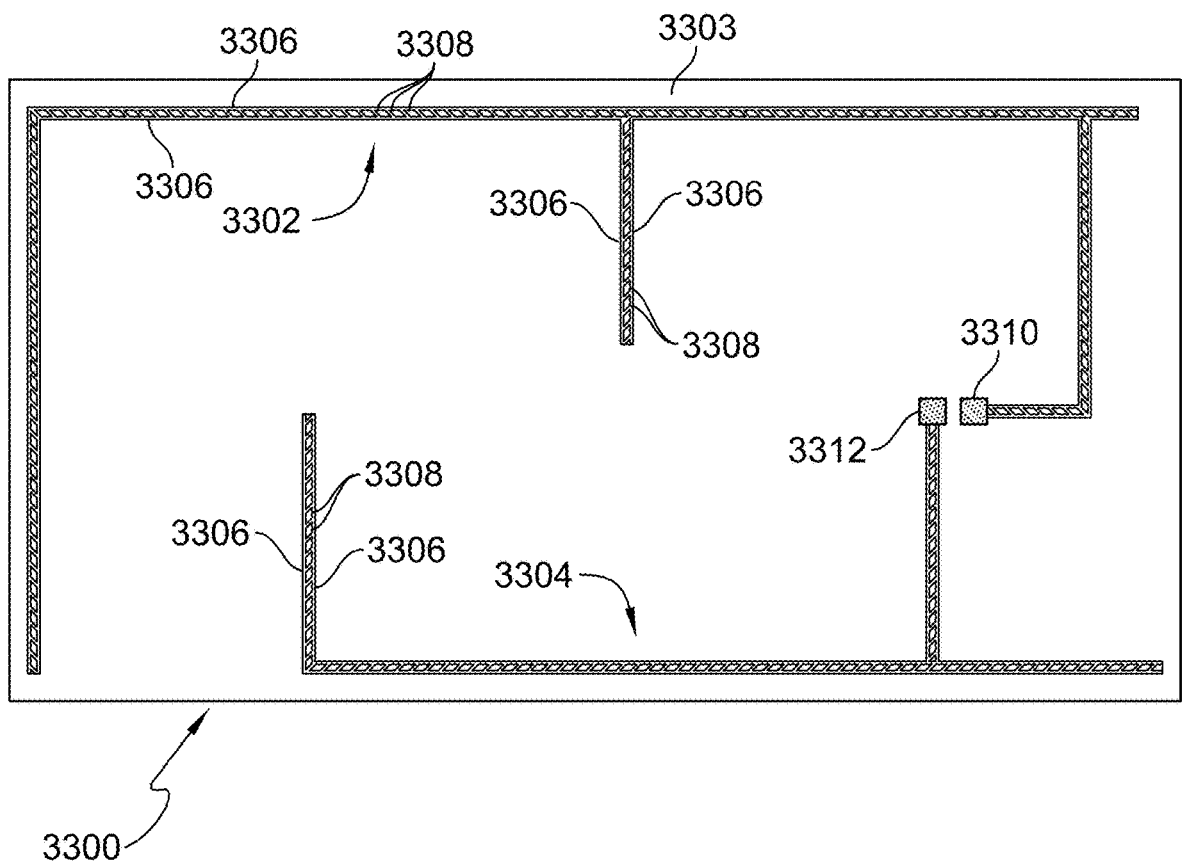
FIG. 43 is a top plan view of another embodiment of a backsheet showing the backsheet having electrode traces formed by pairs of spaced and parallel elongated trace portions and a plurality of angled trace portions that bridge the space between the pair of spaced and parallel elongated trace portions to form a large number of conductive pathways between terminal ends of the electrode traces.

Referring now to FIG. 43, another embodiment of a backsheet 3300 has a substrate 3303 and first and second electrode traces 3302, 3304 formed on the substrate 3303 by pairs of spaced and parallel elongated trace portions 3306 and a plurality of angled trace portions 3308 that bridge the space between the pair of spaced and parallel elongated trace portions 3306 to form a large number of conductive pathways between first and second terminal ends 3310, 3312 of the electrodes 3302, 3304. The angled trace portions 3308 are each non-parallel with, and non-perpendicular to, either of the pair of spaced and parallel elongated trace portions 3306. Thus, in the illustrative example, spaces between adjacent pairs of the plurality of angled traces 3308 are shaped as rhomboids.

Figure 44:
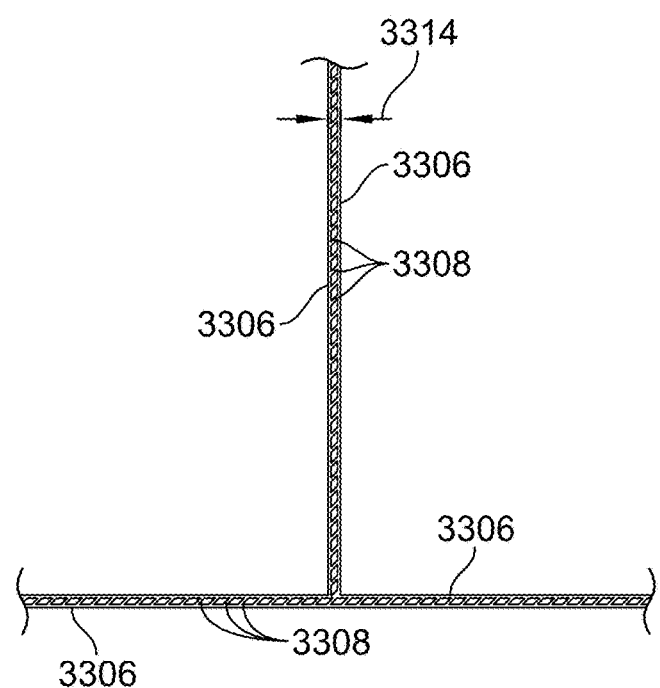
FIG. 44 is a top plan view showing an enlarged part of the electrode trace of FIG. 43.
Figure 46:
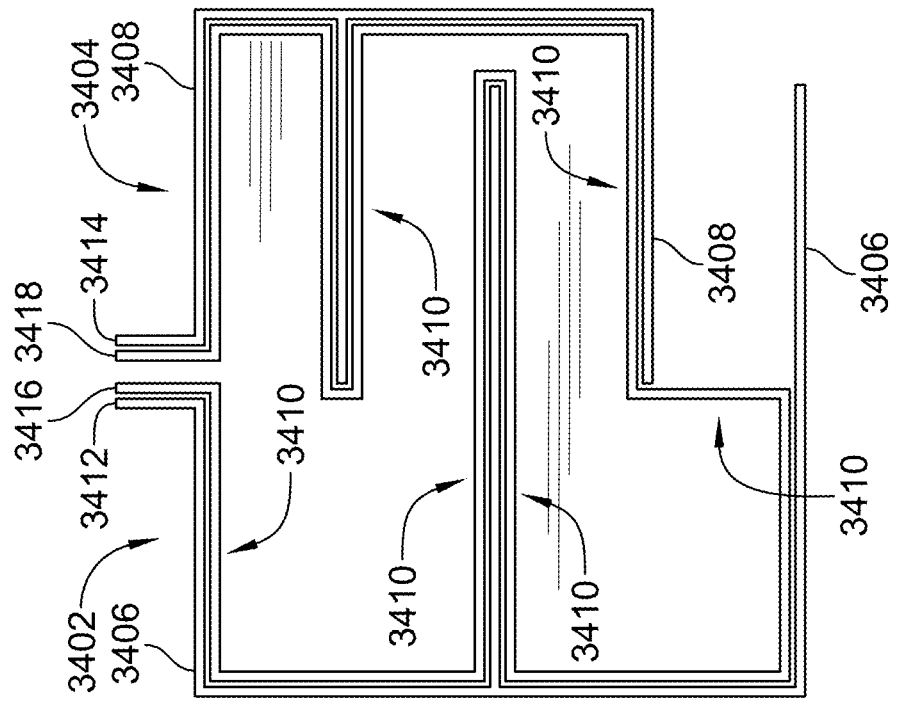
FIG. 46 is a top plan view, similar to FIG. 45, showing a sentinel electrode trace formed closely as a closed loop adjacent the pair of spaced electrodes.

As best shown in FIG. 44, the spaced and parallel elongated trace portions 3306 and the angled trace portions 3308 have substantially equal widths. The widths of portions 3306, 3308 are each about 1 mm. As also shown in FIG. 44, a distance 3314 between outside boundaries of the parallel elongated trace portions 3306 is about 3 mm. It should be appreciated that an RFID tag, such as tag 1512, is attached to the substrate 3303 so that electrical contacts of the RFID tag electrically couple with terminal ends 3310, 3312 of the electrodes 3302, 3304. In some embodiments, substrate 3300 is similar to substrate 3100 in that it comprises a sheet or film of polyethylene on which electrodes 3302, 3304 are printed and a layer of nonwoven material adhered to the sheet or film of polyethylene. According to this disclosure, electrodes having portions 3306, 3308 like those shown in FIGS. 43 and 44 can be substituted for the electrodes of each of the other incontinence detection pads disclosed herein.

By having spaces, illustratively shaped as rhomboids, between trace portions 3306, 3308, less conductive ink is needed to print the electrodes 3302, 3304 than if these traces were 3 mm wide solid lines. Thus, the design of trace portions 3306, 3308 represents a manufacturing cost savings. Also, the thinner widths of trace portions 3306, 3308 allows for faster drying times and/or use of lower curing temperatures due to the increased edge surface area. Thus, less damage to the trace and to the thin backsheet substrate as compared to solid traces of the same width is realized with the trace design of FIGS. 43 and 44.

Figure 45:
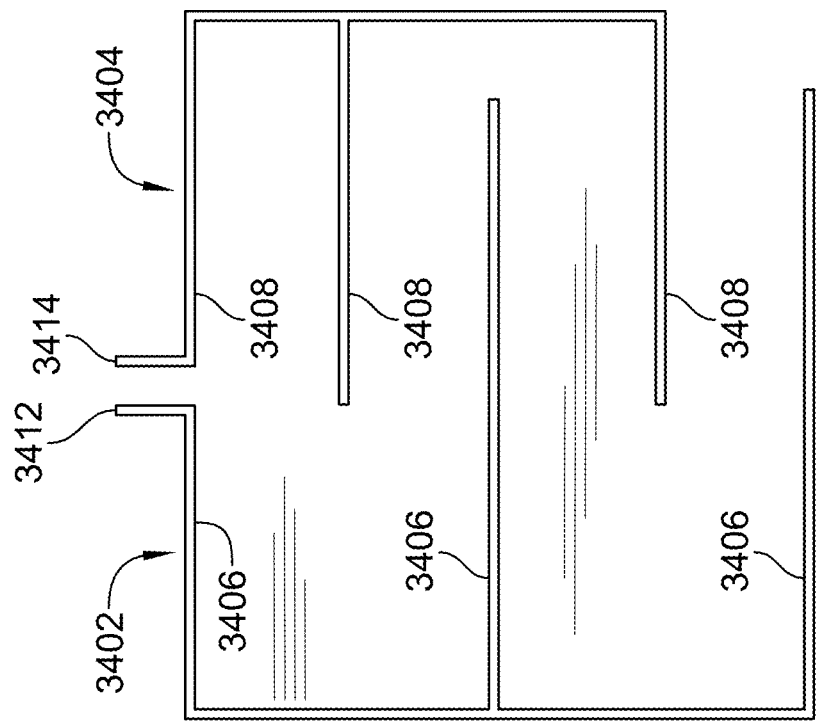
FIG. 45 is a top plan view showing a pair of spaced electrodes having interdigitated trace fingers.

Referring now to FIG. 45, spaced electrodes 3402, 3404 have respective trace segments 3406, 3408, some of which are interdigitated. Electrodes 3402, 3404 are similar to those provided on the various incontinence detection pads disclosed herein. According to this disclosure, a sentinel electrode trace 3410 is formed as a closed loop closely adjacent to the pair of spaced electrodes 3402, 3404. If either of traces 3402, 3404 breaks at any point therealong, the ability of the associated incontinence detection pad to sense wetness is potentially comprised. The closer the break is to terminal ends 3412, 3414 of electrodes 3402, 3404, respectively, the worse the problem. Such breakage in electrodes 3402, 3404 may occur, for example, when an associated incontinence detection pad is used by one or more caregivers (typically two or more) to reposition a patient in bed. When the pad is grabbed by the caregivers, localized stress and deformation of the backsheet occurs which can potentially cause breaks in the electrodes 3402, 3404.

Sentinel trace 3410 provides a means for testing for breaks in traces 3402, 3404. In particular, sentinel trace 3410 is tested from time to time to confirm that a short circuit exists between terminal ends 3416, 3418 of trace 3410. If sentinel trace 3410 passes the short circuit test, the assumption is that electrodes 3402, 3404 are not broken at any point because the sentinel trace 3410 is not broken. However, if sentinel trace 3410 fails the short circuit test, then a break has developed in sentinel trace 3410 which causes the trace 3410 to become an open circuit (assuming there is no wetness on the associated incontinence detection pad that would bridge the break in trace 3410). If trace 3410 fails the short circuit test, then the assumption is that at least one of electrodes 3402, 3404 has also developed a break at an adjacent location to the break in trace 3410.

Figure 47:
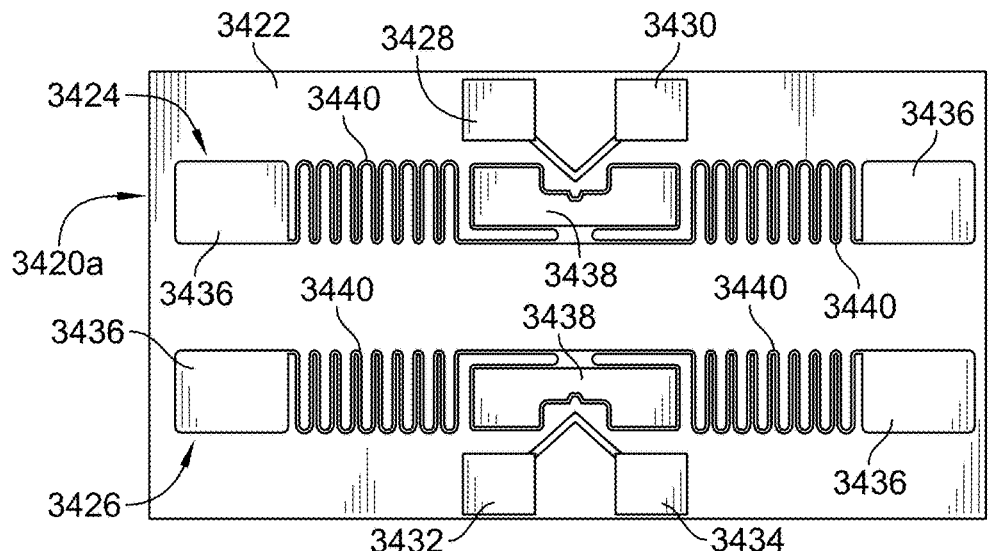
FIG. 47 is a first embodiment of a pair of RFID tags arranged on a common substrate, having a first pair of electrical contacts that couple to terminal ends of the pair of spaced apart electrodes, and having a second pair of electrical contacts that couple to terminal ends of the sentinel electrode trace.
Figure 48:
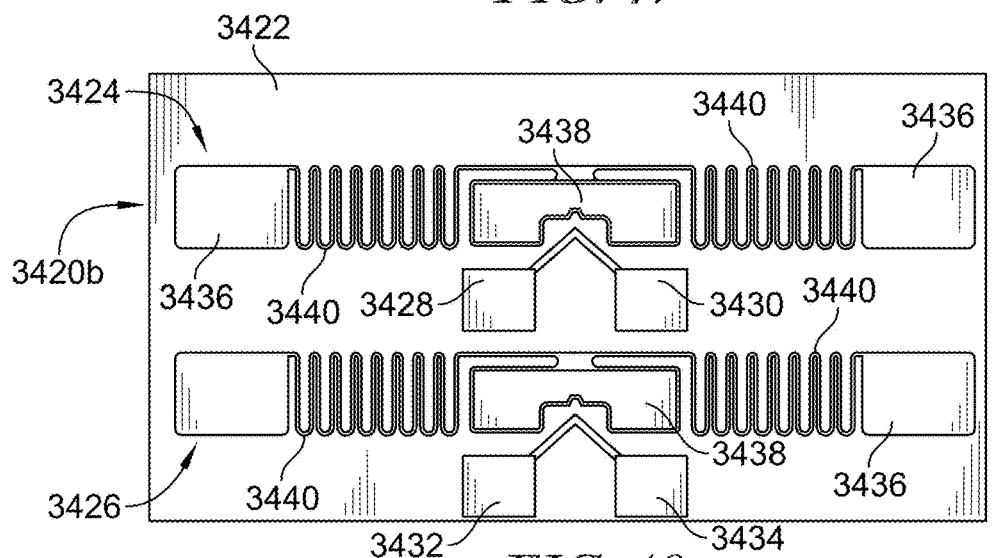
FIG. 48 is a second embodiment of a pair of RFID tags arranged on a common substrate, having a first pair of electrical contacts that couple to terminal ends of the pair of spaced apart electrodes, and having a second pair of electrical contacts that couple to terminal ends of the sentinel electrode trace.
Figure 49:
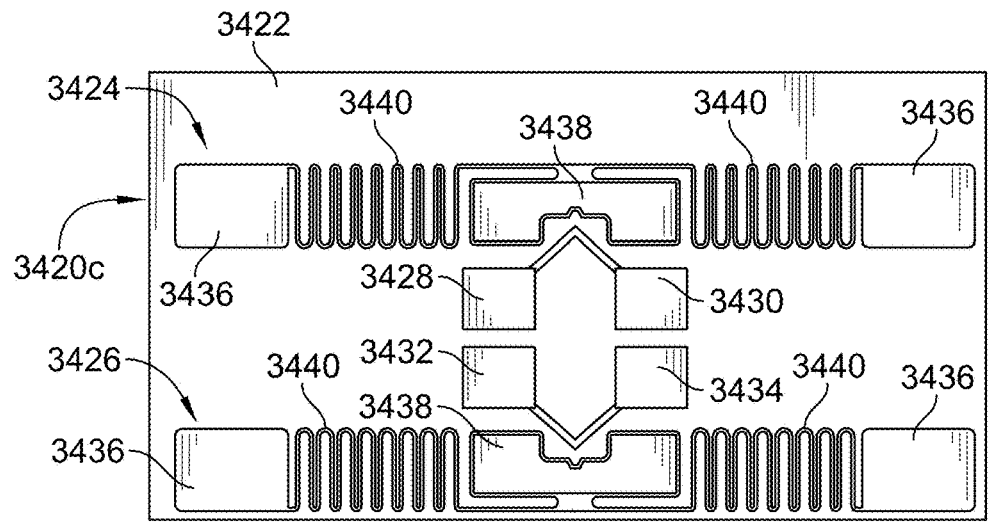
FIG. 49 is a third embodiment of a pair of RFID tags arranged on a common substrate, having a first pair of electrical contacts that couple to terminal ends of the pair of spaced apart electrodes, and having a second pair of electrical contacts that couple to terminal ends of the sentinel electrode trace.

Referring now to FIGS. 47-49, first, second and third embodiments of dual RFID tags 3420a, 3420b, 3420c are shown. Each tag 3420a, 3420b, 3420c has a common substrate 3422 to which first and second antennae 3424, 3426 are coupled. Substrate 3422 also carries a first pair of electrical contacts 3428, 3430 that are associated with antenna 3424 and a second pair of electrical contacts 3432, 3434 that are associated with antenna 3426. Electrical contacts 3428, 3430 couple to terminal ends 3412, 3414 of the pair of spaced apart electrodes 3402, 3404. Electrical contacts 3432, 3434 couple to terminal ends 3416, 3418 of the sentinel electrode trace 3410. In FIG. 47, tag 3420a is configured such that antennae 3424, 3426 are situated between pair of contacts 3428, 3430 and pair of contacts 3432, 3434. In FIG. 48, tag 3420b is configured such that pair of electrical contacts 3428, 3430 is situated between antenna 3424, 3426. In FIG. 49, tag 3420c is configured so that pair of electrical contacts 3428, 3430 and the pair of electrical contacts 3432, 3434 are situated between antennae 3424, 3426.

The end portions of electrodes 3402, 3404, 3410 are routed appropriately in each of embodiments 3420a, 3420b, 3420c so that terminal ends 3412, 3414, 3416, 3418 reach the respective electrical contacts 3428, 3430, 3432, 3434 without any—portions of electrodes 3402, 3404, 3410 extending over any portions of antenna 3424, 3426. Antennae 3424, 3426 each include a pair of spaced apart end patches, 3436, a central patch 3438, and a pair of undulated segments 3440 that interconnect respective patches 3436 with patch 3438. A pair of RFID chips such as those discussed above are included in each of tags 3420a, 3420b, 3420c and interconnect respective pairs of electrical contacts 3428, 3430, 3432, 3434 with the associated antennae 3424, 3436.

Tags 3420a, 3420b, 3420c are configured so that when the pair of RFID chips are interrogated or irradiated with energy, they respond after a random delay period such that the responses occur at different times. This permits the reader to take an inventory to identify the pair of RFID chips included in tags 3420a, 3420b, 3420c. Once the chips are identified by the reader, the reader is able to dictate which chip of the pair of chips of tags 3420a, 3420b, 3420c are to respond to the next successive interrogations. Thus, a single reader is used to read the RFID chip coupled to electrodes 3402, 3404 separately from reading the RFID chip coupled to sentinel electrode 3410. Accordingly, collisions and overlap of the transmissions from the RFID chips of tags 3420a, 3420b, 3420c are avoided.

Figure 52:
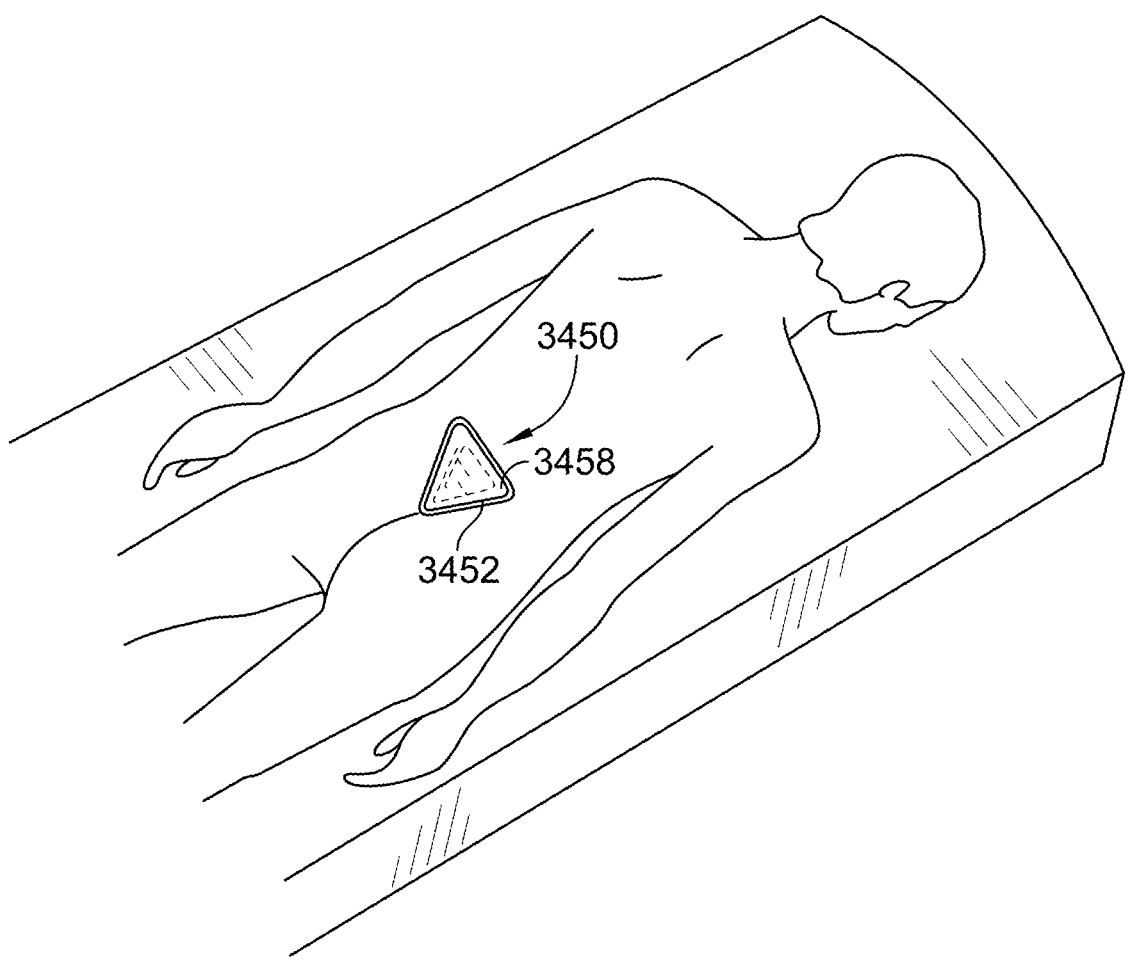
FIG. 52 is a perspective view of the dressing of FIGS. 50 and 51 attached to a sacral region of a patient.

Referring now to FIGS. 50 and 51, a dressing 3450 has a central base sheet 3452 including a pair of electrode traces 3454, 3456 on opposite surfaces for detecting wound moisture and for detecting incontinence. Dressing 3450 further includes a first fluid permeable cover sheet 3458, a first layer of absorbent material 3460, a second layer of absorbent material 3462, and a second fluid permeable cover sheet 3464. Base sheet 3452 has a first RFID tag 3466 on top surface thereof and a second RFID tag 3468 on a bottom surface thereof. Tags 3466, 3468 are electrically coupled to respective electrodes 3454, 3456 on the top and bottom surfaces of base sheet 3452. As shown in FIG. 52, the illustrative dressing 3450 is sized and configured for attachment to a sacral region of a patient. In this regard, base sheet 3452, absorbent material 3460, 3462, and covers 3458, 3463 are each triangular in shape.

Electrodes 3454, 3456 and RFID tag 3468 on the bottom surface of base sheet 3452 serve as a first moisture detection sensor that transmits a first signal in response to detecting moisture, such as blood or wound exudate, from the wound of the patient. Electrodes 3454, 3456 and RFID tag 3466 on the top surface of base sheet 3452 serve as a second moisture detection sensor that transmits a second signal in response to detecting incontinence from the patient. In some embodiments, the base sheet comprises polyethylene. Optionally, a periphery of the base sheet 3452 has adhesive for attachment of the dressing to the patient. Alternatively or additionally, medical tape is used to attach dressing 3450 to the patient. In either case, a peripheral region of the base sheet 3452 extends beyond boundaries of the first and second cover sheets 3458, 3464. Furthermore, a first peripheral region of the first cover sheet 3458 extends beyond a first outer periphery of the first layer of absorbent material 3460 and a second peripheral region of the second cover sheet 3464 extends beyond a second outer periphery of the second layer of absorbent material 3462.

According to this disclosure, the first RFID tag 3466 and the second RFID tag 3468 have random delay times in connection with transmission of data in response to being excited with energy. At least one of the first and second RFID tags 3466, 3468 is configured to receive a wireless message commanding the respective first or second RFID tag 3466, 3468 not to transmit any data in response to a next excitation of energy. In some embodiments, the first electrodes 3454 on the top and bottom surfaces of base sheet 3452 and the second electrodes 3456 on the top and bottom surfaces of base sheet 3452 include conductive ink printed on the respective top and bottom surfaces of the base sheet 3452.

In some embodiments, the base sheet 3452 is made from a single layer of material. In other embodiments, the base sheet 3452 includes a first base sheet layer and a second base sheet layer removably coupled to the first base sheet layer. The first base sheet layer may carry the one of the moisture detection sensors 3454, 3456, 3466, the first layer of absorbent material 3460, and the first cover sheet 3458. The second base sheet layer may carry the other moisture detection sensor 3454, 3456, 3468, the second layer of absorbent material 3462, and the second cover sheet 3464. The first base sheet layer along with the associated moisture detection sensor 3454, 3456, 3466, the first layer of absorbent material 3460, and the first cover sheet 3458 are removable from the second base sheet layer to permit replacement of the first base sheet layer along with the first moisture detection sensor 3454, 3456, 3466, the first layer of absorbent material 3460, and the first cover sheet 3458 after an incontinence event without the need to replace the second base sheet layer carrying the second moisture detection sensor 3454, 3456, 3468, the second layer of absorbent material 3463, and the second cover sheet 3464.

Figure 53A:
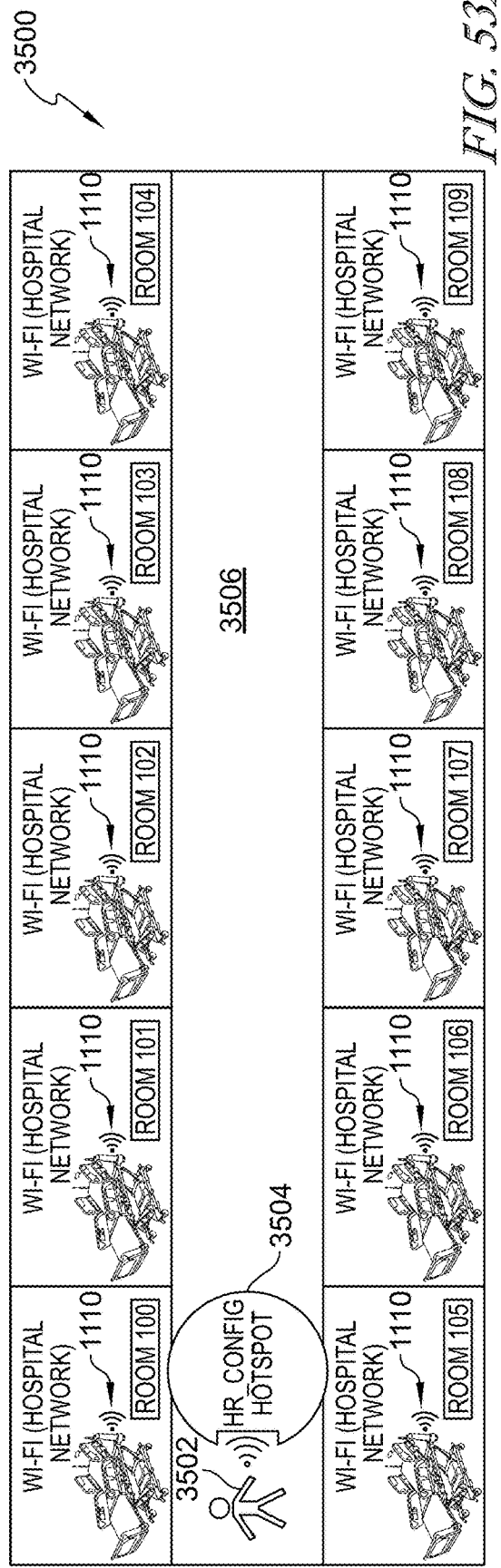
FIG. 53A is a diagrammatic view showing a number of hospital beds located in respective rooms of a healthcare facility and communicating via Wi-Fi with a hospital network and showing a technician carrying a computer which serves as a configuration hotspot.
Figure 53B:
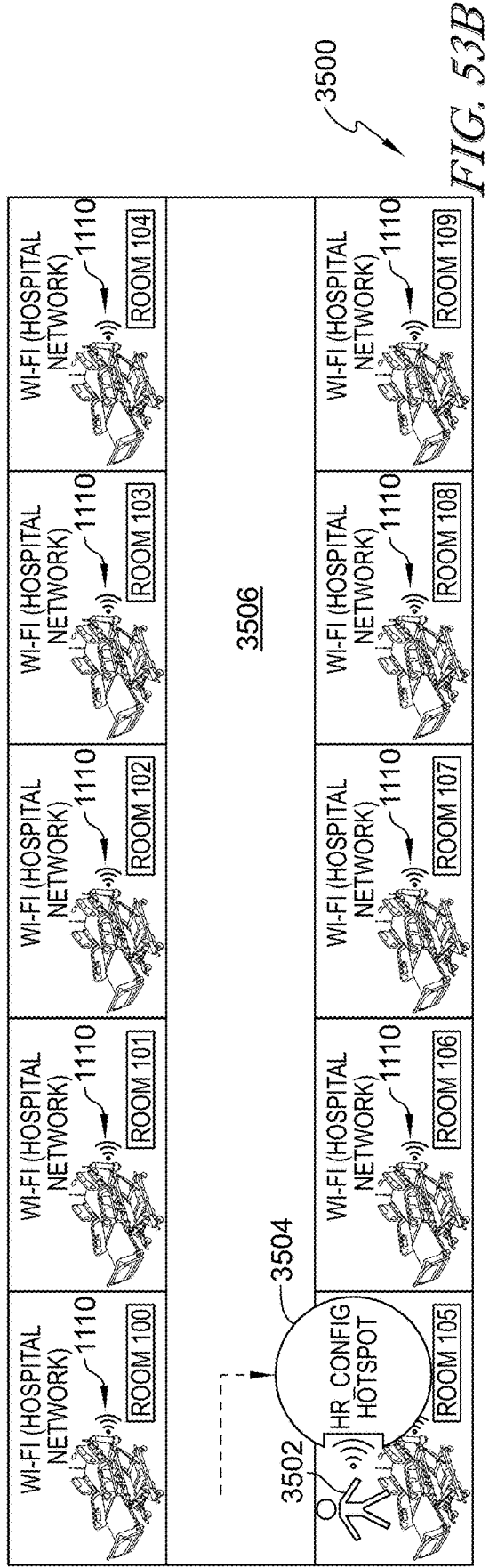
FIG. 53B is a diagrammatic view, similar to FIG. 53A, showing the technician entering room 105 and showing the hospital bed in room 105 no longer communicating with the hospital network but, instead, communicating with the computer carried by the technician.
Figure 54:
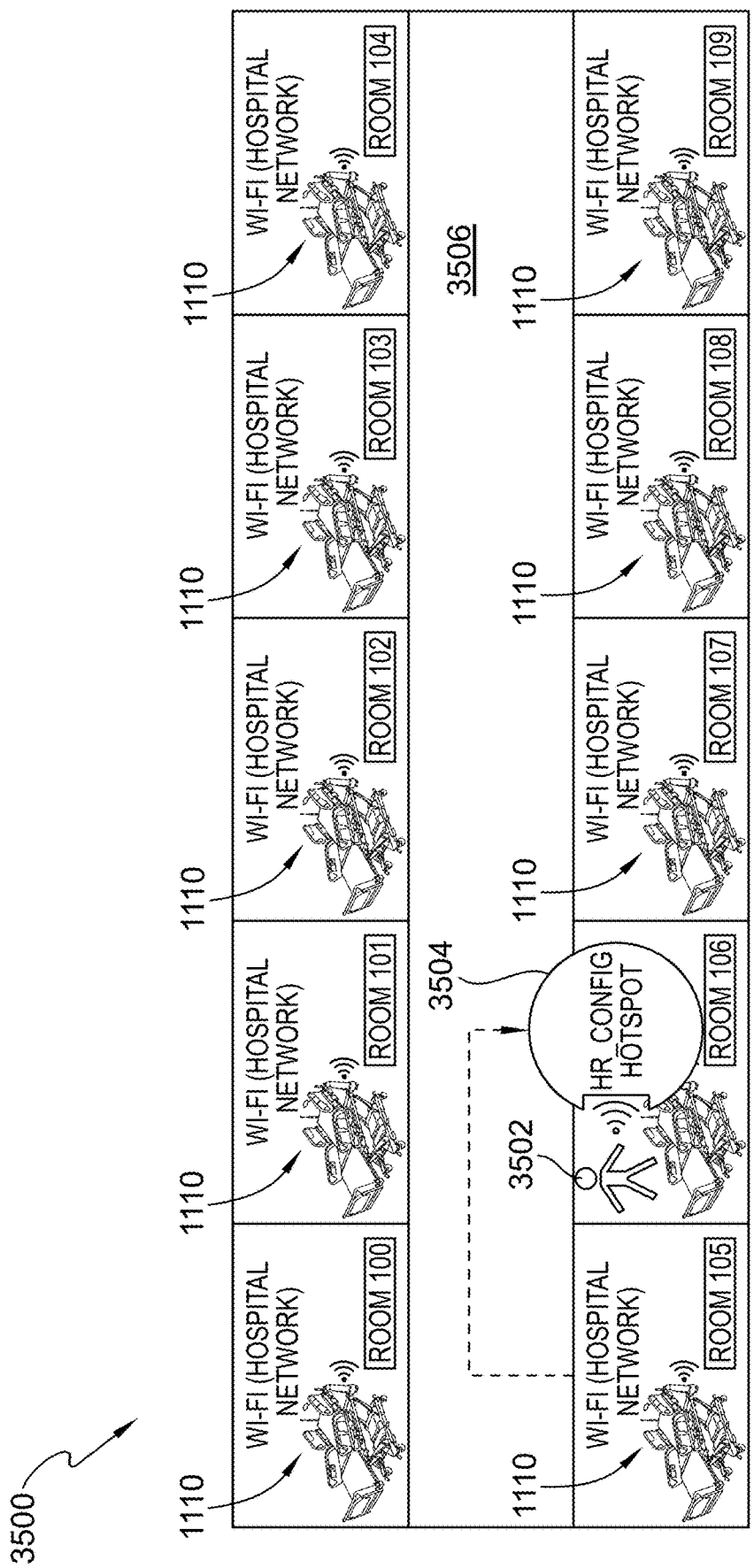
FIG. 54 is a diagrammatic view, similar to FIG. 53B, showing the technician leaving room 105, such that the bed in room 105 once again communicates with the hospital network via Wi-Fi, and entering room 106, such that the bed in room 106 no longer communicates with the hospital network but, instead, communicates with the computer carried by the technician.

Referring now to FIGS. 53A, 53B, and 54, a diagrammatic view of a healthcare facility 3500 has a number of hospital beds 1110 located in respective rooms which are labeled rooms 100-109. In the illustrative example, each bed 1110 has circuitry that is configured to communicate via Wi-Fi with a hospital network. Such circuitry may be the bed control circuitry, such as circuitry 1302 shown diagrammatically in FIG. 13, or may be the circuitry of another system on the bed 1110, such as the circuitry of reader 1112 of incontinence detection system 1100. A technician 3502 carries a computer 3504 which serves as a configuration hotspot according to this disclosure. Computer 3504 is represented diagrammatically as a circle with a notch in FIGS. 53A, 53B, and 54. The discussion below uses the example of computer 3504 linking with the circuitry of beds 1110 for wireless communication but the discussion is equally applicable to computer 3504 linking for wireless communication with other wireless capable devices located in the particular room.

When technician 3502 carries computer 3504 in a hallway 3506 of healthcare facility 3500, such as shown in FIG. 53A, computer 3504 is too far away from the wireless-capable devices, such as beds 1110 and/or incontinence detection systems 1100, located in the patient rooms 100-109, for any wireless communication to occur therebetween. Thus, no wireless communication links exist between computer 3504 and beds 1110 when technician 3502 is in hallway 3506. However, when technician 3502 enters into one of the rooms, such as shown in FIG. 53B in which technician 3502 has entered room 105, computer 3504 and the bed 1110 in room 105 are able to communicate wirelessly once computer 3504 is in close enough proximity with bed 1110. Proximity on the order of 2 to 10 feet is contemplated by this disclosure, for example, to permit wireless communication between computer 3504 and each of beds 1110.

After computer 3504 and the bed 1110 in room 105 have automatically established wireless communications, which occurs within just a few seconds of computer 3504 being brought in close enough proximity to bed 1110, the portable computer 3504 transmits a service set identifier (SSID) to bed 1110 which, in turn, detects the SSID included in the transmission from the portable computer 3504. Once the SSID is detected by bed 1110, the bed disconnects from the hospital network thereby ceasing communications with the network of healthcare facility 3500. The portable computer 3504 then establishes a secure shell (SSH) connection with the bed 1110 in room 105. After the SSH connection is established, computer 3405 or another remote computer of a service network then reconfigures the bed 1110 via the SSH connection. Such reconfiguring includes downloading additional software modules to bed 1110 thereby to provide the bed 1110 with additional or enhanced functionality, replacing existing software modules of bed 1110 with new software modules 1110, and/or replacing all of the software of bed 1110 with new software.

After bed 1110 of room 105 has been reconfigured and the technician 3502 carries computer 3504 away from the bed 1110 by a sufficient distance, bed 1110 of room 105 then automatically reconnects with the network of the healthcare facility. As shown in FIG. 54, the technician 3502 has left room 105 and has entered room 106 where the process just described repeats for the bed 1110 in room 106. Of course, if desired, the technician 3502 carries computer 3504 to each of rooms 100-109 so that the beds 1110 in each room are reconfigured.

Figure 55:
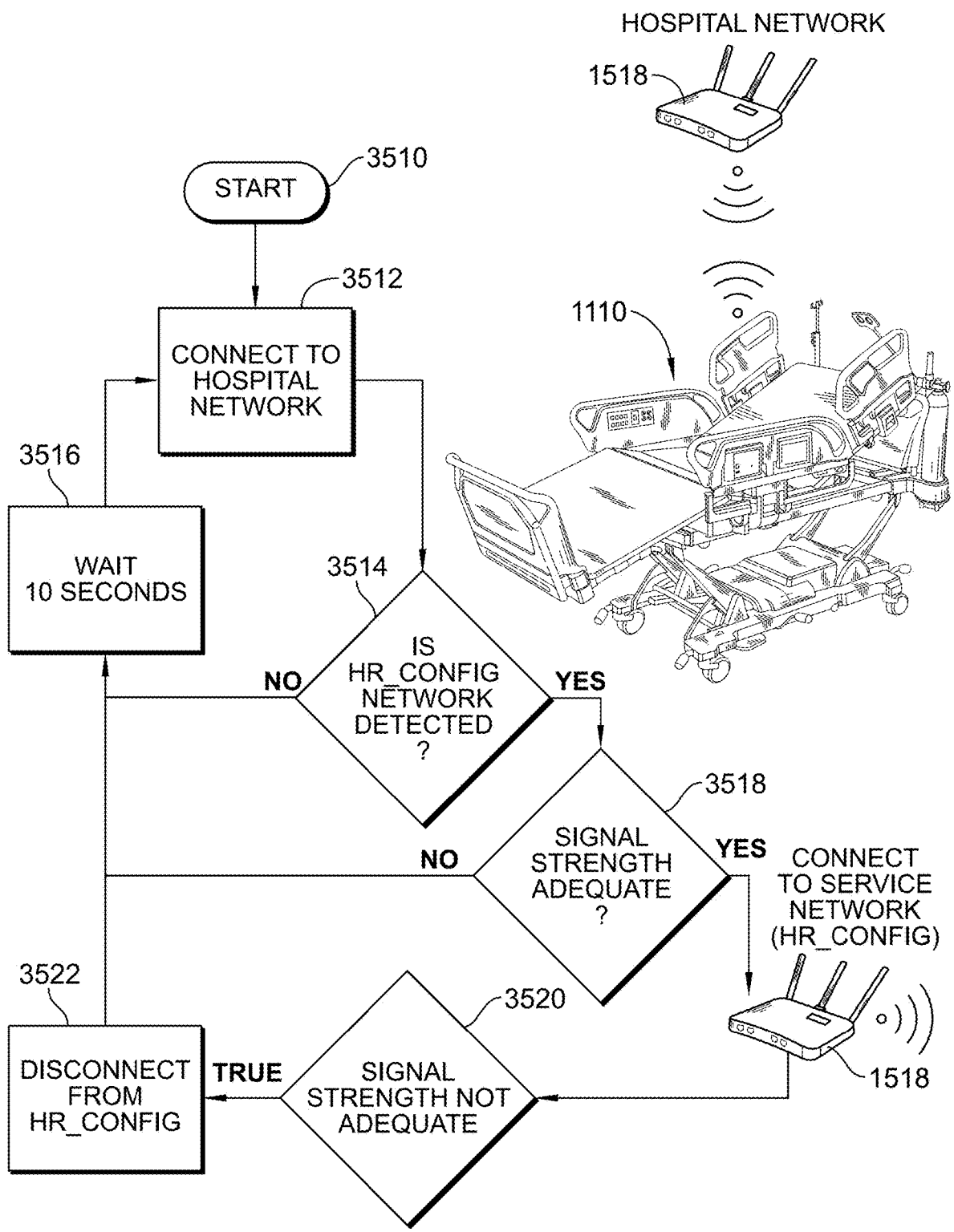
FIG. 55 is a flow chart showing an algorithm used by medical devices, such as the illustrative hospital beds of FIGS. 53A-54, to connect to and disconnect from the computer carried by the technician.
Figure 56A:
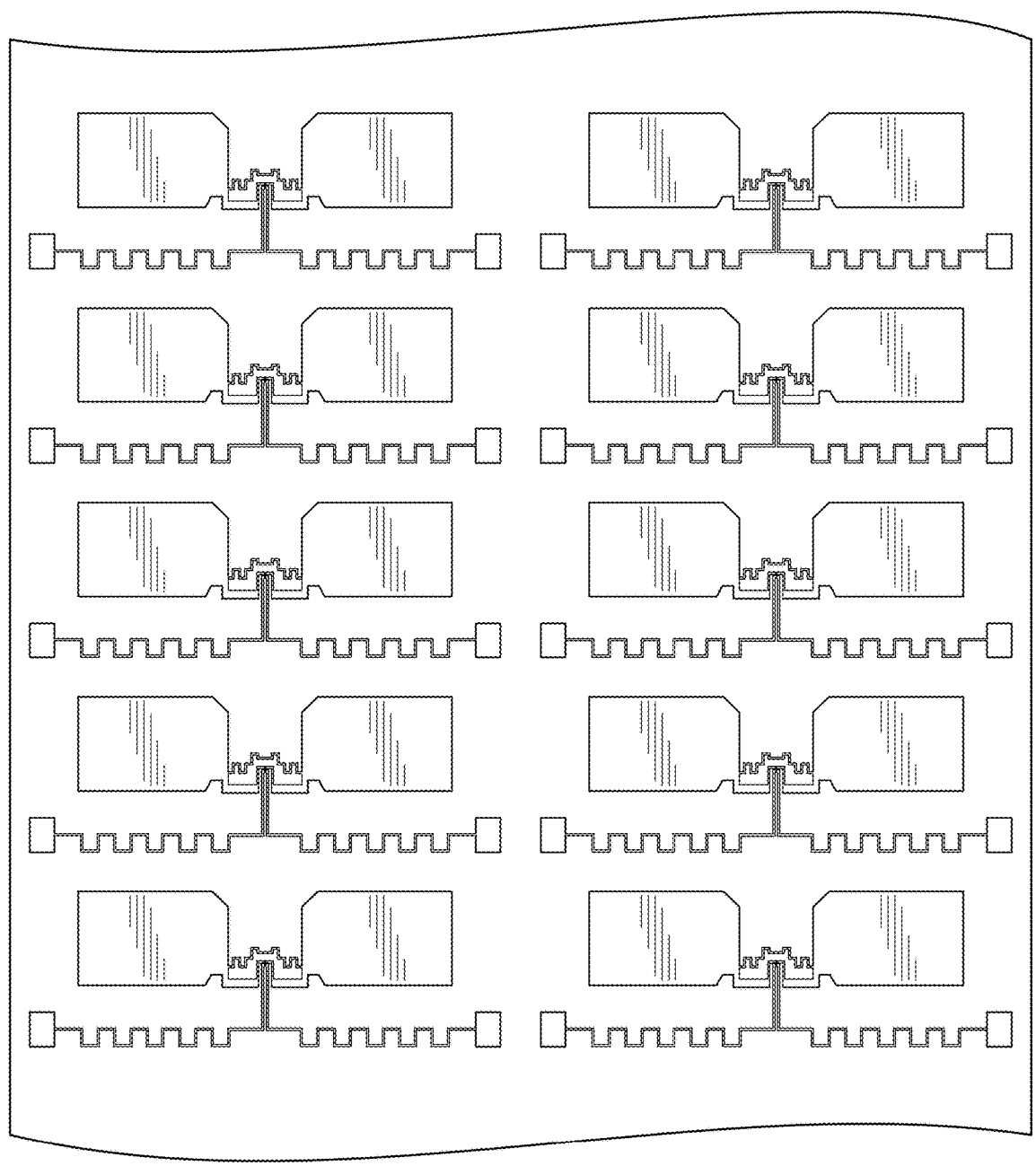
FIG. 56A is a top plan view of a substrate carrying a number of antennae assemblies for attachment to RFID tags used in incontinence detection pads.
Figure 56B:
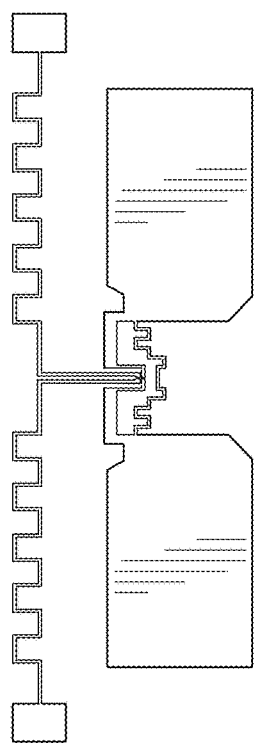
FIG. 56B is a top plan view of one of the antenna assemblies of FIG. 56A.
Figure 56C:
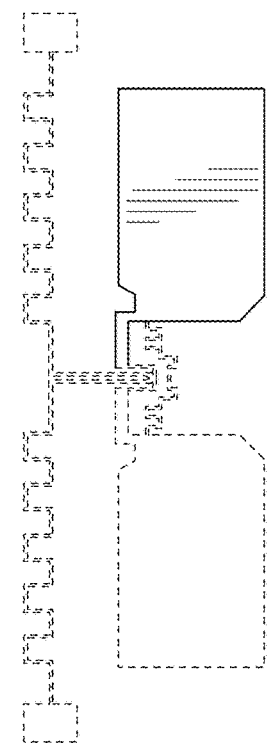
FIG. 56C is a top plan view of the antenna assembly of FIG. 56B showing a first large antenna patch in solid and the rest of the antenna assembly dotted out.
Figure 56D:
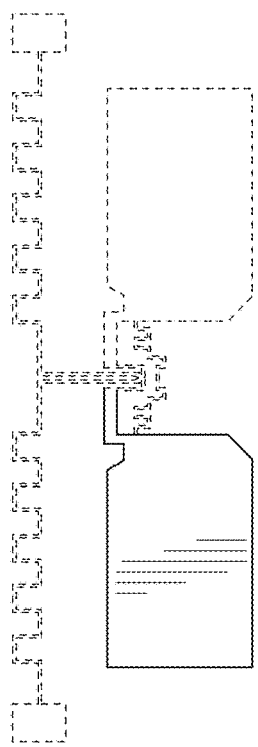
FIG. 56D is a top plan view of the antenna assembly of FIG. 56B showing a second large antenna patch in solid and the rest of the antenna assembly dotted out.
Figure 56E:
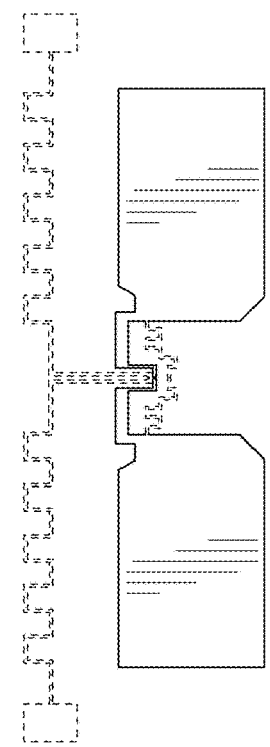
FIG. 56E is a top plan view of the antenna assembly of FIG. 56B showing the first and second large antennae patches in solid and the rest of the antenna assembly dotted out.
Figure 56F:
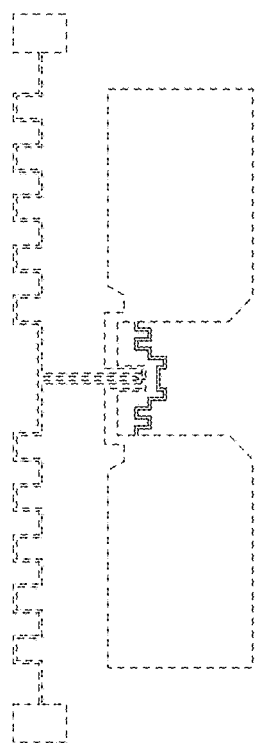
FIG. 56F is a top plan view of the antenna assembly of FIG. 56B showing an upper undulated antenna connection portion in solid and the rest of the antenna assembly dotted out.
Figure 56G:
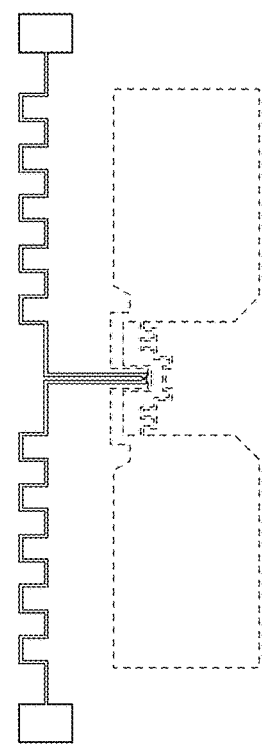
FIG. 56G is a top plan view of the antenna assembly of FIG. 56B showing a lower undulated antenna to electrical contact pad connection portion in solid and the rest of the antenna assembly dotted out.
Figure 56H:
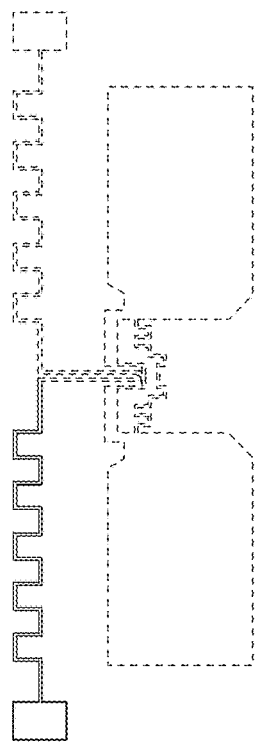
FIG. 56H is a top plan view of the antenna assembly of FIG. 56B showing a first portion of the lower undulated antenna to electrical contact pad connection in solid and the rest of the antenna assembly dotted out.
Figure 56I:
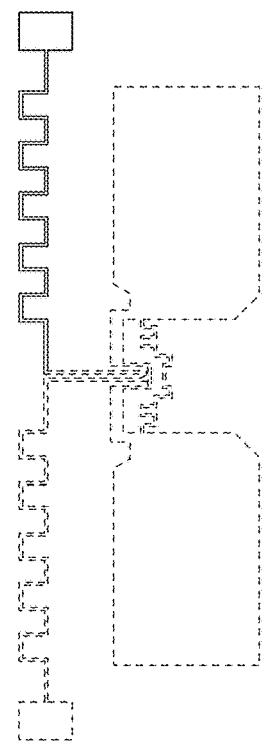
FIG. 56I is a top plan view of the antenna assembly of FIG. 56B showing a second portion of the lower undulated antenna to electrical contact pad connection in solid and the rest of the antenna assembly dotted out.

Referring now to FIG. 55, a flow chart shows an algorithm used by medical devices, such as the illustrative hospital beds 1110 of FIGS. 53A-54, to connect to and disconnect from the computer 3504 carried by the technician 3502. The algorithm starts at block 3510 and proceeds to block 3512 where the hospital bed 1110, one of which is shown next to the flow chart in FIG. 55, connects to the hospital network 1518 which is shown diagrammatically in FIG. 55. The algorithm proceeds from block 3512 to block 3514 where the circuitry of bed 1110 determines whether a configuration network is detected (e.g., whether computer 3504 is in communicative proximity of bed 1110). If the computer 3504 is not detected, the algorithm proceeds to block 3516 and a wait period of some amount of time, 10 seconds in the illustrative example, transpires until the algorithm proceeds back to block 3512.

If at block 3514 the circuitry of bed 1110 does detect computer 3504, the algorithm proceeds to block 3518 to determine whether the signal strength of the transmission(s) from computer 3504 is adequate. If the signal strength is not adequate, the algorithm proceeds back to the wait time block 3516 and proceeds from there. If at block 3518 the circuitry of bed 1110 does determine that the signal strength is adequate, the circuitry of bed 1110 proceeds to connect to the service network (illustratively indicated as being a portion of network 1518 in the FIG. 55 example). The bed 1110 is then reconfigured via the service network and/or computer 3504.

During the reconfiguring process and thereafter, the circuitry of bed 1110 monitors the signal strength of the communications between the bed 1110 and the service network and/or computer 3504 as indicated at block 3520. If the signal strength is not adequate at block 3520, then the circuitry of bed 1110 disconnects from the service network and/or computer 3504 as indicated at block 3522, after which the algorithm proceeds back to the time delay block 3516 and the proceeds from there.

Based on the foregoing, it should be understood that a method according to this disclosure includes providing reconfigurable devices, such as beds 1110 and/or incontinence detection systems 1100, in a plurality of patient rooms, configuring a portable computer 3504 as a WiFi hotspot, programming the portable computer 3504 to transmit a service set identifier (SSID), transporting the portable computer into communicative proximity of a first reconfigurable device so that the reconfigurable device is able to detect the SSID included in a transmission from the portable computer 3504, detecting the SSID in the first reconfigurable device, ceasing communications, in the first reconfigurable device, with network 1518 of healthcare facility 3500, using the portable computer 3504 to establish a secure shell (SSH) connection with the first reconfigurable device, and reconfiguring the reconfigurable device via the SSH connection.

In some embodiments, the method may further include checking, in the reconfigurable device, to determine if a signal strength of the transmission from the portable computer 3504 having the SSID meets a threshold signal strength prior to ceasing communications with the network 1518 of the healthcare facility 3500. Alternatively or additionally, the method may further include transporting the portable computer out of communicative proximity of the first reconfigurable device and, in response, the first reconfigurable device may automatically reconnect to the network 1518 of the healthcare facility 3500. For example, automatically reconnecting to the network 1518 may occur only after a threshold amount of time has passed after the portable computer 3504 is transported out of communicative proximity of the first reconfigurable device. The threshold amount of time may be about ten seconds in some embodiments.

In some embodiments, the portable computer 3504 and the first reconfigurable device communicate via wireless transmissions. The portable computer 3504 and the first reconfigurable device may communicate according to the TCP/IP protocol, for example. Alternatively or additionally, the first reconfigurable device may communicate via wireless transmissions with the network 1518 of the healthcare facility 3500. The plurality of reconfigurable devices may include hospital beds 1110. Alternatively or additionally, the plurality of reconfigurable devices may include incontinence detection systems 1100.

Network 1518 may have, therefore, a first set of computer devices (e.g., a regular hospital network) with which the bed 1110 communicates in the absence of computer 3504 and a second set of computer devices (e.g., a service network) with which bed communicates when computer 3504 is present in the respective room and in close enough proximity to the bed 1110 for successful wireless communications. Software to reconfigure each bed 1110 is stored on computer 3504 and transmitted directly to the bed 1110 from computer 3504 in some embodiments. In other embodiments, the software to reconfigure each bed is transmitted from a remote computer device of the service network to bed 1110 via computer 3504. In further embodiments, the software to reconfigure each bed is transmitted from a remote computer device of the service network to bed 1110 via a wireless access point of the network 1518, for example, without involving computer 3504 in the communication path. However, in such embodiments, computer 3504 is required to be in communicative proximity with the bed 1110 even though it is not in the communication path to the bed 1110 for the software with which the bed 1110 is to be reconfigured.

The bed software reconfiguration system and method disclosed herein is an improvement over reconfiguration systems and methods of the prior art requiring a direct wired connection between beds and a reconfiguration computer such as a lap top. In the contemplated system, service technicians use a tablet PC 3504 with a built-in wireless access point, or "hotspot". This portable PC 3504 gives a lot of mobility to the technician. By utilizing the wireless capabilities of both the tablet PC 3504 and the medical devices, such as beds 1110 and/or incontinence detection systems 1110, a wireless relationship between the clients (the devices) and the service administrative tools (the tablet PC) is formed. By eliminating the need for a physical connection to a device, bed reconfiguration requires less time than when physically interfacing with a device is required. Thus, the contemplated bed reconfiguration system and method permits faster configuration and lower field service cost. In some embodiments, service logic is abstracted from the product and placed onto the configuration device, thereby reducing project costs tied to implementation of service logic. After a device is reconfigured, there is a quick return to standard operation for the reconfigured devices.

To achieve the benefits of the disclosed system and method, a reconfiguration software module is programmed into the reconfigurable device at manufacturing. Such a software module includes a specific, secured wireless profile with the SSID (broadcasted wireless network name), for instance, "HR_Config." A simple script (i.e., software code of the reconfiguration software) checks for the presence of the "HR_Config" SSID at a set interval. If the SSID is detected, the reconfiguration software then checks for the "strength" of the signal. If the strength is acceptable, meaning that the access point 3504 is nearby, it will connect to it. If the reconfigurable device is already connected to the HR_Config SSID, it can monitor the strength of the broadcasted signal and if it becomes too weak, it will disconnect from the HR_Config wireless network and resume normal operation.

By using the strength of the signal of a broadcasted wireless network, decisions can be made as to whether the strength is strong enough that the module should connect to the network, and vice versa, if the strength is weak, to disconnect from the network. What this achieves is, in essence, a controlled "sphere of influence" that surrounds the technician as they navigate a facility with computer 3504. The devices within this sphere of influence are capable of being configured. As soon as the technician 3502 navigates to a new area, and the device is no longer within the sphere of influence, it will automatically disconnect and resume standard operation.

FIGS. 56A-56I, 59A-59G, 60A-60G, 61A-61E, 62A-62D, 63A-63D, 64A-64D, 65A, 65B, 66A, 66B, 67A-67D, 68A-68D, 69A-69L, and 70 show the ornamental features of incontinence detection pads according to the present disclosure and may form the basis for future design patent applications claiming priority to the present disclosure.

Some of the above embodiments may be described in terms of functional block components and various processing steps. Such functional blocks may be realized by any number of hardware and/or software components configured to perform the specified functions. For example, embodiments may employ various integrated circuit components, e.g., memory elements, processing elements, logic elements, look-up tables, and the like, which may carry out a variety of functions under the control of one or more processors, microprocessors or other control devices. Similarly, where the elements of the above embodiments are implemented using software programming or software elements the embodiments may be implemented with any programming or scripting language such as C, C++, Java, assembler, or the like, with the various algorithms being implemented with any combination of data structures, objects, processes, routines or other programming elements. Furthermore, the embodiments could employ any number of conventional techniques for electronics configuration, signal processing and/or control, data processing and the like. The word "mechanism" may be used broadly and is not limited to mechanical or physical embodiments, but can include software routines in conjunction with processors, etc.

The particular implementations shown and described herein are illustrative examples and are not intended to otherwise limit the scope of the claims in any way. For the sake of brevity, conventional electronics, control systems, software development and other functional aspects of the systems (and components of the individual operating components of the systems) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device. Moreover, no item or component disclosed herein is intended to be an essential element. Numerous modifications and adaptations will be readily apparent to those skilled in this art without departing from the spirit and scope of the embodiments.

The order of execution or performance of the operations in embodiments illustrated and described herein is not essential. That is, the operations may be performed in any order, unless otherwise specified, and embodiments as described may include additional or fewer operations than those disclosed herein. For example, it is contemplated that executing or performing a particular operation before, contemporaneously with, or after another operation is within the scope of aspects of the present disclosure.

Embodiments may be implemented with computer-executable instructions. The computer-executable instructions may be organized into one or more computer-executable components or modules. Aspects of the disclosure may be implemented with any number and organization of such components or modules. For example, aspects of the disclosure are not limited to the specific computer-executable instructions or the specific components or modules illustrated in the figures and/or described herein. Other embodiments may include different computer-executable instructions or components having more or less functionality than illustrated and described herein.

Although certain illustrative embodiments have been described in detail above, variations and modifications exist within the scope and spirit of this disclosure as described and as defined in the following claims.

The invention claimed is:

1. An incontinence detection system for use with a patient support apparatus having a head end and a foot end, the incontinence detection system comprising
    an incontinence detection pad having a passive radio frequency identification (RFID) tag,
    a reader attachable to the patient support apparatus and operable to read data from the passive RFID tag,
    a first antenna attachable to the patient support apparatus,
    a second antenna housed separately from the first antenna and attachable to the patient support apparatus at a location spaced from the first antenna, wherein the first and second antenna are electrically coupled to the reader, wherein the passive RFID tag is excited by energy emitted from at least one of the first and second antennae and the data from the RFID tag of the incontinence pad is reflected back to at least one of the first and second antennae, a visual indicator electrically coupled to the reader by a first cable having sufficient length to permit the visual indicator to be mounted adjacent the foot end of the patient support apparatus, and an output port electrically coupled to the reader by a second cable having sufficient length to permit the output port to be mounted adjacent the head end of the patient support apparatus.

2. The incontinence detection system of claim 1, wherein the reader is operable to write data to the passive RFID tag via the first and second antenna.

3. The incontinence detection system of claim 1, wherein a first bit of the data stored in the passive RFID tag is set in response to the incontinence detection pad detecting wetness.

4. The incontinence detection system of claim 3, wherein the first bit is not set if the incontinence detection pad does not detect wetness.

5. The incontinence detection system of claim 4, wherein the first bit changes from being set to not being set in response to the incontinence detection pad becoming sufficiently dry after the incontinence detection pad has detected wetness, wherein a second bit of data stored in the passive RFID tag is set in response to the incontinence detection pad detecting wetness, and wherein the second bit of data remains set even after the incontinence detection pad becomes sufficiently dry after the incontinence detection pad has detected wetness to cause the first bit to change states back to not being set.

6. The incontinence detection system of claim 5, wherein the second bit serves as a kill bit that indicates to the reader that the incontinence detection pad cannot be used again once it becomes dry after having been wet.

7. The incontinence detection system of claim 1, wherein at least a portion of the data transferred between the passive RFID tag and the reader is encrypted.

8. The incontinence detection system of claim 1, wherein the incontinence detection pad comprises a top sheet, a backsheet having a pair of electrodes that are printed on the backsheet and that are electrically coupled to the passive RFID tag, and an absorbent core sandwiched between the top sheet and the backsheet.

9. The incontinence detection system of claim 1, wherein the first antenna is electrically coupled to the reader by a third cable that is routed through a first gap between first and second mattress support deck sections of the patient support apparatus.

10. The incontinence detection system of claim 9, wherein the second antenna is electrically coupled to the reader by a fourth cable that is also routed through the first gap.

11. The incontinence detection system of claim 9, wherein the second antenna is electrically coupled to the reader by a fourth cable that is routed through a second gap between the second mattress support deck section and a third mattress support deck section of the patient support apparatus.

12. The incontinence detection system of claim 1, wherein the first antenna is electrically coupled to the reader by a third cable that is routed through a first hole provided in a first mattress support deck section of the patient support apparatus.

13. The incontinence detection system of claim 12, wherein the second antenna is electrically coupled to the reader by a fourth cable that is routed through a second hole provided in a second mattress support deck section of the patient support apparatus.

14. The incontinence detection system of claim 9, wherein the second antenna is electrically coupled to the reader by a fourth cable that is routed through a second gap between the second mattress support deck section and a third mattress support deck section of the patient support apparatus.

15. The incontinence detection system of claim 1, wherein the output port comprises any one or more of the following: a female ¼ inch receptacle, a multi-contact connector, an RJ-45 connector, a 37-pin connector, or an RS-232 connector.

16. The incontinence detection system of claim 1, wherein the visual indicator is configured to be mounted to a portion of a foot section of the patient support apparatus that extends and retracts, and wherein the first cable is provided with sufficient slack to permit the extension and retraction of the portion of the foot section through its full range of movement.

17. The incontinence detection system of claim 1, wherein, when the incontinence detection pad is in communication with the reader, the visual indicator is illuminated a first color in response to the incontinence detection pad detecting wetness and the visual indicator is illuminated a second color in response to the incontinence detection pad not detecting wetness.

18. The incontinence detection system of claim 17, wherein the visual indicator flashes in response to the incontinence detection pad detecting wetness.

19. The incontinence detection system of claim 17, wherein the first color comprises amber or yellow and the second color comprises green.

20. The incontinence detection system of claim 17, wherein the visual indicator is illuminated a third color if the reader is not in communication with the incontinence detection pad.

* * * * *